(12) United States Patent
Dankulich et al.

(10) Patent No.: US 6,541,505 B1
(45) Date of Patent: Apr. 1, 2003

(54) SUBSTITUTED (AMINOIMINOMETHYL OR AMINOMETHYL) BENZOHETEROARYL COMPOUNDS

(75) Inventors: William P. Dankulich, Collegeville, PA (US); Daniel G. McGarry, Bedminster, NJ (US); Christopher Burns, Malvern, PA (US); Timothy F. Gallagher, Harleysville, PA (US); Francis A. Volz, Philadelphia, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/609,103

(22) Filed: Jun. 30, 2000

Related U.S. Application Data

(63) Continuation of application No. PCT/US99/30623, filed on Dec. 22, 1999.
(60) Provisional application No. 60/113,710, filed on Dec. 24, 1998, now abandoned.

(51) Int. Cl.$^7$ .................. A61K 31/405; A61K 31/4164; C07D 239/02; C07D 233/00
(52) U.S. Cl. ...................... 514/415; 514/428; 514/275; 514/396; 514/397; 514/235.8; 514/354; 544/322; 544/238; 544/335; 544/330; 544/162; 544/405; 548/311.1; 548/335.1; 548/335.5; 548/505; 548/504; 546/314; 546/329; 546/340; 546/277.4
(58) Field of Search ................................. 544/322, 111, 544/333, 149, 335, 162, 330, 170, 176, 405; 548/311.1, 503, 128, 335.1, 504, 335.5, 505, 510; 514/415, 428, 275, 396, 399, 231.5, 235.8, 252.1, 255.05, 397, 354; 546/314, 329, 340, 277.4

(56) References Cited

FOREIGN PATENT DOCUMENTS

| EP | 328200 | * | 8/1989 |
|---|---|---|---|
| EP | 0 568 289 | | 11/1993 |
| EP | 0 328 200 | | 12/1993 |
| FR | 2 400 518 | | 3/1979 |
| FR | 2400518 | * | 3/1979 |
| WO | WO 97/24118 | | 7/1997 |
| WO | WO 98/01428 | | 1/1998 |

OTHER PUBLICATIONS

Merriam Wedster's Collegiate Dictonary, 10th Edn., 1996, pp. 165 and 1320.*
Lape et al., "An Invest. of the Anthyperensive properties . . . ", Arch.Intl. Pharmacodyn, 171/2, 394–414(1968).*
Lape H.E. et al., An Investigation Of The Antihypertensive Properties Of A Series Of Indole And Azaindole Amidoximes with Particular Reference To 7–Azaindoxime and Indole–1–Acetamidoxime, Arch. int. Pharmacodyn., 1968, 171, No. 2. 394–414.

* cited by examiner

Primary Examiner—Mark L. Berch
Assistant Examiner—Sudhaker B. Patel
(74) Attorney, Agent, or Firm—Raymond S. Parker, III; Irving Newman

(57) ABSTRACT

This invention is directed to an (aminoiminomethyl or aminomethyl)benzoheteroaryl compound of formula I which is useful for inhibiting the activity of Factor Xa by combining said compound with a composition containing Factor Xa. The present invention is also directed to compositions containing compounds of the formula I, methods for their preparation, their use, such as in inhibiting the formation of thrombin or for treating a patient suffering from, or subject to, a disease state associated with a physiologically detrimental excess amount of thrombin.

35 Claims, No Drawings

SUBSTITUTED (AMINOIMINOMETHYL OR AMINOMETHYL) BENZOHETEROARYL COMPOUNDS

This is a continuation of International Patent Application No. PCT/US99/30623. filed Dec. 22, 1999, which is, in turn, a continuation of U.S. patent application Ser. No. 60/113,710, filed Dec. 24. 1998, now abandoned.

FIELD OF THE INVENTION

This invention is directed to substituted (aminoiminomethyl or aminomethyl)benzoheteroaryl compounds that inhibit Factor Xa, pharmaceutical compositions comprising these compounds and use of the compounds for inhibiting Factor Xa or otherwise treating a physiological condition in a patient that may be ameliorated by administering these compounds to the patient.

BACKGROUND OF THE INVENTION

Factor Xa is the penultimate enzyme in the coagulation cascade. Both free Factor Xa and Factor Xa assembled in the prothrombinase complex (Factor Xa, Factor Va, calcium and phosphiolipid) are inhibited by compounds of formula I. Factor Xa inhibition is obtained by direct complex formation between the inhibitor and the enzyme and is therefore independent of the plasma co-factor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus fonnation frequently occurs in the veins of the lower extremities following abdominal, knee and hip surgery (deep vein thrombosis, DVT). DVT further predisposes the patient to a higher risk of pulmonary throinboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threateniling clots throughout the microvasculature of several organ systems.

Accumulated experimental evidence has also reflected that prothrombin activation is only one of the biological activities of Factor Xa. EPR-1 (effector cell protease receptor-1, recognizing Factor Xa), is believed to mediate several of the vascular wall interactions by Factor Xa. It has been shown to be expressed on human umbilical vein endothelial cells, rat smooth muscle cells and platelets(CR McKenzie, et al., Arterioscler Thromb Vasc Biol 16 1285–91 (1996); also F Bono, et al., J Cell Physiol 172 36–43 (1997), AC Nicholson, et al., J Biol Chem 271 28407–13 (1996), J. M. Herbert, et al., J Clin Invest 101 993–1000 (1998)). This protease-receptor interaction could mediate not only prothrombinase-catalyzed thrombin generation, but also diverse cellular functions such as cell proliferation, release of PDGF and DNA syntheses. The mitogenic effect of Factor Xa has been reported to be dependent on Factor Xa enzymatic activity (F Bono, et al., J Cell Physiol 172 36–43 (1997), J. M. Herbert, et al., J Clin Invest 101 993–1000 (1998)). TAP for example inhibited the mitogenesis of human and rat cultured vascular smooth muscle cells (F Bono, et al., J Cell Physiol 172 36–43 (1997)). In a study of the rabbit carotid artery air-drying injury model, increased EPR-1 expression was detected after vascular injury. Animals treated with the specific Factor Xa inhibitor, DX-9065a, exhibited less neointimal proliferation. The important regulatory role of Factor Xa in the coagulation process coupled with its mitogenic effects points to Factor Xa's involvement in the formation of thrombin at the luminal surface of the vessel wall and contribution to the atherothrombotic process and abnormal proliferation of vascular cells resulting in restenosis or angiogenesis.

In view of the physiological conditions discussed above related to Factor Xa, inhibitors of Factor Xa would be useful in treating those conditions and others that would be ameliorated by a Factor Xa inhibitor.

Reported Developments

H. E. Lape, et al, Arch. lnt. Pharmacodyn., 171(2) 394414 (1968) disclose the following optionally alkyl substituted indole-(1 or 3)-acetamidoxime compounds wherein X is CH or N, and n is 0–2

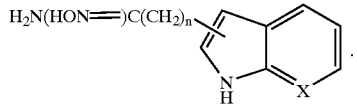

A wide range of antihypertensive activity is noted regarding the compounds. There is no disclosure or suggestion that the acetamidoxime compounds exhibit Factor Xa activity.

European Patent Application Publication No. 568,289 discloses the following 2-carboxamidine benzothiophene compounds wherein at least one of $R^2$, $R^3$, $R^4$ and $R^5$ is an organic group

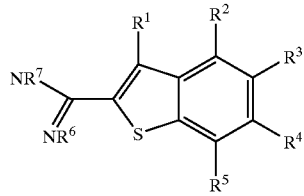

which includes 5 or more carbons, an organic group which contains a sulfur atom or hydroxy, an unsaturated organic group or a cyclic organic group. The compounds are noted to be urokinase inhibitors. European Patent Application Publication No. 568,289 does not disclose or suggest 3-carboxamidine benzothiophene compounds or that the 2-carboxamidine benzothiophene compounds exhibit Factor Xa activity.

SUMMARY OF THE INVENTION

This invention is directed to a compound of formula I:

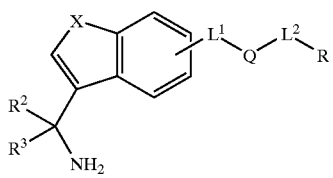

(I)

wherein
X is O, S or NR$^1$;
R is hydrogen, cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl or fused heterocyclylheteroaryl, provided that when L$^2$ is a chemical bond, then Q is attached to R through a carbon atom thereof and, when R is hydrogen then L$^2$ is not a chemical bond;
R$^1$ is hydrogen, alkyl, aralkyl, heteroaralkyl, acyl, aroyl, heteroaroyl, alkoxycarbonyl, aryloxycarbonyl or heteroaryloxycarbonyl;
R$^2$ and R$^3$ are hydrogen, or taken together are =NR$^4$;
R$^4$ is hydrogen, R$^5$O$_2$C—, R$^5$O—, HO—, cyano, R$^5$CO—, HCO—, lower alkyl, nitro, or R$^6$R$^7$N—;
R$^5$ is alkyl, aryl, heteroaryl, aralkyl, or heteroaralkyl;
R$^6$ and R$^7$ are independently hydrogen or alkyl;
L$^1$ is alkylene, alkenylene or alkynylene;
L$^2$ is a chemical bond, alkylene, alkenylene or alkynylene;
Q is —NR$^{8'}$—, —O—, —C(O)—, —C(O)—O—, —O—C(O)—, —NR$^{8'}$C(X$^1$)—, —C(X$^1$)NR$^{8'}$—, —NR$^8$C(X$^1$)O—, —OC(X$^1$)NR$^8$—, —NR$^8$C(X$^1$)NR$^8$—, —NR$^8$C(X$^1$)NR$^8$—, —S(O)$_n$—, —NR$^8$SO$_2$— or —SO$_2$NR$^8$—, provided that a nitrogen atom or oxygen atom of Q is not directly bonded to a carbon atom of L$^1$ or L$^2$ having a double bond or triple bond, or Q—L$^2$—R is cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl or fused heterocyclylheteroaryl, provided that a nitrogen atom or oxygen atom of Q is not directly bonded to a carbon atom of L$^1$ having a double bond or triple bond;
X$^1$ is O or S;
R$^{8'}$ is hydrogen, alkyl, aralkyl, heteroaralkyl, acyl, aroyl, heteroaroyl or alkoxycarbonyl;
R$^8$ is hydrogen, alkyl, aralkyl, heteroaralkyl, acyl, aroyl or heteroaroyl; and
n is 0, 1 or 2, or an oxide thereof, a pharmaceutically acceptable salt thereof, a solvate thereof, or prodrug thereof.

DETAILED DESCRIPTION OF THE INVENTION

As used above, and throughout the description of the invention, the following terms, unless otherwise indicated, shall be understood to have the following meanings:

Definitions

"Patient" includes both human and other mammals.

"Alkyl" means an aliphatic hydrocarbon group which may be straight or branched having about 1 to about 15 carbon atoms in the chain. Preferred alkyl groups have 1 to about 10 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl group may be substituted by one or more halo, hydroxyl, cycloalkyl or cycloalkenyl. Representative alkyl groups include methyl, fluoromethyl, difluoromethyl, trifluoromethyl, cyclopropylmethyl, cyclopentylmethyl, ethyl, n-propyl, i-propyl, n-butyl, t-butyl, n-pentyl, 3-pentyl, heptyl, octyl, nonyl, decyl and dodecyl.

"Alkylene" means a straight or branched bivalent hydrocarbon chain having from 1 to about 10 carbon atoms. The preferred alkylene groups are the lower alkylene groups having from 1 to about 4 carbon atoms. The alkylene group may be substituted by one or more halo, hydroxy, acyl, alkoxycarbonyl or carboxy. Exemplary alkylene groups include methylene, ethylene, propylene or butylene; preferred is ethylene.

"Alkenyl" means an aliphatic hydrocarbon group containing a carbon—carbon double bond and which may be straight or branched having about 2 to about 15 carbon atoms in the chain. Preferred alkenyl groups have 2 to about 10 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain which may be straight or branched. The alkenyl group may be substituted by one or more halo. Representative alkenyl groups include ethenyl, propenyl, n-butenyl, i-butenyl, 3-methylbut-2-enyl, n-pentenyl, heptenyl, octenyl and decenyl.

"Alkenylene" means a straight or branched bivalent hydrocarbon chain having a double bond and from 2 to about 10 carbon atoms. Preferred alkenylene groups are the lower alkenylene groups having from 2 to about 4 carbon atoms. The alkenylene group may be substituted by one or more halo, hydroxy, acyl, alkoxycarbonyl or carboxy, provided the hydroxy is not substituted at a double bond thereof. Exemplary alkenylene groups include ethenylene, propenylene or butenylene.

"Alkynyl" means an aliphatic hydrocarbon group containing a carbon—carbon triple bond and which may be straight or branched having about 2 to about 15 carbon atoms in the chain. Preferred alkynyl groups have 2 to about 10 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain which may be straight or branched. Representative alkynyl groups include ethynyl, propynyl, n-butynyl, 2-butynyl, 3-methylbutynyl, n-pentynyl, heptynyl, oetynyl and decynyl.

"Alkynylene" means a straight or branched bivalent hydrocarbon chain having a double bond and from 2 to about 10 carbon atoms. Preferred alkynylene groups are the lower alkynylene groups having from 2 to about 4 carbon atoms. The alkynylene group may be substituted by one or more halo, hydroxy, acyl, alkoxycarbonyl or carboxy, provided the hydroxy is not substituted at a triple bond thereof. Exemplary alkynylene groups include ethynylene, propynylene or butynylene.

"Carboxy" means a HO(O)C— (caboxylic acid) group.

"Carboxyalkyl" means an HOOC-alkyl- group wherein the alkyl group is as defined herein. Preferred groups include carboxymethyl and carboxyethyl.

"Cycloalkyl" means a non-aromatic mono- or multicyclic ring system of about 3 to about 10 carbon atoms, preferably of about 5 to about 10 carbon atoms. Preferred cycloalkyl rings contain about 5 to about 6 ring atoms. The cycloalkyl is optionally substituted with one or more "ring system substituents" which may be the same or different, and are as defined herein. Representative monocyclic cycloalkyl include cyclopentyl, cyclohexyl, cycloheptyl, and the like. Representative multicyclic cycloalkyl include 1-decalin, norbornyl, adamantyl, and the like.

"Cycloalkylalkyl" means a cycloalkylalkyl group wherein the cycloalkyl and alkyl groups are as herein defined. Representative cycloalkylalkyl groups include cyclopropyl, cyclopentyl, cyclohexyl, cycloheptyl, and the like "Cycloalkenyl" means a non-aromatic mono- or multicyclic ring system of about 3 to about 10 carbon atoms, preferably of about 5 to about 10 carbon atoms which contains at least one carbon—carbon double bond. Preferred cycloalkylene rings contain about 5 to about 6 ring atoms. The cycloalkenyl is optionally substituted with one or more "ring system substituents" which may be the same or different, and are as defined herein. Representative monocyclic cycloalkenyl include cyclopentenyl, cyclohexenyl, cycloheptenyl, and the like. A representative multicyclic cycloalkenyl is norbornylenyl.

"Heterocyclenyl" means a non-aromatic monocyclic or multicyclic ring system of about 3 to about ring atoms, preferably about to about 10 ring atoms, in which one or more of the atoms in the ring system is/are elemnent(s) other than carbon, for example nitrogen, oxygen or sulfur atoms, and which contains at least one carbon—carbon double bond or carbon-nitrogen double bond. Preferred heterocyclenyl rings contain about 5 to about 6 ring atoms. The prefix aza, oxa or thia before heterocyclenyl means that at least a nitrogen, oxygen or sulfur atom respectively is present as a ring atom. The heterocyclenyl is optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 4,5-dihydro-[1,2,4]oxadiazyl, 1,2,3,4-tetrahydropyridinyl, 1,2-dihydropyridyl, 1,4-dihydropyridyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, 2,3-dihydropyridazinyl, 1,6-dihydrotriazinyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like. A heterocyclenyl may also be a "lactam" where the heterocyclenyl is an appropriately dioxo substituted azaheterocyclenyl, for example maleimide.

"Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyls contain about 5 to about 6 ring atoms. The prefix aza, oxa or thia before heterocyclyl means that at least a nitrogen, oxygen or sulfur atom respectively is present as a ring atom. The heterocyclyl is optionally substituted by one or more "ring system substituents" which may be the same or different, and are as defined herein. The nitrogen or sulphur atom of the heterocyclyl is optionally oxidized to the corresponding N-oxide, S-oxide or S,S-dioxide. Representative monocyclic heterocyclyl rings include piperidyl, 2-oxo-hexahydro-pyrimidinyl, imidazolinyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. A heterocyclyl may also be a "lactam" where the heterocyclyl is an appropriately dioxo substituted azaheterocyclyl, for example succinimide.

"Heterocyclyloxy" means a heterocyclyl-O— group in which the heterocyclyl group is as previously described. Exemplary heterocyclyloxy groups include quinuclidyloxy, pentamethylenesulfideoxy, tetrahydropyranyloxy, tetrahydrothiophenyloxy, piperidinyloxy, pyrrolidinyloxy, tetrahydrofuranyloxy or 7-oxabicyclo[2.2.1]heptanyloxy, hydroxytetrahydropyranyloxy and hydroxy-7-oxabicyclo[2.2.1]heptanyloxy.

"Heterocyclyl-alkylene-O—" means a heterocyclyl-alkylene-O— group in which the heterocyclyl and alkylene groups are as previously described. Exemplary heterocyclyl-alkylene-O— groups include pyrrolidinyl-ethoxyl, and piperidinyl-methoxyl.

"Aryl" means an aromatic monocyclic or multicyclic ring system of 6 to about 14 carbon atoms, preferably of about 6 to about 10 carbon atoms. The aryl is optionally substituted with one or more "ring system substituents" which may be the same or different, and are as defined herein. Representative aryl groups include phenyl, naphthyl, substituted phenyl or substituted naphthyl.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example nitrogen, oxygen or sulfur. Preferred heteroaryls contain about 5 to about 6 ring atoms. The "heteroaryl" is optionally substituted by one or more "ring system substituents" which may be the same or different, and are as defined herein. The prefix aza, oxa or thia before heteroaryl means that at least a nitrogen, oxygen or sulfur atom respectively is present as a ring atom. A nitrogen atom of a heteroaryl is optionally oxidized to the corresponding N-oxide. Representative heteroaryls include pyrazinyl, furanyl, thienyl, pyridyl, pyrimidinyl, isoxazolyl, furanopyridyl, pyrrolopyrimidinyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Fused arylcycloalkenyl" means a radical derived from a fused aryl and cycloalkenyl as defined herein by removal of hydrogen atom from the cycloalkenyl portion. Preferred fused arylcycloalkenyls are those wherein aryl is phenyl and the cycloalkenyl consists of about 5 to about 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused arylcycloalkenyl as defined herein by removal of hydrogen atom from the aryl portion. Representative fused cycloalkenylaryl are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyls are those wherein aryl is phenyl and the cycloalkyl consists of about 5 to about 6 ring atoms. The fused arylcycloalkyl is optionally substituted by one or more ring system substituents, wherein "ring system substituent" is as defined herein. Representative fused arylcycloalkyl includes 1,2,3,4-tetrahydronaphthyl, and the like, in which the bond to the parent moiety is through a non-aromatic carbon atom.

"Fused cycloalkylaryl" means a radical derived from a fused arylcycloalkyl as defined herein by removal of a hydrogen atom from the aryl portion. Representative fused cycloalkylaryl are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyls are those wherein aryl is phenyl and the heterocyclenyl consists of about 5 to about 6 ring atoms. The prefix aza, oxa or thia before the heterocyclenyl portion of the fused arylheterocyclenyl means that at least a nitrogen, oxygen or sulfur atom respectively is present as a ring atom. The fused arylheterocyclenyl is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon atom.

"Fused heterocyclenylaryl" means a radical derived from a fused arylheterocyclenyl as defined herein by removal of a hydrogen atom from the aryl portion. Representative fused heterocyclenylaryl are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyls are those wherein aryl is phenyl and the heterocyclyl consists of about 5 to about 6 ring atoms. The prefix aza, oxa or thia before heterocyclyl means that at least a nitrogen, oxygen or sulfur atom respectively is present as a ring atom. The fused arylheterocyclyl is optionally substituted by one or more ring system substituents, wherein "ring system substituent" is as defined herein. The nitrogen or sulphur atom of the heterocyclyl portion of the fused arylheterocyclyl is optionally oxidized to the corresponding N-oxide, S-oxide or S,S-dioxide. Representative preferred fused arylheterocyclyl ring systems include phthalimide, 1,4-benzodioxane, indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon atom.

"Fused heterocyclylaryl" means a radical derived from a fused aryheterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom. A fused heterocyclylaryl may also be a "lactam" where the heterocyclyl is an appropriately dioxo substituted azaheterocyclenyl, for example phthalimide.

"Fused heteroarylcycloalkenyl" means a radical derived from a fused heteroaryl and cycloalkenyl as defined herein by removal of a hydrogen atom from the cycloalkenyl portion. Preferred fused heteroarylcycloalkenyls are those wherein the heteroaryl and the cycloalkenyl each contain about 5 to about 6 ring atoms. The prefix aza, oxa or thia before heteroaryl means that at least a nitrogen, oxygen or sulfur atom respectively is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroarylcycloalkenyl as defined herein by removal of a hydrogen atom from the heteroaryl portion. Representative fused cycloalkenylheteroaryl are as described herein for fused heteroaylcycloalkenyl, except that the bond to the parent moiety is through an aromatic carbon atom.

"Fused heteroarylcycloalkyl" means a radical derived from a fused heteroaryl and cycloalkyl as defined herein by removal of a hydrogen atom from the cycloalkyl portion. Preferred fused heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The fused heteroarylcycloalkyl is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroarylcycloalkyl as defined herein by removal of a hydrogen atom from the heteroaryl portion. Representative fused cycloalkylheteroaryl are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl as defined herein by the removal of a hydrogen atom from the heterocyclenyl portion. Preferred fused heteroarylheterocyclenyls are those wherein the heteroaryl thereof consists of about 5 to about 6 ring atoms and the heterocyclenyl consists of about 5 to about 6 ring atoms. The prefix aza, oxa or thia before heteroaryl or heterocyclenyl means that at least a nitrogen, oxygen or sulfur atom is present respectively as a ring atom. The fused heteroarylheterocyclenyl is optionally substituted by one or more ring system substituents, wherein "ring system substituent" is as defined herein. The nitrogen atom of the heteroaryl portion of the fused heteroarylheterocyclenyl is optionally oxidized to the corresponding N-oxide. The nitrogen or sulphur atom of the heterocyclenyl portion of the fused heteroarylheterocyclenyl is optionally oxidized to the corresponding N-oxide, S-oxide or S,S-dioxide. Representative fused heteroarylheterocyclenyl include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon atom.

"Fused heterocyclenylheteroaryl" means a radical derived from a fused heteroarylheterocyclenyl as defined herein by the removal of a hydrogen atom from the heteroaryl portion. Representative fused heterocyclenylheteroaryl are as described herein for fused heteroarylheterocyclenyl, except that the bond to the parent moiety is through an aromatic carbon atom.

"Fused heteroarylheterocyclyl" means a radical derived from a fused heteroaryl and heterocyclyl as defined herein, by removal of a hydrogen atom from the heterocyclyl portion. Preferred fused heteroarylheterocyclyls are those wherein the heteroaryl thereof consists of about 5 to about 6 ring atoms and the heterocyclyl consists of about 5 to about 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl is optionally substituted by one or more ring system substituents, wherein "ring system substituent" is as defined herein. The nitrogen atom of the heteroaryl portion of the fused heteroarylheterocyclyl is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl include 2,3-dihydro-1H pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2-yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2-yl, 5,6,7,8-tetrahydro[1,7]naphthyridinyl, 1,2,3,4-tetrhydro[2,7]naphthyridyl, 2,3-dihydro[1,4]dioxino[2,3-b]pyridyl, 2,3-dihydro[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]naphthyridinyl, 1,2,3,4-tetrahydro[1,6]naphthyridinyl, 1,2,3,4-tetrahydro[1,7]naphthyridinyl, 1,2,3,4-tetrahydro[1,8]naphthyridinyl, 1,2,3,4-tetrahydro[2,6]naphthyridinyl, and the like, in which the bond to the parent moiety is through a non-aromatic carbon atom.

"Fused heterocyclylheteroaryl" means a radical derived from a fused heteroarylheterocyclyl as defined herein, by removal of a hydrogen atom from the heteroaryl portion. Representative fused heterocyclylheteroaryl are as described herein for fused heterarylheterocyclyl, except that the bond to the parent moiety is through an aromatic carbon atom.

"Aralkyl" means an aryl-alkyl- group in which the aryl and alkyl are as previously described. Preferred aralkyls contain a lower alkyl moiety. Representative aralkyl groups include benzyl, 2-phenethyl and naphthlenemethyl.

"Aralkenyl" means an aryl-alkenyl- group in which the aryl and alkenyl are as previously described. Preferred aralkenyls contain a lower alkenyl moiety. Representative aralkenyl groups include 2-phenethenyl and 2-naphthylethenyl.

"Aralkynyl" means an aryl-alkynyl- group in which the aryl and alkynyl are as previously described. Preferred aralkynyls contain a lower alkynyl moiety. Representative aralkynyl groups include phenacetylenyl and naphthylacetylenyl.

"Heteroaralkyl" means an heteroaryl-alkyl- group in which the heteroaryl and alkyl are as previously described. Preferred heteroaralkyls contain a lower alkyl moiety. Representative aralkyl groups include pyridylmethyl, 2-(furan-3-yl)ethyl and quinolin-3-ylmethyl.

"Heteroaralkenyl" means an heteroaryl-alkenyl- group in which the heteroaryl and alkenyl are as previously described. Preferred heteroaralkenyls contain a lower alkenyl moiety. Representative heteroaralkenyl groups include 2-(pyrid-3-yl)ethenyl and 2-(quinolin-3-yl)ethenyl.

"Heteroaralynyl" means an heteroaryl-alkynyl- group in which the heteroaryl and alkynyl are as previously described. Preferred heteroaralkynyls contain a lower alkynyl moiety. Representative heteroaralkynyl groups include pyrid-3-ylacetylenyl and quinolin-3-ylacetylenyl.

"Hydroxyalkyl" means a HO-alkyl- group in which alkyl is as previously defined. Preferred hydroxyalkyls contain lower alkyl. Other preferred hydroxyalkyls contain more than one hydroxyl group. Representative hydroxyalkyl groups include hydroxymethyl and 2-hydroxyethyl.

"Hydroxyalkylene-O—" means a HO-alkylene-O— group in which the alkylene moiety is as previously defined. Preferred hydroxyalkylene-O— groups contain lower alkylene. Representative hydroxyalkylene-O— groups include hydroxymethoxyl and 2-hydroxyethoxyl.

"Acyl" means an H—CO— or alkyl-CO— group in which the alkyl group is as previously described. Preferred acyls contain a lower alkyl. Representative acyl groups include formyl, acetyl, propanoyl, 2-methylpropanoyl, butanoyl and palmitoyl.

"Aroyl" means an aryl-CO— group in which the aryl group is as previously described. Representative groups include benzoyl and 1- and 2-naphthoyl.

"Heteroaroyl" means a heteroaryl-CO— group in which the heteroaryl group is as previously described. Representative groups include nicotinoyl and pyrrol-2-ylcarbonyl and 3-quinolinccarbonyl.

"Alkoxy" means an alkyl-O— group in which the alkyl group is as previously described.

Representative alkoxy groups include methoxy, ethoxy, n-propoxy, i-propoxy, n-butoxy and heptoxy.

"Alkoxy-alkylene-O—" means an alkoxy-alkylene-O— group in which the alkoxy and alkylene groups are as previously described. Representative alkoxy-alkylene-O— groups include methoxymethoxy, methoxyethoxy, methoxy-n-propoxy, methoxy-n-butoxy and methoxyheptoxy.

"Aryloxy" means an aryl-O— group in which the aryl group is as previously described. Representative aryloxy groups include phenoxy and naphthoxy.

"Aralkyloxy" means an aralkyl-O— group in which the aralkyl groups is as previously described. Representative aralkyloxy groups include benzyloxy and 1- or 2-naphthalenemethoxy.

"Alkylthio" means an alkyl-S— group in which the alkyl group is as previously described. Representative alkylthio groups include methylthio, ethylthio, i-propylthio and heptylthio.

"Arylthio" means an aryl-S— group in which the aryl group is as previously described. Representative arylthio groups include phenylthio and naphthylthio.

"Aralkylthio" means an aralkyl-S— group in which the aralkyl group is as previously described. A representative aralkylthio group is benzylthio.

"$Y^1Y^2N$—" means a substituted or unsubstituted amino group, wherein $y^1$ and $Y^2$ are as described herein. Representative groups include amino ($H_2N$—), methylamino, ethylmethylamino, dimethylamino and diethylamino.

"Alkoxycarbonyl" means an alkyl-O—CO— group. Representative alkoxycarbonyl groups include methoxy- and ethoxycarbonyl.

"Aryloxycarbonyl" means an aryl-O—CO— group. Representative aryloxycarbonyl groups include phenoxy- and naphthoxycarbonyl.

"Aralkoxycarbonyl" means an aralkyl-O—CO— group. A representative aralkoxycarbonyl group is benzyloxycarbonyl.

"$Y^1Y^2NCO$—" means a substituted or unsubstituted carbamoyl group, wherein $Y^1$ and $Y^2$ are as previously described. Representative groups are carbamoyl ($H_2NCO$—) and dimethylcarbamoyl ($Me_2NCO$—).

"$Y^1Y^2NSO_2$—" means a substituted or unsubstituted sulfamoyl group, wherein $Y^1$ and $Y^2$ are as previously described. Representative groups are sulfamoyl ($H_2NSO_2$—) and dimethylsulfamoyl ($Me_2NSO_2$—).

"Sulfo" means an HO—$SO_2$— group.

"Sulfoalkyl" means an HO—$SO_2$-alkyl- group wherein the alkyl group is as herein defined. Exemplary HO—$SO_2$-alkyl- groups include sulfomethyl, sulfoethyl and sulfopropyl.

"Alkylsulfonyl" means an alkyl-$SO_2$— group. Preferred groups are those in which the alkyl group is lower alkyl.

"Alkylsulfinyl" means an alkyl-SO— group. Preferred groups are those in which the alkyl group is lower alkyl.

"Arylsulfonyl" means an aryl-$SO_2$— group.

"Arylsulfinyl" means an aryl-SO— group.

"Halo" means fluoro, chloro, bromo, or iodo. Preferred are fluoro, chloro or bromo, and more preferred are fluoro or chloro.

"Ring system substituent" means a substituent which optionally replaces hydrogen on an aromatic or non-aromatic ring system. Ring system substituents are selected from the group consisting of alkyl, aryl, heteroaryl, aralkyl, aralkenyl, aralkynyl, heteroaralkyl, heteroaralkenyl, heteroaralkynyl, hydroxy, hydroxyalkyl, alkoxy, aryloxy, heteroaryloxy, heterocyclyloxy, heterocyclenyloxy, aralkoxy, acyl, aroyl, halo, nitro, cyano, hydroxy-alkylene-O—, alkoxy-alkylene-O—, $Y^1Y^2$NCO-alkylene-O—, $Y^1Y^2$N-alkylene-O—, heterocyclyl-alkylene-O—, carboxy, carboxyalkyl, alkoxycarbonyl, aryloxycarbonyl, aralkoxycarbonyl, sulfo, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, heterocyclylalkyl, heterocyclenylalkyl, aryidiazo, heteroaryidiazo, amidino, 1-azaheterocyclylcarbonyl, carboxy-alkyl-, $Y^1Y^2N$—, $Y^1Y^2$N-alkyl-, ($Y^1Y^2N$— and hydroxy)alkyl-, $Y^1Y^2$N-alkenyl-, $Y^1Y^2$N-alkynyl-, $Y^1Y^2$NCO—, $Y^1Y^2$NCO-alkyl-, $Y^1Y^2$NCONH—, $Y^1Y^2$NCO$_2$— and $Y^1Y^2$NSO$_2$—, wherein $Y^1$ and $Y^2$ are independently hydrogen, alkyl, alkoxyalkyl, hydroxyalkyl, cycloalkyl, cycloalkyl-alkyl, $Y^1Y^2$N-alkyl, aryl, aralkyl, heteroaralkyl, heterocyclylalkyl, heterocyclenylalkyl, sulfo-alkyl-, or where the substituent is $Y^1Y^2N$— or $Y^1Y^2$N-alkyl-, then one of $Y^1$ and $Y^2$ is H—CO—, alkyl-CO—, aryl-CO—, heterocyclyl-CO—, and the other of $Y^1$ and $Y^2$ is hydrogen, alkyl, aryl, or aralkyl. When a ring system is saturated or partially saturated, the "ring system substituent" further comprises methylene ($H_2C$=), oxo (O=) and thioxo (S=).

"Chemical bond" means a direct bond.

"Solvate" means a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Representative solvates include ethanolates, methanolates, and the like. "Hydrate" is a solvate wherein the solvent molecule(s) is/are $H_2O$.

"Prodrug" means a form of the compound of formula I suitable for administration to a patient without undue toxicity, irritation, allergic response, and the like, and effective for their intended use, including ketal, ester and zwitterionic forms. A prodrug is transformed in vivo to yield the compound of formula 1, for example by hydrolysis in blood. A thorough discussion is provided in T. Higuchi and V. Stella, *Pro-drugs as Novel Delivery Systems*, Vol. 14 of the A. C. S. Symposium Series, and in Edward B. Roche, ed., *Bioreversible Carriers in Drug Design*, American Pharmaceutical Association and Pergamon Press, 1987, both of which are incorporated herein by reference.

"Acid protecting group" means an easily removable group which is known in the art to protect an acid group against undesirable reaction during synthetic procedures and preferably to be selectively removable. The use of acid protecting groups is well known in the art for protecting groups against undesirable reactions during a synthetic procedure and many such protecting groups are known to those skilled in the art, having been extensively used in the protection of carboxyl groups in the penicillin and ceplialosporini fields, as described in U.S. Pat. Nos. 3,840,556 and 3,719,667, the disclosures of which are hereby incorporated herein by reference. For suitable protecting groups see T. W. Green and P. G. M. Wuts in "Protective Groups in Organic Chemistry" John Wiley and Sons, 1991. Examples of carboxylic acid protecting groups include esters such as methoxymethyl, methylthiomethyl, tetrahydropyranyl, substituted and unstibstituted phenacyl, 2,2,2-trichloroethyl, tert-butyl, cinnamyl, dialkylaminoalkyl (e.g., dimethylaminoethyl and the like), trimethylsilyl, and the like, and amides and hydrazides including N,N-dimethyl, 7-nitroindolyl, hydrazide, N-phenylhydrazide, $C_1$ to $C_8$ loweralkyl (e.g., methyl, ethyl or tertiary butyl and the like) and substituted derivatives thereof such as alkoxybenzyl or nitrobenzyl groups and the like; alkanoyloxyalkyl groups such as pivaloyloxymethyl or propionyloxymethyl and the like: aroyloxyalkyl, such as benzoyloxyethyl and the like, alkoxycarbonvylalkyl, such as niethoxycarbonylmethyl, cyclohexyloxy-carbonylmethiyl and the like; alkoxycarbonyloxyalkyl, such as t-butyloxycarbonyloxyinethyl and the like; alkoxycarbonylaminoalkyl, such as t-butyloxycarbonylaminomethiyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylam iiocarbonylmethyl and the like; (5-(loweralkyl)-2-oxo-1,3-dioxolen-4-yl)alkyl, such as (5-t-butyl-2-oxo-1,3-dioxolen-4-yl) metliyl and the like; and (5-phenyl-2-oxo-1,3-dioxolen-4-yl)alkyl, such as (5-phenyl-2-oxo-1,3-dioxolen-4-yl)methyl and the like.

"Amine protecting group" means an easily removable group which is known in the art to protect an amino group against undesirable reaction during synthetic procedures and preferably to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Preferred amine protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxycarbonyl, 9-fluorenylmethoxycarbonyl, 2,2,2-trifluoroethoxycarbonyl, 2-trimethylsilylethxoycarbonyl, vinyloxycarbonyl, allyloxycarbonyl, t-butyloxycarbonyl (BOC), 1,1-dimethylpropynyloxycarbonyl, benzyloxycarbonyl (CBZ), p-nitrobenzyloxycarbony, 2,4-dichlorobenzyloxycarbonyl, and the like.

"Acid labile amine protecting group" means an amine protecting group as defined above which is readily removed by treatment with acid while remaining relatively stable to other reagents. A preferred acid labile amine protecting group is tert-butoxycarbonyl (BOC).

"Hydrogenation labile amine protecting group" means an amine protecting group as defined above which is readily removed by hydrogenation while remaining relatively stable to other reagents. A preferred hydrogenation labile amine protecting group is benzyloxycarbonyl (CBZ).

"Hydrogenation labile acid protecting group" means an acid protecting group as defined above which is readily removed by hydrogenation while remaining relatively stable to other reagents. A preferred hydrogenation labile acid protecting group is benzyl.

"Thiol protecting group" means a thiol protecting group that is readily removed by some reagents while being relatively stable to other reagents. The use of thiol protecting groups is well known in the art for thiol protecting groups against undesirable reactions during a synthetic procedure and many such protecting groups are known, for example, T. H. Greene and P. M. G. Wuts, Protective Groups in Organic Synthesis, 2nd edition, John Wiley & Sons, New York (1991), incorporated herein by reference. Exemplary thiol protecting groups are trityl (Trt), acetamidomethyl (Acm), and the like.

"Hydroxy protecting group" means a hydroxy protecting group that is readily removed by some reagents while being relatively stable to other reagents. The use of hydroxy protecting groups is well known in the art for hydroxy protecting groups against undesirable reactions during a synthetic procedure and many such protecting groups are known, for example, T. H. Greene and P. M. G. Wuts, Protective Groups in Organic Synthesis, 2nd edition, John Wiley & Sons, New York (1991), incorporated herein by reference. Exemplary hydroxy protecting groups are t-butyl, benzyl, tetrahydropyranyl, and the like.

Preferred Embodiments

A preferred embodiment of the invention is a method for treating a physiological condition capable of being modulated by inhibiting the activity of Factor Xa in a patient suffering from said physiological condition by administering to the patient an effective amount of a compound of formula I.

A preferred compound aspect of the invention is a compound of formula I wherein R is aryl, heteroaryl or heterocyclyl; a more preferred R is substituted phenyl.

Another preferred compound aspect of the invention is a compound of formula I wherein R is optionally substituted (phenyl substituted phenyl), optionally substituted (heteroaryl substituted phenyl), optionally substituted (phenyl substituted heteroaryl), optionally substituted (heteroaryl substituted heteroaryl), optionally substituted (phenyl substituted cyclyoalkyl), optionally substituted (heteroaryl substituted cyclyoalkyl), optionally substituted (cyclyoalkyl substituted heteroaryl), optionally substituted (cyclyoalkyl substituted phenyl), optionally substituted (cyclyoalkyl substituted cyclyoalkyl), optionally substituted (phenyl substituted cyclyoalkenyl), optionally substituted (heteroaryl substituted cyclyoalkenyl), optionally substituted (cyclyoalkenyl substituted heteroaryl), optionally substituted (cyclyoalkenyl substituted phenyl), optionally substituted (cyclyoalkenyl substituted cyclyoalkeny), optionally substituted (phenyl substituted heterocyclyl), optionally substituted (heteroaryl substituted heterocyclyl), optionally substituted (cyclyoalkyl substituted heterocyclyl), optionally substituted (heterocyclyl substituted phenyl), optionally substituted (heterocyclyl substituted heterocyclyl), optionally substituted (phenyl substituted heterocyclenyl), optionally substituted (heteroaryl substituted heterocyclenyl), optionally substituted (cyclyoalkenyl substituted heterocyclenyl), optionally substituted (heterocyclenyl substituted phenyl), or optionally substituted (heterocyclenyl substituted heterocyclenyl), wherein the term "optionally substituted" before the term in the parenthesis, denote that the phenyl, heteroaryl, cycloalkyl, cycloalkenyl, heterocyclyl, or heterocyclenyl, portions thereof could be further substituted as noted per their definitions).

A further preferred compound aspect of the invention is a compound of formula I wherein R is optionally substituted (phenyl substituted phenyl), optionally substituted (heteroaryl substituted phenyl), optionally substituted (phenyl substituted heteroaryl), optionally substituted (heteroaryl substituted heteroaryl), optionally substituted (phenyl substituted heterocyclyl), optionally substituted (heteroaryl substituted heterocyclyl), optionally substituted (cyclyoalkyl substituted heterocyclyl), optionally substituted (heterocyclyl substituted phenyl), optionally substituted (heterocyclyl substituted heterocyclyl), optionally substituted (phenyl substituted heterocyclenyl), optionally substituted (heteroaryl substituted heterocyclenyl), optionally substituted (cyclyoalkenyl substituted heterocyclenyl), optionally substituted (heterocyclenyl substituted phenyl), or optionally substituted (heterocyclenyl substituted heterocyclenyl), wherein the term "optionally substituted" before the term in the parenthesis, denote that the phenyl, heteroaryl, cycloalkyl, cycloalkenyl, heterocyclyl, or heterocyclenyl, portions thereof could be further substituted as noted per their definitions).

A formula preferred compound aspect of the invention is a compound of formula I wherein R is optionally substituted (phenyl substituted heteroaryl), optionally substituted (phenyl substituted heterocyclyl), and optionally substituted (phenyl substituted heterocyclenyl).

Another preferred compound aspect of the invention is a compound of formula I wherein R is optionally substituted (phenyl substituted heteroaryl), optionally substituted (phenyl substituted heterocyclyl), and optionally substituted (phenyl substituted heterocyclenyl); $L^2$ is bonded to said phenyl in the 1-position of the phenyl moiety and said heterocyclyl, heterocyclenyl, or heteroaryl, is bonded to said phenyl in the 4-position of the phenyl moiety.

Another preferred compound aspect of the invention is a compound of formula I wherein X is $NR^1$.

Another preferred compound aspect of the invention is a compound of formula I wherein $R^1$ is hydrogen.

Another preferred compound aspect of the invention is a compound of formula I wherein $R^1$ is hydrogen.

Another preferred compound aspect of the invention is a compound of formula I wherein $R^2$ and $R^3$ taken together are $=NR^4$.

Another preferred compound aspect of the invention is a compound of formula I wherein $R^4$ is hydrogen or hydroxy, more preferred is hydrogen.

Another preferred compound aspect of the invention is a compound of formula I wherein $R^5$ is alkyl; more preferred is methyl.

Another preferred compound aspect of the invention is a compound of formula I wherein $R^6$ and $R^7$ are hydrogen.

Another preferred compound aspect of the invention is a compound of formula I wherein $L^1$ is alkylene; more preferred is ethylene.

Another preferred compound aspect of the invention is a compound of formula I wherein $L^1$ is

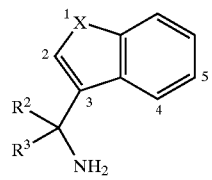

bonded to the 5-position of the moiety.

Another preferred compound aspect of the invention is a compound of formula I wherein $L^2$ is a chemical bond or alkylene.

Another preferred compound aspect of the invention is a compound of formula I wherein $L^2$ is chemical bond.

Another preferred compound aspect of the invention is a compound of formula I wherein $X^1$ is O.

Another preferred compound aspect of the invention is a compound of formula I wherein Q is —$NR^8CO$—, —$CONR^8$—, —$NR^8SO_2$— or —$SO_2NR^8$—; more preferred is —$NR^8CO$—.

Another preferred compound aspect of the invention is a compound of formula I $R^8$ and $R^8$ are hydrogen.

Another preferred compound aspect of the invention is a compound of formula I wherein n is 2.

Another preferred compound aspect of the invention is a compound of formula I wherein $L^1$ is

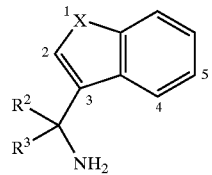

bonded to the 5-position of the moiety;

R is optionally substituted (phenyl substituted pyridinonyl), optionally substituted (phenyl substituted pyrrolopyrimidinyl), optionally substituted (phenyl substituted pyridazinyl), optionally substituted (phenyl substituted pyridazinonyl), optionally substituted (phenyl substituted pyridyl), or optionally substituted (phenyl substituted pyrimidinyl).

Another preferred compound aspect of the invention is a compound of formula I wherein R is substituted (phenyl substituted pyrimidinyl), said pyrimidinyl is substituted with at least one ring system sybstituent selected from the group alkoxy, $Y^1Y^2N$-alkyl-, $Y^1Y^2N$—, azaheterocyclyl, $Y^1Y^2NCO$-alkylene-O—, azaheterocyclyl-alkylene-O—, and $Y^1Y^2N$-alkylene-O—; and $Y^1$ and $Y^2$ are independently hydrogen, alkyl, alkoxyalkyl, hydroxyalkyl, cycloalkyl, cycloalkyl-alkyl, $Y^1Y^2N$-alkyl, aryl, aralkyl, heteroaralkyl, heterocyclylalkyl, heterocyclenylalkyl, or sulfo-alkyl-; or when $Y^1$ is H—CO—, alkyl-CO—, aryl-CO—, or heterocyclyl-CO—, then $Y^2$ is hydrogen, alkyl, aryl, or aralkyl.

Included within the scope of formula I are compounds wherein $R^2$ and $R^3$ taken together are $=NR^4$, wherein $R^4$ is $R^5O_2C$—, $R^5O$—, cyano, $R^5CO$—, optionally substituted lower alkyl, nitro, or $R^6R^7N$—. Such derivatives may themselves comprise the biologically active compound useful for treating a physiological condition capable of being modulated by inhibiting activity of Factor Xa by its administration to a patient suffering from said physiological condition, or may act as pro-drugs to such biologically active compounds which are formed therefrom under physiological conditions.

Species according to the invention are selected from the following:

N-(2-[3-Carbamimidoyl-5-indolyl]ethyl)-4-pyrid-3-ylbenzamide;
N-(2-[3-Carbamimidoyl-5-indolyl]ethyl)-4-(pyrimidin-5-yl)-benzamide);
5-(Pyrid-2-yl)-thiophene-2-carboxylic acid 2-(3-Carbamimidoyl-5-indolyl)ethyl amide;
N-(2-[3-Carbamimidoylindol-5-yl]ethyl)-6-morpholin-4-ylnicotinamide4-(5–2[-{3-Carbamimidoylindol-5-yl}ethylcarbamoyl]pyridin-2-yl)piperazine-1-carboxylic acid ethyl ester;
N-(2-[3-Carbamimidoylindol-5-yl]ethyl)-6-imidazol-1-ylnicotinamide;
N-(2-[3-Carbamimidoylindol-5-yl]ethyl)-4-imidazol-1-ylbenzamide;
N-(2-[3-Carbamimidoylindol-5-yl]ethyl)-4-(3H-imidazol-4-yl)benzamide;
N-(2-[3-Carbamimidoylindol-5-yl]ethyl)-4-(1,2,4)thiadiazol-5-ylbenzamide;
N-[2-(3-Carbamimidoyl-1H-indol-5-yl)-ethyl]-4-(1-carbamoyl-1-methyl-ethyl-benzamide;
N-[2-(3-Carbamimidoyl-1H-indol-5-yl)-ethyl]-4-(1-[N-(2-methoxyethyl)]-carbamoyl-1-methyl-ethyl-benzamide;
N-[2-(3-Carbamimidoyl-1H-indol-5-yl)-ethyl]-4-(t-butyl)-benzamide;
N-[2-(3-Carbamimidoyl-1H-indol-5-yl)-ethyl]-4-(pyridazin-4-yl)-benzamide;
N-[2-(3-Carbamimidoyl-1H-indol-5-yl)-ethyl]-2-methyl-4-(6-oxo-1,6-dihydro-pyridin-3-yl)-benzamide 3',4'-Dimnethoxybiphenyl-4-carboxylic acid (2-[3-Carbamimidoylindol-5-yl]ethyl)amide;
N-(2-[3-Carbamimidoylindol-5-yl]ethyl)-4-(6-methoxypyrid-3-yl)benzamide;
N-(2-[3-Carbamimidoylindol-5-yl]ethyl)-4-(1-oxy-pyrid-4-yl)benzamide;
N-[2-(3-Carbamimidoyl-1H-indol-5-yl)-ethyl]-4-(7H-pyrrolo[2,3-d]pyrimidin-6-yl)-benzamide;
N-[2-(3-Carbamimidoyl-1H-indol-5-yl)-ethyl]-4-(7H-pyrrolo[3,2-c]pyridin-2-yl)-benzamide;
N-[2-(3-Carbamimidoyl-1H-indol-5-yl)-ethyl]-4-furo[3,2-c]pyridin-2-yl-benzamide;
N-[2-(3-Carbamimidoyl-1H-indol-5-yl)-ethyl]-3-chloro-4-(6-oxo-1,6-dihydro-pyridin-3-yl)-benzamide;
N-(2-[3-Carbamimidoyl-1H-indol-5-yl)-ethyl]-4-(6-oxo-1,6-dihydro-pyrid-3-yl)benzamide;
N-(2-[3-Carbamimidoyl-1H-indol-5-yl]ethyl)-4-(6-oxo-1,6-dihydro-pyrid-3-yl)benzamide;
4-(3-Amino-1,1-dimethyl-propyl)-N-[2-(3-Carbamimidoyl-1H-indol-5-yl)-ethyl]-benzamide;
N-[2-(3-Carbamimidoyl-1H-indol-5-yl)-ethyl]-2-(4-chloro-phenyl)-acetamide;
5-chloro-thiophene-2-carboxylic acid[2-(3-Carbamimidoyl-1H-indol-5-yl)-ethyl]-amide;
N-(2-[3-Carbamimidoylindol-5-yl]ethyl)-6-(2-hydroxyethylamino)nicotinamide;
N-(2-[3-Carbamimidoylindol-5-yl]ethyl)-6-(1,2,4)-triazol-1-ylnicotinamide;
N-(2-[3-Carbamimidoylindol-5-yl]ethyl)-6-pyrrol-1-ylnicotinamide;
N-(2-[3-Carbamimidoylindol-5-yl]ethyl)-6-pyrazol-1-ylnicotinamide;
N-(2-[3-Carbamimidoyl-1-methylindol-5-yl]ethyl)-4-(6-methoxypyrid-3-yl)benzamide;
N-[2-(3-Carbamimidoyl-1H-indol-5-yl)-ethyl]-3-chloro-benzamide;
N-[2-(3-Carbamimidoyl-1H-indol-5-yl)-ethyl]-2-(3-chloro-phenyl)-acetamide;
4-(2-Aminomethyl-pyridin-4-yl)-N-[2-(3-Carbamimidoyl-1H-indol-5-yl)-ethyl]-benzamide;
4-{4-[2-(3-Carbamimidoy-1-indol-5-yl)-ethylcarbamoyl]-phenyl-pyridine-2-carboxylic acid amide;
N-[2-(3-Carbamimidoy-1H-indol-5-yl)-ethyl]-4-(2-(N,N-dimethylaminomethyl)-pyridin-4-yl)benzamide);
N-[2-(3-Carbamimidoyl-1H-indol-5-yl)-ethyl]-4-(6-oxo-1,6-dihydro-pyridazin-3-yl)-benzamide;
N-[2-(3-Carbamimidoyl-1H-indol-5-yl)-ethyl]-4-(6-methoxy-pyridazin-3-yl)-benzamide;
N-[2-(3-Carbamimidoyl-1H-indol-5-yl)-ethyl]-4-[1-(2-dimethylamino-ethyl)-6-oxo-1,6-dihydro-pyridazin-3-yl]-benzamide;
N-[2-(3-Carbamimidoyl-1H-indol-5-yl)-ethyl]-4-[1-(3-dimethylamino-propyl)-6-oxo-1,6-dihydro-pyridazin-3-yl]-benzamide;
N-[2-(3-Carbamimidoyl-1H-indol-5-yl)-ethyl]-4-[2-(2-dimethylamino-ethylamino)-pyrimidin-4-yl]-benzamide;
N-[2-(3-Carbamimidoyl-1H-indol-5-yl)-ethyl]-4-[2-methoxy-pyrimidin-4-yl]-benzamide;
N-(2-[3-Carbamimidoylindol-5-yl]ethyl)-4-(1-[2-dimethylaminoethyl]-6-oxo-1,6-dihydropyridin-3-yl)benzamide;
N-(2-[3-Carbamimidoylindol-5-yl]ethyl)-4-(1-carbamoylmethyl-6-oxo-1,6-dihydropyridin-3-yl)benzamide;
4-(3-Amino-[1,2,4]triazin-6-yl)-N-[2-(3-Carbamimidoyl-1-indol-5-yl)-ethyl]-benzamide;
4-(3-Amino-[1,2,4]triazin-5-yl)-N-[2-(3-Carbamimidoyl-1H-indol-5-yl)-ethyl]-benzamide;
N-[2-(3-Carbamimidoyl-1H-indol-5-yl)-ethyl]-4-(3-oxo-2,3-dihydro-[1,2,4]triazin-6-yl)-benzamide;
N-[2-(3-Carbamimidoyl-1H-indol-5-yl)ethyl]-4-(5-oxo-4,5-dihydro-[1,2,4]oxadiazol-3-yl)-benzamide
N-[2-(3-Carbamimidoyl-1H-indol-5-yl)ethyl]-4-(6-oxo-piperidin-3-yl)-benzamide;
N-[2-(3-Carbamimidoyl-1H-indol-5-yl)-ethyl]-4-[2-(morpholin-4-yl-ethylamino)-pyrimidin-4-yl]-benzamide;
N-[2-(3-Carbamimidoyl-1H-indol-5-yl)-ethyl]-4-[2-(3-dimethylamino-propylamino)-pyrimidin-4yl]-benzamide;
N-[2-(3-Carbamimidoyl-1H-indol-5-yl)-ethyl]-4-[2-([2-dimethylamino-ethyl]-methyl-amino)-pyrimidin-4-yl]-benzamide;
2-[(4-{4-[2-(3-Carbamimidoyl-1H-indol-5-yl)-ethylcarbamoyl]-phenyl}-pyrimidin-2-yl)-methyl-amino]-ethanesulfonic acid;
N-[2-(3-Carbamimidoyl-1H-indol-5-yl)-ethyl]-4-{2-[methyl-(2(S),3(R),4(R),5(R),6-pentahydroxy-hexyl)-amino]-pyrimidin-4-yl}-benzamide
N-[2-(3-Carbamimidoyl-1H-indol-5-yl)-ethyl]-4-{2-[methyl-(2(S),3(R),4(S),5(R),6-pentahydroxy-hexyl)-amino]-pyrimidin-4-yl}-benzamide;
N-[2-(3-Carbamimidoyl-1H-indol-5-yl)-ethyl]-4-[2-(2-hydroxy-1-hydroxymethyl-ethylamino)-pyrimidin-4-yl]-benzamide;

2-[(4-{4-[2-(3-Carbamimidoyl-1H-indol-5-yl)-ethylcarbamoyl]-phenyl}-pyrimidin-2-yl)-methyl-amino]-ethanesulfonic acid;

N-[2-(3-Carbamimidoyl-1H-indol-5-yl)-ethyl]-4-[2-(3-imidazol-1-yl-propylamino)-pyrimidin-4-yl]-benzamide;

N-[2-(3-Carbamimidoyl-1H-indol-5-yl)-ethyl]-4-{2-[(2-diethylamino-ethyl)-methyl-amino]-pyrimidin-4-yl}-benzamide;

N-[2-(3-Carbamimidoyl-1H-indol-5-yl)-ethyl]-4-[2-(2-diisopropylamino-ethylamino)-pyrimidin-4-yl]-benzamide;

N-[2-(3-Carbamimidoyl-1H-indol-5-yl)-ethyl]-4-[2-(2-dibutylamino-ethylamino)-pyrimidin-4-yl]-benzamide N-[2-(3-Carbamimidoyl-1-indol-5-yl)-ethyl]-4-[2-(3-morpholin-4-yl-propylamino)-pyrimidin-4-yl]-benzamide;

N-[2-(3-Carbamimidoyl-1H-indol-5-yl)-ethyl]-4-[2-(3-diethylamino-propylamino)-pyrimidin-4-yl]-benzamide;

N-[2-(3-Carbamimidoyl-1H-indol-5-yl)-ethyl]-4-[2-(3-piperidin-1-yl-propylamino)-pyrimidin-4-yl]-benzamide;

N-[2-(3-Carbamimidoyl-1H-indol-5-yl)-ethyl]-4-(2-{[2-(ethyl-methyl-amino)-ethyl]-methyl-amino}-pyrimidin-4-yl)-benzamide;

N-[2-(3-Carbamimidoyl-1H-indol-5-yl)-ethyl]-4-[2-(5-dimethylamino-pentylamino)-pyrimidin-4-yl]-benzamide;

N-[2-(3-Carbamimidoyl-1H-indol-5-yl)-ethyl]-4-[2-(5-morpholin-4-yl-pentylamino)-pyrimidin-4-yl]-benzamide;

N-[2-(3-Carbamimidoyl-1H-indol-5-yl)-ethyl]-4-[2-(5-piperidin-1-yl-pentylamino)-pyrimidin-4-yl]-benzamide;

N-[2-(3-Carbamimidoyl-1H-indol-5-yl)-ethyl]-4-[2-(5-pyrrolidin-1-yl-pentylamino)-pyrimidin-4-yl]-benzamide;

N-[2-(3-Carbamimidoyl-1H-indol-5-yl)-ethyl]-4-(2-oxo-hexahydro-pyrimidin-5-yl)-benzamide;

N-[2-(3-Carbamimidoyl-1H-indol-5-yl)-ethyl]-4-(1,3-dimethyl-2-oxo-hexahydro-pyrimidin-5-yl)-benzamide;

Biphenyl-3,4'-dicarboxylic acid 4'-{[2-(3-Carbamimidoyl-1H-indol-5-yl)-ethyl]-amide}3-[(2-methoxy-ethyl)-amide];

3'-(Morpholine-4-carbonyl)-biphenyl-4-carboxylic acid [2-(3-Carbamimidoyl-1H-indol-5-yl)-ethyl]-amide;

Biphenyl-3,4'-dicarboxylic acid 4'-{[2-(3-Carbamimidoyl-1H-indol-5-yl)-ethyl]-amide}3-[(2-morpholin-4-yl-ethyl)-amide];

Biphenyl-2,4'-dicarboxylic acid 4'-{[2-(3-Carbamimidoyl-1H-indol-5-yl)-ethyl]-amide}2-[(3-diethylamino-propyl)-amide];

Biphenyl-2,4'-dicarboxylic acid 4'-{[2-(3-Carbamimidoyl-1H-indol-5-yl)-ethyl]-amide}2-[(3-morpholin-4-yl-propyl)-amide];

Biphenyl-2,4'-dicarboxylic acid 4'-{[2-(3-Carbamimidoyl-1H-indol-5-yl)-ethyl]-amide}2-[(3-piperidin-1-yl-propyl)-amide];

Biphenyl-2,4'-dicarboxylic acid 4'-{[2-(3-Carbamimidoyl-1H-indol-5-yl)-ethyl]-amide}2-[(4-dimethylamino-butyl)-amide];

Biphenyl-2,4'-dicarboxylic acid 4'-{[2-(3-Carbamimidoyl-1H-indol-5-yl)-ethyl]-amide}2-[(2,3-dihydroxy-propyl)-methyl-amide];

Biphenyl-2,4'-dicarboxylic acid 4'-{[2-(3-Carbamimidoyl-1-indol-5-yl)-ethyl]-amide}2-[(2,3-dihydroxy-propyl)-amide];

N-[2-(3-Carbamimidoyl-1H-indol-5-yl)ethyl]-4-[2-(4-methylpiperazin-1-yl)pyrimidin-4-yl]benzamide;

4-[(4-{4-[2-(3-Carbamimidoyl-1H-indol-5-yl)ethylcarbamoyl]phenyl}pyrimidin-2-yl)methylamino]butyric acid;

N-[2-(3-Carbamimidoyl-1H-indol-5-yl)ethyl]-4-[2-(2,2,2-trifluoroethoxy)pyrimidin-4-yl]benzamide;

N-[2-(3-Carbamimidoyl-1H-indol-5-yl)-ethyl]-4-(2-pyrrolidin-1-ylpyrimidin-4-yl)benzamide;

N-[2-(3-Carbamimidoyl-1H-indol-5-yl)-ethyl]-4-[2-(2-hydroxymethylpyrrolidin-1-yl)-pyrimidin-4-yl]benzamide;

N-[2-(3-Carbamimidoyl-1H-indol-5-yl)ethyl]-4-[2-(carbamoylmethyl-N-methylamino)-pyrimidin-4-yl]benzamide;

N-[2-(3-Carbamimidoyl-1H-indol-5-yl)ethyl]-4-[2-(6-pyrrolidin-1-yl-hexylamino)pyrimidin-4-yl]benzamide;

N-[2-(3-Carbamimidoyl-1H-indol-5-yl)ethyl]-4-[2-(6-piperidin-1-ylhexylamino)pyrimidin-4-yl]benzamide;

N-[2-(3-Carbamimidoyl-1-indol-5-yl)ethyl]-4-[2-(4-piperidin-1-ylbutylamino)pyrimidin-4-yl]benzamide;

N-[2-(3-Carbamimidoyl-1H-indol-5-yl)ethyl]-4-[2-(4-diethylaminobutylamino)pyrimidin-4-yl]benzamide;

N-[2-(3-Carbamimidoyl-1H-indol-5-yl)ethyl]-4-[2-(6-morpholin-4-ylhexylamino)pyrimidin-4-yl]benzamide;

N-[2-(3-Carbamimidoyl-1H-indol-5-yl)ethyl]-4-[2-(6-dimethylaminohexylamino)pyrimidin-4-yl]benzamide;

N-[2-(3-Carbamimidoyl-1H-indol-5-yl)ethyl]-4-[2-(4-dimethylaminobutylamino)pyrimidin-4-yl]benzamide;

4-[2-(Bicyclo[2;2;1]hept-2-ylamino)pyrimidin-4-yl]-N-[2-(3-Carbamimidoyl-1H-indol-5-yl)ethyl]benzamide;

1-(4-{4-[2-(3-Carbamimidoyl-1H-indol-5-yl)ethylcarbamoyl]phenyl}pyrimidin-2-yl)pyrrolidine-2-carboxylic acid amide;

N-[2-(3-Carbamimidoyl-1H-indol-5-yl)ethyl]-4-{2-[(2-hydroxy-ethyl)-N-methylamino]pyrimidin-4-yl}benzamide;

N-[2-(3-Carbamimidoyl-1H-indol-5-yl)-ethyl]-4-(2-morpholin-4-yl-pyrimidin-4-yl)-benzamide;

N-[2-(3-Carbamimidoyl-1H-indol-5-yl)-ethyl]-4-[2-(cyclopropylmethyl-amino)-pyrimidin-4-yl]-benzamide;

N-[2-(Carbamimidoyl-1H-indol-5-yl)-ethyl]-4-[2-[(2-methoxy-ethyl)-methyl-amino]-pyrimidin-4-yl]benzamide;

N-[2-(3-Carbamimidoyl-1H-indol-5-yl)-ethyl]-4-[2-(3-hydroxy-propylamino)-pyrimidin-4-yl]-benzamide;

N-[2-(3-Carbamimidoyl-1H-indol-5-yl)-ethyl]-4-[(2-hydroxy-ethyl)-propyl-amino-pyrimidin-4-yl]-benzamide;

N-[2-(3-Carbamimidoyl-1H-indole-5-yl)-ethyl]-4-(2-piperidin-1-yl-pyrimidin-4-yl)-benzamide;

N-[2-(3-Carbamimidoyl-1H-indol-5-yl)-ethyl]-4-[2-(ethyl-methyl-amino)-pyrimidin-4-yl]-benzamide;

N-[2-(3-Carbamimidoyl-1H-indol-5-yl)-ethyl]-4-[2-(4-hydroxy-piperidin-1-yl)-pyrimidin-4-yl]-benzamide;

N-[2-(3-Carbamimidoyl-1H-indol-5-yl)-ethyl]-4-[2-(2,3-dihydroxy-propylamino)-pyrimidin-4-yl]-benzamide;

N-[2-(3-Carbamimidoyl-1H-indol-5-yl)-ethyl]-4-[2-[(2,3-dihydroxy-propyl)-methyl-amino]-pyrimidin-4-yl]-benzamide;

N-[²-(3-Carbamimidoyl-1H-indol-5-yl)-ethyl]-4-[2-((s)-2-methoxymethyl-pyrrolidin-1-yl)-pyrimidin-4-yl]-benzamide;

N-[2-(3-Carbamimidoyl-1H-indol-5-yl)-ethyl]-4-(2-piperazin-1-yl-pyrimidin-4-yl)-benzamide;

N-[2-(3-Carbamrimridoyl-1H-indol-5-yl)-4-[2-[2-(2-oxo-imidazolidin-1-yl)-ethylamino]-pyrimridin-4-yl]-benzamide;

N-[2-(3-Carbamimidoyl-1H-indol-5-yl)-ethyl]-4-[2-(3-methoxy-propylamino)-pyrimidin-4-yl]-benzamide;

4-[2-(3-Carbamimidoyl-1H-indol-5-yl)-ethyl]-4-[2-(2-hydroxy-ethylamino)-pyrimidin-4-yl]-benzamide;

N-[2-(3-Carbamimidoyl-1H-indol-5-yl)-ethyl]-4-[2-(2-methoxyethoxy)-pyrimidin-4-yl]benzamide;

N-[2-(3-Carbamimidoyl-1H-indol-5-yl)ethyl]-4-[2-(1-carbamoylethoxy)pyrimidin-4-yl]benzamide;

N-[2-(3-Carbamimidoyl-1H-indol-5-yl)ethyl]-4-[2-(6-dimethylaminohexyloxy)pyrimidin-4-yl]benzamide;

N-[2-(3-Carbamimidoyl-1H-indol-5-yl)ethyl]-4-[2-(2-oxopiperidin-3-yloxy)pyrimidin-4-yl]benzamide;

N-[2-(3-Carbamimidoyl-1H-indol-5-yl)ethyl]-4-[2-(2-pyrrolidin-1-yl-ethoxy)pyrimidin-4-yl]benzamide;

N-[2-(3-Carbamimidoyl-1H-indol-5-yl)ethyl]-4-[2-(2-dimethylaminoethoxy)pyrimidin-4-yl]benzamide;

3'-(2-Dimethylaminoethoxy)biphenyl-4-carboxylic acid [2-(3-Carbamimidoyl-1H-indol-5-yl)ethyl]amide;

N-[2-(3-Carbamimidoyl-1H-indol-5-yl)ethyl]-4-(1-oxypyridin-2-yl)benzamide;

2'-(2-Dimethylaminoethoxy)biphenyl-4-carboxylic acid [2-(3-Carbamimidoyl-1H-indol-5-yl)ethyl]amide;

2'-(3-Dimethylaminopropoxy)biphenyl-4-carboxylic acid [2-(3-Carbamimidoyl-1H-indol-5-yl)ethyl]amide;

3'-(3-Dimethylaminopropoxy)biphenyl-4-carboxylic acid [2-(3-Carbamimidoyl-1H-indol-5-yl)ethyl]amide;

N-[2-(3-Carbamimidoyl-1H-indol-5-yl)-ethyl]-4-(1-oxo-pyridin-3-yl)-benzamide;

4-[2-(acetylamino-methyl)-pyridin-4-yl]-N-[2-(3-Carbamimidoyl-1H-indol-5-yl)-ethyl]-benzamide;

Piperidine-4-carboxylic acid (4-[4-[2-(3-Carbamimidoyl-1H-indol-5-yl)-ethylcarbamoyl]-phenyl-]-pyridin-2-ylmethyl)-amide;

N-[2-(3-Carbamimidoyl-1H-indol-5-yl)ethyl]-4-[1-(3-dimethylaminopropyl)-6-oxo-1,6-dihydropyridin-3-yl]benzamide;

N-[2-(3-Carbamimidoyl-1H-indol-5-yl)ethyl]-4-[6-(3-dimethylaminopropoxy)pyridin-3-yl]benzamide;

(5-{4-[2-(3-Carbamimidoyl-1H-indol-5-yl)ethylcarbamoyl]phenyl}-2-oxo-2H-pyridin-1-yl)acetamide;

N-[2-(3-Carbamimidoyl-1H-indol-5-yl)-ethyl]-4-{1-[(2-dimethylaminoethylcarbamoyl)methyl]-6-oxo-1,6-dihydropyridin-3-yl}benzamide;

N-[2-(3-Carbamimidoyl-1H-indol-5-yl)-ethyl]-4-(4-dimethylamino-piperidin-1-yl)-benzamide;

N-[2-(3-Carbamimidoyl-1H-indol-5-yl)-ethyl]-4-[4-(2-dimethylamino-ethylamino)-piperidin-1-yl]-benzamide;

4-(4-Amino-piperidin-1-yl)-N-[2-(3-Carbamimidoyl-1H-indol-5-yl)-ethyl]-benzamide;

N-[2-(3-Carbamimidoyl-1H-indol-5-yl)-ethyl]-4-(4-methoxy-piperidin-1-yl)-benzamide;

4-(4-Acetylamino-piperidin-1-yl)-N-[2-(3-Carbamimidoyl-1H-indol-5-yl)-ethyl]-benzamide;

4-(1-Acetyl-piperidin-4-yl)-N-[2-(3-Carbamimidoyl-1H-indol-5-yl)-ethyl]-benzamide;

4-{4-[2-(3-Carbamimidoyl-1H-indol-5-yl)-ethylcarbamoyl]-phenyl}-piperidine-1-carboxylic acid amide;

N-[2-(3-Carbamimidoyl-1H-indol-5-yl)-ethyl]-4-(1-methyl-1-oxy-piperidin-4-yl)-benzamide;

N-[2-(3-Carbamimidoyl-1H-indol-5-yl)-ethyl]-4-(1-methyl-piperidin-4-yl)-benzamide;

N-[2-(3-Carbamimidoyl-1H-indol-5-yl)-ethyl]-4-(1-methanesulfonyl-piperidin-4-yl)-benzamide;

4-(2-Acetylamino-1,1-dimethyl-ethyl)-N-[2-(3-Carbamimidoyl-1H-indol-5-yl)-ethyl]-benzamide;

N-[2-(3-Carbamimidoyl-1H-indol-5-yl)-ethyl]-4-(2-methanesulfonylamino-1,1-dimethyl-ethyl)-benzamide;

Piperidine-4-carboxylic acid (2-{4-[2-(3-Carbamimidoyl-1H-indol-5-yl)-ethylcarbamoyl]-phenyl}-2-methyl-propyl)-amide;

N-[2-(3-Carbamimidoyl-1H-indol-5-yl)-ethyl]-4-(1,1-dimethyl-2-ureido-ethyl)-benzamide;

N-[2-(3-Carbamimidoyl-1H-indol-5-yl)-ethyl]-4-[2-(3-ethyl-ureido)-1,1-dimethyl-ethyl]-benzamide;

N-[2-(3-Carbamimidoyl-1H-indol-5-yl)-ethyl]-4-(2-dimethylamino-3,4,5,6-tetrahydro-pyrimidin-4-yl)-benzamide;

N-[2-(3-Carbamimidoyl-1H-indol-5-yl)-ethyl]-4-(1-oxy-pyridin-4-yloxy)-benzamide;

N-[2-(3-Carbamimidoyl-1H-indol-5-yl)-ethyl]-4-(1-methyl-piperidin-4-yloxy)-benzamide;

N-[2-(3-Carbamimidoyl-1H-indol-5-yl)ethyl]-4-(1,2,3,6-tetrahydropyridin-4-yl)-benzamide;

N-[2-(3-Carbamimidoyl-1H-indol-5-yl)ethyl]-4-piperidin-4-yl-benzamide;

4-(2-Amino-1,1-dimethylethyl)-N-(2-[3-Carbamimidoylindol-5-yl]ethyl)benzamide;

N-(2-[3-Carbamimidoylindol-5-yl]ethyl)-4-(6-[2-dimethylaminoethoxy]pyridin-3-yl)benzamide;

N-(2-[3-Carbamimidoylindol-5-yl]ethyl)-4-pyrid-4-ylbenzamide;

N-(2-[3-Carbamimidoylindol-5-yl]ethyl)-4-(4-carbamoyl-phenyl)-benzamide;

N-(2-[3-Carbamimidoyl indol-5-yl]ethyl)-4-(4-methoxy-phenyl)-benzamide;

N-(2-[3-Carbamimidoyl indol-5-yl]ethyl)-(5-methoxy-indol-2-yl)-carboxamide;

N-(2-[3-Carbamimidoyl indol-5-yl]ethyl)-(6-chloro-benzothiophen-2-yl)-carboxamide;

N-(2-[3-Carbamimidoyl indol-5-yl]ethyl)-4-(4-benzyloxy-phenyl)-benzamide;

N-(2-[3-Carbamimidoyl indol-5-yl]ethyl)-4-chloro-benzamide;

N-(2-[3-Carbamimidoyl indol-5-yl]ethyl)-4-(methylsulphonyl)-benzamide;

N-(2-[3-Carbamimidoylindol-5-yl]ethyl)-4-(aminosulphonyl)-benzamide;

4-(3-Aminoprop-1-ynyl)-N-[2-(3-Carbamimidoyl-1H-indol-5-yl)-ethyl]-benzamide;

5-{4-[2-(3-Carbamimidoyl-1H-indol-5-yl)ethylcarbamoyl]phenyl}-2-oxo-2H-pyridin-1-yl)acetic acid; and 3-Carbamimidoyl-5-{2-[4-(6-oxo-1,6-dihydro-pyridin-3-yl)-benzoylamino]-propyl}-indole.

More preferred species according to the invention are compounds:

N-[2-(3-Carbamimidoyl-1H-indol-5-yl)-ethyl]-4-(pyridazin-4-yl)-benzamide;

N-[2-(3-Carbamimidoyl-1H-indol-5-yl)-ethyl]-2-methyl-4-(6-oxo-1,6-dihydro-pyridin-3-yl)-benzamide;

N-(2-[3-Carbamimidoylindol-5-yl]ethyl)-4-(6-methoxypyrid-3-yl)benzamide;

N-(2-[3-Carbamimidoylindol-5-yl]ethyl)-4-(1-oxy-pyrid-4-yl)benzamide;

N-[2-(3-carbamimidoyl-1H-indol-5-yl)-ethyl]-4-(7H-pyrrolo[2,3-d]pyrimidin-6-yl)-benzamide;

N-[2-(3-carbamimidoyl-1H-indol-5-yl)-ethyl]-4-(1H-pyrrolo[3,2-c]pyridin-2-yl)-benzamide;

N-[2-(3-carbamimidoyl-1H-indol-5-yl)-ethyl]-3-chloro-4-(6-oxo-1,6-dihydro-pyridin-3-yl)-benzamide;

N-(2-[3-Carbamimidoylindol-5-yl]ethyl)-4-(6-oxo-1,6-dihydropyrid-3-yl)benzamide;

4-(3-Amino-1,1-dimethyl-propyl)-N-[2-(3-carbamimidoyl-1H-indol-5-yl)-ethyl]-benzamide;

4-(2-Aminomethyl-pyridin-4-yl)-N-[2-(3-carbamimidoyl-1H-indol-5-yl)-ethyl]-benzamide;

4-{4-[2-(3-Carbamimidoy-1H-indol-5-yl)-ethylcarbamoyl]-phenyl-pyridine-2-carboylic acid amide;

N-[2-(3-Carbamimidoy-1H-indol-5-yl-ethyl]-4-(2-(N,N-dimethylaminomethyl)-pyridin-4-yl)benzamide);

N-[2-(3-carbamimidoyl-1H-indol-5-yl)-ethyl]-4-(6-oxo-1,6-dihydro-pyridazin-3-yl)-benzamide;

N-[2-(3-carbamimidoyl-1H-indol-5-yl)-ethyl]-4-(6-methoxy-pyridazin-3-yl)-benzamide;

N-[2-(3-carbamimidoyl-1H-indol-5-yl)-ethyl]-4-[1-(2-dimethylamino-ethyl)-6-oxo-1,6-dihydro-pyridazin-3-yl]-benzamide;

N-[2-(3-carbamimidoyl-1H-indol-5-yl)-ethyl]-4-[1-(3-dimethylamino-propyl)-6-oxo-1,6-dihydro-pyridazin-3-yl]-benzamide;

N-[2-(3-Carbamimidoyl-1H-indol-5-yl)-ethyl]-4-[2-(2-dimethylamino-ethylamino)-pyrimidin-4-y]-benzamide;

N-[2-(3-Carbamimidoyl-1H-indol-5-yl)-ethyl]-4-[2-methoxy-pyrimidin-4-yl]-benzamide;

N-(2-[3-Carbamimidoylindol-5-yl]ethyl)-4-(1-[2-dimethylaminoethyl]-6-oxo-1,6-dihydropyridin-3-yl) benzamide;

N-[2-(3-Carbamimidoyl-1H-indol-5-yl)ethyl-4-(6-oxo-piperidin-3-yl)-benzamide;

N-[2-(3-Carbamimidoyl-1H-indol-5-yl)-ethyl]-4-[2-(morpholin-4-yl-ethylamino)-pyrimidin-4-yl]-benzamide;

N-[2-(3-Carbamimidoyl-1H-indol-5-yl)-ethyl]-4-[2-(3-dimethylamino-propylamino)-pyrimidin-4-yl]-benzamide;

N-[2-(3-Carbamimidoyl-1H-indol-5-yl)-ethyl]-4-[2-([2-dimethylamino-ethyl]-methyl-amino)-pyrimidin-4-yl]-benzamide;

2-[(4-{4-[2-(3-Carbamimidoyl-1H-indol-5-yl)-ethylcarbamoyl]-phenyl}-pyrimidin-2-yl)-methyl-amino]-ethanesulfonic acid;

N-[2-(3-Carbamimidoyl-1H-indol-5-yl)-ethyl]-4-{2-[methyl-(2(S),3(R),4(R),5(R),6-pentahydroxy-hexyl)-amino]-pyrimidin-4-yl}-benzamide;

N-[2-(3-Carbamimidoyl-1H-indol-5-yl)-ethyl]-4-{2-[methyl-(2(S),3 (R),4(S),5(R),6-pentahydroxy-hexyl)-amino]-pyrimidin-4-yl}-benzamide;

N-[2-(3-Carbamimidoyl-1H-indol-5-yl)-ethyl]-4-[2-(2-hydroxy-1-hydroxymethyl-ethylamino)-pyrimidin-4-yl]-benzamide;

N-[2-(3-Carbamimidoyl-1H-indol-5-yl)-ethyl]-4-[2-(3-imidazol-1-yl-propylamino)-pyrimidin-4-yl]-benzamide;

N-[2-(3-Carbamimidoyl-1H-indol-5-yl)-ethyl]-4-{2-[(2-diethylamino-ethyl)-methyl-amino]-pyrimidin-4-yl}-benzamide;

N-[2-(3-Carbamimidoyl-1H-indol-5-yl)-ethyl]-4-[2-(2-diisopropylamino-ethylamino)-pyrimidin-4-yl]-benzamide;

N-[2-(3-Carbamimidoyl-1H-indol-5-yl)-ethyl]-4-[2-(2-dibutylamino-ethylamino)-pyrimidin-4-yl]-benzamide;

N-[2-(3-Carbamimidoyl-1H-indol-5-yl)-ethyl]-4-[2-(3-morpholin-4-yl-propylamino)-pyrimidin-4-yl]-benzamide;

N-[2-(3-Carbamimidoyl-1H-indol-5-yl)-ethyl]-4-[2-(3-diethylamino-propylamino)-pyrimidin-4-y]-benzamide;

N-[2-(3-Carbamimidoyl-1H-indol-5-yl)-ethyl]-4-[2-(3-piperidin-1-yl-propylamino)-pyrimidin-4-yl]-benzamide;

N-[2-(3-Carbamimidoyl-1H-indol-5-yl)-ethyl]-4-(2-{[2-(ethyl-methyl-amino)-ethyl]-methyl-amino}-pyrimidin-4-yl)-benzamide;

N-[2-(3-Carbamimidoyl 1H-indol-5-yl)-ethyl]-4-[2-(5-dimethylamino-pentylamino)-pyrimidin-4-yl]-benzamide;

N-[2-(3-Carbamimidoyl-1H-indol-5-yl)-ethyl]-4-[2-(5-morpholin-4-yl-pentylamino)-pyrimidin-4-yl]-benzamide;

N-[2-(3-Carbamimidoyl-1H-indol-5-yl)-ethyl]-4-[2-(5-piperidin-1-yl-pentylamino)-pyrimidin-4-yl]-benzamide;

N-[2-(3-Carbamimidoyl-1H-indol-5-yl)-ethyl]-4-[2-(5-pyrrolidin-1-yl-pentylamino)-pyrimidin-4-yl]-benzamide;

N-[2-(3-Carbamimidoyl-1H-indol-5-yl)-ethyl]-4-(2-oxo-hexahydro-pyrimidin-5-yl)-benzamide;

N-[2-(3-Carbamimidoyl-1H-indol-5-yl)-ethyl]-4-(1,3-dimethyl-2-oxo-hexahydro-pyrimidin-5-yl)-benzamide;

Biphenyl-3,4'-dicarboxylic acid 4'-{[2-(3-carbamimidoyl-1H-indol-5-yl)-ethyl]-amide}3-[(2-methoxy-ethyl)-amide];

Biphenyl-3,4'-dicarboxylic acid 4'-{[2-(3-carbamimidoyl-1H-indol-5-yl)-ethyl]-amide}3-[(2-morpholin-4-yl-ethyl)-amide];

N-[2-(3-Carbamimidoyl-1H-indol-5-yl)ethyl]-4-[2-(4-methylpiperazin-1-yl)pyrimidin-4-yl]benzamide;

4-[(4-{4-[2-(3-Carbamimidoyl-1H-indol-5-yl)ethylcarbamoyl]phenyl}pyrimidin-2-yl)methylamino] butyric acid;

N-[2-(3-Carbamimidoyl-1H-indol-yl)ethyl]-4-[2-(2,2,2-trifluoroethoxy)pyrimidin-4-yl]benzamide;

N-[2-(3-Carbamimidoyl-1H-indol-5-yl)-ethyl]-4-(2-pyrrolidin-1-ylpyrimidin-4-yl)benzamide;

N-[2-(3-Carbamimidoyl-1H-indol-5-yl)-ethyl]-4-[2-(2-hydroxymethylpyrrolidin-1-yl)pyrimidin-4-yl]benzamide;

N-[2-(3-Carbamimidoyl-1H-indol-5-yl)-ethyl]-4-[2-(carbamoylmethyl-N-methylamino)-pyrimidin-4-yl]benzamide;

N-[2-(3-Carbamimidoyl-1H-indol-5-yl)ethyl]-4-[2-(6-pyrrolidin-1-yl-hexylamino)pyrimidin-4-yl]benzamide;

N-[2-(3-Carbamimidoyl-1H-indol-5-yl)ethyl]-4-[2-(6-piperidin-1-ylhexylamino)pyrimidin-4-yl]benzamide;

N-[2-(3-Carbamimidoyl-1H-indol-5-yl)ethyl]-4-[2-(4-piperidin-1-ylbutylamino)pyrimidin-4-yl]benzamide;

N-[2-(3-Carbamimidoyl-1H-indol-5-yl)ethyl]-4-[2-(4-diethylaminobutylamino)pyrimidin-4-yl]benzamide;

N-[2-(3-Carbamimidoyl-1H-indol-5-yl)ethyl]-4-[2-(6-morpholin-4-ylhexylamino)pyrimidin-4-yl]benzamide;

N-[2-(3-Carbamimidoyl-1H-indol-5-yl)ethyl]-4-[2-(6-dimethylaminohexylamino)pyrimidin-4-yl]benzamide;

N-[2-(3-Carbamimidoyl-1H-indol-5-yl)ethyl]-4-[2-(4-dimethylaminobutylamino)pyrimidin-4-yl]benzamide;

4-[2-(Bicyclo[2;2;1]hept-2-ylamino)pyrimidin-4-yl]-N-[2-(3-carbamimidoyl-1H-indol-5-yl)ethyl]benzamide;

N-[2-(3-Carbamimidoyl-1H-indol-5-yl)ethyl]-4-{2-[(2-hydroxy-ethyl)-N-methylamino]pyrimidin-4-yl}benzamide;

N-[2-(3-carbamimidoyl-1H-indol-5-yl)-ethyl]-4-(2-morpholin-4-yl-pyrmidin-4-yl)-benzamide;

N-[2-(3-carbamimidoyl-1H-indol-5-yl)-ethyl]-4-[2-(cyclopropylmethyl-amino)-pyrimidin-4-yl]-benzamide;

N-[2-(carbamimidoyl-1H-indol-5-yl)-ethyl]-4-[2-[(2-methoxy-ethyl)-methyl-amino]-pyrimidin-4-yl]-benzamide;

N-[2-(3-carbamimidoyl-1H-indol-5-yl)-ethyl]-4-[2-(3-hydroxy-propylamino)-pyrimidin-4-yl]-benzamide;

N-[2-(3-carbamimidoyl-1H-indol-5-yl)-ethyl]-4-[(2-hydroxy-ethyl)-propyl-amino]-pyrimidin-4-yl]-benzamide;

N-[2-(3-Carbamimidoyl-1H-indole-5-yl)-ethyl]-4-(2-piperidin-1-yl-pyrimidin-4-yl)-benzamide;

N-[2-(3-carbamimidoyl-1H-indol-5-yl)-ethyl]-4-[2-(ethyl-methyl-amino)-pyrimidin-4-yl]-benzamide;

N-[2-(3-carbamimidoyl-1H-indol-5-yl)-ethyl]-4-[2-(4-hydroxy-piperidin-1-yl)-pyrimidin-4-yl]-benzamide;

N-[2-(3-carbamimidoyl-1H-indol-5-yl)-ethyl]-4-[2-(2,3-dihydroxy-propylamino)-pyrimidin-4-yl]-benzamide;

N-[2-(3-carbamimidoyl-1H-indol-5-yl)-ethyl]-4-[2-[(2,3-dihydroxy-propyl)-methyl-amino]-pyrimidin-4-yl]-benzamide;

N-[2-(3-carbamimidoyl-1H-indol-5-yl)-ethyl]-4-[2-((s)-2-methoxymethyl-pyrrolidin-1-yl)-pyrimidin-4-yl]-benzamide;

N-[2-(3-carbamimidoyl-1H-indol-5-yl)-ethyl]-4-(2-piperazin-1-yl-pyrimidin-4-yl)-benzamide;

N-[2-(3-carbamimidoyl-1H-indol-5-yl)-4-[2-[2-(2-oxo-imidazolidin-1-yl)-ethylamino]-pyrimidin-4-yl]-benzamide;

N-[2-(3-carbamimidoyl-1H-indol-5-yl)-ethyl]-4-[2-(3-methoxy-propylamino)-pyrimidin-4-yl]-benzamide;

4-[2-(3-carbamimidoyl-1H-indol-5-yl)-ethyl]-4-[2-(2-hydroxy-ethylamino)-pyrimidin-4-yl]-benzamide;

N-[2-(3-Carbamimidoyl-1H-indol-5-yl)-ethyl]-4-[2-(2-hydroxyethy)-pyrimidin-4-yl]benzamide;

N-[2-(3-Carbamimidoyl-1H-indol-5-yl)ethyl]-4-[2-(2-carbamoylethoxy)pyrimidin-4-yl]benzamide;

N-[2-(3-Carbamimidoyl-1H-indol-5-yl)ethyl]-4-[2-(6-dimethylaminohexyloxy)pyrimidin-4-yl]benzamide;

N-[2-(3-Carbamimidoyl-1H-indol-5-yl)ethyl]-4-[2-(2-dimethylaminoethoxy)pyrimidin-4-yl]benzamide;

N-[2-(3-Carbamimidoyl-1H-indol-5-yl)ethyl]-4-[2-(2-pyrroldin ethoxy)pyrimidin-4-yl]benzamide;

N-[2-(3-Carbamimidoyl-1H-indol-5-yl)ethyl]-4-(1-oxypyridin-2-yl)benzamide;

2'-(2-Dimethylaminoethoxy)biphenyl-4-carboxylic acid [2-(3-carbamimidoyl-1H-indol-5-yl)ethyl]amide;

2'-(3-Dimethylaminopropoxy)biphenyl-4-carboxylic acid [2-(3-carbamimidoyl-1H-indol-5-yl)ethyl]amide;

N-[2-(3-carbamimidoyl-1H-indol-5-yl)-ethyl]-4-(1-oxo-pyridin-3-yl)-benzamide;

4-[2-(acetylamino-methyl)-pyridin-4-yl]-N-[2-(3-carbamimidoyl-1H-indol-5-yl)-ethyl]-benzamide;

Piperidine-4-carboxylic acid (4-[4-[2-(3-carbamimidoyl-1H-indol-5-yl)-ethylcarbamoyl]-phenyl-]-pyridin-2-ylmethyl)-amide;

N-[2-(3-Carbamimidoyl-1H-indol-5-yl)ethyl]-4-[1-(3-dimethylaminopropyl)-6-oxo-1,6-dihydropyridin-3-yl]benzamide;

4-(2-Amino-1,1-dimethylethyl)-N-(2-[3-carbamimidoylindol-5-yl]ethyl)benzamide; and N-(2-[3-Carbamimidoylindol-5-yl]ethyl)-4-pyrid-4-ylbenzamide.

It is to be understood that this invention covers all appropriate combinations of the particular and preferred groupings referred to herein.

Compounds of formula I may be prepared by the application or adaptation of known methods, by which is meant methods used heretofore or described in the literature, or by methods according to the invention described herein.

One aspect of this invention involves the syntheses of variously substituted indole, benzofuran and benzothiophene heterocycles. These syntheses are achieved, for example, by functionalization of specific precursors followed by ring synthesis or by derivatization of a preformed ring system. There are numerous approaches to the synthesis and functionalization of the aforementioned heterocycles in the chemical literature (For reviews, see (a) Katritzky, A. R.; Rees, C. W.; Scriven, E. F. V. Eds. Comprehensive Heterocyclic Chemstry II, Vol 2, 119, 607. Elsevier Science 1996 and references therein. (b) Ketcha, D. M. Prog. Heterocycl. Chem. 1997, 9, 97 and references therein. (c) Hughes, D. L. Org. Prep. Proced. Int. 1993, 25, 607).

A particularly useful preparative method according to the invention is outlined in Scheme 1. Bromo-indoles can be metalated using sodium hydride or other strong base at or around room temperature followed by treatment (at lower temperature, typically below 0° C.) with an alkyl lithium reagent. Suitable solvents for this method include THF or diethyl ether, either alone or as mixtures with additives such as HMPA, TMEDA or DABCO. The resulting nucleophile is then reacted with a variety of appropriately functionalized/substituted and/or protected electrophiles, for example, such as aldehydes, ketones, alkyl halides, oxiranes, aziridines, ?,β-unsaturated carbonyls or ?,β-usaturated esters (Scheme 1) to provide indoles substituted with a variety of functionalized/substituted and/or protected side chains, i.e., wherein $Q^1$ is —$NR^8P^1$, —$OP^1$, —C(O)(H or alkyl), —C(O)—$OP^1$ or —$SP^1$, wherein $P^1$ is hydrogen or a protecting group as defined herein. (For representative examples see Moyer, M. P.; Shiurba, J. F.; Rapaport, H. J. Org. Chem., 1986, 51, 5106).

Scheme 1

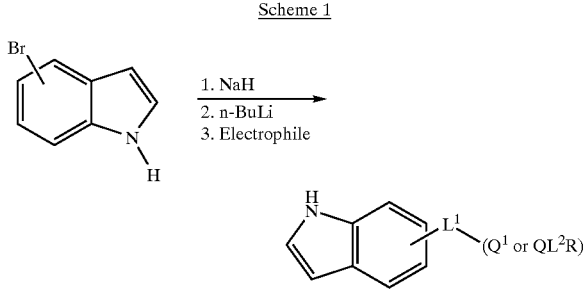

Alternatively, as shown in Scheme 2, bromo-indoles are reacted with terminal olefins ($Q^1L^{1b}H$, wherein $Q^1$ is as defined herein and $L^{1b}$ is an alkenylene having at least a terminal double bond), terminal acetylenes ($Q^1L^{1a}H$, wherein $Q^1$ is as defined herein and $L^{1a}$ is an alkynylene having at least a terminal triple bond), or metalated derivatives thereof (particularly zinc tin and boron), under palladium or nickel catalysis (for examples see J. Tsuji, Palladium Reagents and Catalysts, J. Wiley Publications, 1996. Also Harrington, P. J.; Hegedus, L. S. J. Org. Chem., 1984, 49, 2657), with or without a base, to produce vinyl or acetylenic substituted indoles. The choice of catalyst depends on the substrate employed but is most commonly tetrakistriphenylphosphine palladium, bis(triphenylphosphine)palladium chloride, 1,1'-bis(diphenylphosphino)ferrocene/bis-dibenzylideneacetone palladium or 1,2 bis-(diphenylphosphino)-ethane/bis(acetonitrile)dichloropalladium. In certain cases, addition of a copper (I) salt as co-catalyst is also required (Rossi, R.; Carpita, A.; Bellina, F. Org. Prep. Proced. Int. 1995, 27, 127). These coupling reactions are performed in various solvents, including toluene, THF, DME, DMSO, DMF, dimethylacetamide and HMPA, at about 20 to about 150 ° C.

The indole side chains incorporated as described above, can contain, or be converted to, a variety of functional groups (using one or more steps) including amines, alcohols, aldehydes, ketones, carboxylic acids, esters, olefins, amides, imides, urethanes, carbamates, sulfonamides, sulfones, sulfoxides and sulfides. These interconversions employ standard synthetic methods described in the chemical literature (For example, see Larock, C. L. Comprehensive Organic Transformations, VCH Publishers 1989 and Greene, T. W.; Wuts, P. M. G. Protective Groups in Organic Synthesis, John Wiley Publications 1991). In particular, an alcohol in the indole side chain is converted, for example, to the corresponding amine by a sequence (Scheme 3) involving treatment with toluenesulfonyl chloride/DMAP and a base such as triethylamine or diisopropylethylamine in a solvent such as dichloromethane, DMF or pyridine at about room temperature. Alternatively, the alcohol is treated with NBS/$Ph_3P$, $NCS/Ph_3P$, $I_2/Ph_3P$/imidazole, $CBr_4/Ph_3P$ to provide the corresponding alkyl halide (For a review see Castro, B. R. Org. React., 1983, 29, 1). The product is then reacted with sodium azide in a solvent such as DMF, dimethyl acetamide, DMPU or ethanol at about 20 to about 80 ° C. The resulting azide is then reduced with a reagent such as triphenylphosphine/water in THF or boron trifluoride etherate/1,3-propane-dithiol in a solvent such as dichloromethane to the corresponding amine.

Scheme 3

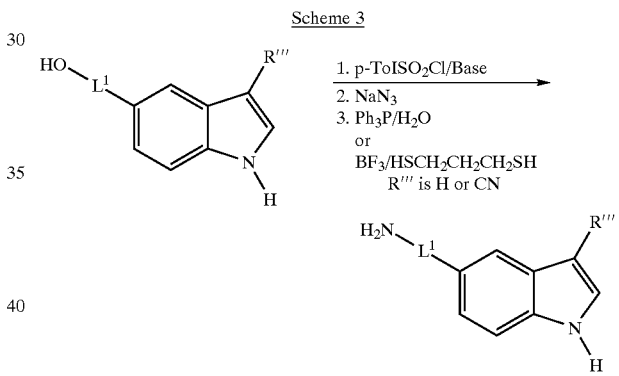

An amino moiety can also be introduced into the indole side chain (Scheme 4) by conversion of an appropriate side Scheme 2

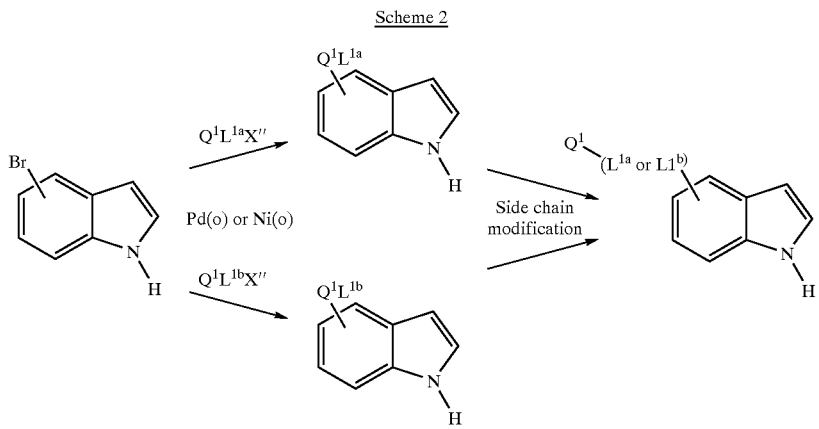

X" = H, Zn, Sn, B chain alkene double bond ($L^{1bb}$ is an alkenylene having at least a double bond at the terminal end thereof distal to its attachment to the indole moiety), first to an alcohol, using a hydroboration oxidation sequence, (For examples see (a) Beletskaya, I; Pelter, A. Tetrahedron, 1997, 53, 4957 and references therein. (b) Brown, H. C.; Kramer, G. W.; Levy, M. B.; Midland, M. M., Organic Synthesis via Boranes, Wiley Interscience, N.Y. 1973.), then oxidation of the alcohol to the corresponding ketone using any of a number of common oxidation reagents such as Swern's reagent. (For a review, see Hudlicky, T. Oxidations in Organic Chemistry, ACS Publications 1990) and finally reductive amination of the ketone (Abdel-Magid, A. F.; Maryanoff, C. A. Reductions in Organic Synthesis, ACS Symp. Ser., 641, p201, ACS Publications 1996) with an appropriate amine and a reducing agent such as sodium cyanoborohydride or sodium triacetoxyborohydride in a solvent such as methanol, THF, acetonitrile, HMPA, or water either alone or as cosolvents. In certain cases, the amine moiety may be part of the indole side chain, in which case, a heterocyclyl can be formed.

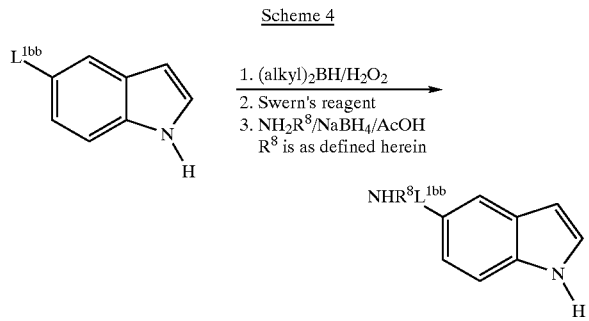

Another convenient method for introduction of an amino moiety into the side chain involves treatment of a side chain carboxylic acid with diphenylphosphoryl azide and a base such as triethylamine, diisopropylamine in a solvent such as dichloromethane or THF toluene or benzene usually at about 0° C. to about room temperature. (For a review, see Banthrope, The Chemistry of the Azido Group, S. Patai Ed. Wiley Interscience N.Y. 1971). Subsequent thermolysis of the resulting acyl azide at about room temperature to about 140° C. in the presence of an alcohol such as t-butanol, benzyl alcohol or allyl alcohol provides the corresponding carbamate which can be cleaved to the amine using standard protecting group chemistry. Thermolysis of the acyl azide in the absence of an alcohol produces the corresponding isocyanate which may be subsequently reacted with a variety of amines to provide urethanes (for a modification which also provides a convenient preparation of secondary amines see Pfister, J. R.; Wymann, W. E. Synthesis, 1983, 38). Alternatively, a urethane may be incorporated by reaction of a side chain amino moiety with an appropriate isocyanate.

According to Scheme 5, a ketone may also be incorporated into the side chain by hydroboration of an appropriate alkyne ($L^{1aa}$ is an alkynylene having at least a triple bond at the terminal end thereof distal to its attachment to the indole moiety) with catechol borane in a solvent such as THF at about room temperature to about 67° C., followed by oxidative cleavage of the resulting product with hydrogen peroxide in the presence of a base such as sodium hydroxide.

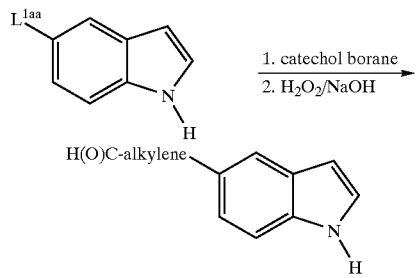

An imide moiety may be incorporated by reaction of a side chain alcohol with a preformed, N-unsubstituted-imide using Mitsunobu's reagent (Mitsunobu. O., Synthesis, 1981, 1, an imide, so formed, can also be converted to the corresponding amine by treatment with hydrazine in a solvent such as ethanol). Alternatively, the imide group may be introduced by acylation of a side chain amide with an acid chloride (or an activated ester) in the presence of a base such as sodium hydride.

An amide linkage may be introduced into the indole side chain by reaction of an amine (incorporated using a method such as described above) with a carboxylic acid. Suitable conditions for effecting this transformation involve activation of the acid with a reagent such as thionyl chloride, isopropyl chloroformate, oxalylchloride/DMF, TBTU, DCC, DICC/HOBT, CDI, BOP, EEDQ or PyBroP (For reviews see (a) Blackburn, C.; Kates, S. A. Methods Enzymol. 1997, 289, 175. (b) Bodanszky, M.; Trost, B. M. Principles of Peptide Synthesis 2nd Ed., Springer Verlag, N.Y. 1993) usually in the presence of a base such as triethylamine, diisopropylethylamine and/or DMAP in a solvent such as dichloromethane, DMF, dimethylacetamide or DMPU at about or above room temperature. The reverse orientation of the amide unit may be prepared by reaction of an indole side chain containing an acid moiety with an amine. An acid moiety may be formed in the side chain by oxidation of a side chain alcohol, first to the aldehyde, then oxidation of the aldehyde to the corresponding carboxylic acid. A particularly suitable reagent for this transformation is sodium chlorate (Lidgren, B. O.; Hilsson, T. Acta. Chem. Scand. 1973, 58, 238). Alternatively, an aldehyde may be generated by oxidation of an olefin using osmium tetroxide with a co-catalyst such as sodium periodate in a solvent such as THF/water or t-butanol/water. A carboxylic acid may also be obtained by hydrolysis of the corresponding ester using standard protecting group methodology.

A sulfonamide linkage may be introduced into the side chain by reaction of a side chain amino functionality with a sulfonyl chloride in the presence of a base such as pyridine, triethylamine, diisopropylethylamine or sodium hydroxide in a solvent such as dichloromethane, pyridine, DMF or an alcohol such as ethanol or isopropanol. The reverse orientation of the sulfonamide linkage may be produced by the method of Liskamp (Moree, W. J.; Van der Marel, G. A.; Liskamp, R. J. J. Org. Chem. 1995, 60, 1995.) from a side chain thioacetate. The thioacetate moiety may be prepared by displacement of a halide or sulfonate with sodium thioacetate in a solvent such as DMF, DMPU, HMPA or DMSO.

A sulfide linkage may be incorporated into the side chain by saponification of the thioacetate functional group followed by alkylation of the resulting thiol with an appropriate alkyl halide, or sulfonate(such as tosylate, triflate or mesylate). Alternatively, the sulfide linkage may be incorporated by direct reaction of a side chain alkyl chloride, bromide, iodide, tosylate or mesylate with a thiolate ion in a solvent such as benzene, DMF, DMPU, HMPA or DMSO. In certain cases, a sulfide can be formed from an appropriate disulfide and a side chain alcohol in the presence of tributylphosphine in a solvent such as THF.

The sulfoxide and sulfone linkages may be introduced by mild oxidation of the sulfides with a reagent such as m-chloroperbenzoic acid in dichloromethane chloroform or benzene at about or below room temperature.

An ether linkage (for a review see Comprehensive Organic Chemistry Vol 1, p 799, Ed. Barton, D.; Ollis, W. D., Pergamon Press, 1979) may be prepared from a side chain alcohol and an alkyl halide, sulfonate or unsaturated ketone derivative and a base such as sodium hydride potassium hydride in a solvent such as DMF DMSO THF DMPU or HMPA. Alternatively, an ether linkage may be obtained using a side chain alkyl halide, sulfonate or ?,β-unsaturated ketone and an appropriate alcohol under the same conditions. Another method of ether formation involves formation of a thiono-ester from a side chain ester or lactone by reaction with a thionating reagent, such as Lawesson's reagent (For a review see Cava, M. P.; Levinson, M. I. Tetrahedron (1985), 41(22), 5061–87), followed by reduction of the thiono group with a hydride reducing agent such as tributyltin hydride, usually in the presence of a free radical initiator such as AIBN.

Introduction of a nitrile at C-3 of the indole ring system (Scheme 6) may be accomplished by first formylation at C-3 using a reagent combination such as phosphorous oxychloride in DMF, at or above room temperature, followed by conversion of the resulting aldehyde to the corresponding oxime with hydroxylamine hydrochloride in a solvent such as toluene or xylene in the presence of a catalyst such as toluene sulfonic acid and a desiccant such as magnesium sulfate according to the method of Ganbao and Palomo (Ganbao, I.; Palomo, C. Syn. Commun. 1983, 13, 219. For alternatives to this procedure see Wang, E-C.; Lin, G-J. Tetrahedron Lett. 1998, 39, 4047 and references therein) Heating the oxime with these reagents at about 80° C. to about 150° C. then results in dehydration to form the corresponding nitrile. In certain favorable cases, the formylation conditions described above also result in conversion of a side chain alcohol into the corresponding alkyl chloride.

Scheme 6

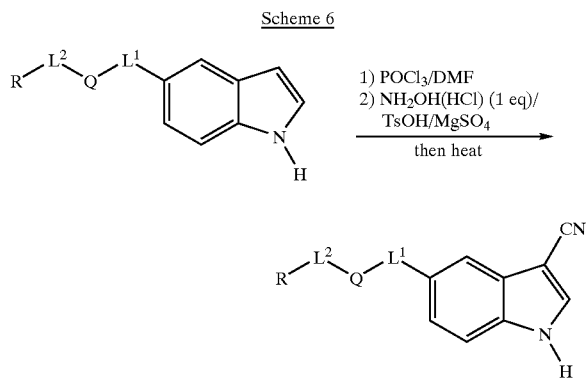

Introduction of the C-3 nitrile, as described above, may be carried out either before or after derivatization of the side chain(s) at other positions on the indole ring depending on the nature of the functionality present.

Another embodiment of this invention involves the use of a benzothiophene in place of an indole scaffold. A variety of methods can be applied to the synthesis of benzothiophenes (for examples see Katritzky, A. R.; Rees, C. W.; Scriven, E. F. V. Eds. Comprehensive Heterocyclic Chemistry II, Vol. 2, p 607, Elsevier Science 1996 and references therein). A particularly useful protocol with reference to the current invention is outlined in Scheme 7. Starting from an appropriate bromo-thiophenol, alkylation of the thiol with bromo-acetaldehyde diethyl acetal in the presence of a base such as NaH in a solvent such as DMF, THF, TBTU, DMSO or HMPA followed by cyclization with an acid such as polyphosphoric acid provides the corresponding bromo-benzothiophene (for examples see Titus, R. L.; Choi, M.; Hutt, M. P. J. Heterocycl. Chem. 1967, 4, 651. and Clark, P. D.; Kirk, A.; Yee, J. G. K. J. Org. Chem. 1995, 60, 1936). This structure may be manipulated using many of the same procedures used to install and functionalize the side chain of the indole scaffold described above. Introduction of a nitrile at C-3 of the benzothiophene ring may be effected by treatment with bromine in a solvent such as acetic acid or chloroform. The resulting 3-bromo-benzothiophene can then be converted to the 3-cyano-derivative using zinc cyanide and a palladium catalyst, preferably tetrakis (triphenylphosphine) palladium(o) in DMF at about 70° C. to about 90° C.

Scheme 7

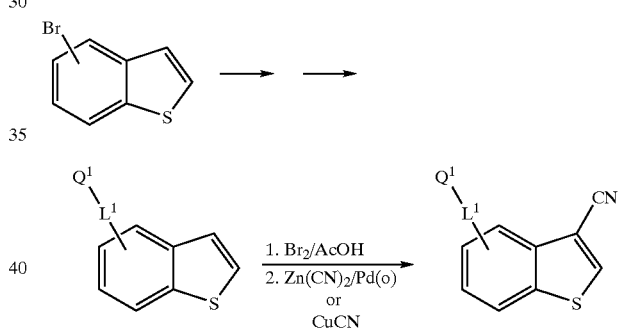

In certain cases, it is convenient to prepare a specifically substituted heteroaryl scaffold by direct ring synthesis. A particularly suitable ring synthesis protocol employs an adaptation of the method of Yamanaka (Sakamoto, K.; Nagano, T.; Kondo, Y.; Yamanaka, H. Synthesis, 1990, 215). In this approach, an appropriately substituted aniline, thiophenol or phenol is first brominated or more preferably, iodinated ortho to the nitrogen/sulfur/oxygen substituent on the ring (Scheme 8). Suitable reagents for effecting this transformation include bromine in the presence of either acid (such as acetic acid) or a base (such as sodium acetate, sodium carbonate, triethylamine or pyridine), iodine or iodine monochloride in the presence of a soft Lewis acid such as silver sulfate or a base such as calcium carbonate, morpholine, dimethylamine or pyridine. Suitable solvents for this process include water, methanol, ethanol or dichloromethane at about or below room temperature. Addition of the acrylonitrile functionality to the ring heteroatom can be effected following the procedures of Scotti and Frazza (Scotti, F.; Frazza, E. J. J. Org. Chem., 1964, 29, 1800)

Scheme 8

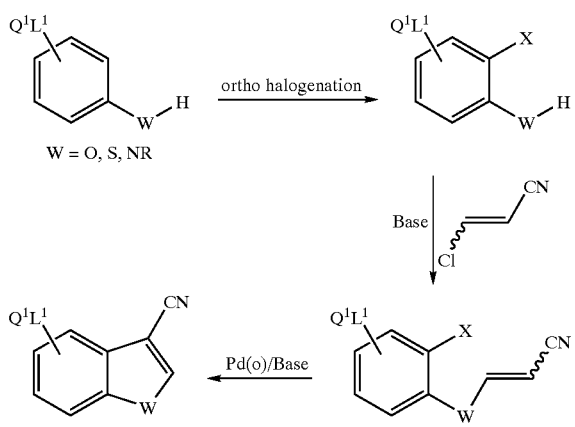

A particular embodiment of the current invention employs indoles/benzothiophenes/benzofurans substituted with a side chain which contains (aryl or heteroaryl)-substituted aryl or heteroaryl appendages. These latter structural motifs can be prepared by cross coupling (Scheme 9) of an appropriately substituted (heteroaryl or aryl)halide or triflate with a (heteroaryl or aryl)aryl organometallic (most commonly zinc, boron, magnesium and tin derivatives) under catalysis by Pd(o) or Ni(o) employing conditions described above for derivatization of 5-bromo-indole.

Scheme 9

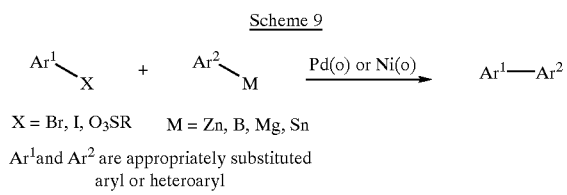

$X = Br, I, O_3SR$    $M = Zn, B, Mg, Sn$ $Ar^1$ and $Ar^2$ are appropriately substituted aryl or heteroaryl Aryl and heteroaryl substituted heterocycles can also be prepared by direct ring synthesis. A wide variety of methods and conditions for this kind of process are known in the chemical literature (for examples see(a) Katritzky, A. R.; Rees, C. W.; Scriven, E. F. V. Eds. Comprehensive Heterocyclic Chemstry II, Elsevier Science 1996).

In another embodiment of this invention the indole/benzothiophene/benzofuran side chain is substituted with a substituted aryl group. One particularly useful aryl substitution comprises of a 1,1-dimethyl alkyl chain further substituted with a heteroatom, a heteroatom cluster (such as a diol or amino-alcohol) or a heteroaryl (such as imidazole). These systems can be prepared from 2-(4-furan-2-yl-phenyl)-2-methyl-propionic acid methyl ester or 2-(4-bromo-phenyl)-2-methyl-propionic acid methyl ester a shown in scheme 10.

Scheme 10

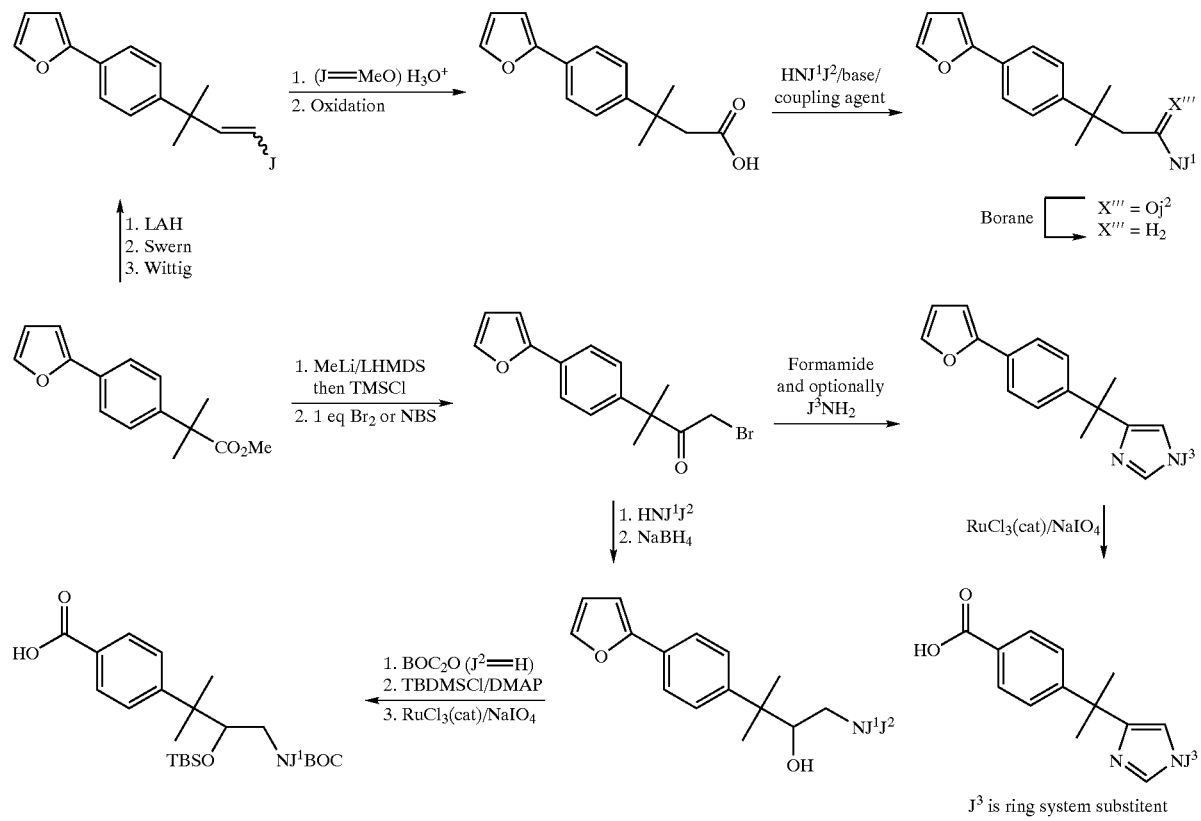

$J^3$ is ring system substitent

-continued

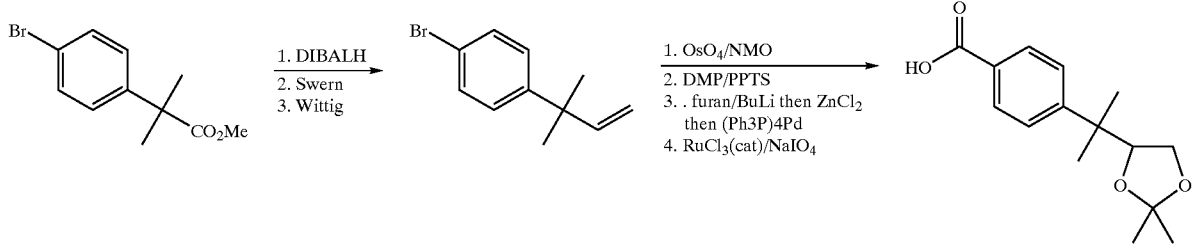

Treatment of 2-(4-furan-2-yl-phenyl)-2-methyl-propionic acid methyl ester with methyl lithium in the presence of lithium hexamethyldisilazide at about or below room temperature and reaction of the resulting enolate with TMS chloride provides the corresponding silylenol ether. Reaction of this intermediate with 1 eq of bromine at low temperature (typically at α-bromoketone. This compound can be treated with formamide at elevated temperatures (from about 50° C. to about 180° C.) to provide imidazole. Alternatively, the bromo ketone can be reacted with sodium azide followed by reduction with sodium borohydride to provide the amino alcohol. After, protection of the amino alcohol as a BOC derivative of the amine and a TBS ether of the alcohol, the furan ring can be oxidatively cleaved to provide the benzoic acid derivative. This unit can then be attached to the heteroaryl scaffold as described above. Reduction of 2-(4-furan-2-yl-phenyl)-2-methyl-propionic acid methyl ester with lithium aluminum hydride in a solvent such as THF followed by oxidation of the resulting primary alcohol to the corresponding aldehyde and Wittig or Horner-Emmons olefin reactions provides access to chain extended alkenes (For a review see Cadogan, J. I. G. Organophosphorus Reagents in Organic Synthesis, Academic Press, 1979). In the case where R=Ome, this system can be hydrolyzed to the corresponding aldehyde with dilute HCl then oxidized to the carboxylic acid as previously described. Amide formation followed by reduction with a reagent such as borane in THF provides a series of amines. Subsequent oxidative cleavage of the furan ring as described above provides a useful functional group for attachment to the heterocyclic scaffold. Additionally, treatment of 2-(4-bromo-phenyl)-2-methyl-propionic acid methyl ester with diisobutylaluminum hydride at −78° C. in dichloromethane followed by Swern oxidation of the resulting alcohol and Wittig reaction on the aldehyde provides the one carbon chain extended olefin. Osmylation of this species, followed by protection of the resulting diol as an acetonide allows oxidation of the furan ring to the carboxylic acid which provides an attachment point for coupling to the heteroaryl scaffold.

It is often useful to introduce conformational constraints into a linker to optimize the availability of a bioactive conformer. These constraining groups can also interact favorably with a target protein providing an additional advantage. An example of the synthesis of a system which can produce such effects is shown in Scheme 11. Two carbon chain extension of the bromo indole by adaptation of the method of Migata (Kosugi, M; Negishi, Y.; Kameyama, M.; Migata, T.; Bull, Chem. Soc. Jpn., 1985, 58, 3383; Agnelli, F., Sulikowski, G. A. Tetrahedron Letts 1998, 39, 8807) then treatment of the resulting ester with TMS triflate and triethylamine in ether at 0° C. provides the silyl ketene acetal. Reaction of this species with an amine acetal in dichloromethane in the presence of TMS triflate as a catalyst, generates the substituted ?,β-amino ester (for representative examples see Okano, K.; Morimoto, T.; Sekiya, M. J. Chem Soc., Chem. Commun., 1984, 883 and Colvin, E. W.; McGarry, D. G.; Nugent, M. J. Tetrahedron, 1988, 44, 4157). Acylation of the amino group then provides access to a variety of amide substituted scaffolds.

Scheme 11

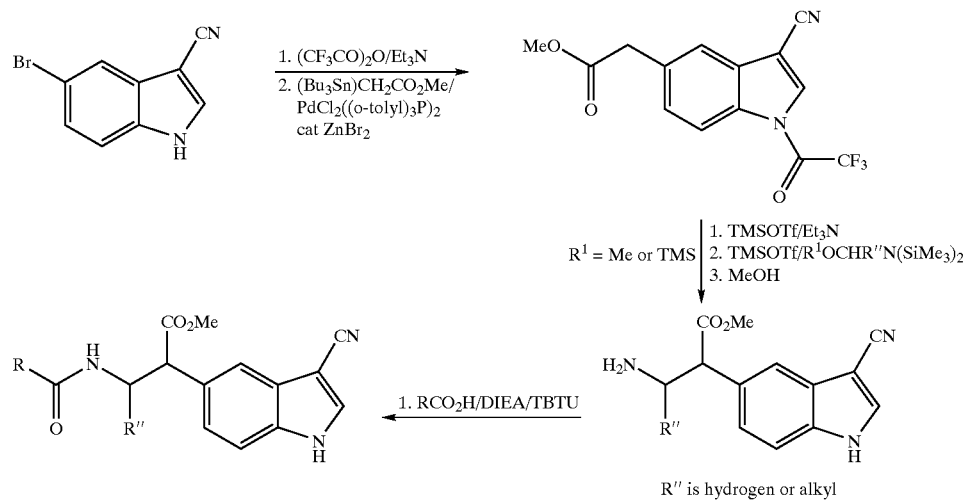

Transformation of the C-3 nitrile into the corresponding amidine can be carried out employing a number of standard procedures. (for examples see Judkins, B. D.; Allen, D. G.; Cook, T. A.; Evans, B.; Sardharwala, T. E. Syn. Comm. 1996, 26, 4351 and references therein). Treatment of the nitrile (Scheme 12) with HCl in a solvent such as methanol or ethanol at about or above room temperature provides the imidate ester intermediate which can then be converted to the amidine by treatment with ammonia or an alkylamine in a solvent such as methanol or ethanol. Alternatively, reaction of the nitrile with hydrogen sulfide in a solvent such as pyridine, followed by alkylation of the resulting thioamide with an alkylating agent such as methyl iodide in a solvent such as acetone at a temperature at or above room temperature and treatment of this product with ammonia or ammonium acetate in a solvent such as methanol at about or above room temperature provides the final amidine.

It will be apparent to those skilled in the art that certain compounds of formula I can exhibit isomerism, for example geometrical isomerism, e.g., E or Z isomerism, and optical isomerism, e.g., R or S configurations. Geometrical isomers include the cis and trans forms of compounds of the invention having alkenyl moieties. Individual geometrical isomers and stereoisomers within formula I, and their mixtures, are within the scope of the invention.

Such isomers can be separated from their mixtures, by the application or adaptation of known methods, for example chromatographic techniques and recrystallization techniques, or they are separately prepared from the appropriate isomers of their intermediates, for example by the application or adaptation of methods described herein.

The compounds of the present invention are useful in the form of the free base or acid or in the form of a pharmaceutically acceptable salt thereof. All forms are within the scope of the invention.

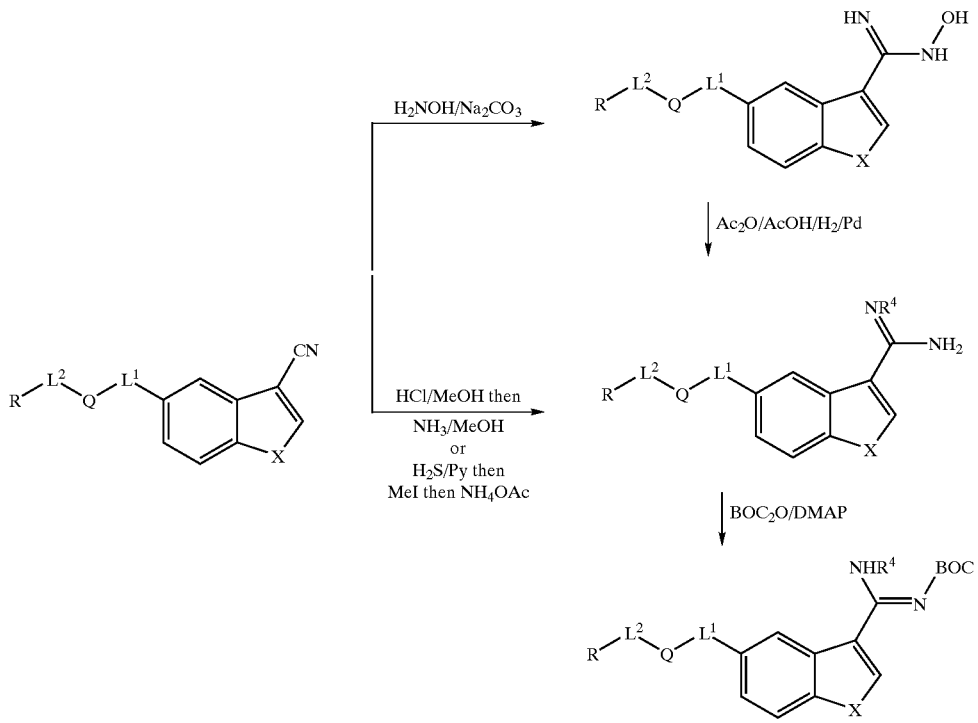

Scheme 12

An amidine can also be prepared by addition of hydroxylamine to the nitrile to form the corresponding N-hydroxyamidine followed by acylation and hydrogenolysis of the N—O bond using hydrogen/acetic acid/acetic anhydride in the presence of a catalyst such as palladium on carbon. For certain transformations of the side chain, it may be necessary or preferable to protect the indole nitrogen as an inert derivative (Protective Groups in Organic Synthesis, T. W. Greene and P. G. M. Wuts; John Wiley Publications 1991). A particularly suitable derivative for this purpose is the t-butyloxy-carbamate. This can be prepared by reaction of the appropriate indole with di-t-butyidicarbonate in THF or dichloromethane in the presence of a base such as DMAP/triethylamine or diisopropylethylamine at about or above room temperature. The nitrogen of the amidine functional group can be protected using essentially the same conditions described above for the indole nitrogen. Cleavage of these BOC derivatives can be accomplished by treatment with TFA in dichloromethane or with HCl in ethyl acetate.

Where the compound of the present invention is substituted with a basic moiety, acid addition salts are formed and are simply a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects on Factor Xa inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrohalides, e.g. hydrochloride and hydrobromide, sulfate, phosphate, nitrate, sulfamate, acetate, citrate, lactate, tartarate, malonate, oxalate, salicylate, propionate, succinate, fumarate, maleate, methylene-bis-β-hydroxy-naphthoates, gentisates, mesylates, isethionates, di-p-toluoyltartrates, methanesulfonate, ethanesulfonate, benzenesulfonate, p-toluenesulfonate, cyclohexylsulfamate and quinate, respectively.

According to a further feature of the invention, acid addition salts of the compounds of this invention are prepared by reaction of the free base with the appropriate acid, by the application or adaptation of known methods. For example, the acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Where the compound of the invention is substituted with an acidic moiety, base addition salts may be formed and are simply a more convenient form for use; and in practice, use of the salt form inherently amounts to use of the free acid form. The bases which can be used to prepare the base addition salts include preferably those which produce, when combined with the freeacid, pharmaceutically acceptable salts, that is, salts whose cations are non-toxic to the animal organism in pharmaceutical doses of the salts, so that the beneficial inhibitory effects on Factor Xa inherent in the free acid are not vitiated by side effects ascribable to the cations. Pharmaceutically acceptable salts, including for example alkali and alkaline earth metal salts, within the scope of the invention are those derived from the following bases: sodium hydride, sodium hydroxide, potassium hydroxide, calcium hydroxide, aluminum hydroxide, lithium hydroxide, magnesium hydroxide, zinc hydroxide, ammonia, ethylenediamine, N-methyl-glucamine, lysine, arginine, omithine, choline, N,N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, and the like.

Metal salts of compounds of the present invention may be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous or organic solvent with the free acid form of the compound. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The the compounds of this invention can be regenerated from the salts by the application or adaptation of known methods. For example, parent compounds of the invention can be regenerated from their base addition salts by treatment with an acid, e.g. hydrochloric acid.

Pharmaceutically acceptable salts also include quaternary lower alkyl ammonium salts. The quaternary salts are prepared by the exhaustive alkylation of basic nitrogen atoms in compounds, including nonaromatic and aromatic basic nitrogen atoms, according to the invention, i.e., alkylating the non-bonded pair of electrons of the nitrogen moieties with an alkylating agent such as methylhalide, particularly methyl iodide, or dimethyl sulfate. Quatemarization results in the nitrogen moiety becoming positively charged and having a negative counter ion associated therewith.

As will be self-evident to those skilled in the art, some of the compounds of this invention do not form stable salts. However, acid addition salts are most likely to be formed by compounds of this invention having a nitrogen-containing heteroaryl group and/or wherein the compounds contain an amino group as a substituent. Preferable acid addition salts of the compounds of the invention are those wherein there is not an acid labile group.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The starting materials and intermediates are prepared by the application or adaptation of known methods, for example methods as described in the Reference Examples or their obvious chemical equivalents, or by methods according to this invention.

The present invention is further exemplified but not limited by the following illustrative examples which illustrate the preparation of the compounds according to the invention.

EXPERIMENTAL SECTION

Unless otherwise stated, all starting materials are obtained from commercial suppliers and are used without further purification. Reactions are routinely carried out under an inert atmosphere of nitrogen or argon using anhydrous solvents obtained from Aldrich Chemical Company. Flash column chromatography is performed on Merck silica gel (230–400 mesh) eluting with the specified solvent mixture. Reverse phase FFPLC is performed using Dynamax C-18 (60A) columns, eluting with a water/acetonitrile gradient (containing a fixed 0.1% v/v trifluoroacetic acid additive) with UV detection (λ=220, 254, 294 nM). $^1$H NMR spectra are recorded at a frequency of 300 MHz in the specified deuterated solvent. Chemical shifts are in ppm relative to the resonance frequency of tetramethylsilane δ=0.00. The following conventions are used throughout to describe NMR spectra: s=singlet, d=doublet, t=triplet, q=quartet, m=multiplet, b=broad. Coupling constants are designated with the symbol J and are measured in Hz.

Example 1a

N-(2-[3-Carbamimidoyl-5-indolyl]ethyl)-4-pyrid-3-ylbenzamide. A stream of HCl gas is bubbled through a cooled (0° C.) slurry of N-(2-[3-Cyano-5-indolyl]ethyl)-4-pyrid-3-ylbenzamide (reference example 1a) in MeOH (10 mL) for seven minutes, after which the reaction is capped and allowed to stir overnight at room temperature. After purging with a stream of nitrogen, the reaction is concentrated, and 15 mL 7N $NH_3$ in MeOH is added. After stirring overnight, the reaction is purged with nitrogen and concentrated, The residue is chromatographed (3:1 $CH_2Cl_2$: 7N $NH_3$ in MeOH) to afford partially purified product. Further purification by reverse phase HPLC provided 0.298 g of the title compound as a white solid. m.p. 55–58° C.; $^1$H NMR ($CD_3OD$): δ 3.09 (2H, t, J=7 Hz), 3.71 (2H, t, J=7 Hz), 7.26 (1H, d, J=8 Hz), 7.49 (1H, d, J=8 Hz), 7.80 (1H, s), 7.87 (2H, d, J=8 Hz), 7.97 (2H, d, J=8 Hz), 8.00 (1H, m), 8.09 (1H, s), 8.69 (1H, d, J=8 Hz), 8.80 (1H, br, m), 9.14 (1H, br, s). MS (ion spray) m/z 384 (M+H)$^+$. Anal. calcd for $C_{23}H_{21}N_5O.(C_2HF_3O_2)_2.(H_2O)_3$: C, 48.7; H, 4.4; N, 10.5. Found: C, 48.5; H,3.9; N, 10.3.

The following compounds are prepared using essentially the same procedure described in example 1a except using the specified nitrile:

Example 1b

N-(2-[3-Carbamimidoyl-5-indolyl]ethyl)-4-(pyrimidin-5-yl)-benzamide). Using the product from reference example 1b. m.p. 97–100° C.; $^1$H NMR ($CD_3OD$): δ 3.09 (2H, t, J=7 Hz), 3.71 (2H, t, J=7 Hz), 7.26 (1H, d, J=8 Hz), 7.49 (1H, d, J=8 Hz), 7.79 (1H, s), 7.82 (2H, d, J=8 Hz), 7.94 (2H, d, J=8 Hz), 8.08 (1H, s), 9.23 (3H, br). MS (ion spray) m/z 385 (M+H)$^+$.

Example 1c 5-(Pyrid-2-yl)-thiophene-2-carboxylic acid 2-(3-carbamimidoyl-5-indolyl)ethyl amide. Using the product from reference example 1c. m.p. 198–200° C.; $^1$H NMR ($CD_3OD$): δ 3.07 (2H, t J=7 Hz), 3.66 (2H, t, J=7 Hz), 7.25 (1H, d, J=8 Hz), 7.33 (1H, m), 7.48 (1H, d, J=8 Hz), 7.63 (1H, m), 7.66 (1H, m), 7.78 (1H, s), 7.83 (1H, m), 7.87 (1H, m), 8.07 (1H, s), 8.52 (1H, d, J=5 Hz). MS (ion spray) m/z 390 (M+H)$^+$. Anal. calcd for $C_{21}H_{19}N_5OS.(C_2HF_3O)_2.(H_2O)_{0.5}$: C, 47.9; H, 3.5; N, 11.2. Found: C, 48.1; H, 3.4; N, 11.0.

Example 1d

N-(2-[3-Carbamimidoylindol-5-yl]ethyl)-6-morpholin-4-yinicotinamide. Using the product from reference example 1d. m.p. 130–132° C.; $^1$H NMR ($D_2O$): δ 2.88 (2H, t, J=6 Hz), 3.50 (2H, t, J=6 Hz), 3.56 (2H, t, J=4 Hz), 3.73 (2H, t, J=4 Hz), 7.07–7.12 (2H, m), 7.37 (1H, d, J=8 Hz), 7.55 (1H, s), 7.88–7.96 (2H, m), 8.00 (1H, s). MS (ion spray) m/z 393 (M+H)$^+$. Anal. calcd. for $C_{21}H_{24}N_6O_2.(C_2HF_3O)_2.(H_2O)_2$: C, 45.1; H, 4.7; N, 12.6. Found: C, 44.9; H, 4.2; N, 12.4.

Example 1e 4-(5-2[-{3-Carbamimidoylindol-5-yl}ethylcarbamoyl]pyridin-2-yl)piperazine-1-carboxylic acid ethyl ester. Using the product from reference example 24b. m.p. 85–87° C. $^1$H NMR ($CD_3OD$): δ 1.28 (3H, t, J=7 Hz), 3.05 (2H, t, J=7 Hz), 3.55–3.73 (10H, m), 4.16 (2H, q, J=7 Hz), 6.97 (1H, d, J=9 Hz), 7.23 (1H, d, J=8 Hz), 7.47 (1H, d, J=8 Hz), 7.76 (1H, s), 8.06 (1H, d, J=9 Hz), 8.80 (1H, s), 8.50 (1H, d, J=2 Hz). MS (ion spray) m/z 464 (M+H)$^+$. Anal. calcd. for $C_{24}H_{29}N_7O_3.(C_2HF_3O)_2.(H_2O)_{4.5}$: C, 43.5; H, 5.2; N, 12.7. Found: C, 43.5; H, 4.4; N, 12.6.

Example 1f

N-(2-[3-Carbamimidoylindol-5-yl]ethyl)-6-imidazol-1-yinicotinamide. Using the product from reference example 1f. m.p. 94–97° C. $^1$H NMR ($CD_3OD$): δ 3.09 (2H, t, J=7 Hz), 3.72 (2H, m), 7.26 (1H, d; J=9 Hz), 7.49 (1H, d, J=9 Hz), 7.71 (1H, s, br), 7.79 (1H, s), 7.99 (1H, d, J=9 Hz), 8.09 (1H, s), 8.37 (1H, s, br), 8.43 (1H, d, J=9 Hz), 8.95 (1H, s), 9.66 (1H, s, br). MS (FAB) m/z 374 (M+H)$^+$. Anal. calcd. for $C_{20}H_{19}N_7O.(C_2HF_3O)_2.(H_2O)_2$: C, 45.2; H, 3.9; N, 15.4. Found: C, 45.2; H, 3.5; N, 15.3.

Example 1g

N-(2-[3-Carbamimidoylindol-5-yl]ethyl)-4-imidazol-1-ylbenzamide. Using the product from reference example 1g. m.p. 191–194° C. $^1$H NMR ($CD_3OD$): δ 3.09 (2H, m), 3.71 (2H, m), 7.26 (1H, d, J=8 Hz), 7.48 (1H, d, J=8 Hz), 7.73 (1H, s, br), 7.77–7.86 (3H, m), 8.01–8.16 (4H, m), 9.38 (1H, s, br). MS (ion spray) m/z 373 (M+H)$^+$. Anal. calcd. for $C_{21}H_{20}N_6O.(C_2HF_3O)_2.(H_2O)_5.(CH_3CN)_{0.5}$: C, 43.9; H, 4.7; N, 12.8. Found: C, 43.6; H, 4.0; N, 13.1.

Example 1h

N-(2-[3-Carbamimidoylindol-5-yl]ethyl)-4-(3H-imidazol-4-yl)benzamide. Using the product from reference example 1h. m.p. 52–54° C. $^1$H NMR ($D_2O$): δ 2.89 (2H, m), 3.52 (2H, m), 7.13 (1H, d, J=8 Hz), 7.39 (1H, d, J=8 Hz), 7.49–7.57 (5H, m), 7.65 (1H, s), 7.90 (1H, s), 8.62 (1H, s). MS (ion spray) m/z 373 (M+H)$^+$.

Example 1i

N-(2-[3-Carbamimidoylindol-5-yl]ethyl)-4-(1,2,4)thiadiazol-5-ylbenzamide. Using the product from reference example 1i m.p. 222–224° C. $^1$H NMR (DMSO-$d_6$): δ 2.99 (2H, t, J=7 Hz), 3.60 (2H, m), 7.20 (1H, d, J=8 Hz), 7.50 (1H, d, J=8 Hz), 7.74 (1H, s), 8.01 (2H, d, J=8 Hz), 8.16 (2H, d, J=8 Hz), 8.20 (1H, d, J=3 Hz), 9.03 (1H, s). MS (ion spray) m/z 391 (M+H)$^+$. Anal. calcd. for $C_{20}H_{18}N_6OS.C_2HF_3O.(H_2O)_{1.5}$: C, 49.7; H, 4.2; N, 15.8. Found: C, 49.9; H, 4.0; N, 15.7.

Example 1j

N-[2-(3-Carbamimidoyl-1H-indol-5-yl)-ethyl]-4-(1-carbamoyl-1-methyl-ethyl-benzamide. Using the product from reference example 1j. $^1$H NMR ($CD_3OD$) d 1.56 (s, 6H), 3.06 (t, J=7 Hz, 2H), 3.67 (t, J=7 Hz, 2H), 7.22 (d, J=8 Hz, 1H), 7.48 (m, 3H), 7.76 (m, 3H), 8.07 (s, 1H), 8.28 (bs, 1H), 8.6 (bs, 1H). MS (ion spray) m/z 392 (M+H). Combustion Analysis $C_{22}H_{25}N_5O_2;(C_2HF_3O)_2;(H_2O)$ requires C 52.8, H 5.4, N 13.3. Found C 52.8, H 5.3, N 13.2.

Example 1k

N-[2-(3-Carbamimidoyl-1H-indol-5-yl)-ethyl]-4-(1-[N-(2-methoxyethyl)]-carbamoyl-1-methyl-ethyl-benzamide. Using the product from reference example 1k. $^1$H NMR ($CD_3OD$) d 1.54 (s, 6H), 3.05 (t, J=7 Hz, 2H), 3.28 (s, 3H), 3.34 (m, 2H), 3.40 (m, 2H), 3.67 (t, J=7 Hz, 2H), 7.22 (dd, J=7, 1 Hz, 1H), 7.44 (m, 3H), 7.75 (m, 3H), 8.07 (s, 1H). MS (ion spray) m/z 450 (M+H). Combustion Analysis $C_{25}H_{31}N_5O_3;(C_2HF_3O_2)1.4$ requires C 54.9, H 5.4, N 11.5. Found C 54.6, H 5.5, N 11.8.

Example 1l

N-[2-(3-Carbamimidoyl-1H-indol-5-yl)-ethyl]-4-(t-butyl)-benzamide. Using the product from reference example 1l $^1$H NMR (DMSO) d 1.29 (s, 9H), 2.96 (t, J=7 Hz, 2H), 3.53 (q, J=7 Hz, 2H), 7.18 (d, J=8 Hz, 1H), 7.45 (m, 3H), 7.75 (m, 3H), 8.21 (s, 1H), 8.52 (bt, 1H), 8.70 (bs, 4H), 12.3 (bs, 1H). MS (ion spray) m/z 363 (M+H). Combustion Analysis $C_{22}H_{26}N_4O;[C_2HF_3O_2]_{1.3}$ requires C 57.8, H 5.4, N 11.0. Found C 57.6, H 5.3, N 11.0.

Example 1m

N-[2-(3-Carbamimidoyl-1H-indol-5-yl)-ethyl]-4-(pyridazin-4-yl)-benzamide. Using the product from reference example 1m. $^1$H NMR (DMSO) d 3.0 (t, J=7 Hz, 2H), 3.60 (q, J=7 Hz, 2H), 7.20 (d, J=8 Hz, 1H), 7.50 (d, J=8 Hz, 1H), 7.74 (s, 1H), 8.04 (m, 5H), 8.20 (d, J=3 Hz, 1H), 8.54 (bs, 2H), 8.70 (bs, 2H), 8.77 (bt, J=7 Hz, 1H), 9.33 (d, J=5 Hz, 1H), 9.71 (s, 1H), 12.28 (bs, 1H). MS (ion spray) m/z 385 (M+H). Combustion Analysis $C_{22}H_{20}N_6O;(C_2HF_3O_2)_2$ requires C 51.0, H 3.6, N 13.7. Found C 50.7, H 4.1, N 13.7.

Example 1n

N-[2-(3-Carbamimidoyl-1H-indol-5-yl)-ethyl]-2-methyl-4-(6-oxo-1,6-dihydro-pyridin-3-yl)-benzamide. Using the product from reference example 36a. $^1$H NMR (CD$_3$OD) d 2.30 (s, 3H), 3.07 (t, J=7 Hz, 2H), 3.69 (t, J=7 Hz, 2H), 6.63 (d, J=9 Hz, 1H), 7.34–7.40 (m, 4H), 7.50 (d, J=8 Hz, 1H), 7.71 (d, J=2 Hz, 1H), 7.80 (s, 1H), 7.93 (dd, J=9, 2, 1H), 8.08 (s, 1H). MS (ion spray) m/z 414 (M+H).

Example 1o

3',4'-Dimethoxybiphenyl-4-carboxylic acid (2-[3-carbamimidoylindol-5-yl]ethyl)amide. Using the product from reference example 1o but without HPLC purification. Instead, the crude product is chromatographed on silica gel then washed with distilled water to remove inorganic salts and dried by lyophilization. m.p. >250° C. $^1$H NMR (DMSO): δ 2.99 (2H, m), 3.57 (2H, m), 3.80 (3H, s), 3.86 (3H, s), 7.06 (1H, d, J=9 Hz), 7.20 (1H, d, J=8 Hz), 7.27–7.29 (2H, m), 7.50 (1H, d, J=9 Hz), 7.71–7.76 (3H, m), 7.90 (2H, d, J=8 Hz), 8.23 (1H, d, J=3 Hz). MS (ion spray) m/z 443 (M+H)$^+$. Anal. calcd. for $C_{26}H_{26}N_4O_3 \cdot HCl(H_2O)_{1.25}$: C, 62.3; H, 5.9; N, 11.2. Found C, 62.2; H, 5.8; N, 10.9.

Example 1p

N-(2-[3-Carbamimidoylindol-5-yl]ethyl)-4-(6-methoxypyrid-3-yl)benzamide. Using the product from reference example 1p. m.p. 164–167° C. $^1$H NMR (3:1 D$_2$O:CD$_3$OD): δ 2.81 (2H, m), 3.43 (2H, m), 3.70 (3H, s), 6.76 (1H, d, J=8 Hz), 7.06 (1H, d, J=8 Hz), 7.38 (1H, d, J=8 Hz), 7.35–7.46 (5H, m), 7.78 (1H, m), 7.81 (1H, s), 8.09 (1H, s). MS (FAB) m/z 414 (M+H)$^+$. Anal. calcd. for $C_{24}H_{23}N_5O_2 \cdot C_2HO_2F_3 \cdot (H_2O)_2$: C, 55.4; H, 5.0; N, 12.4. Found C, 55.3; H, 4.5; N, 12.1.

Example 1q

N-(2-[3-Carbamimidoylindol-5-yl]ethyl)-4-(1-oxy-pyrid-4-yl)benzamide. Using the product from reference example 1q. m.p. 99–101° C. $^1$H NMR (3:1 D$_2$O:CD$_3$OD): δ 2.80 (21H, m), 3.44 (2H, m), 7.03 (1H, d, J=8 Hz), 7.28 (1H, d, J=8 Hz), 7.34–7.67 (7H, m), 7.82 (1H, s), 8.13 (2H, br, m). MS (ion spray) m/z 400 (M+H)$^+$.

Example 1r

N-[2-(3-carbamimidoyl-1H-indol-5-yl)-ethyl]-4-(7H-pyrrolo[2,3-d]pyrimidin-6-yl)-benzamide. Using the product from reference example 1r. $^1$H NMR (DMSO) δ 2.98 (m, 2H), 3.59 (m, 2H), 7.20 (d, J=9 Hz, 1H), 7.33 (s, 1H), 7.50 (d, J=8 Hz, 1H), 7.74 (s, 1H), 7.96 (d, J=8 Hz, 2H), 8.10 (d, J=8 Hz, 2H), 8.20 (d, J=3 Hz, 1H), 8.68 (m, 4H), 8.95 (s, 1H), 9.19 (bs, 1H), 12.30 (bs, 1H), 13.22 (bs, 1H). MS (ion spray) m/z 424 (M+H)$^+$. Combustion Analysis: $C_{24}H_{21}N_7O;(C_2HF_3O_2)_2;(H_2O)_{0.5}$ requires C 50.9, H 3.7, N 14.8. Found C 50.7, H 3.7, N 14.4

Example 1s

N-[2-(3-carbamimidoyl-1H-indol-5-yl)-ethyl]-4-(1H-pyrrolo[3,2-c]pyridin-2-yl)-benzamide. Using the product from reference example 1s. $^1$H NMR (DMSO) δ 3.02 (bt, 2H), 3.58 (m, 2H), 7.22 (s, 1H), 7.52 (d, J=8 Hz, 1H), 7.60 (s, 1H), 7.77 (s, 1H), 7.98 (d, J=6 Hz, 1H), 8.02 (d, J=8 Hz, 2H), 8.13 (d, J=8 Hz, 2H), 8.24 (d, J=4 Hz, 1H), 8.45 (d, J=7 Hz, 1H), 8.76 (m, 5H), 9.31 (s, 1H), 12.36 (s, 1H), 13.64 (s, 1H). MS (ion spray) m/z 423 (M+H)$^+$. Combustion Analysis: $C_{25}H_{22}N_6O;(C_2HF_3O_2)_2;(H_2O)_{3.5}$ requires C 48.8, H 4.4, N 11.8. Found C 48.5, H 4.0, N 11.8.

Example 1t

N-[2-(3-carbamimidoyl-1H-indol-5-yl)-ethyl]-4-furo[3,2-c]pyridin-2-yl-benzamide. Using the product from reference example 1t. $^1$H NMR (DMSO) δ 2.98 (bt, 2H), 3.59 (m, 2H), 7.20 (d, J=8 Hz, 1H), 7.50 (d, J=8 Hz, 1H), 7.74 (s, 1H), 7.85 (s, 1H), 8.00 (d, J=8 Hz, 2H), 8.05 (d, J=6 Hz, 1H), 8.10 (d, J=8 Hz, 2H), 8.20 (d, J=3 Hz, 1H), 8.59 (bs, 2H), 8.67 (m, 2H), 8.76 (bt, 1H), 9.24 (s, 1H), 12.29 (bs, 1H). MS (ion spray) m/z 424 (M+H)$^+$. Combustion analysis: $C_{25}H_{21}N_5O_2;(C_2HF_3O_2)_2;(H_2O)_{1.5}$ requires C 51.3, H 3.9, N 10.3. Found C 51.2, H 3.7, N 10.4.

Example 1u

N-[2-(3-carbamimidoyl-1H-indol-5-yl)-ethyl]-3-chloro-4-(6-oxo-1,6-dihydro-pyridin-3-yl)-benzamide. Using the product from reference example 36c. $^1$H NMR (DMSO) δ 2.98 (bt, 2H), 3.56 (m, 2H), 6.42 (d, J=9 Hz, 1H), 7.20 (d, J=8 Hz, 1H), 7.56 (m, 4H), 7.74 (s, 1H), 7.82 (d, J=8 Hz, 1H), 7.96 (s, 1H), 8.22 (d, J=3 Hz, 1H), 8.54 (bs, 2H), 8.70 (bs, 2H), 8.76 (bt, 1H), 12.28 (bs, 1H). MS (ion spray) m/z 434/436 (M+H)$^+$, Cl.

Example 1v

N-(2-[3-carbamimidoyl-1H-indol-5-yl]ethyl)-4-(6-oxo-1,6-dihydro-pyrid-3-yl)benzamide. Using the product from reference example 36b. m.p. 152–156° C. $^1$H NMR (CD$_3$OD): δ 3.08 (2H, m), 3.69 (2H, m), 6.66 (1H, d, J=9 Hz), 7.26 (1H, d, J=8 Hz), 7.48 (1H, d, J=8 Hz), 7.62 (2H, d, J=8 Hz), 7.78 (1H, s), 7.79 (1H, s), 7.84 (2H, d, J=8 Hz), 7.99 (1H, d, J=9 Hz), 8.08 (1H, s). MS (FAB) m/z calcd. for $C_{23}H_{22}N_5O_2$ (M+H)$^+$400.1773, found 400.1778.

Example 1w 4-(3-Amino-1,1-dimethyl-propyl)-N-[2-(3-carbamimidoyl-1H-indol-5-yl)-ethyl]-benzamide. Using the product from reference example 1w. $^1$H NMR (DMSO) δ 1.31 (s, 1H), 1.93 (m, 2H), 2.50 (m, 2H), 2.97 (m, 2H), 3.57 (m, 2H), 7.18 (d, J=8 Hz, 1H), 7.44 (d, J=8 Hz, 2H), 7.50 (d, J=9 Hz, 1H), 7.72 (m, 3H), 7.80 (d, J=8 Hz, 2H), 8.22 (d, J=3 Hz, 1H), 8.59 (bt, 1H), 8.72 (s, 1H), 8.77 (s, 2H), 12.35 (s, 1H). MS (ion spray) m/z 392 (M+H)$^+$. Combustion Analysis: $C_{23}H_{29}N_5O;(C_2HF_3O_2)_{2.5}$ requires C 49.7, H 4.7, N 10.4. Found C 50.0, H 4.8, N 10.7.

Example 1x

N-[2-(3-Carbamimidoyl-1H-indol-5-yl)-ethyl]-2-(4-chloro-phenyl)-acetamide. Using the product from reference example 1x. $^1$H NMR (CD$_3$OD) δ 2.94 (t, J=7 Hz, 2H), 3.39 (s, 2H), 3.55 (q, J=7 Hz, 2H), 7.04 (d, J=8 Hz, 2H), 7.14 (m, 3H), 7.44 (d, J=8 Hz, 1H), 7.67 (s, 1H), 8.09 (s, 1H). MS (ion spray) m/z 355/357 (M+H, Cl pattern). Combustion analysis: C$_{19}$H$_{19}$N$_4$OCl;(C$_2$HF$_3$O$_2$)$_{1.3}$ requires C 51.6, H 4.1, N 11.1. Found C 51.6, H 4.1, N 11.2.

Example 1y 5-chloro-thiophene-2-carboxylic acid [2-(3-carbamimidoyl-1H-indol-5-yl)-ethyl]-amide. Using the product from reference example 1y. $^1$H NMR (CD$_3$OD) δ 3.0 (t, J=7 Hz, 2H), 3.61 (q, J=7 Hz, 2H), 6.98 (d, J=4 Hz, 1H), 7.21 (d, J=8 Hz, 1H), 7.46 (m, 2H), 7.75 (s, 1H), 8.07 (s, 1H). MS (ion spray) m/z 347/349 (M+H, Cl pattern). Combustion analysis: C$_{16}$H$_{15}$N$_4$OSCl;(C$_2$HF$_3$O$_2$)$_{1.5}$ requires C 44.1, H 3.2, N 10.8. Found C 44.1, H 3.2, N 10.9.

Example 1z

N-(2-[3-Carbamimidoylindol-5-yl]ethyl)-6-(2-hydroxyethylamino)nicotinamide. Using the product from reference example 1z m.p. 102–105° C. $^1$H NMR (D$_2$O): δ 2.88 (2H, t, J=6.0 Hz), 3.39 (2H, t, J=4 Hz), 3.49 (2H, t, J=6.0 Hz), 3.64 (2H, t, J=4 Hz), 6.88 (1H, d, J=9 Hz), 7.09 (1H, d, J=8 Hz), 7.37 (1H, d, J=8 Hz), 7.54 (1H, s), 7.79 (1H, d, J=9 Hz), 7.91 (1H, s), 7.92 (1H, s). MS (ion spray) m/z 367 (M+H)$^+$.

Example 1aa

N-(2-[3-Carbamimidoylindol-5-yl]ethyl)-6-(1,2,4) triazol-1-ylnicotinamide. Using the product from reference example 1aa. m.p. 196–199° C. $^1$H NMR (DMSO-d$_6$): δ 2.99 (2H, m), 3.59 (2H, m), 7.21 (1H, d, J=8 Hz), 7.51 (1H, d, J=8 Hz), 7.74 (1H, s), 7.98 (1H, d, J=8 Hz), 8.21 (1H, d, J=3 Hz), 8.37 (1H, s), 8.45 (1H, dd, J=8, 2 Hz), 8.51 (1H, s, br), 8.71 (2H, s, br), 8.92 (2H, m, br), 9.47 (1H, s). MS (ion spray) m/z 375 (M+H)$^+$. Anal. calcd. for C$_{19}$H$_{18}$N$_8$O.(C$_2$HO$_2$F$_3$).(H$_2$O)$_{0.5}$: C, 45.2; H, 3.5; N, 18.3. Found: C, 45.0; H, 3.5; N, 18.7.

Example 1ab

N-(2-[3-Carbamimidoylindol-5-yl]ethyl)-6-pyrrol-1-ylnicotinamide. Using the product from reference example 1ab. m.p. 213–214° C. $^1$H NMR (CD$_3$OD): δ 3.08 (2H, d, J=7 Hz), 3.70 (2H, d, J=7 Hz), 6.33 (2H, s), 7.26 (1H, d, J=7 Hz), 7.49 (1H, d, J=7 Hz), 7.58–7.62 (3H, m), 7.77 (1H, s), 8.07 (1H, s), 8.19 (1H, d, J=8 Hz), 8.75 (1H, s). MS (ion spray) m/z 373 (M+H)$^+$. Anal. calcd. for C$_{21}$H$_{20}$N$_5$O.C$_2$HO$_2$F$_3$.(H$_2$O)$_{1.25}$: C, 54.3; H, 4.6; N, 16.5. Found: C, 54.1; H, 4.3; N, 16.3.

Example 1ac

N-(2-[3-Carbamimidoylindol-5-yl]ethyl)-6-pyrazol-1-ylnicotinamide. Using the product from reference example 1ac. m.p. 235–236° C. $^1$H NMR (CD$_3$OD): δ 3.08 (2H, m), 3.69 (2H, m), 6.56 (1H, s), 7.26 (1H, d, J=8 Hz), 7.49 (1H, d, J=8 Hz), 7.77 (1H, s), 7.80 (1H, s), 7.98 (1H, d, J=8 Hz), 8.07 (1H, s), 8.24 (1H, d, J=8 Hz), 8.64 (1H, s), 8.70–8.79 (2H, m). MS (ion spray) m/z 374 (M+H)$^+$. Anal. calcd. for C$_{20}$H$_{19}$N$_7$O.C$_2$HO$_2$F$_3$.(H$_2$O)$_2$: C, 50.5; H, 4.6; N, 18.7. Found: C, 50.5; H, 4.0; N, 18.5.

Example 1ad

N-(2-[3-Carbamimidoyl-1-methylindol-5-yl]ethyl)-4-(6-methoxypyrid-3-yl)benzamide. Using the product from reference example 55. m.p. 237–238° C. $^1$H NMR (CD$_3$OD): δ 3.09 (2H, m), 3.71 (2H, m), 3.92 (3H, s), 3.96 (3H, s), 6.90 (1H, d, J=9 Hz), 7.32 (1H, d, J=9 Hz), 7.52 (1H, d, J=9 Hz), 7.68 (2H, d, J=8 Hz), 7.79 (1H, s), 7.85 (2H, d, J=8 Hz), 8.00 (1H, d, J=9 Hz), 8.02 (1H, s), 8.43 (1H, s), 8.62 (1H, m, br). MS (ion spray) m/z 428 (M+H)$^+$. Anal. calcd. for C$_{25}$H$_{25}$N$_5$O$_2$.C$_2$HO$_2$F$_3$.(H$_2$O)$_{1.25}$: C, 57.5; H, 5.1%; N, 12.4. Found: C, 57.5; H, 4.8; N, 12.3.

Example 1ae

N-[2-(3-Carbamimidoyl-1H-indol-5-yl)-ethyl]-3-chloro-benzamide. Using the product from reference example 1ae. $^1$H NMR (DMSO) δ 2.96 (t, J=7 Hz, 2H), 3.59 (q, J=7 Hz, 2H), 7.14 (d, J=8 Hz, 1H), 7.3–7.45 (m, 3H), 7.59 (d, J=7 Hz, 1H), 7.65 (m, 2H), 7.98 (s, 1H), 8.57 (bt, 1H). MS (ion spray) m/z 341/343 (M+H Cl pattern). Combustion analysis: C$_{18}$H$_{17}$N$_4$OCl;(C$_2$HF$_3$O$_2$)$_{1.2}$ requires C 51.3, H 3.8, N 11.7. Found C 51.4, H 3.9, N 11.7.

Example 1af

N-[2-(3-Carbamimidoyl-1H-indol-5-yl)-ethyl]-2-(3-chloro-phenyl)-acetamide. Using the product from reference example 1af. $^1$H NMR (DMSO) δ 2.82 (t, J=7 Hz, 2H), 3.35 (q, J=7 Hz, 2H), 3.40 (s, 2H), 7.11 (m, 2H), 7.25 (m, 2H), 7.45 (d, J=8 Hz, 1H), 7.67 (s, 1H), 8.22 (m, 2H), 8.62 (bs, 2H), 8.69 (bs, 2H). MS (ion spray) m/z 355/357 (M+H, Cl pattern).

Example 1ag 4-(2-Aminomethyl-pyridin-4-yl)-N-[2-(3-carbamimidoyl-1H-indol-5-yl)-ethyl]-benzamide. Using the product from reference example 1ag. $^1$H NMR (DMSO) δ 3.0 (t, J=7.5 Hz, 2H), 3.61 (q, J=7 Hz, 2H), 4.29 (q, J=6 Hz, 2H), 7.20 (d, J=8 Hz, 1H), 7.50 (d, J=8 Hz, 1H), 7.82 (d, J=5 Hz, 1H), 7.93 (m, 3H), 8.0 (m, 2H), 8.22 (d, J=3 Hz, 1H), 8.40 (bs, 3H), 8.7 (m, 6H), 12.34 (bs, 1H). MS (ion spray) m/z 527 (M+H$^+$TFA), 413 (M+H). Combustion analysis: C$_{24}$H$_{24}$N$_6$O;(C$_2$HF$_2$)$_3$ (NH$_4$Cl)$_{0.3}$ requires C 46.8, H 3.7, N 11.4. Found C 46.6, H 3.9, N 11.5.

Example 1ah

4-{4-[2-(3-Carbamimidoy-1H-indol-5-yl)-ethylcarbamoyl]-phenyl-pyridine-2-carboxylic acid amide. Using the product from reference example 1ah. $^1$H NMR (DMSO) δ 3.0 (t, J =7 Hz, 2H), 3.61 (q, J=7 Hz, 2H), 7.21 (d, J=8 Hz, 1H), 7.50 (d, J=8 Hz, 1H), 7.75 (m, 2H), 8.0 (m, 4H), 8.23 (m, 2H), 8.35 (bs, 1H), 8.55 (bs, 2H), 8.75 (m, 5H). MS (ion spray) m/z 427 (M+H).

Example 1ai

N-[2-(3-Carbamimidoy-1H-indol-5-yl)-ethyl]-4-(2-(N,N-dimethylaminomethyl)-pyridin-4-yl)benzamide). Using the product from reference example 1ai. $^1$H NMR (CD$_3$OD) δ 3.00 (s, 6H), 3.10 (t, J=7 Hz, 2H), 3.70 (t, J=7 Hz, 2H), 4.56 (s, 2H), 7.25 (dd, J=8, 2 Hz, 1H), 7.49 (d, J=8 Hz, 1H), 7.80 (m, 2H), 7.83 (s, 1H), 7.88 (m, 2H), 7.93 (m, 2H), 8.09 (s, 1H), 8.75 (d, J=5 Hz, 1H). MS (ion spray) m/z 441 (M+H). Combustion analysis: C$_{26}$H$_{28}$N$_6$O;(C$_2$HF$_3$O$_2$)$_3$ requires C 49.1, H 4.0, N 10.7. Found C 49.4, H 4.3, N 10.9.

Example 1aj

N-[2-(3-carbamimidoyl-1H-indol-5-yl)-ethyl]-4-(6-oxo-1,6-dihydro-pyridazin-3-yl)-benzamide. Using the product from reference example 36d. $^1$H NMR (DMSO) δ 2.98 (bt, 2H), 3.58 (m, 2H), 7.02 (d, J=9 Hz, 1H), 7.20 (d, J. =9 Hz, 1H), 7.50 (d, J=8 Hz, 1H), 7.74 (s, 1H), 7.95 (m, 4H), 8.10 (d, J=10 Hz, 1H), 8.21 (s, 1H), 8.60 (bs, 1H), 8.71 (bs, 3H), 12.30 (s, 1H), 13.31 (s, 1H). MS (ion spray) m/z 401 (M+H)$^+$. Combustion Analysis: $C_{22}H_{20}N_6O_2$; $(C_2HF_3O_2)_2$; $(NH_4Cl)_{1.5}$ requires C 44.1, H 4.0, N 14.8. Found C 44.5, H 4.1, N 14.4.

Example 1ak

N-[2-(3-carbamimidoyl-1H-indol-5-yl)-ethyl]-4-(6-methoxy-pyridazin-3-yl)-benzamide. Using the product from reference example 1ak. $^1$H NMR (DMSO) δ 3.00 (bt, 2H), 3.58 (m, 2H), 4.10 (s, 3H), 7.20 (d, J=9 Hz, 1H), 7.36 (d, J=9 Hz, 1H), 7.50 (d, J=8 Hz, 1H), 7.76 (s, 1H), 7.98 (d, J=8 Hz, 2H), 8.17 (d, J=8 Hz, 2H), 8.23 (d, J=5 Hz, 1H), 8.63 (bs, 2H), 8.73 (bs, 3H), 12.32 (bs, 1H). MS (ion spray) m/z 415 (M+H)$^+$. Combustion Analysis: $C_{23}H_{22}N_6O_2$; $(C_2HF_3O_2)_{2.5}$;$(NH_4Cl)_{0.5}$ requires C 46.3, H 3.7, N 12.5. Found C 46.2, H 3.8, N 12.6.

Example 1al

N-[2-(3-carbamimidoyl-1H-indol-5-yl)-ethyl]-4-[1-(2-dimethylamino-ethyl)-6-oxo-1,6-dihydro-pyridazin-3-yl]-benzamide. Using the product from reference example 1al. $^1$H NMR (DMSO) δ 2.88 (bs, 6H), 2.98 (bt, 2H), 3.58 (m, 4H), 4.52 (bt, 2H), 7.14 (d, J=10 Hz, 1H), 7.18 (d, J=9 Hz, 1H), 7.49 (d, J=8 Hz, 1H), 7.74 (s, 1H), 7.94 (d, J=9 Hz, 2H), 8.02 (d, J=9 Hz, 2H), 8.16 (d, J=10 Hz, 1H), 8.22 (d, J=3 Hz, 1H), 8.74 (m, 3H), 9.74 (bs, 1H), 12.34 (d, J=3 Hz, 1H). MS (ion spray) m/z 472 (M+H)$^+$. Combustion Analysis: $C_{26}H_{29}N_7O_2$;$(C_2HF_3O_2)_3$;$(NH_4Cl)_{0.1}$;$(H_2O)_2$ requires C 45.0, H 4.0, N 11.6. Found C 45.1, H 3.8, N 11.3.

Example 1am

N-[2-(3-carbamimidoyl-1H-indol-5-yl)-ethyl]-4-[1-(3-dimethylamino-propyl)-6-oxo-1,6-dihydro-pyridazin-3-yl]-benzamide. Using the product from reference example 1am. $^1$H NMR (DMSO) δ 2.16 (m, 2H), 2.77 (s, 3H), 2.78 (s, 3H), 2.98 (bt, 2H), 3.15 (m, 2H), 3.56 (m, 2H), 4.22 (bt, 2H), 7.10 (d, J=10 Hz, 1H), 7.18 (d, J=8 Hz, 1H), 7.49 (d, J=9 Hz, 1H), 7.74 (s, 1H), 7.94 (d, J=8 Hz, 2H), 8.00 (d, J=8 Hz, 2H), 8.14 (d, J=10 Hz, 1H), 8.22 (d, J=3 Hz, 1H), 8.74 (m, 3H), 9.72 (bs, 1H), 12.34 (s, 1H). MS (ion spray) m/z 485 (M+H)$^+$. Combustion Analysis: $C_{27}H_{31}N_7O_2$;$(C_2HF_3O_2)_3$;$(NH_4Cl)_{0.1}$;$(H_2O)_{0.5}$ requires C 47.1, H 4.2, N 11.8. Found C 46.8, H 4.2, N 11.8.

Example 1an

N-[2-(3-Carbamimidoyl-1H-indol-5-yl)-ethyl]-4-[2-(2-dimethylamino-ethylamino)-pyrimidin-4-yl]-benzamide. Using the product from reference example 1an. $^1$H NMR (CD$_3$OD) δ 2.97 (s, 6H), 3.08 (t, J=7 Hz, 2H), 3.44 (t, J=6 Hz, 2H), 3.70 (t, J=7 Hz, 2H), 3.87 (bt, J=6 Hz, 2H), 7.28 (m, 2H), 7.49 (d, J=8 Hz, 1H), 7.80 (s, 1H), 7.90 (d, J=8 Hz, 2H), 8.09 (s, 1H), 8.18 (d, J=8 Hz, 2H), 8.44 (bm, 1H). MS (ion spray) m/z 471 (M+H)$^+$. Combustion Analysis: $C_{26}H_{30}N_8O$;$(C_2HF_3O_2)_{3.2}$ requires C 46.6, H 4.0, N 13.4. Found C 46.6, H 4.1, N 13.7.

Example 1ao

N-[2-(3-Carbamimidoyl-1H-indol-5-yl)-ethyl]-4-[2-methoxy-pyrimidin-4-yl]-benzamide. Using the product from reference example 1ao and purifying by flash chromatography (eluting with 10% MeOH in CH$_2$Cl$_2$ then 20% MeOH/10% 7N NH$_3$ in MeOH/70% CH$_2$Cl$_2$) isolated as the hydrochloride salt. $^1$H NMR (CD$_3$OD) δ 3.09 (t, J=7 Hz, 2H), 3.70 (t, J=7 Hz, 2H), 4.10 (s, 3H), 7.25 (d, J=8 Hz, 1H), 7.48 (d, J=8 Hz, 1H), 7.63 (d, J=5 Hz, 1H), 7.78 (s, 1H), 7.90 (d, J=8 Hz, 2H), 8.09 (s, 1H), 8.23 (d, J=8 Hz, 2H), 8.61 (d, J=5 Hz, 1H). MS (ion spray) m/z (ion spray) m/z 415 (M+H). Combustion Analysis: $C_{23}H_{22}N_6O_2$;$(HCl)_2$ requires C 56.7, H 5.0, N 17.2. Found C 57.1, H 4.9, N 17.0.

Example 1ap

N-(2-[3-Carbamimidoylindol-5-yl]ethyl)-4-(1-[2-dimethylaminoethyl]-6-oxo-1,6-dihydropyridin-3-yl) benzamide. Using the product from reference example 1ap. m.p. 94–97° C. $^1$H NMR (D$_2$O): δ 2.61 (2H, m), 2.80 (6H, s), 3.25 (2H, m), 3.32 (2H, m), 4.14 (2H, m), 6.45 (1H, d, J=9.0 Hz), 6.96 (1H, d, J=8.2 Hz), 7.22–7.31 (4H, m), 7.40 (2H, d, J=8.0 Hz), 7.55–7.69 (3H, m), 7.78 (1H, s). MS (ion spray) m/z 471 (M+H)$^+$. Anal. calcd. for $C_{27}H_{30}N_6O_2 \cdot 3C_2HO_2F_3$: C, 48.8; H, 4.1; N, 10.3. Found: C, 48.8; H, 4.1; N, 10.6.

Example 1aq

N-(2-[3-Carbamimidoylindol-5-yl]ethyl)-4-(1-carbamoylmethyl-6-oxo-1,6-dihydropyridin-3-yl) benzamide. Using the product from reference example 1aq. m.p. 244–245° C. $^1$H NMR (CD$_3$OD): δ 2.97 (2H, t, J=7 Hz), 3.59 (2H, m), 4.67 (2H, s), 6.56 (1H, d, J=9 Hz), 7.16 (1H, d, J=8 Hz), 7.38 (1H, d, J=8 Hz), 7.54 (2H, d, J=8 Hz), 7.67 (1H, s), 7.73 (2H, d, J=8 Hz), 7.85 (1H, d, J=9 Hz), 7.91 (1H, s), 7.98 (1H, s). MS (ion spray) m/z 457 (M+H)$^+$.

Example 1ar 4-(3-Amino-[1,2,4]triazin-6-yl)-N-[2-(3-carbamimidoyl-1H-indol-5-yl)-ethyl]-benzamide. Using the product from reference example 1ar $^1$H NMR (CD$_3$OD) d 3.09 (2H, t, J=7 Hz), 3.72 (2H, t, J=7 Hz), 7.23 (1H, d, J=8 Hz), 7.49 (1H, d, J=8 Hz), 7.79 (1H, s), 7.93 (2H, d, J=7 Hz), 8.13 (1H, s), 8.28 (2H, d, J=7 Hz), 9.15 (1H, s); MS, m/z (ion spray) 401 (M +H)$^+$.

Example 1as 4-(3-Amino-[1,2,4]triazin-5-yl)-N-[2-(3-carbamimidoyl-1H-indol-5-yl)-ethyl]-benzamide. Using the product from reference example 1as. $^1$H NMR (CD$_3$OD) d 3.08 (2H, t, J=7 Hz), 3.68 (2H, m), 7.25 (1H, d, J=9 Hz), 7.49 (1H, d, J=9 Hz), 7.7–8.3 (7H, m); MS, m/z (ion spray) 401 (M+H)$^+$.

Example 1at

N-[2-(3-Carbamimidoyl-1H-indol-5-yl)-ethyl]-4-(3-oxo-2,3-dihydro-[1,2,4]triazin-6-yl)-benzamide. Using the product from reference example 1at. $^1$H NMR (DMSO-d$_6$) d 2.99 (2H, t, J=5 Hz), 3.05 (2H, m), 6.58 (1H, m), 7.22 (1H, d, J=8 Hz), 7.52 (1H, d, J=8 Hz), 7.75 (1H, d, J=3 Hz), 7.94 (2H, d, J=8 Hz), 8.02 (1H, d, J=3 Hz), 8.04 (2H, d, J=7 Hz), 8.22 (1H, d, J=3 Hz), 8.49 (1H, s), 8.70 (1H, s), 8.81 (1H, t, J=5 Hz), 11.12 (1H, s), 12.28 (1H, s); MS, m/z (ion spray) 420 [(M+18)+H]$^+$.

Example 1au

N-[2-(3-Carbamimidoyl-1H-indol-5yl)ethyl]-4-(5-oxo-4,5-dihydro-[1,2,4]oxadiazol-3-yl)-benzamide. Using the product from reference example 1au. $^1$H NMR (CD$_3$OD) d 3.11 (2H, t, J=8 Hz), 3.72 (2H, m), 7.27 (1H, d, J=9 Hz), 7.49 (1H, d, J=9 Hz), 7.78 (1H, s), 7.90 (4H, q, J=8 Hz, J=16 Hz), 8.08 (1H, s), 8.76 (1H, m); MS, m/z (ion spray) 391 [(M+H]$^+$.

Example 1av

N-[2-(3-Carbamimidoyl-1H-indol-5-yl)ethyl-4-(6-oxo-piperidin-3-yl)-benzamide. Using the product from reference example 64a. $^1$H NMR (CD$_3$OD) δ 2.08 (m, 2H), 2.43 (m, 2H), 3.10 (m, 3H), 3.42 (m, 2H), 3.65 (m, 2H), 7.13 (m, 1H), 7.20 (m, 1H), 7.38 (m, 2H), 7.45 (m, 1H), 7.72 (m, 3H), 8.07 (m, 1H). MS (Ion spray) m/z 387 (M+H)$^+$.

Example 1aw

N-[2-(3-Carbamimidoyl-1H-indol-5-yl)-ethyl]-4-[2-(morpholin-4yl-ethylamino)-pyrimidin-4-yl]-benzamide. Using the product from reference example 1aw. $^1$H NMR (DMSO) δ 2.99 (t, J=7 Hz, 2H), 3.40 (m, 2H), 3.53–4.1 (m, 12H), 7.20 (d, J=8 Hz, 1H), 7.34 (d, J=5 Hz, 1H), 7.50 (m, 2H), 7.73 (s, 1H), 7.95 (d, J=8 Hz, 2H), 8.21 (m, 3H), 8.45 (d, J=5 Hz, 1H), 8.52 (bs, 2H), 8.72 (bs, 2H), 8.77 (bt, 1H). MS (ion spray) m/z=513 (M+H)$^+$.

Example 1ax

N-[2-(3-Carbamimidoyl-1H-indol-5-yl)-ethyl]-4-[2-(3-dimethylamino-propylamino)-pyrimidin-4-yl]-benzamide. Using the product from reference example 1ax. $^1$H NMR (DMSO) δ 1.95 (m, 2H), 2.77 (s, 3H), 2.79 (s, 3H), 3.0 (t, J=7 Hz, 2H), 3.15 (m, 2H), 3.43 (m, 2H), 3.60 (q, J=7 Hz, 2H), 7.21 (d, J=8 Hz, 1H), 7.25 (d, J=5 Hz, 1H), 7.45 (bm, 1H), 7.50 (d, J=8 Hz, 1H), 7.74 (s, 1H), 7.95 (d, J=8 Hz, 2H), 8.20 (d, J=1 5 8 Hz, 2H), 8.21 (d, J=5 Hz, 1H), 8.41 (d, J=5 Hz, 1H), 8.70 (bm, 5H). MS (ion spray) m/z 485 (M+H)$^+$.

Example 1ay

N-[2-(3-Carbamimidoyl-1H-indol-5-yl)-ethyl]-4-[2-([2-dimethylamino-ethyl]-methyl-amino)-pyrimidin-4-yl]-benzamide. Using the product from reference example 1ay $^1$H NMR (DMSO) δ 2.9 (bs, 6H), 3.0 (bt, J=7 Hz, 2H), 3.24 (s, 3H), 3.40 (bm, 2H), 3.59 (bq, J=7 Hz, 2H), 4.05 (bm, 2H), 7.20 (d, J=8 Hz, 1H), 7.35 (d, J=5 Hz, 1H), 7.51 (d, J=8 Hz, 1H), 7.77 (s, 1H), 7.98 (d, J=8 Hz, 2H), 8.24 (m, 3H), 8.52 (d, J=5 Hz, 1H), 8.7 (bm, 5H). MS (ion spray) m/z 485 (M+H)$^+$.

Example 1az

2-[(4-{4-[2-(3-Carbamimidoyl-1H-indol-5-yl)-ethylcarbamoyl]-phenyl}-pyrimidin-2-yl)-methyl-amino]-ethanesulfonic acid. Using the product from reference example 92d. $^1$H NMR (DMSO) δ 2.95 (bm, 4H), 3.17 (s, 3H), 3.48 (m, 2H), 3.96 (bm, 2H), 7.18 (d, J=8 Hz, 1H), 7.24 (dd, J=5, 1 Hz, 1H), 7.47 (dd, J=8, 1 Hz, 1H), 7.81 (bd, 2H), 7.92 (bs, 1H), 8.17 (bt, J=1 Hz, 1H), 8.31 (bd, J=8 Hz, 2H), 8.51 (bs, 1H), 8.61 (bs, 2H), 9.11 (bs, 1H). MS (ion spray) m/z 522 (M+H)$^+$.

Example 1aaa

N-[2-(3-Carbamimidoyl-1H-indol-5-yl)-ethyl]-4-{2-[methyl-(2(S),3(R),4(R),5(R),6-pentahydroxy-hexyl)-amino]-pyrimidin-4-yl}-benzamide. Using the product from reference example 92e. $^1$H NMR (DMSO) δ 2.99 (t, J=7 Hz, 2H), 3.24 (bs, 3H), 3.38 (m, 1H), 3.42–3.67 (m, 9H), 4.05 (bm), 7.19 (d, J=8 Hz, 1H), 7.22 (d, J=5 Hz, 1H), 7.49 (d, J=8 Hz, 1H), 7.71 (s, 1H), 7.91 (d, J=8 Hz, 2H), 8.20 (m, 3H), 8.45 (m, 3H), 8.70 (m, 3H). MS (ion spray) m/z 578 (M+H)$^+$.

Example 1aab

N-[2-(3-Carbamimidoyl-1H-indol-5-yl)-ethyl]-4-{2-[methyl-(2 (S),3 (R),4 (S),5 (R),6-pentahydroxy-hexyl)-amino]-pyrimidin-4-yl}-benzamide. Using the product from reference example 92f. $^1$H NMR (DMSO) δ 2.99 (t, J=7 Hz, 2H), 3.26 (bs, 3H), 3.39 (m, 3H), 3.55 (m, 3H), 3.63–4.2 (bm, 8H), 7.20 (m, 2H), 7.50 (d, J=8 Hz, 1H), 7.72 (s, 1H), 7.93 (d, J=8 Hz, 2H), 8.20 (m, 3H), 8.42 (m, 3H), 8.70 (m, 3H). MS (ion spray) m/z 578 (M+H)$^+$.

Example 1aac

N-[2-(3-Carbamimidoyl-1H-indol-5-yl)-ethyl]-4-[2-(2-hydroxy-1-hydroxymethyl-ethylamino)-pyrimidin-4-yl]-benzamide. Using the product from reference example 92g. $^1$H NMR (DMSO) δ 2.95 (t, J=7 Hz, 2H), 3.55 (m, 4H), 3.6–4.1 (bm, 5H), 6.75 (bs, 1H), 7.20 (m, 2H), 7.48 (d, J=8 Hz, 1H), 7.70 (s, 1H), 7.90 (d, J=8 Hz, 2H), 8.18 (m, 3H), 8.40 (d, J=5 Hz, 1H), (m, 2H), 8.70 (m, 3H). MS (ion spray) m/z 474 (M+H)$^+$.

Example 1aad

2-[(4-{4-[2-(3-Carbamimidoyl-1H-indol-5-yl)-ethylcarbamoyl]-phenyl}-pyrimidin-2-yl)-methyl-amino]-ethanesulfonic acid. Using the product from reference example 92h. The title compound was purified by precipitation from the reaction medium. $^1$H NMR (DMSO) δ 2.95 (m, 4H), 3.18 (s, 3H), 3.50 (bm, 2H), 4.00 (bm, 2H), 7.18 (d, J=8 Hz, 1H), 7.24 (dd, J=5, 1 Hz, 1H), 7.47 (dd, J=8, 2 Hz, 1H), 7.81 (d, J=8 Hz, 1H), 7.92 (bs, 1H), 8.15 (t, J=1 Hz, 1H), 8.30 (d, J=8 Hz, 2H), 8.40 (dd, J=8, 2 Hz, 1H), 8.52 (m, 1H), 8.64 (bs, 2H). 9.11 (bs, 2H). MS (ion spray) m/z 522 (M+H)$^+$.

Example 1aae

N-[2-(3-Carbamimidoyl-1H-indol-5-yl)-ethyl]-4-[2-(3-imidazol-1-yl-propylamino)-pyrimidin-4-yl]-benzamide. Using the product from reference example 92i. $^1$H NMR (DMSO) δ 2.10 (m, 2H), 2.95 (t, J=7 Hz, 2H), 3.36 (bm, 2H), 3.56 (q, J=7 Hz, 2H), 4.30 (t, J=7 Hz, 2H), 7.18 (d, J=8 Hz, 1H), 7.24 (d, J=5 Hz, 1H), 7.48 (d, J=8 Hz, 1H), 7.50 (bs, 1H), 7.70 (s, 1H), 7.75 (s, 1H), 7.82 (s, 1H), 7.94 (d, J=8 Hz, 2H), 8.14 (d, J=8 Hz, 2H), 8.21 (d, J=1 Hz, 1H), 8.39 (d, J=5 Hz, 1H), 8.75 (m, 5H) 9.15 (s, 1H). MS (ion spray) m/z 508 (M+H)$^+$.

Example 1aaf

N-[2-(3-Carbamimidoyl-1H-indol-5-yl)-ethyl]-4-{2-[(2-diethylamino-ethyl)-methyl-amino]-pyrimidin-4-yl}-benzamide. Using the product from reference example 92j. $^1$H NMR (DMSO) δ 1.60 (t, J=7 Hz, 6H), 2.95 (t, J=7 Hz, 2H), 3.12–3.4 (m, 9H), 3.59 (q, J=7 Hz, 2H), 4.0 (bt, 2H), 7.18 (d, J=8 Hz, 1H), 7.32 (d, J=5 Hz, 1H), 7.49 (d, J=8 Hz, 1H), 7.75 (s, 1H), 7.94 (d, J=8 Hz, 2H), 8.20 (m, 3H), 8.50 (d, J=5 Hz, 1H), 8.70 (bs, 4H), 8.74 (bt, 1H), 9.40 (bs, 1H). MS (ion spray) m/z 513 (M+H)$^+$.

Example 1aag

N-[2-(3-Carbamimidoyl-1H-indol-5-yl)-ethyl]-4-[2-(2-diisopropylamino-ethylamino)-pyrimidin-4-yl]-benzamide. Using the product from reference example 92k. $^1$H NMR (DMSO) δ 1.29 (d, J=7 Hz, 12H), 2.97 (t, J=7 Hz, 2H), 3.22 (bt, 2H), 3.57 (q, J=7 Hz, 2H), 3.68 (m, 4H), 7.18 (d, J=8 Hz, 1H), 7.39 (d, J=5 Hz, 1H), 7.42 (bm, 1H), 7.48 (d, J=8 Hz, 1H), 7.73 (s, 1H), 7.95 (d, J=8 Hz, 2H), 8.15 (d, J=8 Hz, 2H), 8.20 (d, J=3 Hz, 1H), 8.44 (d, J=5 Hz, 1H), 8.71 (bs, 4H), 8.74 (bt, 1H). MS (ion spray) m/z 527 (M+H)$^+$.

Example 1aah

N-[2-(3-Carbamimidoyl-1H-indol-5-yl)-ethyl]-4-[2-(2-dibutylamino-ethylamino)-pyrimidin-4-yl]-benzamide.

Using the product from reference example 92l. ¹H NMR (DMSO) δ 0.85 (t, J=7 Hz, 6H), 1.29 (m, 4H), 1.60 (m, 4H), 2.97 (t, J=7 Hz, 2H), 3.12 (m, 4H), 3.30 (m, 2H), 3.58 (q, J=7 Hz, 2H), 3.73 (m, 2H), 7.17 (d, J=8 Hz, 1H), 7.30 (d, J=5 Hz, 1H), 7.45 (d, J=8 Hz, 2H), 7.48 (d, J=8 Hz, 1H), 7.72 (s, 1H), 7.95 (d, J=8 Hz, 2H), 8.15 (d, J=8 Hz, 2H), 8.20 (d, J=3 Hz, 1H), 8.44 (d, J=5 Hz, 1H), 8.65–8.8 (bm, 5H), 8.74 (bs, 1H). MS (ion spray) m/z 555 (M+H)⁺.

Example 1aai

N-[2-(3-Carbamimidoyl-1H-indol-5-yl)-ethyl]-4-[2-(3-morpholin-4-yl-propylamino)-pyrimidin-4-yl]-benzamide. Using the product from reference example 92m. ¹H NMR (DMSO) δ 1.95 (m, 2H), 2.9–3.14 (m, 4H), 3.19 (m, 2H), 3.40 (m, 4H), 3.59 (m, 4H), 7.17 (d, J=8 Hz, 1H), 7.21 (d, J=5 Hz, 1H), 7.40 (bt, J=7 Hz, 1H), 7.48 (d, J=8 Hz, 1H), 7.72 (s, 1H), 7.93 (d, J=8 Hz, 2H), 8.14 (m, 3H), 8.44 (d, J=5 Hz, 1H), 8.55 (bs, 2H), 8.71 (bm, 3H).

Example 1aaj

N-[2-(3-Carbamimidoyl-1H-indol-5-yl)-ethyl]-4-[2-(3-diethylamino-propylamino)-pyrimidin-4-yl]-benzamide. Using the product from reference example 92n. ¹H NMR (DMSO) δ 1.15 (t, J=7 Hz, 6H), 2.99 (t, J=7 Hz, 2H), 3.13 (m, 6H), 3.43 (m, 2H), 3.58 (m, 2H), 7.18 (d, J=8 Hz, 1H), 7.21 (d, J=5 Hz, 1H), 7.40 (bt, J=7 Hz, 1H), 7.48 (d, J=8 Hz, 1H), 7.73 (s, 1H), 7.94 (d, J=8 Hz, 2H), 8.16 (m, 3H), 8.40 (d, J=5 Hz, 1H), 8.60 (bs, 2H), 8.71 (bm, 3H). MS (ion spray) m/z 513 (M+H)⁺.

Example 1aak

N-[2-(3-Carbamimidoyl-1H-indol-5-yl)-ethyl]-4-[2-(3-piperidin-1-yl-propylamino)-pyrimidin-4-yl]-benzamide. Using the product from reference example 92p. ¹H NMR (DMSO) δ 1.50–1.73 (m, 4H), 1.80 (m, 2H), 1.96 (m, 2H), 2.85 (m, 2H), 2.96 (m, 2H), 3.13 (m, 2H), 3.42 (m, 4H), 3.56 (m, 2H), 7.18 (d, J=8 Hz, 1H), 7.22 (d, J=5 Hz, 1H), 7.40 (bt, J=7 Hz, 1H), 7.48 (d, J=8 Hz, 1H), 7.73 (s, 1H), 7.95 (d, J=8 Hz, 2H), 8.16 (m, 3H), 8.38 (d, J=5 Hz, 1H), 8.6–8.78 (bm, 5H). MS (ion spray) m/z 525 (M+H)⁺.

Example 1aal

N-[2-(3-Carbamimidoyl-1H-indol-5-yl)-ethyl]-4-(2-{[2-(ethyl-methyl-amino)-ethyl]-methyl-amino}-pyrimidin-4-yl)-benzamide. Using the product from reference example 92q. ¹H NMR (DMSO) δ 1.15 (t, J=7 Hz, 3H), 2.77 (s, 3H), 2.78 (s, 3H), 2.96 (t, J=7 Hz, 2H), 3.10 (m, 2H), 3.57 (q, J=7 Hz, 2H), 3.69 (m, 4H), 7.18 (d, J=8 Hz, 1H), 7.24 (d, J=5 Hz, 1H), 7.49 (d, J=8 Hz, 1H), 7.72 (s, 1H), 7.94 (d, J=8 Hz, 2H), 8.18 (m, 3H), 8.38 (d, J=5 Hz, 1H), 8.6–8.75 (bm, 5H), 9.6 (bs, 1H).

Example 1aam

N-[2-(3-Carbamimidoyl-1H-indol-5-yl)-ethyl]-4-[2-(5-dimethylamino-pentylamino)-pyrimidin-4-yl]-benzamide. Using the product from reference example 92r. ¹H NMR (DMSO) δ 1.35 (m, 2H), 1.58 (m, 4H), 2.71 (s, 3H), 2.72 (s, 3H), 3.0 (m, 4H), 3.37 (m, 2H), 3.45–3.8 (bs, solvent), 7.18 (m, 2H), 7.32 (bm, 1H), 7.48 (d, J=8 Hz, 1H), 7.72 (s, 1H), 7.94 (d, J=8 Hz, 2H), 8.15 (m, 3H), 8.37 (d, J=5 Hz, 1H), 8.57 (bs, 2H), 8.70 (bm, 3H), 9.35 (bs, 1H). MS (ion spray) m/z 513 (M+H)⁺.

Example 1aan

N-[2-(3-Carbamimidoyl-1H-indol-5-yl)-ethyl]-4-[2-(5-morpholin-4-yl-pentylamino)-pyrimidin-4-yl]-benzamide. Using the product from reference example 92s. ¹H NMR (DMSO) δ 1.36 (m, 2H), 1.61 (m, 4H), 2.9–3.1 (m, 8H), 3.35 (m, 4H), 3.5–3.7 (m, 4H), 7.18 (m, 2H), 7.40 (bm, 1H), 7.48 (d, J=8 Hz, 1H), 7.71 (s, 1H), 7.92 (d, J=8 Hz, 2H), 8.15 (m, 3H), 8.38 (d, J=5 Hz, 1H), 8.62 (bs, 2H), 8.70 (bm, 3H), 9.85 (bs, 1H). MS (ion spray) m/z 555 (M+H)⁺.

Example 1aap

N-[2-(3-Carbamimidoyl-1H-indol-5-yl)-ethyl]-4-[2-(5-piperidin-1-yl-pentylamino)-pyrimidin-4-yl]-benzamide. Using the product from reference example 92t. ¹H NMR (DMSO) δ 1.35 (m, 4H), 1.5–1.95 (m, 8H), 2.80 (m, 2H), 2.95 (m, 4H), 3.38 (m, 4H), 3.55 (q, J=7 Hz, 2H), 7.19 (m, 2H), 7.40 (bm, 1H), 7.46 (d, J=8 Hz, 1H), 7.71 (s, 1H), 7.92 (d, J=8 Hz, 2H), 8.19 (m, 3H), 8.39 (d, J=5 Hz, 1H), 8.62–8.80 (bm, 5H), 9.20 (bs, 1H). MS (ion spray) m/z 553 (M+H)⁺.

Example 1aaq

N-[2-(3-Carbamimidoyl-1H-indol-5-yl)-ethyl]-4-[2-(5-pyrrolidin-1-yl-pentylamino)-pyrimidin-4-yl]-benzamide. Using the product from reference example 92u. ¹H NMR (DMSO) δ 1.37 (m, 4H), 1.60 (m, 4H), 1.80 (m, 2H), 1.94 (m, 2H), 2.94 (m, 4H), 3.08 (m, 2H), 3.33 (m, 2H), 3.50 (m, 4H), 7.19 (m, 2H), 7.40 (bm, 1H), 7.48 (d, J=8 Hz, 1H), 7.70 (s, 1H), 7.91 (d, J=8 Hz, 2H), 8.15 (m, 3H), 8.36 (d, J=5 Hz, 1H), 8.62 (bs, 2H), 8.7 (bm, 3H), 9.60 (bs, 1H). MS (ion spray) m/z 539 (M+H)⁺.

Example 1aar

N-[2-(3-Carbamimidoyl-1H-indol-5-yl)-ethyl]-4-(2-oxo-hexahydro-pyrimidin-5-yl)-benzamide. Using the product from reference example 1aaa. ¹H NMR (DMSO) δ 2.91 (t, J=7 Hz, 2H), 3.08 (m, 1H), 3.25 (m, 4H), 3.53 (q, J=7 Hz, 2H), 6.33 (bs, 2H), 7.17 (d, J=8 Hz, 1H), 7.38 (d, J=8 Hz, 2H), 7.46 (d, J=8 Hz, 1H), 7.69 (s, 1H), 7.75 (d, J=8 Hz, 2H), 8.17 (d, J=3 Hz, 1H), 8.42 (bm, 2H), 8.52 (bt, J=7 Hz, 1H), 8.67 (bs, 2H). MS (ion spray) m/z 407 (M+H)⁺.

Example 1aas

N-[2-(3-Carbamimidoyl-1H-indol-5-yl)-ethyl]-4-(1,3-dimethyl-2-oxo-hexahydro-pyrimidin-5-yl)-benzamide. Using the product from reference example 1aab. ¹H NMR (CD₃OD) 2.95 (s, 6H), 3.06 (t, J=7 Hz, 2H), 3.36–3.55 (m, 5H), 3.66 (m, 2H), 7.23 (d, J=8 Hz, 1H), 7.39 (d, J=8 Hz, 2H), 7.47 (d, J=8 Hz, 1H), 7.77 (m, 3H), 8.07 (d, J=3 Hz, 1H), 8.30 (bm, 2H), 8.52 (bt, J=7 Hz, 1H), 8.68 (bs, 2H). MS (ion spray) m/z 433 (M+H)⁺.

Example 1aat

Biphenyl-3,4'-dicarboxylic acid 4'-{[2-(3-carbamimidoyl-1H-indol-5-yl)-ethyl]-amide} 3-[(2-methoxy-ethyl)-amide]. Using the product from reference example 99a. ¹H NMR (CD₃OD) δ 3.09 (t, J=7 Hz, 2H), 3.40 (s, 3H), 3.60 (bs, 4H), 3.71 (q, J=7 Hz, 2H), 7.28 (d, J=8 Hz, 1H), 7.48 (d, J=8 Hz, 1H), 7.56 (t, J=8 Hz, 1H), 7.77 (m, 3H), 7.87 (m, 4H), 8.07 (s, 1H), 8.13 (s, 1H), 8.65 (bt, 1H). MS (ion spray) m/z 484 (M+H)⁺.

Example 1aau

3'-(Morpholine-4-carbonyl)-biphenyl-4-carboxylic acid [2-(3-carbamimidoyl-1H-indol-5-yl)-ethyl]-amide. Using the product from reference example 99b. ¹H NMR (DMSO) δ 2.98 (t, J=7 Hz, 2H), 3.3–3.8 (bs, solvent), 7.20 (d, J=814z, 114), 7.43 (d, J=8 Hz, 1H), 7.50 (d, J=8 Hz, 114), 7.56 (t, J=8 Hz, 1H), 7.73 (bs, 2H), 7.80:(m, 3H), 7.91 (d, J=8 Hz, 2H), 8.20 (d, J=1 Hz, 1H), 8.50 (bs, 2H), 8.70 (m, 3H). MS (ion spray) m/z 496 (M+H)$^+$.

Example 1aav

Biphenyl-3,4'-dicarboxylic acid 4'-{[2-(3-carbamimidoyl-1H-indol-5-yl)-ethyl]-amide} 3-[(2-morpholin-4-yl-ethyl)amide]. Using the product from reference example 99c. $^1$H NMR (CD$_3$OD) δ 3.08 (t, J=7 Hz, 2H), 3.15–3.3 (bm, 2H), 3.45 (t, J=7 Hz, 2H), 3.70 (m, 2H), 3.6–3.95 (bm, 4H), 3.81 (t, J=7 Hz, 2H), 4.06 (bm, 2H), 7.27 (d, J=8 Hz, 1H), 7.50 (d, J=8 Hz, 1H), 7.61 (t, J=8 Hz, 1H), 7.77 (m, 3H), 7.90 (m, 4H), 8.1 (s, 1H), 8.20 (bs, 1H), 8.7 (bt, 1H). MS (ion spray) m/z 539 (M+H)$^+$.

Example 1aaw

Biphenyl-2,4'-dicarboxylic acid 4'-{[2-(3-carbamimidoyl-1H-indol-5-yl)-ethyl]-amide} 2-[(3-diethylamino-propyl)-amide]. Using the product from reference example 99d. MS (ion spray) m/z 539 (M+H)$^+$.

Example 1aax

Biphenyl-2,4'-dicarboxylic acid 4'-{[2-(3-carbamimidoyl-1H-indol-5-yl)-ethyl]-amide} 2-[(3-morpholin-4-yl-propyl)-amide]. Using the product from reference example 99e. MS (ion spray) m/z 553 (M+H)$^+$.

Example 1aaaa

Biphenyl-2,4'-dicarboxylic acid 4'-{[2-(3-carbamimidoyl-1H-indol-5-yl)-ethyl]-amide} 2-[(3-piperidin-1-yl-propyl)-amide]. Using the product from reference example 99f. MS (ion spray) mlz 551 (M+H)$^+$.

Example 1aab

Biphenyl-2,4'-dicarboxylic acid 4'-{[2-(3-carbamimidoyl-1H-indol-5-yl)-ethyl]-amide} 2-[(4-dimethylamino-butyl)-amide]. Using the product from reference example 99g. MS (ion spray) m/z 525 (M+H)$^+$.

Example 1aaac

Biphenyl-2,4'-dicarboxylic acid 4'-{[2-(3-carbamimidoyl-1H-indol-5-yl)-ethyl]-amide} 2-[(2,3-dihydroxy-propyl)-methyl-amide]. Using the product from reference example 99h. MS (ion spray) m/z 514 (M+H)$^+$.

Example 1aaad

Biphenyl-2,4'-dicarboxylic acid 4'-{[2-(3-carbamimidoyl-1H-indol-5-yl)-ethyl]-amide} 2-[(2,3-dihydroxy-propyl)-amide]. Using the product from reference example 99i. MS (ion spray) m/z 500 (M+H)$^+$.

Example 1aae

N-[2-(3-Carbamimidoyl-1H-indol-5-yl)ethyl]-4-[2-(4-methylpiperazin-1-yl)pyrimidin-4-yl]benzamide. Using the product from reference example 92v. m.p. 111–113° C. $^1$H NMR (DMSO-d$_6$): δ 2.50 (s, 3H), 2.86 (s, 4H), 2.98 (t, 2H, J=9 Hz), 3.30 (t, 2H, J=12 Hz), 3.57 (m, 4H), 7.20 (d, 1H, J=9 Hz), 7.43 (d, 1H, J=6 Hz), 7.50 (d, 1H, J=9 Hz), 7.74 (s, 1H), 7.97 (d, 2H, J=9 Hz), 8.22 (d, 1H, J=3 Hz), 8.26 (d, 2H, J=91 Hz), 8.55 (s, 1H), 8.57 (d, 1H, J=6 Hz), 8.72 (s, 2H), 8.77 (t, 1H, J=6 Hz). MS (ion spray) m/z 483 (M+H)$^+$. Anal. calcd for C$_{27}$H$_{30}$N$_8$O.3C$_2$HF$_3$O$_2$.1.5H$_2$O: C, 46.5%; H, 4.3%; N, 13.2%. Found: C, 46.3%; H, 4.1%; N, 13.4%.

Example 1aaaf

4-[(4-{4-[2-(3-Carbamimidoyl-1H-indol-5-yl)ethylcarbamoyl]phenyl}pyrimidin-2-yl)methylamino]butyric acid. Using the product from reference example 92w. m.p. 100–104° C. $^1$H NMR (DMSO-d$_6$): δ 1.85 (t, 2H, J=6 Hz), 2.26 (t, 2H, J=6 Hz), 3.00 (t, 2H, J=6 Hz), 3.18 (s, 3H), 3.56 (m, 2H), 3.71 (m, 2H), 7.22 (t, 1H, J=6 Hz), 7.50 (d, 1 1, J=6 Hz), 7.74 (s, 1H), 8.00 (d, 2H, J=8 Hz), 8.24 (s, 1H), 8.25 (d, 214, J=8 Hz), 8.45 (d, 2H, J=6 Hz), 8.71 (s, 21H). MS (ion spray) m/z 500 (M+H)$^+$. Anal. calcd for C$_{27}$H$_{29}$N$_7$O$_3$. 2.5C$_2$HF$_3$O$_2$.0.5H$_2$O: C, 48.4%; H, 4.1%; N, 12.4%. Found: C, 48.7%; H, 4.1%; N, 12.1%.

Example 1aaag

N-[2-(3-Carbamimidoyl-1H-indol-5-yl)ethyl]-4-[2-(2,2,2-trifluoroethoxy)pyrimidin-4-yl]benzamide. Using the product from reference example 92x. m.p. 194–195° C. $^1$H NMR (DMSO-d$_6$): δ 3.02 (t, 2H, J=6 Hz), 3.60 (m, 2H), 5.10 (d, 1H, J=9 Hz), 5.19 (d, 1H, J=9 Hz), 7.21 (d, 1H, J=9 Hz), 7.52 (d, 1H, J=9 Hz), 7.72 (s, 1H), 7.93 (d, 1H, J=3 Hz), 8.00 (d, 2H, J=6 Hz), 8.20 (d, 1H, J=3 Hz), 8.32 (d, 2H, J=6 Hz), 8.44 (s, 1H), 8.71 (s, 2H), 8.80 (m, 2H). MS (ion spray) m/z 483 (M+H)$^+$.

Example 1aaah

N-[2-(3-Carbamimidoyl-1H-indol-5-yl)-ethyl]-4-(2-pyrrolidin-1-ylpyrimidin-4-yl)benzamide. Using the product from reference example 92y. m.p. 134–136° C. $^1$H NMR (DMSO-d$_6$): δ 2.00 (m, 4H), 3.00 (t, 2H, J=6 Hz), 3.55 (m, 6H), 7.21 (m, 2H), 7.53 (d, 1H, J=6 Hz), 7.72 (s, 1H), 7.93 (d, 2H, J=6 Hz), 8.20 (m, 3H), 8.42 (m, 2H), 8.71 (s, 2H). MS (ion spray) m/z 454 (M+H)$^+$. >98% pure by analytical HPLC.

Example 1aaaj

N-[2-(3-Carbamimidoyl-1H-indol-5-yl)-ethyl]-4-[2-(2-hydroxymethylpyrrolidin-1-yl)-pyrimidin-4-yl]benzamide. Using the product from reference example 92z. m.p. 117–120° C. $^1$H NMR (DMSO-d$_6$): δ 2.01 (m, 4H), 2.98 (t, 2H, J=6 Hz), 3.40 (s, 1H), 3.58 (m, 4H), 3.70 (s, 1H), 4.19 (s, 1H), 7.20 (d, 1H, J=6 Hz), 7.25 (d, 1H, J=6 Hz), 7.50 (d, 1H, J=6 Hz), 7.73 (s, 1H), 7.94 (d, 2H, J=9 Hz), 8.21 (t, 3H, J=9 Hz), 8.46 (d, 2H, J=6 Hz), 8.71 (s, 2H). MS (ion spray) m/z 484 (M+H)$^+$. Anal. calcd for C$_{27}$H$_{29}$N$_7$O$_2$.2.5C$_2$HF$_3$O$_2$.0.5H$_2$O: C, 49.4%; H, 4.2%; N, 12.6%. Found: C, 49.2%; H, 4.2%; N, 12.6%.

Example 1aaak

N-[2-(3-Carbamimidoyl-1H-indol-5-yl)-ethyl]-4-[2-(carbamoylmethyl-N-methylamino)-pyrimidin-4-yl]benzamide. Using the product from reference example 92aa. m.p. 96–98° C. $^1$H NMR (DMSO-d$_6$): δ 2.99 (t, 2H, J=6 Hz), 3.23 (s, 3H), 3.59 (m, 2H), 3.80 (s, 2H), 7.21 (d,1H, J=9 Hz), 7.30 (m, 1H), 7.50 (d, 1H, J=6 Hz), 7.74 (s, 1H), 7.93 (d, 2H, J=9 Hz), 8.20 (m, 3H), 8.45 (s, 2H), 8.71 (s, 2H). MS (ion spray) m/z 471 (M+H)$^+$. Anal. calcd for C$_{25}$H$_{26}$N$_8$O$_2$.3C$_2$HF$_3$O$_2$.H$_2$O: C, 44.8%; H, 3.8%; N, 13.5%. Found: C, 44.9%; H, 4.0%; N, 13.5%.

Example 1aaal

N-[2-(3-Carbamimidoyl-1H-indol-5-yl)ethyl]-4-[2-(6-pyrrolidin-1-yl-hexylamino)-pyrimidin-4-yl]benzamide. Using the product from reference example 92ab. m.p. 159–161° C. $^1$H NMR (DMSO-d$_6$): δ 1.38 (m, 4H), 1.62 (m, 4H), 1.87 (m, 2H), 2.02 (m, 2H), 2.53 (m, 4H), 3.00 (m, 2H), 3.12 (m, 2H), 3.38 (m, 2H), 3.57 (m, 2H), 7.20 (m, 2H), 7.30 (m, 1H), 7.50 (d, 1H, J=6 Hz), 7.72 (s, 1H), 7.93 (d, 2H, J=6 Hz), 8.19 (m, 3H), 8.40 (d, 1H, J=3 Hz), 8.50 (s, 1H), 8.72 (m, 3H). MS (ion spray) m/z 553 (M+H)$^+$. >98% pure by analytical HPLC.

Example 1aaam

N-[2-(3-Carbamimidoyl-1H-indol-5-yl)ethyl]-4-[2-(6-piperidin-1-ylhexylamino)pyrimidin-4-yl]benzamide. Using the product from reference example 92ac. m.p. 110–113° C. $^1$H NMR (DMSO-d$_6$): δ 1.36 (m, 4H), 1.63 (m, 6H), 1.97 (m, 2H), 1.98 (m, 2H), 2.50 (m, 4H), 2.80 (m, 2H), 2.98 (m, 2H), 3.40 (m, 2H), 3.67 (m, 2H), 7.22 (m, 2H), 7.30 (m, 1H), 7.55 (d, 1H, J=6 Hz), 7.70 (s, 1H), 7.97 (d, 2H, J=6 Hz), 8.20 (m, 3H), 8.40 (d, 1H, J=3 Hz), 8.50 (s, 1H), 8.75 (m, 3H). MS (ion spray) m/z 567 (M+H)$^+$. >99% pure by analytical HPLC.

Example 1aaan

N-[2-(3-Carbamimidoyl-1H-indol-5-yl)ethyl]-4-[2-(4-piperidin-1-ylbutylamino)pyrimidin-4-yl]benzamide. Using the product from reference example 92ad. m.p. 94–96° C. $^1$H NMR (DMSO-d$_6$): δ 1.52–1.86 (m, 10H), 2.50 (m, 4H), 2.82 (m, 2H), 2.98 (m, 2H), 3.40 (m, 2H), 3.61 (m, 2H), 7.20 (m, 2H), 7.35 (m, 1H), 7.50 (d, 1H, J=6 Hz), 7.75 (s, 1H), 7.95 (d, 2H, J=6 Hz), 8.20 (m, 3H), 8.40 (d, 1H, J=3 Hz), 8.48 (s, 1H), 8.7 (m, 3H). MS (ion spray) m/z 539 (M+H)$^+$. >99% pure by analytical HPLC.

Example 1aaap

N-[2-(3-Carbamimidoyl-1H-indol-5-yl)ethyl]-4-[2-(4-diethylaminobutylamino)pyrimidin-4-yl]benzamide. Using the product from reference example 92ae. m.p. 73–76° C. $^1$H NMR (D$_2$O): δ 1.03 (t, 6H, J=8 Hz), 1.60 (s, 4H), 2.81 (m, 2H), 2.97 (m, 6H), 3.45 (m, 4H), 7.08 (d, 1H, J=6 Hz), 7.18 (d, 1H, J=3 Hz), 7.35 (d, 1H, J=9), 7.42 (s, 1H), 7.55 (m, 3H), 7.86 (s, 1H), 7.98 (m, 2H), 8.10 (m, 1H). MS (ion spray) m/z 527 (M+H)$^+$. >97% pure by analytical HPLC.

Example 1aaaq

N-[2-(3-Carbamimidoyl-1H-indol-5-yl)ethyl]-4-[2-(6-morpholin-4-ylhexylamino)pyrimidin-4-yl]benzamide. Using the product from reference example 92af. m.p. 129–130° C. $^1$H NMR (DMSO-d$_6$): δ 1.38 (m, 4H), 1.62 (m, 4H), 2.50 (m, 6H), 3.01 (m, 2H), 3.10 (m, 2H), 3.50 (m, 6H), 7.20 (m, 2H), 7.31 (m, 1H) 7.50 (d, 1H, J=3 Hz), 7.65 (s, 1H), 7.95 (d, 2H, J=9 Hz), 8.10 (m, 3H), 8.40 (m, 1H), 8.5 (s, 1H), 8.72 (m, 3H). MS (ion spray) m/z 569 (M+H)$^+$. >99% pure by analytical HPLC.

Example 1aaar

N-[2-(3-Carbamimidoyl-1H-indol-5-yl)ethyl]-4-[2-(6-dimethylaminohexylamino)pyrimidin-4-yl]benzamide. Using the product from reference example 92ag. m.p. 89–91° C. $^1$H NMR (DMSO-d$_6$): δ 1.36 (m, 4H), 1.59 (m, 4H), 2.75 (s, 3H), 2.76 (s, 3H), 2.95 (m, 4H), 3.28 (m, 2H), 3.60 (m, 2H), 7.21 (m, 2H), 7.32 (m, 1H), 7.51 (d, 1H, J=9 Hz), 7.74 (s, 1H), 7.95 (d, 2H, J=9 Hz), 8.18 (d, 2H, J=9 Hz), 8.21 (d, 1H, J=3 Hz), 8.37 (d, 1H, J=6 Hz), 8.49 (s, 1H), 8.72 (m, 3H). MS (ion spray) m/z 527 (M+H)$^+$. Anal. calcd for C$_{30}$H$_{38}$N$_8$O.3C$_2$HF$_3$O$_2$.2H$_2$O: C, 47.8%; H, 5.0%; N, 12.4%. Found: C, 47.8%; H, 4.6%; N, 12.3%.

Example 1aaas

N-[2-(3-Carbamimidoyl-1H-indol-5-yl)ethyl]-4-[2-(4-dimethylaminobutylamino)pyrimidin-4-yl]benzamide. Using the product from reference example 92ah. m.p. 156–159° C. $^1$H NMR (DMSO-d$_6$): δ 1.62 (m, 2H), 1.68 (m, 2H), 2.76 (s, 3H), 2.77 (s, 3H), 2.98 (t, 2H, J=6 Hz), 3.07 (m, 2H), 3.99 (m, 2H), 3.59 (m, 2H), 7.21 (m, 2H), 7.32 (m, 1H), 7.52 (d, 1H, J=9 Hz), 7.74 (s, 1H), 7.95 (d, 2H, J=9 Hz), 8.18 (d, 2H, J=9 Hz), 8.21 (d, 1H, J=3 Hz), 8.37 (d, 1H, J=6 Hz), 8.49 (s, 1H), 8.72 (m, 3H). MS (ion spray) m/z 499 (M+H)$^+$. Anal. calcd for C$_{28}$H$_{34}$N$_8$O.3C$_2$HF$_3$O$_2$.2H$_2$O: C, 46.6%; H, 4.7%; N, 12.8%. Found: C, 46.5%; H, 4.5%; N, 12.6%. >99% pure by analytical HPLC.

Example 1aaat

4-[2-(Bicyclo[2.2.1]hept-2-ylamino)pyrimidin-4-yl]-N-[2-(3-carbamimidoyl-1H-indol-5-yl)ethyl]benzamide. Using the product from reference example 92ai. m.p. 152–155° C. $^1$H NMR (DMSO-d$_6$): δ 1.14 (m, 2H), 1.33 (m, 2H), 1.46 (m, 2H), 1.63 (m, 1H), 1.97 (m, 1H), 2.20 (m, 2H), 2.97 (t, 2H, J=6 Hz), 3.56 (m, 2H), 4.09 (m, 1H), 7.20 (m, 2H), 7.37 (m, 1H), 7.53 (d, 1H, J=9 Hz), 7.73 (s, 1H), 7.94 (d, 2H, J=9 Hz), 8.19 (d, 2H, J=9 Hz), 8.20 (d, 1H, J=3 Hz), 8.39 (d, 1H, J=6 Hz), 8.45 (s, 1H), 8.70 (m, 3H). MS (ion spray) m/z 494 (M+H)$^+$. Anal. calcd for C$_{29}$H$_{31}$N$_7$O.2C$_2$HF$_3$O$_2$.1.5H$_2$O: C, 52.9%; H, 4.8%; N, 13.1%. Found: C, 53.0%; H, 4.7%; N, 12.9%. >98% pure by analytical HPLC.

Example 1aaau 1-(4-{4-[2-(3-Carbamimidoyl-1H-indol-5-yl)ethylcarbamoyl]phenyl}pyrimidin-2-yl)pyrrolidine-2-carboxylic acid amide. Using the product from reference example 92aj. m.p. 139–141° C. $^1$H NMR (D$_2$O): δ 1.98 (m, 2H), 2.28 (m, 1H), 2.81 (t, 2H, J=6 Hz), 3.44 (t, 2H, J=6 Hz), 3.62 (m, 1H), 4.40 (m, 1H), 7.07 (d, 1H, J=9 Hz), 7.12 (m, 1H), 7.38 (d, 1H, J=9 Hz), 7.47 (s, 1H), 7.48 (d, 2H, J=9 Hz), 7.89 (m, 3H), 8.16 (d, 1H, J=6 Hz). MS (ion spray) m/z 497 (M+H)$^+$. Anal. calcd for C$_{27}$H$_{28}$N$_8$O$_2$.3C$_2$HF$_3$O$_2$NH$_3$: C, 46.3%; H, 4.0%; N, 14.7%. Found: C, 46.6%; H, 4.0%; N, 14.2%.

Example 1aaav

N-[2-(3-Carbamimidoyl-1H-indol-5-yl)ethyl]-4-{2-[(2-hydroxy-ethyl)-N-methylamino]pyrimidin-4-yl}benzamide. Using the product from reference example 92ak. m.p. 97–100° C. $^1$H NMR (DMSO-d$_6$): δ 2.99 (t, 2H, J=7 Hz), 3.24 (s, 3H), 3.58 (m, 2H), 3.64 (t, 2H, J=7 Hz), 3.75 (m, 2H), 7.21 (m, 2H), 7.50 (d, 1H, J=9 Hz), 7.74 (s, 1H), 7.94 (d, 2H, J=9 Hz), 8.21 (m, 3H), 8.44 (d, 1H, J=5 Hz), 8.52 (s, 1H), 8.72 (s, 2H). MS (ion spray) m/z 458 (M+H)$^+$. Anal. calcd for C$_{25}$H$_{27}$N$_7$O$_2$.3C$_2$HF$_3$O$_2$NH$_3$: C, 47.1%; H, 4.1%; N, 13.7%. Found: C, 47.2%; H, 4.3%; N, 13.7%.

Example 1aaaw

N-[2-(3-carbamimidoyl-1H-indol-5-yl)-ethyl]-4-(2-morpholin-4-yl-pyrmidin-4-yl)-benzamide. Using the product from reference example 92al. $^1$H NMR (DMSO) δ 3.0 (bt, 2H); 3.59 (m, 2H); 3.71 (m, 4H); 3.80 (m, 4H); 7.20 (d, 1H, J=8 Hz); 7.32 (d, J=5 Hz, 1H); 7.50 (d, J=8 Hz, 1H); 7.74 (s, 1H); 7.94 (d, 2H, J=9 Hz); 8.22 (m, 3H); 8.51 (m, 2H); 8.73 (m, 3H); 12.28 (bs, 1H). MS (ion spray) m/z 470 (M+H)$^+$.

Example 1aaax

N-[2-(3-carbamimidoyl-1H-indol-5-yl)-ethyl]-4-[2-(cyclopropylmethyl-amino)-pyrimidin-4-yl]-benzamide. Using the product from reference example 92am. $^1$H NMR (DMSO) δ 0.26 (m, 2H); 0.43 (d, 2H, J=7 Hz); 1.12 (bt, H); 2.98 (t, 2H, J=7 Hz); 3.25 (bs, 2H); 3.57 (m, 2H); 7.20 (m, 2H); 7.50 (d, 1H, J=9 Hz); 7.74 (s, 1H); 7.94 (d, 2H, J=9 Hz); 8.19 (m, 3H); 8.39 (d, 1H, J=5 Hz); 8.53 (bs, 2H); 8.71 (bs, 3H); 12.28 (bs, 1H). MS (ion spray) m/z 454 (M+H)$^+$.

Example 1aaay

N-[2-(carbamimidoyl-1H-indol-5-yl)-ethyl]-4-[2-[(2-methoxy-ethyl)-methyl-amino]-pyrimidin-4-yl]-benzamide. Using the product from reference example 92an $^1$H NMR (DMSO) δ 2.99 (bt, 2H); 3.22 (s, 3H); 3.58 (m, 4H); 3.86 (m, 2H); 7.24 (m, 2H); 7.50 (d, 1H, J=8 Hz); 7.76 (s, 1H); 7.96 (d, 2H, J=9 Hz); 8.46 (d, 1H, J=5 Hz); 8.65 (bs, 1H); 8.76 (bs, 3H); 12.37 (bs, 1H). MS (ion spray) m/z 472 (M+H)$^+$.

Example 1aaaz

N-[2-(3carbamimidoyl-1H-indol-5-yl)-ethyl]-4-[2-(3-hydroxy-propylamino)-pyrimidin-4-yl]-benzamide. Using the product from reference example 92ap. $^1$H NMR (DMSO) δ 1.74 (bt, 2H); 2.98 (bt, 2H); 3.42 (bs, 2H); 3.50 (t, 2H, J=6 Hz); 3.56 (m, 2H); 7.20 (m, 2H); 7.50 (d, 1H, J=9 Hz); 7.74 (s, 1H); 7.94 (d, 2H, J=8 Hz); 8.19 (m, 3H); 8.39 (d, 1H, J=5 Hz); 8.52 (bs, 2H); 8.71 (m, 3H); 12.28 (bs, 1H). MS (ion spray) m/z 458 (M+H)$^+$.

Example 1aaaaa

N-[2-(3-carbamimidoyl-1H-indol-5-y)-ethyl]-4-[(2-hydroxy-ethyl)-propyl-amino]-pyrimidin-4-yl]-benzamide. Using the product from reference example 92aq. $^1$H NMR (DMSO) δ 5.90 (t, 3H); 1.63 (bd, 2H); 2.99 (t, 2H); 3.61 (m, 8H); 4.70 (bs, 1H); 7.20 (m, 2H); 7.49 (d, 1H, J=8 Hz); 7.73 (s, 1H); 7.92 (d, 2H, J 8 Hz); 8.18 (m, 3H); 8.42 (d, 1H, J=5 Hz); 8.50 (bs, 2H); 8.70 (bs, 2H); 12.26 (bs, 1H). MS (ion spray) m/z 469 (M+H)$^+$.

Example 1aaaab

N-[2-(3-Carbamimidoyl-1H-indole-5yl)-ethyl]-4-(2-piperidin-1-yl-pyrimidin-4-yl)-benzamide. Using the product from reference example 92ar. $^1$H NMR (DMSO) δ 1.61 (m, 6H); 2.98 (m, 2H); 3.57 (m, 2H); 3.84 (m, 4H); 7.20 (m, 2H); 7.50 (m, 2H); 7.74 (s, 1H); 7.94 (d, 2H, J=8 Hz); 8.20 (m, 3H); 8.45 (d, 1H, J=5 Hz); 8.50 (bs, 1H); 8.71 (bs, 3H); 12.28 (bs, 1H). MS (ion spray) m/z 468 (M+H)$^+$.

Example 1aaaac

N-[2-(3-carbamimidoyl-1H-indol-5-yl)-ethyl]-4-[2-(ethyl-methyl-amino)-pyrimidin-4-yl]-benzamide. Using the product from reference example 92as. $^1$H NMR (DMSO) δ 1.15 (t, 3H, J=7 Hz); 2.98 (bt, 2H); 3.18 (s, 3H); 3.59 (m, 2H); 3.73 (m, 2H); 7.21 (m, 2H); 7.50 (d, 1H, J=8 Hz); 7.74 (s, 1H); 7.94 (d, 2H, J=8 Hz); 8.21 (m, 3H); 8.45 (d, 1H, J=5 Hz); 8.53 (bs, 2H); 8.72 (bs, 3H); 12.29 (bs, 1H). MS (ion spray) m/z 442 (M+H)$^+$.

Example 1aaaad

N-[2-(3-carbamimidoyl-1H-indol-5-yl)-ethyl]-4-[2-(4-hydroxy-piperidin-1-yl)-pyrimidin-4-yl]-benzamide. Using the product from reference example 92at. $^1$H NMR (DMSO) δ 1.38 (m, 2H); 1.82 (m, 2H); 2.99 (t, 2H, J=7 Hz); 3.34 (t, 2H, J=7 Hz); 3.58 (m, 2H); 3.76 (m, 1H); 4.39 (bd, 2H); 7.22 (m, 2H); 7.50 (d, 1H, J=8 Hz); 7.75 (s, 1H); 7.94 (d, 2H, J=8 Hz); 8.20 (m, 3H); 8.45 (d, 1H, J=5 Hz); 8.57 (bs, 1H); 8.73 (bs, 3H); 12.29 (bs, 1H). MS (ion spray) m/z 484 (M+H)$^+$.

Example 1aaaae

N-[2-(3-carbamimidoyl-1H-indol-5-yl)-ethyl]-4-[2-(2,3-dihydroxy-propylamino)-pyrimidin-4-yl]-benzamide. Using the product from reference example 92au. $^1$H NMR (DMSO) δ 2.98 (bt, 2H); 3.3 (m, 1H); 3.39 (m, 2H); 3.57 (m, 3H); 3.70 (bs, 1H); 7.22 (m, 3H); 7.50 (d, 1H, J=8 Hz); 7.74 (s, 1H); 7.94 (d, 2H, J=9 Hz); 8.21 (m, 3H); 8.40 (d, 1H, J=5 Hz); 8.53 (bs, 1H); 8.72 (m, 3H); 12.29 (bs, 1H). MS (ion spray) m/z 474 (M+H)$^+$.

Example 1aaaaf

N-[2-(3-carbamimidoyl-1H-indol-5-yl)-ethyl]-4-[2-[(2,3-dihydroxy-propyl)-methyl-amino]-pyrimidin-4-yl]-benzamide. Using the product from reference example 92av. $^1$H NMR (DMSO) δ 2.98 (t, 2H, J=7 Hz); 3.25 (s, 3H); 3.38 (d, 2H, J=5 Hz); 3.54 (m, 3H); 3.85 (bs, 2H); 7.22 (m, 2H); 7.50 (d, 1H, J=8 Hz); 7.74 (s, 1H); 7.94 (d, 2H, J=8 Hz); 8.22 (m, 3H); 8.45 (d, 1H, J=5 Hz); 8.53 (bs, 1H); 8.71 (bs, 3H); 12.28 (bs, 1H). MS (ion spray) m/z 488 (M+H)$^+$.

Example 1aaaag

N-[2-(3-carbamimidoyl-1H-indol-5-yl)-ethyl]-4-[2-((s)-2-methoxymethyl-pyrrolidin-1-yl)-pyrimidin-4-yl]-benzamide. Using the product from reference example 92aw. $^1$H NMR (DMSO) δ 2.04 (m, 4H); 2.98 (t, 2H, J=7 Hz); 3.33 (m, 5H); 3.60 (m, 4H); 4.35 (bs, 1H); 7.20 (d, 1H, J=8 Hz); 7.28 (d, 1H, J=8 Hz); 7.50 (d, 1H, J=8 Hz); 7.74 (s, 1H); 7.95 (d, 2H, J=8 Hz); 8.22 (m, 3H); 8.47 (d, 1H, J=5 Hz); 8.52 (bs, 1H); 8.72 (bs, 3H); 12.28 (bs, 1H). MS (ion spray) m/z 498 (M+H)$^+$.

Example 1aaaah

N-[2-(3-carbamimidoyl-1H-indol-5-yl)-ethyl]-4-(2-piperazin-1-yl-pyrimidin-4-yl)-benzamide. Using the product from reference example 92ax. $^1$H NMR (DMSO) δ 2.98 (bt, 2H, J=7 Hz); 3.24 (bs, 4H); 3.59 (m, 2H); 4.06 (bs, 4H); 7.20 (d, 1H, J=9 Hz); 7.40 (d, 1H, J=5 Hz); 7.50 (d, 1H, J=8 Hz); 7.75 (s, 1H); 7.96 (d, 2H, J=8 Hz); 8.24 (m, 3H); 8.56 (d, 1H, J=5 Hz); 8.63 (bs, 1H); 8.74 (m, 2H); 8.95 (bs, 2H); 12.30 (bs, 1H). MS (ion spray) m/z 469 (M+H)$^+$.

Example 1aaaai

N-[2-(3-carbamimidoyl-1H-indol-5-yl)-4-[2-[2-(2-oxo-imidazolidin-1-yl)-ethylamino]-pyrimidin-4-yl]-benzamide. Using the product from reference example 92ay. $^1$H NMR (DMSO) δ 2.98 (bt, 2H); 3.24 (m, 4H); 3.50 (m, 6H); 6.28 (bs, 1H); 7.22 (m, 2H); 7.39 (bs, 1H); 7.50 (d, 1H, J=8 Hz); 7.74 (s, 1H); 7.94 (d, 2H, J=9 Hz); 8.20 (m, 3H); 8.40 (bs, 1H); 8.50 (bs, 2H); 8.73 (m, 3H); 12.28 (bs, 1H). MS (ion spray) m/z 512 (M+H)$^+$.

Example 1aaaaj

N-[2-(3-carbamimidoyl-1H-indol-5-yl)-ethyl]-4-[2-(3-methoxy-propylamino)-pyrimidin-4-yl]-benzamide. Using the product from reference example 92az. $^1$H NMR (DMSO) δ 1.80 (m, 2H); 2.98 (t, 2H, J=7 Hz); 3.23 (s, 3H); 3.40 (t, 4H, J=6 Hz); 3.55 (m, 2H); 7.20 (m, 2H); 7.50 (d, 1H, J=9 Hz); 7.73 (s, 1H); 7.94 (d, 2H, J=9 Hz); 8.18 (m, 3H); 8.38 (d, 1H, J=5 Hz); 8.54 (bs, 2H); 8.71 (m, 3H); 12.28 (bs, 1H). MS (ion spray) m/z 472 (M+H)$^+$.

Example 1aaaak

4-[2-(3-carbamimidoyl-1H-indol-5-yl)-ethyl]-4-[2-(2-hydroxy-ethylamino)-pyrimidin-4-yl]-benzamide. Using the product from reference example 92aaa. $^1$H NMR (DMSO) δ 2.98 (t, 2H, J=7 Hz); 3.44 (bs, 2H); 3.56 (m, 4H); 4.80 (bs, 1H); 7.20 (m, 2H); 7.49 (d, 1H, J=9 Hz); 7.72 (s, 1H); 7.93

(d, 2H, J=8 Hz); 8.18 (m, 3H); 8.38 (d, 1H, J=5 Hz); 8.50 (bs, 2H); 8.70 (m, 3H); 12.26 (bs, 1H). MS (ion spray) m/z 444 (M+H)$^+$.

Example 1aaaal

N-[2-(3-Carbamimidoyl-1H-indol-5-yl)-ethyl]-4-[2-(2-methoxyethoxy)-pyrimidin-4-yl]benzamide. Using the product from reference example 100a. m.p. 122–124° C. $^1$H NMR (DMSO-d$_6$): δ 2.50 (s, 3H), 2.99 (t, 2H, J=9 Hz), 3.59 (m, 2H), 3.74 (m, 2H), 4.51 (m, 2H), 7.22 (d, 1H, J=9 Hz), 7.50 (d, 1H, J=9 Hz), 7.73 (s, 1H), 7.79 (d, 1H, J=6 Hz), 7.97 (d, 2H, J=6 Hz), 8.20 (d, 1H, J=3 Hz), 8.28 (d, 2H, J=6 Hz), 8.41 (s, 1H), 8.71 (m, 3H), 8.76 (t, 1H, J=6 Hz). MS (ion spray) m/z 459 (M+H)$^+$. Anal. calcd for C$_{25}$H$_{26}$N$_6$O$_3$.2.5C$_2$HF$_3$O$_2$.0.5NH$_3$: C, 50.1%; H, 4.3%; N, 13.1%. Found: C, 50.1%; H, 4.5%; N, 13.0%.

Example 1aaaam

N-[2-(3-Carbamimidoyl-1H-indol-5-yl)ethyl]-4-[2-(1-carbamoylethoxy)pyrimidin-4-yl]benzamide. Using the product from reference example 100b. m.p. 159–161° C. $^1$H NMR (DMSO-d$_6$): δ 1.52 (d, 3H, J=6 Hz), 3.00 (t, 2H, J=6 Hz), 3.60 (m, 2H), 5.21 (q, 1H, J=6 Hz), 7.21 (d, 1H, J=6 Hz), 7.51 (d, 1H, J=6 Hz), 7.60 (s, 1H), 7.82 (d, 2H, J=6 Hz), 7.97 (d, 2H, J=9 Hz), 8.20 (d, 1H, J=3 Hz), 8.29 (d, 2H, J=9 Hz), 8.44 (s, 1H), 8.71 (m, 2H), 8.80 (m, 1H). MS (ion spray) m/z 472 (M+H)$^+$.

Example 1aaaan

N-[2-(3-Carbamimidoyl-1H-indol-5-yl)ethyl]-4-[2-(6-dimethylaminohexyloxy)pyrimidin-4-yl]benzamide. Using the product from reference example 100c. m.p. 82–84° C. $^1$H NMR (DMSO-d$_6$): δ 1.40 (m, 2H), 1.49 (m, 2H), 1.68 (m, 2H), 1.81 (m, 2H), 2.76 (s, 3H), 2.78 (s, 3H), 3.01 (m, 4H), 3.56 (m, 2H), 7.21 (d, 1H, J=9 Hz), 7.50 (d, 1H, J=9 Hz), 7.74 (s, 1H), 7.78 (d, 1H, J=6 Hz), 7.98 (d, 2H, J=9 Hz), 8.21 (d, 1H, J=3 Hz), 8.27 (d, 2H, J=9 Hz), 8.55 (s, 1H), 8.70 (m, 3H), 8.78 (m, 2H). MS (ion spray) m/z 528 (M+H)$^+$. >99% pure by analytical HPLC.

Example 1aaaap

N-[2-(3-Carbamimidoyl-1H-indol-5-yl)ethyl]-4-[2-(2-oxopiperidin-3-yloxy)pyrimidin-4-yl]benzamide. Using the product from reference example 100d. m.p. 145–147° C. $^1$H NMR (DMSO-d$_6$): δ 1.92 (m, 2H), 2.20 (m, 1H), 2.25 (m, 1H), 3.00 (t, 2H, J=3 Hz), 3.22 (m, 2H), 3.52 (m, 2H), 5.55 (m, 1H), 7.20 (d, 1H, J=6 Hz), 7.50 (d, 1H, J=6 Hz), 7.70 (s, 1H), 7.75 (d, 1H, J=3 Hz), 7.97 (d, 2H, J=9 Hz), 8.20 (d, 1H, J=3 Hz), 8.26 (d, 2H, J=9 Hz), 8.45 (s, 1H), 8.70 (m, 3H), 8.77 (t, 1H, J=3 Hz). MS (ion spray) m/z 498 (M+H)$^+$.

Example 1aaaaq

N-[2-(3-Carbamimidoyl-1H-indol-5-yl)ethyl]-4-[2-(2-pyrrolidin-1-yl-ethoxy)pyrimidin-4-yl]benzamide. Using the product from reference example 100e. m.p. 104–105° C. $^1$H NMR (DMSO-d$_6$): δ 1.89 (m, 2H), 2.05 (m, 2H), 2.98 (t, 2H, J=3 Hz), 3.19 (m, 2H), 3.50–3.66 (m, 6H), 4.73 (m, 2H), 7.22 (d, 1H, J=6 Hz), 7.50 (d1H, J=6 Hz), 7.73 (s, 1H), 7.88 (d, 2H, J=6 Hz), 8.01 (d, 2H, J=9 Hz), 8.25 (d, 1H, J=3 Hz), 8.30 (d, 2H, J=9 Hz), 8.51 (s, 1H), 8.71 (s, 2H), 8.76 (m, 1H), 8.77 (m, 1H). MS (ion spray) m/z 498 (M+H)$^+$. Anal. calcd for C$_{28}$H$_{31}$N$_7$O$_2$.2.5C$_2$HF$_3$O$_2$.H$_2$O: C, 49.5%; H, 4.5%; N, 12.3%. Found: C, 49.6%; H, 4.4%; N, 12.2%.

Example 1aaaar

N-[2-(3-Carbamimidoyl-1H-indol-5-yl)ethyl]-4-[2-(2-dimethylaminoethoxy)pyrimidin-4-yl]benzamide. Using the product from reference example 100f. m.p. 106–107° C. $^1$H NMR (DMSO-d$_6$): δ 2.89 (s, 3H), 2.91 (s, 3H), 3.59 (m, 4H), 4.75 (t, 2H, J=3 Hz), 7.20 (d, 1H, J=6 Hz), 7.51 (d, 1H, J=9 Hz), 7.74 (s, H), 7.87 (d, 1H, J=6 Hz), 8.00 (d, 2H, J=9 Hz), 8.20 (d, 1H, J=3 Hz), 8.30 (d, 2H, J=9 Hz), 8.45 (s, 1H), 8.72 (s, 2H), 8.77 (d, 1H, J=6 Hz), 8.79 (m, 1H). MS (ion spray) m/z 472 (M+H)$^+$. >99% pure by analytical HPLC.

Example 1aaaas

3'-(2-Dimethylaminoethoxy)biphenyl-4-carboxylic acid [2-(3-carbamimidoyl-1H-indol-5-yl)ethyl]amide. Using the product from reference example 1aae. m.p. 99–101° C. $^1$H NMR (D$_2$O): δ 2.88 (s, 6H), 2.94 (t, 2H, J=61 Hz), 3.55 (m, 4H), 4.32 (t, 2H, J=3 Hz), 6.99 (d, 1H, J=9 Hz), 7.20 (m, 2H), 7.39 (d, 1H, J=6 Hz), 7.45 (d, 1H, J=6 Hz), 7.55 (m, 4H), 7.94 (s, 1H). MS (ion spray) m/z 470 (M+H). >99% pure by analytical HPLC.

Example 1aaaat

N-[2-(3-Carbamimidoyl-1H-indol-5-yl)ethyl]-4-(1-oxypyridin-2-yl)benzamide. Using the product from reference example 1aaf. m.p. 164–167° C. $^1$H NMR (DMSO-d$_6$): δ 2.98 (t, 2H, J=7 Hz), 3.58 (m, 2H), 7.20 (d, 1H, J=8 Hz), 7.44 (m, 2H), 7.47 (d, 1H, J=8 Hz), 7.74 (s, 1H), 7.92 (s, 4H), 8.20 (d, 1H, J=3 Hz), 8.37 (m, 1H), 8.45 (s, 1H), 8.71 (s, 2H). MS (ion spray) m/z 400 (M+H)$^+$. Anal. calcd for C$_{23}$H$_{21}$N$_5$O$_2$.1.5C$_2$HF$_3$O$_2$.0.5H$_2$O: C, 53.9%; H, 4.1%; N, 12.1%. Found: C, 54.1%; H, 4.6%; N, 12.5%.

Example 1aaaau

2'-(2-Dimethylaminoethoxy)biphenyl-4-carboxylic acid [2-(3-carbamimidoyl-1H-indol-5-yl)ethyl]amide. Using the product from reference example 1aag. m.p. 73–76° C. $^1$H NMR (D$_2$O): δ NMR 2.57 (s, 6H), 2.95 (t, 2H, J=3 Hz), 3.32 (t, 2H, J=3 Hz), 3.60 (t, 2H, J=6 Hz), 4.20 (m, 2H), 7.00 (d, 2H, J=6 Hz), 7.20 (d, 1H, J=3 Hz), 7.25 (d, 1H, J=3 Hz), 7.35 (m, 1H), 7.46 (m, 3H), 7.52 (d, 2H, J=6 Hz), 7.60 (s, 1H), 7.95 (s, 1H). MS (ion spray) m/z 470 (M+H)$^+$. >94% pure by analytical HPLC.

Example 1aaaav

2'-(3-Dimethylaminopropoxy)biphenyl-4-carboxylic acid [2-(3-carbamimidoyl-1H-indol-5-yl)ethyl]amide. Using the product from reference example 1aah. m.p. 76–78° C. $^1$H NMR (D$_2$O): δ 1.95 (m, 2H), 2.45 (s, 6H), 2.88 (t, 2H, J=9 Hz), 2.96 (t, 2H, J=9 Hz), 3.59 (t, 2H, J=9 Hz), 4.00 (t, 2H, J=9 Hz), 7.06 (m, 2H), 7.23 (m, 1H), 7.31 (m, 1H), 7.42 (m, 3H), 7.56 (d, 3H, J=9 Hz), 7.61 (s, 1H), 7.96 (s, 1H). MS (ion spray) m/z 484 (M+H)$^+$. >98% pure by analytical HPLC.

Example 1aaaaw

3'-(3-Dimethylaminopropoxy)biphenyl-4-carboxylic acid [2-(3-carbamimidoyl-1H-indol-5-yl)ethyl]amide. Using the product from reference example 1aai. m.p. 84–86° C. $^1$H NMR (D$_2$O): δ 2.06 (m, 2H), 2.76 (s, 6H), 2.85 (t, 2H, J=6 Hz), 3.18 (t, 2H, J=6 Hz), 3.47 (t, 2H, J=6 Hz), 4.00 (t, 2H, J=6 Hz), 6.88 (d, 1H, J=6 Hz), 7.02 (s, 1H), 7.12 (m, 2H), 7.25 (t, 1H, J=9 Hz), 7.36 (d, 1H, J=9 Hz), 7.45 (m, 4H), 7.86 (s, 1H). MS (ion spray) m/z 484 (M+H)$^+$. 100% pure by analytical HPLC.

Example 1aaaax

N-[2-(3-carbamimidoyl-1H-indol-5-yl)-ethyl]-4-(1-oxo-pyridin-3-yl)-benzamide. Using the product from reference example 1aaj. ¹H NMR (DMSO) δ 3.01 (bt, 2H); 3.56 (m, 2H); 7.20 (d, 1H, J=9 Hz); 7.52 (m, 2H); 7.73 (m, 2H); 7.86 (d, 2H, J=9 Hz); 7.94 (d, 2H, J=9 Hz); 8.20 (s, 1H); 8.27 (d, 1H, J=7 Hz); 8.67 (s, 1H); 8.56 (s, 2H); 8.71 (m, 2H); 12.28 (bs, 1H). MS (ion spray) m/z 400 (M+H)⁺.

Example 1aaaay

4-[2-(acetylamino-methyl)-pyridin-4-yl]-N-[2-(3-carbamimidoyl-1H-indol-5-yl)-ethyl]-benzamide. Using the product from reference example 1aak. ¹H NMR (DMSO) δ 1.94 (s, 3H); 2.99 (bt, 2H); 4.49 (d, 2H, J=5 Hz); 7.20 (d, 1H, J=8 Hz); 7.50 (d, 1H, J=8 Hz); 7.74 (s, 1H); 7.83 (m, 214); 7.94 (d, 2H, J=8 Hz); 8.00 (d, 2H, J=8 Hz); 8.22 (d, 1H, J=3 Hz); 8.53 (m, 2H); 8.74 (m, 31H); 12.29 (bs, 1H). MS (ion spray) m/z 455 (M+H)⁺.

Example 1aaaaz

Piperidine-4-carboxylic acid (4-[4-[2-(3-carbamimidoyl-1H-indol-5-yl)-ethylcarbamoyl]-phenyl-]-pyridin-2-ylmethyl)-amide. Using the product from reference example 1aal. ¹H NMR (DMSO) δ 1.75 (m, 2H); 1.94 (m, 2H); 2.58 (m, 1H); 2.94 (m, 5H); 3.30 (m, 2H); 3.62 (m, 2H); 4.54 (bd, 2H); 7.20 (d, 1H, J=8 Hz); 7.51 (d, 1H, J=8 Hz); 7.76 (s, H); 7.88 (m, 2H); 7.94 (d, 2H, J=9 Hz); 8.03 (d, 2H, J=9 Hz); 8.24 (s, 1H); 8.44 (bs, 1H); 8.77 (m, 3H); 12.35 (bs, 1H). MS (ion spray) m/z 524 (M+H)⁺.

Example 1aaaaaa

N-[2-(3-Carbamimidoyl-1H-indol-5-yl)ethyl]-4-[-(3-dimethylaminopropyl)-6-oxo-1,6-dihydropyridin-3-yl]benzamide. Using the product from reference example 1aam. m.p. 129–130° C. ¹H NMR (DMSO-d₆): δ 2.07 (t, 2H, J=6 Hz), 2.72 (s, 6H), 2.84 (t, 2H, J=6 Hz), 3.03 (t, 2H, J=6 Hz), 3.46 (t, 2H, J=6 Hz), 3.98 (t, 2H, J=6 Hz), 6.58 (d, 1H, J=12 Hz), 7.12 (d, 1H, J=9 Hz), 7.38 (m, 3H), 7.47 (m, 3H), 7.81 (m, 2H), 7.88 (s, 1H). MS (ion spray) m/z 485 (M+H)⁺. Anal. calcd for $C_{28}H_{32}N_6O_2\cdot 3C_2HF_3O_2\cdot 0.5H_2O$: C, 48.9%; H, 4.3%; N, 10.1%. Found: C, 48.6%; H, 4.3%; N, 10.4%.

Example 1aaaaab

N-[2-(3-Carbamimidoyl-1H-indol-5-yl)ethyl]-4-[6-(3-dimethylaminopropoxy)pyridin-3-yl]benzamide. Using the product from reference example 1aan. m.p. 84–86° C. ¹H NMR (D₂O): δ 2.11 (m, 2H), 2.78 (s, 6H), 2.90 (t, 2H, J=3 Hz), 3.21 (m, 2H,), 3.51 (t, 2H, J=3 Hz), 4.23 (m, 2H), 6.85 (d, 1H, J=6 Hz), 7.05 (d, 1H, J=6 Hz), 7.40 (d, 1H, J=6 Hz), 7.48–7.55 (m, 5H), 7.89 (m, 2H), 8.23 (s, 1H). MS (ion spray) m/z 485 (M+H)⁺. Anal. calcd for $C_{28}H_{32}N_6O_2\cdot 3C_2HF_3O_2$: C, 49.4%; H, 4.3%; N, 10.2%. Found: C, 49.3%; H, 4.6%; N, 10.4%.

Example 1aaaaac (5-{4-[2-(3-Carbamimidoyl-1H-indol-5-yl)ethylcarbamoyl]phenyl}-2-oxo-2H-pyridin-1-yl)acetamide. Using the product from reference example 1aap. MS (ion spray) m/z 457 (M+H)⁺.

Example 1aaaaad

N-[2-(3-Carbamimidoyl-1H-indol-5-yl)-ethyl]-4-{1-[(2-dimethylaminoethylcarbamoyl)methyl]-6-oxo-1,6-dihydropyridin-3-yl}benzamide. Using the product from reference example 1aaq. m.p. 71–75° C. ¹H NMR (D₂O): δ 2.75 (s, 6H), 3.16 (m, 2H), 3.37 (m, 2H), 3.50 (m, 2H), 4.55 (s, 2H), 4.63 (m 2H), 6.48 (d, 1H, J=9 Hz), 7.03 (d, 1H, J=9 Hz), 7.25 (m, 3H), 7.38 (m, 3H), 7.63 (s, 1H), 7.65 (m, 1H), 7.79 (s, 1H). MS (ion spray) m/z 528 (M+H)⁺. >94% pure by analytical HPLC.

Example 1aaaaae

N-[2-(3-Carbamimidoyl-1H-indol-5-yl)-ethyl]-4-(4-dimethylamino-piperidin-1-yl)-benzamide. Using the product from reference example 1aas. ¹H NMR (CD₃OD): δ 8.04 (s, 1H0, 7.71 (brs, 1H), 7.59 (d, 2H), 7.47 (d, 1H), 7.19 (dd, 1H), 6.92 (d, 2H), 3.93 (d, 2H), 3.59 (t, 2H), 3.29 (m, 1H), 2.96 (t, 2H), 2.80 (dt, 2H), 2.74 (s, 6H), 2.06 (m, 2H), 1.68 (dq, 2H). MS (ion spray) m/z 433 (M+H)+. 92% pure by analytical HPLC.

Example 1aaaaaf

N-[2-(3-Carbamimidoyl-1H-indol-5-yl)-ethyl]-4-[4-(2-dimethylamino-ethylamino)-piperidin-1-yl]-benzamide. Using the product from reference example 1aat. ¹H NMR (CD₃OD): d 8.04 (s, 1H), 7.86 (d, 1H), 7.71 (s, 1H), 7.68 (d, 1H), 7.59 (d, 1H), 7.19 (d, 1H), 6.91 (d, 2H), 4.02 (d, 2H), 3.64 (t, 2H), 3.56 (brs, 2H); 3.42 (m, 1H), 2.98 (s, 6H), 2.90 (m, 2H), 2.20 (brd, 2H), 1.79 (q, 2H). MS (ion spray) m/z 476 (M+H)+. >97% pure by analytical HPLC Example 1aaaaag 4-(4-Amino-piperidin-1-yl)-N-[2-(3-carbamimidoyl-1H-indol-5-yl)-ethyl]-benzamide. Using the product from reference example 1aav. ¹H NMR (CD₃OD): δ 8.08 (s, 1H), 7.78 (s, 1H), 7.71 (d, 2H), 7.48 (d, 1H), 7.24 (dd, 1H), 6.99 (d, 2H), 3.96 (brd, 2H), 3.65 (t, 2H), 3.05 (t, 2H), 2.93 (dt, 2H), 2.07 (brd, 2H), 1.70 (dq, 2H). MS (ion spray) m/z 405 (M+H)+. >99% pure by HPLC.

Example 1aaaaah

N-[2-(3-Carbamimidoyl-1H-indol-5-yl)-ethyl]-4-(4-methoxy-piperidin-1-yl)-benzamide. Using the product from reference example 1aaw. ¹H NMR (CD₃OD): d 8.07 (s, H), 7.76 (s, H), 7.72 (d, 2H), 7.46 (d, H), 7.33 (dd, H), 7.08 (d, 2H), 3.60–3.72 (m, 3H), 3.44–3.52 (m, H), 3.29 (s, 3H), 3.10–3.20 (m, 2H), 3.04 (t, 2H), 1.97–2.08 (m, 2H), 1.54–1.65 (m, 2H). MS (CI) m/z 420 (M+H)+.

Example 1aaaaai 4-(4-Acetylamino-piperidin-1-yl)-N-[2-(3-carbamimidoyl-1H-indol-5-yl)-ethyl]-benzamide. Using the product from reference example 125. ¹H NMR (CD₃OD): δ 8.08 (s, 1H), 7.76 (s, 1H), 7.69 (d, 2H), 7.48 (d, 1H), 7.24 (dd, 1H), 7.01 (d, 2H), 3.83 (brd, 2H), 3.65 (t, 2H), 3.05 (t, 2H), 2.98 (dt, 2H), 1.97 (m, 2H), 1.94 (s, 3H), 1.58 (dq, 2H). MS (CI) m/z 447 (M+H)+.

Example 1aaaaaj 4-(1-Acetyl-piperidin-4-yl)-N-[2-(3-carbamimidoyl-1H-indol-5-yl)-ethyl]-benzamide. Using the product from reference example 1aay. ¹H NMR (CD₃OD): δ 8.06 (s, 1H), 7.76 (d, 2H), 7.47 (d, 1H), 7.32 (d, 2H), 7.23 (dd, 1H), 4.02 (d, 1H), 4,64 (t, 2H), 3.05 (t, 2H), 2.81–2.93 (m, 1H), 2.64–2.75 (dt, 1H), 1.82–1.92 (m, 2H), 1.55–1.75 (m, 2H), 1.37 (m, 1H). MS (ion spray) m/z 432 (M+H)+. >96% pure by analytical HPLC.

Example 1aaaaak

4-{4-[2-(3-Carbamimidoyl-1H-indol-5-yl)-ethylcarbamoyl]-phenyl}-piperidine-1-carboxylic acid amide. Using the product from reference example 1aaz. $^1$H NMR (CD$_3$OD): δ 8.07 (s, 1H), 7.76 (s, 1H), 7.70 (d, 2H), 7.47 (d, 1H), 7.31 (brd, 2H), 7.24 (dd, 2H), 4.14 (m, 2H), 3.66 (t, 2H), 3.08 (t, 2H), 2.80–2.97 (m, 2H), 1.80–1.88 (m, 2H), 1.58–1.68 (m, 2H). MS (ion spray) m/z 433 (M+H)$^+$. 95% pure by analytical HPLC.

Example 1aaaaal

N-[2-(3-Carbamimidoyl-1H-indol-5-yl)-ethyl]-4-(1-methyl-1-oxy-piperidin-4-yl)-benzamide. Using the product from reference example 1aaaa. $^1$H NMR (DMSO): 3 8.69 (brs, 1H), 8.46 (brs, 1H), 8.19 (s, 1H), 7.80 (d, 1H), 7.70 (s, 1H), 7.48 (d, 1H), 7.37 (d, 1H), 7.18 (d, 1H), 3.75 (d, 2H), 3.50 (s, 3H), 3.45–3.72 (m, 8H), 2.94 (m, 1H), 1.97 (m, 1H). MS (ion spray) m/z 420 (M+H)+. 96% pure by analytical HPLC.

Example 1aaaaam

N-[2-(3-Carbamimidoyl-1H-indol-5-yl)-ethyl]-4-(1-methyl-piperidin-4-yl)-benzamide. Using the product from reference example 1aaab. $^1$H NMR (DMSO): δ 9.55 (brs, 1H), 8.62 (d, 2H), 8.18 (d, 1H), 7.77 (d, 1H), 7.69 (s, 1H), 7.46 (d, 1H), 7.29 (d, 1H), 7.15 (d, 1H), 3.47–3.52 (m, 2H), 3.02–3.06 (m, 1H), 2.89–2.95 (m, 2H), 2.78–2.80 (m, 4H), 1.97–2.01 (m, 1H), 1.79–1.82 (m, 1H), 1.20–1.24 (m, 1H). MS (ion spray) m/z 404 (M+H)+.

Example 1aaaaan

N-[2-(3-Carbamimidoyl-1H-indol-5-yl)-ethyl]-4-(1-methanesulfonyl-piperidin-4-yl)-benzamide. Using the product from reference example 1aaac. $^1$H NMR (CD$_3$OD): d 8.06 (s, 1H), 7.76 (s, 1H), 7.72 (d, 2H), 7.47 (d, 1H), 7.34 (d, 2H), 7.23 (d, 1H), 3.84 (d, 2H), 3.67 (m, 2H), 3.04 (t, 2H), 2.71–2.89 (m, 3H), 2.84 (s, 3H), 1.92 (m, 2H), 1.78 (dq, 2H). MS (ion spray) m/z 468 (M+H)+.

Example 1aaaaao 4-(2-Acetylamino-1,1-dimethyl-ethyl)-N-[2-(3-carbamimidoyl-1H-indol-5-yl)-ethyl]-benzamide. Using the product from reference example 1aaad. $^1$H NMR (DMSO) δ 1.24 (s, 6H); 1.77 (s, 3H); 2.96 (t, 2H); 3.27 (d, J=6 Hz); 3.55 (m, 2H); 7.20 (d, J=9 Hz, 1H); 7.44 (d, J=9 Hz, 2H); 7.50 (d, J=9 Hz, 1H); 7.65 (t, 1H); 7.77 (m, 3H); 8.20 (d, J=3 Hz, 1H); 8.52 (m, 2H); 8.70 (bs, 1H); 12.28 (bs, 1H). MS (ion spray) m/z 420 (M+H)$^+$.

Example 1aaaaap

N-[2-(3-Carbamimidoyl-1H-indol-5-yl)-ethyl]-4-(2-methanesulfonylamino-1,1-dimethyl-ethyl)-benzamide. Using the product from reference example 106. $^1$H NMR (DMSO) δ 1.28 (s, 6H); 2.74 (s, 3H); 2.96 (t, J=7 Hz, 2H); 3.11 (d, J=7 Hz, 2H); 3.54 (m, 2H); 6.85 (t, J=7 Hz, 1H); 7.18 (d, J=9 Hz, 1H); 7.48 (m, 3H); 7.76 (m, 3H); 8.20 (d, J=3 Hz, 1H); 8.54 (m, 2H); 8.70 (bs, 1H); 12.27 (d, J=3 Hz, 1H). MS (ion spray) m/z 456 (M+H)$^+$.

Example 1aaaaaq

Piperidine-4-carboxylic acid (2-{4-[2-(3-carbamimidoyl-1H-indol-5-yl)-ethylcarbamoyl]-2-methylpropyl}-phenyl)-amide. Using the product from reference example 1aaaf. $^1$H NMR (DMSO) δ 1.24 (s, 6H); 1.68 (m, 4H); 2.42 (m, 1H); 2.84 (m, 2H); 2.96 (m, 2H); 3.28 (m, 4H); 3.54 (m, 2H); 3.90 (bs, 1H); 7.18 (d, J=8 Hz, 1H); 7.44 (d, J=8 Hz, 2H); 7.50 (d, J=8 Hz, 1H); 7.76 (m, 4H); 8.22 (s, 1H); 8.58 (m, 2H); 8.71 (bs, 1H); 12.30 (bs, 1H). MS (ion spray) m/z 489 (M+H)$^+$.

Example 1aaaaar

N-[2-(3-Carbamimidoyl-1H-indol-5-yl)-ethyl]-4-(1,1-dimethyl-2-ureido-ethyl)-benzamide. Using the product from reference example 107a. $^1$H NMR (DMSO) δ 1.23 (s, 6H); 2.96 (t, 2H); 3.23 (d, J=6 Hz, 2H); 3.55 (m, 2H); 4.19 (bs, 2H); 5.72 (t, 1H); 7.19 (d, J=9 Hz, 1H); 7.46 (m, 3H); 7.75 (m, 3H); 8.20 (d, J=3 Hz, 1H); 8.53 (m, 2H); 8.70 (bs, 1H); 12.26 (d, J=3 Hz, 1H). MS (ion spray) m/z 421 (M+H)$^+$.

Example 1aaaaas

N-[2-(3-Carbamimidoyl-1H-indol-5-yl)-ethyl]-4-[2-(3-ethyl-ureido)-1,1-dimethyl-ethyl]-benzamide. Using the product from reference example 107b. $^1$H NMR (DMSO) δ 0.93 (t, J=7 Hz, 3H); 1.22 (s, 6H); 2.96 (m, 4H); 3.25 (m, 2H); 3.56 (m, 2H); 5.54 (bt, 1H); 5.78 (bs, 1H); 7.18 (d, J=8 Hz, 1H); 7.43 (d, J=8 Hz, 2H); 7.72 (d, J=8 Hz, 1H); 7.76 (m, 3H); 8.21 (bs, 1H); 8.51 (m, 2H); 8.70 (bs, 1H); 12.27 (s, 1H). MS (ion spray) m/z 449 (M+H)$^+$.

Example 1aaaaat

N-[2-(3-Carbamimidoyl-1H-indol-5-yl)-ethyl]-4-(2-dimethylamino-3,4,5,6-tetrahydro-pyrimidin-4-yl)-benzamide. Using the product from reference example 1aaai. $^1$H NMR (DMSO) δ 1.88 (m, 1H); 2.11 (m, 1H); 2.98 (m, 10H); 3.33 (m, 1H); 3.57 (m, 2H); 4.80 (bs, 1H); 7.18 (d, J=9 Hz, 1H); 7.42 (d, J=8 Hz, 2H); 7.50 (d, J=8 Hz, 1H); 7.86 (d, J=8 Hz, 2H); 8.05 (s, 1H); 8.22 (d, J=3 Hz, 2H); 8.64 (bs, 2H); 8.71 (bs, 1H); 12.31 (s, 1H). MS (ion spray) m/z 432 (M+H)$^+$.

Example 1aaaaau

N-[2-(3-Carbamimidoyl-1H-indol-5-yl)-ethyl]-4-(1-oxy-pyridin-4-yloxy)-benzamide. Using the product from reference example 1aaaj. $^1$H NMR (CDCl$_3$): δ 8.07 (s, 1H); 7.74 (s, 1H); 7.64 (d, 2H); 7.46 (d, 1H); 7.22 (dd, 2H); 6.79 (d, 2H); 3.63 (t, 2H); 3.03 (t, 2H). MS (ion spray) m/z 416 (M+H)+.

Example 1aaaaav

N-[2-(3-Carbamimidoyl-1H-indol-5-yl)-ethyl]-4-(1-methyl-piperidin-4-yloxy)-benzamide. Using the product from reference example 1aaak. $^1$H NMR (CD$_3$OD): d 8.07 (s, 1H), 7.74–7.79 (m, 3H), 7.46 (d, 1H), 7.23 (dd, 1H), 6.99–7.09 (m, 2H), 3.59–3.67 (m, 2H), 3.34–3.45 (m, 2H), 3.12–3.23 (m, 1H), 3.04 (t, 2H), 2.91 (t, 3H), 2.38 (brd, 1H), 2.20–2.26 (m, 2H), 2.06–2.10 (m, 2H), 1.89 (brq, 1H). MS (ion spray) m/z 420 (M+H)+. 94% pure by analytical HPLC.

Example 1aaaaaw and 1aaaaax

N-[2-(3-Carbamimidoyl-1H-indol-5-yl)ethyl]-4-(1,2,3,6-tetrahydropyridin-4-yl)-benzamide. Using the product from reference example 67b. $^1$H NMR (300 MHz, DMSO-d$_6$) d 12.27 (bs, 1H), 8.89 (bs, 2H), 8.70 (bs, 2H), 8.56 (t, 1H), 8.21 (bs, 2H), 8.20 (d, J=3 Hz, 1H), 7.84 (d, J=8 Hz, 2H), 7.72 (s, 1H), 7.57 (d, J=8 Hz, 2H), 7.48 (d, J=8 Hz, 1H), 7.18 (d, J=8 Hz, 1H), 6.32 (bs, 1H), 3.78 (bs, 2H), 3.57–3.49 (m, 2H), 3.3 (obsc, 2H), 2.94 (t, J=8 Hz, 2H), 2.69 (bm, 2H); MS (electrospray) m/z 388 (M+H$^+$). A solution of N-[2-(3-carbamimidoyl-1H-indol-5-yl)ethyl]-4-(1,2,3,6-tetrahydropyridin-4-yl)-benzamide (5 mg,) in MeOH (2 mL) is purged with N$_2$ and 10% palladium on carbon (9 mg) added and the reaction again purged with N$_2$. The reaction is then purged with H$_2$ and is vigorously stirred 30 minutes.

The reaction is purged with $N_2$, filtered through Celite, washed with MeOH and concentrated to provide N-[2-(3-Carbamimidoyl-1H-indol-5-yl)ethyl]-4-piperidin-4-yl-benzamide.: $^1$H NMR (300 MHz, DMSO-$d_6$) d 12.31 (bs, 1H), 8.72–8.84 (m, 7H), 8.21 (s, 1H), 7.79 (d, J=7 Hz, 2H), 7.72 (s, 1H), 7.47 (d, J=8 Hz, 1H), 7.30 (d, J=7 Hz, 2H), 7.17 (d, J=8 Hz, 1H), 3.52 (m, 2H), 3.3 (obsc, 2H), 3.05–3.85 (m, 5H), 1.96–1.72 (m, 4H); MS (ion spray) m/z 390 (M+H$^+$).

Example 1aaaaay 4-(2-Amino-1,1-dimethylethyl)-N-(2-[3-carbamimidoylindol-5-yl]ethyl)benzamide. To a solution of 4-(2-[tert-Butoxycarbonylamino]-1,1-dimethylethyl)-N-(2-[1-tert-butoxycarbonyl-3-tert-butoxycarbonylcarbamimidoylindol-5-yl]ethyl)benzamide (0.092 g, 0.14 mmol, reference example 1aaal) in $CH_2Cl_2$ (8 mL) is added distilled water (0.1 mL) and trifluoroacetic acid (2 mL). After stirring six hours, the reaction mixture is concentrated and then placed under high vacuum to give a quantitative yield of the title compound as a white solid (m.p. 67–70° C). $^1$H NMR ($D_2O$): δ 1.29 (6H, s), 2.91 (2H, t, J=7 Hz), 3.12 (2H, s), 3.53 (2H, t, J=7 Hz), 7.14 (1H, d, J=8 Hz), 7.36–7.46 (5H, m), 7.54 (1H, s), 7.93 (1H, s). MS (FAB) m/z 378 (M+H)$^+$. Anal. calcd. for $C_{22}H_{27}N_5O.3C_2HO_2F_3$: C, 46.7; H, 4.2; N, 9.7. Found: C, 46.8; H, 4.5; N, 9.8.

Using essentially the same procedure as used in Example 1aaaaay, except using the specified substrate, there is prepared

Example 1aaaaaz

N-(2-[3-Carbamimidoylindol-5-yl]ethyl)-4-(6-[2-dimethylaminoethoxy]pyridin-3-yl)benzamide. Using the product from reference example 1aaam. Purified by HPLC (96.8% pure by analytical HPLC). m.p. 57–59° C. $^1$H NMR ($D_2O$): δ 2.77–2.89 (8H, m), 3.39–3.54 (4H, m), 4.44 (2H, m), 6.86 (1H, d, J=9 Hz), 7.09 (1H, d, J=8 Hz), 7.35 (1H, d, J=8 Hz), 7.40–7.49 (5H, m), 7.84 (1H, s), 7.88 (1H, d, J=9 Hz), 8.16 (1H, s). MS (ion spray) m/z 471 (M+H)$^+$.

Example 1aaaaaaa

N-(2-[3-Carbamimidoylindol-5-yl]ethyl)-4-pyrid-4-ylbenzamide. Using the product from reference example 1aaan. m.p. 113–116° C. $^1$H NMR ($D_2O$): δ 2.19 (2H, t, J=6 Hz), 3.56 (2H, t, J=6 Hz), 7.16 (1H, d, J=8 Hz), 7.42 (1H, d, J=8 Hz), 7.54 (1H, s), 7.62 (2H, d, J=8 Hz), 7.79 (2H, d, J=8 Hz), 7.92 (1H, s), 8.19 (2H, m), 8.67 (2H, br, m). MS (ion spray) m/z 384 (M+H)$^+$. Anal. calcd. for $C_{23}H_{21}N_5O.(C_2HO_2F_3)_3(H_2O)_{0.5}$: C, 47.4; H, 3.4; N, 9.5. Found: C, 47.2; H, 3.7; N, 9.8.

Example 1aaaaaab

N-(2-[3-Carbamimidoylindol-5-yl]ethyl)-4-(4-carbamoyl-phenyl)-benzamide. Using the product from reference example 1aaao. MS m/z 426 (M+H).

Example 1aaaaaac

N-(2-[3-Carbamimidoylindol-5-yl]ethyl)-4-(4-methoxy-phenyl)-benzamide. Using the product from reference example 1aaap. MS m/z 413 (M+H).

Example 1aaaaaad

N-(2-[3-Carbamimidoylindol-5-yl]ethyl)-(5-methoxy-indol-2-yl)-carboxamide. Using the product from reference example 1aaaq. MS m/z 375 (M+H).

Example 1aaaaaae

N-(2-[-Carbamimidoylindol-5-yl]ethyl)-(6-chloro-benzothiophen-2-y)-carboxamide. Using the product from reference example 1aaar. MS m/z 397 (M+H).

Example 1aaaaaaf

N-(2-[3-Carbamimidoylindol-5-yl]ethyl)-4-(4-benzyloxy-phenyl)-benzamide. Using the product from reference example 1aaas. MS m/z 413 (M+H).

Example 1aaaaaag

N-(2-[3-Carbamimidoylindol-5-yl]ethyl)-4-chloro-benzamide. Using the product from reference example 1aaat. MS m/z 341 343 (M+H, Cl pattern).

Example 1aaaaaah

N-(2-[3-Carbamimidoylindol-5-yl]ethyl)-4-(methylsulphonyl)-benzamide. Using the product from reference example 1aaau. MS m/z 385 (M+H).

Example 1aaaaaai

N-(2-[3-Carbamimidoylindol-5-yl]ethyl)-4-(amino-sulphonyl)-benzamide. Using the product from reference example 1aaav. MS m/z 386 (M+H).

Example 1aaaaaaj 4-(3-Aminoprop-1-ynyl)-N-[2-(3-carbamimidoyl-1H-indol-5-yl)-ethyl]-benzamide. Using the product from reference example 64d. $^1$H NMR (300 MHz, $CD_3OD$) d 8.09 (s, 1H) 7.78 (d, J=8 Hz, 3H), 7.56 (d, J=8 Hz, 2H), 7.48 (d, J=8 Hz, 1H), 7.24 (d, J=7 Hz, 1H), 4.06 (s, 2H), 3.67 (t, J=8 Hz, 2H), 3.05 (t, J=8 Hz, 2H). MS (ion spray) m/z 360 (M+H$^+$).

Example 1aaaaaak

5-{4-[2-(3-Carbamimidoyl-1H-indol-5-yl) ethylcarbamoyl]phenyl}-2-oxo-2H-pyridin-1-yl)acetic acid. Stirred a solution of (5-{4-[2-(3-Carbamimidoyl-1H-indol-5-yl)ethylcarbamoyl]phenyl}-2-oxo-2H-pyridin-1-yl) acetamide (0.507g, 1.11 mmoles Example 1aaaaac) in 5M HCl (40 mL) and and methanol (20 mL) at 50° C. for 42 hours. The reaction mixture was concentrated and taken up in 9:1 $H_2O$:AcCN (30 mL). The solid impurities were filtered off, and the effluent was purified on an HPLC to give 3.60 mg of the title compound as a white solid. m.p. >250° C. $^1$H NMR ($CD_3OD$): δ 3.07 (t, 2H, J=6 Hz), 3.68 (m, 2H), 4.82 (m, 2H), 6.68 (d, 1H, 9 Hz), 7.26 (d, 1H, J=9 Hz), 7.50 (d, 1H, J=9 Hz), 7.63 (d, 2H, J=8 Hz), 7.78 (s, 1H), 7.83 (d, 2H, J=8 Hz), 7.97 (d, 1H, J=9 Hz), 8.07 (m, 2H), 8.65 (m, 1H). MS (ion spray) m/z 458 (M+H)$^+$. >90% pure by analytical HPLC.

Example 2

Using essentially the same procedure used to prepare example 1a except using the product from reference example 67c there is prepared 3-Carbamimidoyl-5-{2-[4-(6-oxo-1,6-dihydro-pyridin-3-yl)-benzoylamino]-propyl}-indole. $^1$H NMR (300 MHz, DMSO-$d_6$) d 12.24 (bs, 1H), 8.68 (bs, 2H), 8.49 (bs, 2H), 8.33 (d, J=8 Hz, 1H), 8.17 (d, J=3 Hz, 1H), 7.88 (dd, J=10, 3 Hz, 1H), 7.83–7.81 (m, 3H), 7.72 (s, 1H), 7.63 (d, J=8 Hz, 2H), 7.45 (d, J=8 Hz, 1H), 7.19 (d, J=8 Hz, 1H), 6.44 (d, J=9 Hz, 1H), 4.34–4.25 (m, 1H), 3.00 (dd, J=13, 7 Hz, 1H), 2.81 (dd, J=13, 7 Hz, 1H), 1.15 (d, J=7 Hz, 3H); MS (ion spray) m/z 414 (M+H$^+$).

Reference Example 1a

N-(2-[3-Cyano-5-indolyl]ethyl)-4-pyridin-3-ylbenzamide. To a suspension of 4-pyrid-3-ylbenzoic acid (0.430 g, 2.16 mmol, reference example 11b) and diisopropylethylamine (DIEA) (0.42 mL, 2.4 mmol) in $CH_2Cl_2$ (10 mL) is added O-Benzotriazol-1yl-N,N,N',N',-tetramethyluronium tetrafluoro-borate (TBTU) (0.706 g, 2.20 mmol). After 30 minutes, 3-cyano-5-(2-aminoethyl) indole (0.4 g, 2.16 mmol, reference example 2) and DIEA (0.42 mL, 2.4 mmol) are added, followed fifteen minutes later by another portion of DIEA (0.42 mL) in $CH_2Cl_2$ (5 mL) After stirring overnight the solution is concentrated, and the resulting residue chromatographed (10:1 $CH_2Cl_2$:MeOH) to provide the product with some DIEA contamination. This crude product is used without further purification. MS (ion spray) m/z 367 (M+H)$^+$.

The following compounds are prepared using essentially the same procedure described in reference example 1a except using the specified acid:

Reference Example 1b

N-(2-[3-Cyano-5-indolyl]ethyl)-4-pyrimid-5-yl-benzamide. Using the product from reference example 11c. Used without further purification. MS (ion spray) m/z 368 (M+H)$^+$.

Reference Example 1c 5-(Pyridin-2-yl)-thiophene-2-carboxylic acid 2-(3-cyano-5-indolyl)ethylamide. Used without further purification. MS (FAB) m/z 373 (M+H)$^+$.

Reference Example 1d

N-(2-[3-Cyanoindol-5-yl]ethyl)-6-morpholin-4-ylnicotinamide. Using the product from reference example 24a. Used 4:1 methylene chloride: DMF as solvent. Used without further purification. MS (ion spray) m/z 376 (M+H)$^+$.

Reference Example 1e

N-(2-[3-Cyanoindol-5-yl]ethyl)-6-chloronicotinamide. Using commercially available 6-chloronicotinic acid. Used without further purification. MS (EI) m/z 324, 326 (M[$^{35}$Cl, $^{37}$Cl])$^+$.

Reference Example 1f

N-(2-[3-Cyanoindol-5-yl]ethyl)-6-imidazol-1-yl-nicotinamide. Using commercially available 6-imidazol-1-yl-nicotinic acid. Used without further purification. MS (ion spray) m/z 357 (M+H)$^+$.

Reference Example 1g

N-(2-[3-Cyanoindol-5-yl]ethyl)-4-imidazol-1-yl-benzamide. Used without further purification. MS (ion spray) m/z 357 (M+H)$^+$.

Reference Example 1h

N-(2-[3-Cyanoindol-5-yl]ethyl)-4-(3H-imidazol-4-yl) benzamide. Using the product from reference example 35b. Used without further purification. MS (ion spray) m/z 356 (M+H)$^+$.

Reference Example 1i

N-(2-[3-Cyanoindol-5-yl]ethyl)-4-(1,2,4)thiadiazol-5-ylbenzamide. Using the product from reference example 35a. Used without further purification. MS (ion spray) m/z 374 (M+H)$^+$.

Reference Example 1j

N-[2-(3-Cyano-1H-indol-5-yl)-ethyl]-4-(1-carbamoyl-1-methyl-ethyl-benzamide. Using the product from reference example 25a. $^1$H NMR (CDCl$_3$/CD$_3$OD) d 1.58 (s, 6H), 3.05 (t, J=7 Hz, 2H), 3.67 (q, J=7 Hz, 2H), 7.21 (d, J=8 Hz, 1H), 7.44 (m, 3H), 7.56 (s, 1H), 7.75 (d, J=8 Hz, 2H), 7.81 (s, 1H), 8.28 (bt, 1H). MS (ion spray) m/z 375 (M+H).

Reference Example 1k

N-[2-(3-Cyano-1H-indol-5-yl)-ethyl]-4-(1-[N-(2-methoxyethyl)]-carbamoyl-1-methyl-ethyl-benzamide. Using the product from reference example 25b. $^1$H NMR (CDCl$_3$/CD$_3$OD) d 1.58 (s, 6H), 3.05 (t, J=7 Hz, 2H), 3.28 (s, 3H), 3.37 (m, 4H), 3.70 (q, J=7 Hz, 1H), 6.3 (bt, 1H), 7.20 (d, J=10 Hz, 1H), 7.41 (m, 3H), 7.57 (s, 1H), 7.57 (bt, J=7 Hz, 1H), 7.74 (m, 3H). MS (ion spray) m/z 433 (M+H).

Reference Example 1l

N-[2-(3-Cyano-1H-indol-5-yl)-ethyl]-4-(t-butyl)-benzamide. Using commercially available 4-(t-butyl)-benzoic acid. $^1$H NMR (CDCl$_3$) d 1.30 (s, 9H), 3.04 (t, J=7 Hz, 2H), 3.76 (q, J=7 Hz, 2H), 6.32 (bt, J=7 Hz, 1H), 7.11 (dd, J=9, 1 Hz, 1H), 7.27 (d, J=9 Hz, 1H), 7.42 (m, 2H), 7.65 (m, 4H), 9.9 (bs, 1H). MS (ion spray) m/z 346 (M+H).

Reference Example 1m

N-[2-(3-Cyano-1H-indol-5-yl)ethyl]-4-(pyridazin-4-yl)-benzamide. Using the product from reference example 11e. $^1$H NMR (DMSO) d 2.98 (t, J=7 Hz, 2H), 3.59 (q, J=7 Hz, 2H), 7.20 (d, J=8 Hz, 1H), 7.50 (m, 2H), 8.05 (m, 5H), 8.23 (s, 1H), 8.74 (bt, J=7 Hz, 1H), 9.31 (d, J=5 Hz, 1H), 9.7 (bs, 1H). MS (ion spray) m/z 368 (M+H).

Reference Example 1n

N-[2-(3-Cyano-1H-indol-5-yl)-ethyl]-4-(2-methoxy-pyridin-5-yl)-2-methyl-benzamide. Using the product from reference example 33a. $^1$H NMR (DMSO) d 2.30 (s, 3H), 2.96 (t, J=7 Hz, 2H), 3.52 (q, J=7 Hz, 2H), 3.90 (s, 3H), 6.91 (d, J=8 Hz, 1H), 7.20 (d, J=8 Hz, 1H), 7.32 (d, J=8 Hz, 1H), 7.50 (m, 4H), 8.01 (dd, J=8, 3 Hz, 1H), 8.21 (d, J=3 Hz, 1H), 8.33 (t, J=7 Hz, 1H), 8.49 (d, J=3 Hz, 1H). MS (ion spray) m/z 411 (M+H).

Reference Example 1o

3',4'-Dimethoxybiphenyl-4-carboxylic acid (2-[3-cyanoindol-5-yl]ethyl)amide. Using the product from reference example 33b. Used without further purification. MS (ion spray) m/z 426 (M+H)$^+$.

Reference Example 1p

N-(2-[3-Cyano-1H-indol-5-yl]ethyl)-4-(6-methoxypyrid-3-yl)benzamide. Using the product from reference example 33c. Used without further purification. MS (FAB) m/z 397 (M+H)$^+$.

Reference Example 1q

N-(2-[3-Cyano-1H-indol-5-yl]ethyl)-4-(1-oxy-pyrid-4-yl)benzamide. Using the product from reference example 17a. Used without further purification. MS (ion spray) m/z 383 (M+H)$^+$.

Reference Example 1r

N-[2-(3-Cyano-1H-indol-5-yl)-ethyl]-4-(7H-pyrrolo[2,3-d]pyrimidin-6-yl)-benzamide. Using the product from reference example 42a. ¹H NMR (DMSO) δ 2.99 (bt, 2H), 3.56 (m, 2H), 7.20 (m, 2H), 7.50 (m, 2H), 7.94 (d, J=8 Hz, 2H), 8.06 (d, J=8 Hz, 2H), 8.21 (s, 1H), 8.65 (bt, 1H), 8.78 (s, 1H), 9.02 (bs, 1H), 12.13 (bs, 1H), 12.71 (bs, 1H). MS (ion spray) m/z 407 (M+H)⁺.

Reference Example 1s

N-[2-(3-cyano-1H-indol-5-yl)-ethyl]-4-(1H-pyrrolo[3,2-c]pyridin-2-yl)-benzamide. Using the product from reference example 42b. ¹H NMR (DMSO) δ 2.99 (bt, 2H), 3.55 (m, 2H), 7.22 (d, J=8 Hz, 1H), 7.30 (s, 1H), 7.52 (m, 3H), 7.95 (d, J=9 Hz, 2H), 8.02 (d, J=9 Hz, 2H), 8.21 (d, J=3 Hz, 1H), 8.26 (d, J=6 Hz, 1H), 8.66 (bt, 1H), 8.98 (s, 1H), 12.13 (s, 1H), 12.49 (bs, 1H). MS (ion spray) m/z 406 (M+H)⁺.

Reference Example 1t

N-[2-(3-cyano-1H-indol-5-yl)-ethyl]-4-furo[3,2-c]pyridin-2-yl-benzamide. Using the product from reference example 42c. ¹H NMR (DMSO) δ 2.99 (bt, 2H), 3.57 (m, 2H), 7.19 (d, J=8 Hz, 1H), 7.49 (m, 2H), 7.74 (m, 2H), 7.98 (d, J=8 Hz, 2H), 8.06 (d, J=8 Hz, 2H), 8.20 (d, J=3 Hz, 1H), 8.51 (d, J=5 Hz, 1H), 8.71 (bt, 1H), 9.00 (s, 1H), 12.10 (bs, 1H). MS (ion spray) m/z 407 (M+H)⁺.

Reference Example 1u

N-[2-(3-cyano-1H-indol-5-yl)-ethyl]-3-chloro-4-(6-methoxy-pyridin-3-yl)-benzamide. Using the product from reference example 33d. ¹H NMR (DMSO) δ 2.98 (bt, 2H), 3.56 (m, 2H), 3.91 (s, 3H), 6.94 (d, J=9 Hz, 1H), 7.18 (d, J=8 Hz, 1H), 7.48 (d, J=9 Hz, 2H), 7.55 (d, J=8 Hz, 1H), 7.86 (d, J=9 Hz, 2H), 7.99 (s, 1H), 8.20 (s, 1H), 8.27 (s, 1H), 8.74 (bt, 1H), 12.12 (bs, 1H). MS (ion spray) m/z 431 (M+H)⁺.

Reference Example 1w (3-{4-[2-(3-cyano-1H-indol-5-yl)-ethylcarbamoyl]-phenyl}-3-methyl-butyl)-carbamic acid tert-butyl ester. Using the product from reference example 25d. ¹H NMR (DMSO) δ 1.27 (s, 6H), 1.33 (s, 9H), 1.74 (m, 2H), 2.65 (m, 2H), 2.95 (t, J=7 Hz, 2H), 3.51 (q, J=7 Hz, 2H), 6.67 (bt, 1H), 7.18 (d, J=8 Hz, 1H), 7.42 (d, J=8 Hz, 2H), 7.46 (s, 1H), 7.50 (s, 1H), 7.76 (d, J=8 Hz, 2H), 8.20 (d, J=3 Hz, 1H), 8.50 (bt, 1H), 12.12 (s, 1H). MS (ion spray) m/z 475 (M+H)⁺.

Reference Example 1x

N-[2-(3-Carbamimidoyl-1H-indol-5-yl)-ethyl]-2-(4-chloro-phenyl)-acetamide. Using commercially available 2-(4-chloro-phenyl) acetic acid. ¹H NMR (CD₃OD) δ 2.90 (t, J=7 Hz, 2H), 3.40 (s, 2H), 3.48 (q, J=7 Hz, 2H), 7.10 (m, 3H), 7.20 (m, 2H), 7.40 (d, J=8 Hz, 1H), 7.45 (s, 1H), 7.91 (s, 1H). (MS (ion spray) m/z 338/340 (M+H, Cl pattern).

Reference Example 1y 5-chloro-thiophene-2-carboxylic acid [2-(3-cyano-1H-indol-5-yl)-ethyl]-amide. Using commercially available 5-chloro-thiophene-2-carboxylic acid. ¹H NMR (DMSO) δ 2.93 (t, J=7 Hz, 2H), 3.48 (q, J=7 Hz, 2H), 7.16 (m, 2H), 7.50 (m, 2H), 7.61 (d, J=4 Hz, 1H), 8.20 (d, J=3 Hz, 1H), 8.7 (bt, J=7 Hz, 1H), 12.14 (bs, 1H). MS (ion spray) m/z 330/332 (M+H, Cl pattern).

Reference Example 1z

N-(2-[3-Cyanoindol-5-yl]ethyl)-6-(2-hydroxyethylamino)nicotinamide. Using the product from reference example 24c MS (ion spray) m/z 350 (M+H)⁺.

Reference Example 1aa

N-(2-[3-Cyanoindol-5-yl]ethyl)-6-(1,2, 4)-triazol-1-ylnicotinamide. Using commercially available 6-(1,2,4)-triazol-1-ylnicotinic acid. MS (ion spray) m/z 358 (M+H)⁺.

Reference Example 1ab

N-(2-[3-Cyano-indol-5-yl]ethyl)-6-pyrrol-1-ylnicotinamide. Using commercially available 6-(pyrrol-1-yl)-nicotinic acid. MS (ion spray) m/z 356 (M+H)⁺.

Reference Example 1ac

N-(2-[3-Cyanoindol-5-yl]ethyl)-6-pyrazol-1-ylnicotinamide). Using commercially available 6-pyrazol-1-ylnicotinic acid. MS (ion spray) m/z 357 (M+H)⁺.

Reference Example 1ae

N-[2-(3-cyano-1H-indol-5-yl)-ethyl]-3-chloro-benzamide. Using commercially available 3-chloro-benzoic acid. ¹H NMR (DMSO) δ 2.98 (t, J=7 Hz, 2H), 3.53 (q, J=7 Hz, 2H), 7.18 (d, J=8 Hz, 1H), 7.50 (m, 3H), 7.60 (m, 1H), 7.79 (d, J=8 Hz, 1H), 7.82 (s, 1H), 8.20 (d, J=2 Hz, 1H), 8.70 (bt, J=7 Hz, 1H). MS (EI) m/z 323/325 (M+, Cl pattern).

Reference Example 1af

N-[2-(3-Cyano-1H-indol-5-yl)-ethyl]-2-(3-chloro-phenyl)-acetamide. Using commercially available 2-(3-chloro-phenyl) acetic acid. ¹H NMR (CD₃OD) δ 2.90 (t, J=7 Hz, 2H), 3.42 (s, 2H), 3.48 (q, J=7 Hz, 2H), 7.10 (m, 2H), 7.21 (m, 3H), 7.40 (d, J=8 Hz, 1H), 7.45 (s, 1H), 7.91 (s, 1H), 8.11 (bs, 1H). MS (ion spray) m/z 338/340 (M+H, Cl pattern).

Reference Example 1ag 4-(2-t-Butyloxycarbonylamino-methyl)-pyridin-4-yl)-N-[2-(3-cyano-1H-indol-5-yl)-ethyl]-benzamide. Using the, product from reference example 33e. ¹H NMR (DMSO) δ 1.38 (s, 9H), 2.96 (t, J=7 Hz, 2H), 3.55 (q, J=7 Hz, 2H), 4.27 (d, J=6 Hz, 2H), 7.16 (d, J=8 Hz, 1H), 7.45 (m, 3H), 7.59 (m, 2H), 7.80 (d, J=8 Hz, 2H), 7.94!(d, J=8 Hz, 2H), 8.17 (d, J=3 Hz, 1H), 8.55 (d, J=5 Hz, 1H), 8.65 (t, J=7 Hz, 1H). MS (ion spray) m/z 496 (M+H).

Reference Example 1ah

4-{4-[2-(3-Cyano-1H-indol-5-yl)-ethylcarbamoyl]-pyridine-2-carboylic acid amide. Using the product from reference example 33f. ¹H NMR (DMSO) δ 3.0 (t, J=7 Hz, 2H), 3.57 (q, J=7 Hz, 2H), 7.19 (d, J=8 Hz, 1H), 7.50 (d, J=8 Hz, 1H), 7.51 (s, 1H), 7.75 (bs, 1H), 8.0 (m, 5H), 8.2 (bs, 2H), 8.35 (s, 1H), 8.73 (m, 2H). MS (ion spray) m/z 410 (M+H).

Reference Example 1ai

N-[2-(3-Cyano-1H-indol-5-yl)ethyl-]-4-(2-dimethylaminomethyl-pyridin-4-yl)benzamide). Using the product from reference example 33g. ¹H NMR (CD₃OD) δ 2.63 (s, 6H), 3.06 (t, J=7 Hz, 2H), 3.67 (t, J=7 Hz, 2H), 4.08 (s, 2H), 7.24 (d, J=8 Hz, 1H), 7.45 (d, J=8 Hz, 1H), 7.55 (s, 1H), 7.70 (d, J=5 Hz, 1H), 7.81 (s, 1H), 7.84 (d, J=8 Hz, 2H), 7.91 (d, J=8 Hz, 2H), 8.64 (d, J=5 Hz, 1H). MS (ion spray) m/z 424 (M+H).

Reference Example 1ak

N-[2-(3-cyano-1H-indol-5-yl)-ethyl]-4-(6-methoxy-pyridazin-3-yl)-benzamide. Using the product from reference example 11f. ¹H NMR (DMSO) δ 3.00 (t, J=7 Hz, 2H), 3.57 (m, 2H), 4.10 (s, 3H), 7.20 (d, J=8 Hz, 1H), 7.36 (d, J=9 Hz, 1H), 7.48 (d, J=8 Hz, 1H), 7.52 (s, 1H), 7.96 (d, J=9 Hz, 2H), 8.20 (m, 4H), 8.68 (bt, 1H), 12.10 (bs, 1H). MS (ion spray) m/z 398 (M+H)⁺.

Reference Example 1al

N-[2-(3-cyano-1H-indol-5-yl)-ethyl]-4-[1-(2-dimethylamino-ethyl)-6-oxo-1,6-dihydro-pyridazin-3-yl]-benzamide. Using the product from reference example 61a. ¹H NMR (DMSO) δ 2.49 (s, 6H), 2.98 (bt, 2H), 3.06 (m, 2H), 3.55 (m, 2H), 4.37 (bt, 2H), 7.10 (d, J=10 Hz, 1H), 7.18 (d, J=8 Hz, 1H), 7.48 (d, J=8 Hz, 1H), 7.51 (s, 1H), 7.94 (d, J=9 Hz, 2H), 8.00 (d, J=9 Hz, 2H), 8.12 (d, J=10 Hz, 1H), 8.20 (d, J=2 Hz, 1H), 8.68 (bt, 1H), 12.12 (s, 1H). MS (ion spray) m/z 455 (M+H)⁺.

Reference Example 1am

N-[2-(3-cyano-1H-indol-5-yl)-ethyl]-4-[1-(3-dimethylamino-propyl)-6-oxo-1,6-dihydro-pyridazin-3-yl]-benzamide. Using the product from reference example 61b. ¹H NMR (DMSO) δ 2.05 (m, 2H), 2.51 (s, 6H), 2.79 (bt, 2H), 2.98 (bt, 2H), 3.56 (m, 2H), 4.21 (bt, 2H), 7.10 (d, J=10 Hz, 1H), 7.19 (d, J=8 Hz, 1H), 7.49 (m, 2H), 7.94 (d, J=8 Hz, 2H), 8.00 (d, J=8 Hz, 2H), 8.14 (d, J=10 Hz, 1H), 8.22 (d, J=3 Hz, 1H), 8.68 (m, 1H), 12.12 (bs, 1H). MS (ion spray) m/z 469 (M+H)⁺.

Reference Example 1an

N-[2-(3-Cyano-1H-indol-5-yl)-ethyl]-4-[2-(2-dimethylamino-ethylamino)-pyrimidin-4-yl]-benzamide. Using the product from reference example 83 ¹H NMR (DMSO) δ 2.20 (s, 6H), 2.95 (t, J=7 Hz, 2H), 3.31 (m, 2H), 3.44 (bm, 2H), 3.51 (bm, 2H), 7.07 (t, J=7 Hz, 1H), 7.18 (m, 2H), 7.45 (d, J=8 Hz, 1H), 7.50 (s, 1H), 7.90 (d, J=8 Hz, 2H), 8.17 (d, J=8 Hz, 2H), 8.18 (s, 1H), 8.37 (d, J=6 Hz, 1H), 8.67 (t, J=7 Hz, 1H). MS (ion spray) m/z 454 (M+H).

Reference Example 1ao

N-[2-(3-Cyano -1H-indol-5-yl)-ethyl]-4-[2-methoxy-pyrimidin-4-yl]-benzamide. Using the product from reference example 17b. ¹H NMR (DMSO) δ 2.96 (t, J=7 Hz, 2H), 3.54 (q, J=7 Hz, 2H), 4.0 (s, 3H), 7.17 (d, J=8 Hz, 1H), 7.46 (m, 2H), 7.78 (d, J=5 Hz, 1H), 7.95 (d, J=8 Hz, 2H), 8.18 (d, J=3 Hz, 1H), 8.26 (d, J=8 Hz, H), 8.70 (d, J=5 Hz, 1H), 8.75 (t, J=7 Hz, 1H). MS (ion spray) m/z 398 (M+H).

Reference Example 1ap

N-(2-[3-Cyanoindol-5-yl]ethyl)-4-(1-[2-dimethylaminoethyl)-6-oxo-1,6-dihydropyridin-3-yl)benzamide. Using the product from reference example 17c ¹H NMR (1:1 CD₃OD: CDCl₃): δ 2.46 (6H, s), 2.86 (2H, m), 3.08 (2H, m), 3.70 (2H, m), 4.23 (2H, m), 6.70 (1H, d, J=9 Hz), 7.24 (1H, d, J=8 Hz), 7.49 (1H, d, J=9 Hz), 7.54–7.61 (3H, m), 7.79–7.92 (4H, m), 7.92 (1H, s). MS (ion spray) m/z 454 (M+H)⁺.

Reference Example 1aq

N-(2-[3-Cyanoindol-5-yl]ethyl)-4-(1-carbamoylmethyl-6-oxo-1,6-dihydropyridin-3-yl)benzamide. Using the product from reference example 17d. MS (ion spray) m/z 440 (M+H)⁺.

Reference Example 1ar 4-(3-Amino-[1,2,4]triazin-6-yl)-N-[2-(3-cyano-1H-indol-5-yl)-ethyl]-benzamide. Using the appropriate product from reference example 86a ¹H NMR (DMSO-d₆) d 2.98 (2H, t, J=6 Hz), 3.56 (2H, m), 7.15–7.55 (5H), 7.90–8.35 (6H), 8.75 (1H, t, J=5 Hz), 9.28 (1H, s); MS, m/z (ion spray) 384 (M+H)⁺.

Reference Example 1as 4-(3-Amino-[1,2,4]triazin-5-yl)-N-[2-(3-cyano-1H-indol-5-yl)-ethyl]-benzamide. Using the appropriate product from reference example 86a.

Reference Example 1at

N-[2-(3-Cyano-1H-indol-5-yl)-ethyl]-4-(3-oxo-2,3-dihydro-[1,2,4]triazin-6-yl)-benzamide. Using the product from reference example 86b: MS, m/z (ion spray) 403 [(M+18)+H]⁺.

Reference Example 1au

N-[2-(3-Cyano-1H-indol-5yl)ethyl]-4-(5-oxo-4,5-dihydro-[1,2,4]oxadiazol-3-yl)-benzamide. Using the product from reference example 86c. MS, m/z (ion spray) 374 [(M+H]⁺.

Reference Example 1av

Ethyl 4-(1-carbamoylmethyl-6-oxo-1,6-dihydropyridin-3-yl)benzoate. Using the product from reference example 67a as the acid component and ammonia as the amine. ¹H NMR (1:2 CD₃OD: CDCl₃): δ 1.43 (3H, t, J=7 Hz), 4.41 (2H, q, J=7 Hz), 4.72 (2H, s), 6.72 (1H, d, J=9 Hz), 7.58 (2H, d, J=8 Hz), 7.82 (1H, d, J=2 Hz), 7.85 (1H, dd, J=9, 2 Hz), 8.09 (2H, d, J=8 Hz). MS (ion spray) m/z 301 (M+H)⁺.

Reference Example 1aw

N-[2-(3-Cyano-1H-indol-5-yl)-ethyl]-4-[2-(morpholin-4yl-ethylamino)-pyrimidin-4-yl]-benzamide. Using the product from reference example 92a. ¹H NMR (DMSO): δ 2.46 (bm, 6H), 2.99 (t, J=7 Hz, 2H), 3.42–3.62 (m, 8H), 7.09 (bt, J=5 Hz, 1H), 7.20 (m, 2H), 7.92 (d, J=8 Hz, 2H), 8.20 (m, 3H), 8.39 (m, 1H), 8.69 (t, J=5 Hz, 1H). MS (ion spray) m/z 496 (M+H)⁺.

Reference Example 1ax

N-[2-(3-Cyano-1H-indol-5-yl)-ethyl]-4-[2-(3-dimethylamino-propylamino)-pyrimidin-4-yl]-benzamide. Using the product from reference example 92b. ¹H NMR (CD₃OD): δ 1.90 (m, 2H), 2.59 (t, J=7 Hz, 2H), 3.05 (t, J=7 Hz, 2H), 3.50 (t, J=7 Hz, 2H), 3.66 (t, J=7 Hz, 2H), 7.13 (d, J=5 Hz, 1H), 7.23 (d, J=8 Hz, 1H), 7.45 (d, J=8 Hz, 1H), 7.56 (s, 1H), 7.86 (d, J=8 Hz, 2H), 7.90 (s, 1H), 8.16 (d, J=8 Hz, 2H), 8.30 (d, J=5 Hz, 1H). MS (ion spray) m/z 468 (M+H)⁺.

Reference Example 1ay

N-[2-(3-Cyano-1H-indol-5-y)-ethyl]-4-[2-([2-dimethylamino-ethyl]-methyl-amino)-pyrimidin-4-yl]-benzamide. Using the product from reference example 92c. ¹H NMR (CDCl₃): δ 2.35 (s, 6H), 2.60 (t, J=7 Hz, 2H), 3.05 (t, J=7 Hz, 2H), 3.23 (s, 3H), 3.77 (q, J=7 Hz, 2H), 3.85 (t, J=7 Hz, 2H), 6.25 (bt, J=7 Hz, 1H), 6.90 (d, J=5 Hz, 1H), 7.17 (bd, J=8 Hz, 1H), 7.36 (bd, J=8 Hz, 1H), 7.61 (bs, 1H), 7.67 (bs, 1H), 7.75 (d, J=8 Hz, 2H), 8.04 (d, J=8 Hz, 2H), 8.35 (d, J=5 Hz, 1H), 9.3 (bs, 1H). MS (ion spray) m/z 468 (M+H)⁺.

Reference Example 1az

N-[2-(3-Cyano-1H-indol-5-yl)-ethyl]-4-[2-chloro-pyrimidin-4-yl]-benzamide. Using the product from reference example 11g. The crude reaction product was filtered and washed with water dried under vacuum and used without further purification. $^1$H NMR (CDCl$_3$): δ 2.99 (t, J=7 Hz, 2H), 3.55 (q, J=7 Hz, 2H), 7.18 (d, J=8 Hz, 1H), 7.5 (m, 2H), 8.01 (d, J=8 Hz, 2H), 8.27 (m, 4H), 8.77 (t, J=7 Hz, 1H), 8.87 (d, J=5 Hz, 1H), 12.1 (bs, 1H). MS (ion spray) m/z 402 (M+H)$^+$.

Reference Example 1aaa

N-[2-(3-Cyano-1H-indol-5-yl)-ethyl]-4-(2-oxo-hexahydro-pyrimidin-5-yl)-benzamide. Using the product from reference example 17f. MS (ion spray) m/z 388 (M+H)$^+$.

Reference Example 1aab

N-[2-(3-Cyano-1H-indol-5-yl)-ethyl]-4-(1,3-dimethyl-2-oxo-hexahydro-pyrimidin-5-yl)-benzamide. Using the product from reference example 17g. MS (ion spray) m/z 416 (M+H)$^+$.

Reference Example 1aac

Biphenyl-3,4'-dicarboxylic acid 4'-{[2-(3-cyano-1H-indol-5-yl)-ethyl]-amide} 3-methyl ester. Using the product from reference example 11i. $^1$H NMR (DMSO): δ 2.96 (t, J=7 Hz, 2H), 3.54 (q, J=7 Hz, 2H), 3.88 (s, 3H), 7.16 (d, J=8 Hz, 1H), 7.46 (m, 2H), 7.64 (t, J=8 Hz, 1H), 7.78 (d, J=8 Hz, 2H), 7.9–8.01 (m, 4H), 8.19 (d, J=1 Hz, 1H), 8.22 (s, 1H), 8.64 (bt, J=7 Hz, 1H). MS (ion spray) m/z 424 (M+H)$^+$.

Reference Example 1aad

Biphenyl-2,4'-dicarboxylic acid 4'-{[2-(3-cyano-1H-indol-5-yl)-ethyl]-amide} 2-methyl ester. Using the product from reference example 11j. $^1$H NMR (DMSO): δ 2.97 (t, J=7 Hz, 2H), 3.55 (q, J=7 Hz, 2H), 3.60 (s, 3H), 7.20 (d, J=8 Hz, 1H), 7.36 (d, J=8 Hz, 2H), 7.50 (m, 4H), 7.66 (t, J=8 Hz, 1H), 7.80 (d, J=8 Hz, 1H), 7.85 (d, J=8 Hz, 2H), 8.20 (d, J=1 Hz, 1H), 8.65 (bt, J=7 Hz, 1H). MS (ion spray) m/z 424 (M+H)$^+$.

Reference Example 1aae

3'-(2-Dimethylaminoethoxy)biphenyl-4-carboxylic acid [2-(3-cyano-1H-indol-5-yl)ethyl]amide. Using the product from reference example 101a. MS (ion spray) m/z 453 (M+H)$^+$.

Reference Example 1aaf

N-[2-(3-Cyano-1H-indol-5-yl)ethyl]-4-(1-oxypyridin-2-yl)benzamide. Using the product from reference example 101b. MS (ion spray) m/z 383 (M+H)$^+$.

Reference Example 1aag

2'-(2-Dimethylaminoethoxy)biphenyl-4-carboxylic acid [2-(3-cyano-1H-indol-5-yl)ethyl]amide. Using the product from reference example 101c. MS (ion spray) m/z 453 (M+H)$^+$.

Reference Example 1aah

2'-(3-Dimethylaminopropoxy)biphenyl-4-carboxylic acid [2-(3-cyano-1H-indol-5-yl)ethyl]amide. Using the product from reference example 101d. MS (ion spray) m/z 467 (M+H)$^+$.

Reference Example 1aai

3'-(3-Dimethylaminopropoxy)biphenyl-4-carboxylic acid [2-(3-cyano-1H-indol-5-yl)ethyl]amide. Using the product from reference example 101e. MS (ion spray) m/z 467 (M+H)$^+$.

Reference Example 1aaj

N-[2-(3-cyano-1H-indol-5-yl)-ethyl]-4-(1-oxo-pyridin-3-yl)-benzamide. Using the product from reference example 101f $^1$H NMR (DMSO) δ 2.98 (bt, 2H); 3.56 (m, 2H); 7.18 (d, 1H, J=9 Hz); 7.51 (m, 3H); 7.72 (d, 1H, J=9 Hz); 7.86 (d, 2H, J=8 Hz); 7.94 (d, 2H, J=8 Hz); 8.25 (d, 1H, J=7 Hz); 8.65 (s, 1H); 8.72 (bt, 1H); 12.22 (bs, 1H). MS (ion spray) m/z 383 (M+H)$^+$.

Reference Example 1aak

4-[2-(acetylamino-methyl)-pyridin-4-yl]-N-[2-(3-cyano-1H-indol-5-yl)-ethyl]-benzamide. Using the product from reference example 17j $^1$H NMR (DMSO) δ 1.92 (s, 3H); 3.08 (bt, 2H); 3.55 (m, 2H); 4.42 (d, 2H, J=6 Hz); 7.18 (d, 1H, J=9 Hz); 7.49 (m, 3H); 7.63 (s, 2H); 7.86 (d, 2H, J=8 Hz); 7.96 (d, 2H, J=8 Hz); 8.20 (d, 1H); 8.48 (bt, 1H); 8.58 (m, 1H); 8.70 (bt, 1H); 12.17 (bs, 1H). MS (ion spray) m/z 438 (M+H)$^+$.

Reference Example 1aal

4-[[4-[4-[2-(3-cyano-1H-indol-5-yl)-ethylcarbamoyl]-phenyl-]-pyridin-2-ylmethyl]-carbamoyl]-piperidine-1-carboxylic acid tert-butyl ester. Using the product from reference example 17k. $^1$H NMR (CD$_3$OD) δ 1.45 (s, 9H); 1.62 (m, 2H); 1.82 (m, 2H); 2.51 (m, 1H); 2.99 (s, 2H); 3.06 (t, 2H, J=7 Hz); 3.67 (t, 2H, J=7 Hz); 4.12 (m, 2H); 4.54 (s, 2H); 7.22 (d, 1H, J=8 Hz); 4.46 (d, 1H, J=8 Hz); 7.58 (m, 3H); 7.78 (d, 2H, J=9 Hz); 7.90 (m, 3H); 7.97 (s, 2H); 8.54 (d, 1H, J=5 Hz). MS (ion spray) m/z 607 (M+H)$^+$.

Reference Example 1aam

N-[2-(3-Cyano-1H-indol-5-yl)ethyl]-4-[1-(3-dimethylaminopropyl)-6-oxo-1,6-dihydropyridin-3-yl]benzamide. Using the product from reference example 17l. MS (esi loop) m/z 468 (M+H)$^+$.

Reference Example 1aan

N-[2-(3-Cyano-1H-indol-5-yl)ethyl]-4-[6-(3-dimethylaminopropoxy)pyridin-3-yl]benzamide. Using the product from reference example 17m. MS (ion spray) m/z 468 (M+H)$^+$.

Reference Example 1aap tert-Butyl (5-{4-[2-(3-cyano-1H-indol-5-yl)ethylcarbamoyl]phenyl}-2-oxo-2H-pyridin-1-yl)acetate. Using the product from reference example 7b. MS (ion spray) m/z 497 (M+H)$^+$.

Reference Example 1aaq

N-[2-(3-Cyano-1H-indol-5-yl)-ethyl]-4-{1-[(2-dimethylaminoethylcarbamoyl)methyl]-6-oxo-1,6-dihydropyridin-3-yl}benzamide. Using the product from reference example 17n. MS (ion spray) m/z 511 (M+H)$^+$.

Reference Example 1aar

Ethyl 4-{1-[(2-dimethylaminoethylcarbamoyl)methyl]-6-oxo-1,6-dihydropyridin-3-yl}benzoate. Using the product from reference Example 103b. MS (ion spray) m/z 372 (M+H)$^+$.

Reference Example 1aas

N-[2-(3-Cyano-1H-indol-5-yl)-ethyl]-4-(4-dimethylamino-piperidin-1-yl)-benzamide. Using the product from reference example 113a. MS (ion spray) m/z 416 (M+H)+.

Reference Example 1aat

N-[2-(3-Cyano-1H-indol-5-yl)-ethyl]-4-[4-(2-dimethylamino-ethyl-tert-butyloxycarbonyl-amino)-piperidin-1-yl]-benzamide. Using the product from reference example 120. MS (ion spray) m/z 559 (M+H)+.

Reference Example 1aav 4-(4-Tert-butoxycarbonylamino-piperidin-1-yl)-N-[2-(3-carbamimidoyl-1H-indol-5-yl)-ethyl]-benzamide. Using the product from reference example 115. MS (ion spray) m/z 488 (M+H)+.

Reference Example 1aaw

N-[2-(3-Cyano-1H-indol-5-yl)-ethyl]-4-(4-methoxy-piperidin-1-yl)-benzamide. Using the product from reference example 121. MS (Cl) m/z 403 (M+H) +.

Reference Example 1aay 4-(1-Acetyl-piperidin-4-yl)-N-[2-(3-cyano-1H-indol-5-yl)-ethyl]-benzamide. Using the product from reference example 110. MS (ion spray) m/z 415 (M+H)+.

Reference Example 1aaz

4-{4-[2-(3-Cyano-1H-indol-5-yl)-ethylcarbamoyl]-phenyl}-piperidine-1-carboxylic acid amide. Using the product from reference example 107c. MS (ion spray) m/z 416 (M+H)$^+$.

Reference Example 1aaaa

N-[2-(3-Cyano-1H-indol-5-yl)-ethyl]-4-(1-oxo-1-methyl-piperidin-4-yl)-benzamide. Using the product from reference example 112. MS (ion spray) m/z 403 (M+H)$^+$.

Reference Example 1aaab

N-[2-(3-Cyano-1H-indol-5-yl)-ethyl]-4-(1-methyl-piperidin-4-yl)-benzamide. Using the product from reference example 111. MS (ion spray) m/z 387 (M+H)$^+$.

Reference Example 1aaac

N-[2-(3-Cyano-1H-indol-5-yl)-ethyl]-4-(1-methanesulfonyl-piperidin-4-yl)-benzamide. Using the product from reference example 17p. MS (ion spray) m/z 451 (M+H)+.

Reference Example 1aaad 4-(2-Acetylamino-1,1-dimethyl-ethyl)-N-[2-(3-cyano-1H-indol-5-yl)-ethyl]-benzamide. Using the product from reference example 105 and acetic acid as substrates. MS (ion spray) m/z 403 (M+H)$^+$.

Reference Example 1aaaf

N-BOC-Piperidine-4-carboxylic acid (2-{4-[2-(3-cyano-1H-indol-5-yl)-ethylcarbamoyl]-phenyl}-2-methyl-propyl)-amide. Using the product from reference example 105 and N-BOC piperidine-4-carboxylic acid as substrates. MS (ion spray) m/z 572 (M+H)$^+$.

Reference Example 1aaai

N-[2-(3-Cyano-1H-indol-5-yl)-ethyl]-4-(2-dimethylamino-3,4,5,6-tetrahydro-pyrimidin-4-y)-benzamide. Using the product from reference example 108. MS (ion spray) m/z 415 (M+H)$^+$.

Reference Example 1aaaj

N-[2-(3-Cyano-1H-indol-5-yl)-ethyl]-4-(1-oxy-pyridin-4-yloxy)-benzamide. Using the product from reference example 118. MS (ion spray) m/z 399 (M+H)+.

Reference Example 1aaak

N-[2-(3-Cyano-1H-indol-5-yl)-ethyl]-4-(1-methyl-piperidin-4-yloxy)-benzamide. Using the product from reference example 17o. MS (ion spray) m/z 403 (M+H)+.

Reference Example 1aaal 4-(2-[tert-Butoxycarbonylamino]-1,1-dimethylethyl)-N-(2-[1-tert-butoxycarbonyl-3-tert-butoxycarbonylcarbamimidoylindol-5-yl]ethyl)benzamide. Using the products from reference example 25c and 7a. $^1$H NMR (CDCl$_3$): δ 1.31 (6H, s), 1.37 (9H, s), 1.56 (9H, s), 1.66 (9H, s), 3.08 (2H, t, J=6.6 Hz), 3.31 (2H, d, J=6.2 Hz), 3.81 (2H, m), 4.27 (1H, br, m), 6.18 (1H, br, m), 7.25 (1H, d, J=8.4 Hz), 7.37 (2H, d, J=8.2 Hz), 7.64 (2H, d, J=8.2 Hz), 7.88 (1H, s), 8.17 (1H, d, J=8.4 Hz), 8.24 (1H, s). MS (ion spray) m/z 678 (M+H)$^+$.

Reference Example 1aaam

N-(2-[1-tert-Butoxycarbonyl-3-tert-butoxycarbonylcarbamimidoylindol-5-yl]ethyl)-4-(6-[2-dimethylamino-ethoxy]pyridin-3-yl)benzamide. Using the product from reference example 7a as the amine component and the product from reference example 17e as the acid component. MS (ion spray) m/z 671 (M+H)$^+$.

Reference Example 1aaan

N-(2-[1-tert-Butoxycarbonyl-3-tert-butoxycarbonylcarbamimidoylindol-5-yl]ethyl)-4-pyrid-4-ylbenzamide. Using the product from reference examples 11a and 7a. $^1$H NMR (CDCl$_3$): δ 1.55 (9H, s), 1.66 (9H, s), 3.10 (2H, t, J=6.6 Hz), 3.83 (2H, m), 6.32 (1H, br, m), 7.25 (1H, d, J=8.5 Hz), 7.50 (2H, d, J=4.9 Hz), 7.65 (2H, d, J=8.2 Hz), 7.80 (2H, d, J=8.2 Hz), 7.92 (1H, s), 8.17 (1H, d, J=8.5 Hz), 8.23 (1H, s), 8.68 (2H, br, m). MS (ion spray) m/z 584 (M+H)$^+$.

Reference Example 1aaao–1aaav

A solution of N-(2-[1-tert-Butoxycarbonyl-3-tert-butoxycarbonylcarbamimidoylindol-5-yl]ethyl)-amine (1 mL, 0.01M in DMF) (reference example 7a) is added to 30 mg of acylated resin (0.5 mmol/g, reference example 54) and the mixture shaken for 48 hours then filtered. The resin is washed with a further portion of DMF (1 mL) then the combined filtrates concentrated under high vacuum. The residue is used without further purification.

The following compounds are prepared using this procedure:

Reference Example 1aaao

N-(2-[1-tert-butoxycarbonyl-3-tert-butoxycarbonylcarbamimidoylindol-5-yl]ethyl)-4-(4-carbamoyl-phenyl)-benzamide.

Reference Example 1aaap

N-(2-[1-tert-butoxycarbonyl-3-tert-butoxycarbonylcarbamimidoylindol-5-yl]ethyl)-4-(4-methoxyl-phenyl)-benzamide.

Reference Example 1aaaq

N-(2-[1-tert-butoxycarbonyl-3-tert-butoxycarbonylcarbamimidoylindol-5-yl]ethyl)-(5-methoxyindol-2-yl)-carboxamide.

Reference Example 1aaar

N-(2-[1-tert-butoxycarbonyl-3-tert-butoxycarbonylcarbamimidoylindol-5-yl]ethyl)-(6-chloro-benzothiophen-2-yl)-carboxamide.

Reference Example 1aaas 4-(4-benzyloxyl-phenyl)-N-(2-[1-tert-butoxycarbonyl-3-tert-butoxycarbonyl-carbamimidoylindol-5-yl]ethyl)-benzamide.

Reference Example 1aaat

N-(2-[1-tert-butoxycarbonyl-3-tert-butoxycarbonylcarbamimidoylindol-5-yl]ethyl)-4-chloro-benzamide.

Reference Example 1aaau

N-(2-[1-tert-butoxycarbonyl-3-tert-butoxycarbonyl-carbamimidoylindol-5-yl]ethyl)-4-(methylsulphonyl)-benzamide.

Reference Example 1aaav

N-(2-[1-tert-butoxycarbonyl-3-tert-butoxycarbonyl-carbamimidoylindol-5-yl]ethyl)-4-(amino-sulphonyl)-benzamide.

Reference Example 2

3-Cyano-5-(2-aminoethyl)indole. A solution of 1.01 g (4.78 mmol) 3-cyano-5-(2-azidoethyl)indole (reference example 3) and 1.38 g (5.26 mmol) triphenylphosphine in 20 mL THF is stirred overnight to give a white precipitate. Another 20 mL THF and 1 mL distilled water is added. After stirring overnight the resulting solution is concentrated, and the residue chromatographed (10:1 $CH_2Cl_2$:7N $NH_3$ in MeOH) to provide 0.870 g of the product as a white solid in 98% yield. $^1$H NMR ($CD_3OD$): δ 2.87–2.97 (4H, m), 7.17 (1H, d, J=8 Hz), 7.45 (1H, d, J=8 Hz), 7.50 (1H, s), 7.90 (1H, s). MS (EI) m/z 185 $M^+$, 169 $(M-NH_3)^+$, 155 $(M-CH_2NH_2)^+$.

Reference Example 3

3-Cyano-5-(2-azidoethyl)indole. A mixture of 1.92 g (9.38 mmol) 3-cyano-5-(2-chloroethyl)indole (reference example 4) and 1.53 g (23.5 mmol) sodium azide in 10 mL DMF is heated to 80° C. for three hours, followed by azeotroping with toluene. The resulting residue is chromatographed (2:1 hexane:ethyl acetate) to provide 1.89 g of the product as a brown solid in 95% yield. $^1$H NMR ($CDCl_3$): δ 3.03 (2H, t, J=7.1 Hz), 3.57 (2H, t, J=7 Hz), 7.20 (1H, dd, J=8, 1 Hz), 7.43 (1H, d, J=8 Hz), 7.62 (1H, s), 7.73 (1H, d, J=3 Hz), 8.81 (1H, br). MS (ion spray) m/z 212 $(M+H)^+$, 169 $(M-N_3)^+$.

Reference Example 4

3-Cyano-5-(2-chloroethyl)indole. A mixture of 3.29 g (15.8 mmol) 5-(2-chloroethyl)indole-3-carboxaldehyde (reference example 5), 1.15 g (16.6 mmol) hydroxylamine hydrochloride, 6.27 g (52.1 mmol) magnesium sulfate, and 0.601 g (3.16 mmol) p-toluenesulfonic acid monohydrate in 10 mL DMF is heated to 150° C. for 30 minutes. The reaction mixture is azeotroped with toluene, and the resulting residue chromatographed (2:1, then 1:1 hexane:ethyl acetate) to provide 3.08 g of product as a white solid in 95% yield. $^1$H NMR ($CDCl_3$): δ 3.20 (2H, t, J=7 Hz), 3.77 (2H, t, J=7 Hz), 7.21 (1H, dd, J=8, 1 Hz), 7.43 (1H, d, J=8 Hz), 7.63 (1H, s), 7.73 (1H, d, J=3 Hz), 8.66 (1H, br). MS (EI) m/z 204, 206 $(M[^{35}Cl, ^{37}Cl])^+$, 155 $(M-CH_2Cl)^+$.

Reference Example 5

5-(2-Chloroethyl)indole-3-carboxaldehyde. A solution of 1.46 mL (15.7 mmol) phosphorous oxychloride in 5 mL DMF is stirred for 20 minutes. A solution of 2.11 g (13.1 mmol) 5-(2-hydroxyethyl)indole (reference example 6) in 5 mL DMF is added, and the reaction mixture is heated to 80° C. for ten minutes. The reaction is quenched with solid sodium bicarbonate and diluted with 250 mL 1:1 $CH_2Cl_2$:MeOH. The inorganic solids are filtered off, and the filtrate concentrated. The resulting residue is refluxed in 75 mL 1N HCl solution for one hour, then extracted with $CH_2Cl_2$. The organic extracts are combined and concentrated, and the residue chromatographed (20:1 $CH_2Cl_2$:MeOH) to provide 2.45 g of the product as a brown solid in 90% yield. $^1$H NMR ($CDCl_3$): δ 3.19 (2H, t, J=7 Hz), 3.76 (2H, t, J=7 Hz), 7.20 (1H, dd, J=8, 1 Hz), 7.40 (1H, d, J=8 Hz), 7.85 (1H, d, J=3 Hz), 8.19 (1H, s), 8.98 (1H, br), 10.05 (1H, s). MS (EI) m/z 207, 209 $(M[^{35}Cl, ^{37}Cl])^+$, 158 $(M-CH_2Cl)^+$.

Reference Example 6

5-(2-Hydroxyethyl)indole. To a cooled (0° C.) mixture of 1.56 g (38.9 mmol) of a 60% dispersion of sodium hydride in 10 mL THF is slowly added a solution of 5.05 g (25.9 mmol) 5-bromoindole (Acros) in 20 mL THF. After $H_2$ evolution stopped (~10 min) the mixture is cooled to −78° C., and 25.9 mL (64.8 mmol) of a 2.5 M hexane solution of n-butyllithium is added dropwise. After five minutes, added 16.8 mL (38.9 mmol) of a 2.3 M THF stock solution of ethylene oxide and removed cooling bath. After 90 minutes, quenched with 5 mL distilled water. The organic layer is then poured away from the inorganic salts and concentrated. The resulting residue is chromatographed (1:1 hexane:ethyl acetate) to provide 2.24 g of the product as a yellow oil in 54% yield. $^1$H NMR ($CDCl_3$): δ 2.96 (2H, t, J=6.5 Hz), 3.88 (2H, m), 6.51 (1H, m), 7.06 (1H, dd, $J_1$=8.5 Hz, $J_2$=1.5 Hz), 7.19 (1H, m), 7.33 (1H, d, J=8.5 Hz), 7.49 (1H, s), 8.19 (1H, br). MS (EI) m/z 161 $M^+$, 130 $(M-CH_2OH)^+$.

Reference Example 7a 1-tert-Butoxycarbonyl-3-(tert-butoxycarbonylcarbamimidoyl)-5-(2-aminoethyl)indole. A solution of 1-tert-Butoxycarbonyl-3-(tert-butoxycarbonylcarbamimidoyl)-5-(2-[allyloxycarbonylamino]ethyl)indole (reference example 8) (0.199 g, 0.409 mmol), 50 mg tetrakis(triphenylphosphine) palladium (0), and 0.078 mL (0.90 mmol) morpholine in 20 mL $CH_2Cl_2$ is stirred for one hour. TLC showed some starting material present, so another 50 mg palladium catalyst is added. After stirring 45 minutes, the reaction mixture is concentrated, and the residue chromatographed (10:1 $CH_2Cl_2$:7N $NH_3$ in MeOH) to provide the product as a yelow solid. $^1$H NMR ($CDCl_3$): δ 1.57 (9H, s), 1.64 (9H, s), 2.88 (4H, m), 7.23 (1H, dd, $J_1$=8.7 Hz, $J_2$=1.2 Hz), 7.77 (1H, s), 8.16 (1H, d, J=8.7 Hz), 8.25 (1H, s). MS (EI) m/z 402 $M^+$.

Reference Example 7b 4-(1-[tert-Butoxycarbonylmethyl]-2-oxo-2H-pyridin-5-yl)benzoic acid. Prepared using essentially the same procedure used in reference example 7a except using Allyl 4-(1-[tert-butoxycarbonylmethyl]-2-oxo-2H-pyridin-5-yl) benzoate (reference example 85d) as substrate. MS (ion spray) m/z 330 $(M+H)^+$.

Reference Example 8

1-tert-Butoxycarbonyl-3-(tert-butoxycarbonyl-carbamimidoyl)-5-(2-[allyloxycarbonylamino]ethyl)indole. A solution of 0.346 g (0.999 mmol) 3-Carbamimidoyl-5-(2-

[allyloxycarbonylamino]ethyl)indole (reference example 9) 0.655 g (3.00 mmol) di-tert-butyl dicarbonate, and 0.49 mL (3.5 mmol) triethylamine in 40 mL 1:1 $CH_2Cl_2$:THF is stirred at 40° C. for seven hours, then at room temperature overnight, then at 40° C. for four more hours, followed by concentration. The resulting residue is chromatographed (2:1 hexane:ethyl acetate) to provide the product as a white solid in 36% yield. $^1$H NMR ($CDCl_3$): δ 1.56 (9H, s), 1.66 (9H, s), 2.95 (2H, t, J=6.5 Hz), 3.56 (2H, m), 4.51 (2H, d, J=5.4 Hz), 5.21 (2H, m), 5.85 (1H, m), 7.21 (1H, d, J=8.3 Hz), 7.76 (1H, s), 8.15 (1H, d, J=8.3 Hz), 8.40 (1H, s). MS (ion spray) m/z 487 (M+H)$^+$.

Reference Example 9

3-Carbamimidoyl-5-(2-[allyloxycarbonylamino]ethyl) indole. A stream of hydrogen sulfide is bubbled through a solution of 0.392 g (1.11 mmol) 1-Allyloxycarbonyl-3-cyano-5-(2-[allyloxycarbonylamino]ethyl)indole (reference example 10) in 10 mL 9:1 pyridine:triethylamine for fifteen minutes. The reaction is capped and stirred for 36 hours, followed by removal of solvent by distillation. The residue is dissolved in 10 mL acetone, and 1.82 mL iodomethane is added. The reaction vessel is fitted with a cooled condenser and heated to 60° C. for one hour. The reaction is concentrated, and 10 mL MeOH and 0.940 g (12.2 mmol) are added. This mixture is stirred at 60° C. for four hours, then at room temperature overnight, followed by concentration and chromatography (5:1 $CH_2Cl_2$:MeOH) to provide the product as the acetate salt in 90% yield. $^1$H NMR ($CD_3OD$): δ 1.98 (3H, s), 2.94 (2H, t, J=7.2 Hz), 3.41 (2H, t, J=7.2 Hz), 4.49 (2H, d, J=4.9 Hz), 5.19 (2H, m), 5.87 (1H, m), 7.20 (1H, d, J=8.3 Hz), 7.50 (1H, d, J=8.3 Hz), 7.73 (1H, s), 8.14 (1H, s). MS (ion spray) m/z 287 (M+H)$^+$.

This compound can also be prepared directly, from 3-cyano-5-(2-[allyloxycarbonylamino]ethyl)indole (reference example 23) using essentially the same procedure as described above.

Reference Example 10

1-Allyloxycarbonyl-3-cyano-5-(2-[allyloxycarbonylamino]ethyl)indole. A solution of 1.89 g (8.95 mmol) 3-cyano-5-(2-azidoethyl)-indole (reference example 3) and 2.58 g (9.85 mmol) triphenylphosphine in 40 mL THF is stirred overnight to give a white precipitate. To this is added 0.32 mL $H_2O$, and stirring is continued overnight. Then 4.75 g (44.8 mmol) sodium bicarbonate and 15 mL $H_2O$, followed by 2.1 mL (20 mmol) allyl chloroformate, is added. After stirring overnight another 2 mL allyl chloroformate is added, followed by stirring overnight. The reaction mixture is diluted with ethyl acetate and washed with distilled water. The organic layer is concentrated, and the resulting residue chromatographed (3:1, then 1:1 hexane:ethyl acetate) to provide the product as a white solid in 61.7% yield. $^1$H NMR ($CDCl_3$): δ 2.96 (2H, t, J=7.0 Hz), 3.50 (2H, m), 4.56 (2H, d, J=5.4 Hz), 4.97 (2H, d, J=5.9 Hz), 5.25 (2H, m), 5.46 (2H, m), 5.91 (1H, m), 6.06 (1H, m), 7.31 (1H, d, J=8.6 Hz), 7.54 (1H, s), 8.14 (1H, d, J=8.6 Hz), 8.15 (1H, s). MS (EI) m/z 353 M$^+$, 268 (M–$CO_2$Allyl)$^+$.

Reference Example 11a

4-[Pyridin-4-yl]-Benzoic Acid. To a suspension of 4-[pyridin-4-yl]-benzaldehyde (approx. 2.8 g, 15 mmol) (reference example 12a) in t-butanol (100 mL) is added 2-methy-but-2-ene (15 mL) followed by a solution comprised of $NaClO_2$ (14.7 g, tech.grade) and $NaH_2PO_4 \cdot H_2O$ (14.7 g, 105 mmol) in $H_2O$ (100 mL). This mixture is stirred for 20 minutes then the precipitated solid filtered off. This solid is washed with water then set aside. The organic phase of the mother liquor is separated, then washed with brine, dried over $MgSO_4$ and concentrated to give a solid. This material is combined with the solid obtained by filtration and dried under vacuum to give 2.34 g of the title compound. $^1$H NMR (DMSO) d 7.77 (d, J=6 Hz, 2H), 7.93 (d, J=8 Hz, 2H), 8.06 (d, J=8 Hz, 2H), 8.70 (d, J=6 Hz, 2H). MS (EI) m/z 199 (M)$^+$.

Reference Example 11b

By employing essentially the same procedure as used in reference example 11a, except using the product from reference example 12b, there is prepared 4-[Pyridin-3-yl]-Benzoic Acid. $^1$H NMR (DMSO) d 7.52 (dd, J=8, 5 Hz, 1H), 7.87 (d, J=8 Hz, 2H), 8.06 (d, J=8 Hz, 2H), 8.15 (dd, J=8, 2 Hz, 1H), 8.62 (dd, J=5, 2 Hz, 1H), 8.96 (s, 1H), 13.05 (bs, 1H). MS (EI) m/z 199 (M)$^+$.

Reference Example 11c

By employing essentially the same procedure as used in reference example 11a, except using the product from reference example 12c, there is prepared 4-[Pyrimidin-5-yl]-Benzoic Acid. $^1$H NMR (DMSO) d 7.95 (d, J=8 Hz, 2H), 8.10 (d, J=8 Hz, 2H), 9.23 (s, 21H), 9.25 (s, 1H), MS (EI) m/z 200 (M)$^+$.

Reference Example 11d

By employing essentially the same procedure as used in reference example 11a, except using the product from reference example 12d, there is prepared 4-[Pyridazin-3-yl]-Benzoic Acid. $^1$H NMR (DMSO) d 7.85 (dd, J=8, 4 Hz. 1H), 8.1 (d, J=8 Hz, 2H), 8.29 (d, J=8 Hz, 2H), 8.31 (d, J=8 Hz, 1H), 9.26 (d, J=4 Hz, 1H). MS (EI) m/z 200 (M)$^+$.

Reference Example 11e

By employing essentially the same procedure as used in reference example 11a, except using the product from reference example 12e, there is prepared 4-[Pyridazin-4-yl]-Benzoic Acid. $^1$H NMR (DMSO) d 8.10 (m, 5H), 9.33 (d, J=4 Hz, 1H), 9.67 (bs, 1H). MS (EI) m/z 200 (M)$^+$.

Reference Example 11f

By employing essentially the same procedure as used in reference example 11a, except using the product from reference example 12f, there is prepared 4-(6-methoxy-pyridazin-3-yl)-benzoic acid. $^1$H NMR (DMSO) δ 4.10 (s, 3H), 7.36 (d, J=9 Hz, 1H), 8.08 (d, J=8 Hz, 2H), 8.20 (d, J=8 Hz, 2H), 8.26 (d, J=9 Hz, 1H), 13.00 (bs, 1H). MS (EI) m/z 230 (M$^+$).

Reference Example 11g

By employing essentially the same procedure as used in reference example 11a, except using the product from reference example 12g, there is prepared 4-[2-chloro-pyrimidin-4-yl]-benzoic acid. $^1$H NMR (DMSO) δ 8.09 (d, J=8 Hz, 2H), 8.21 (d, J=5 Hz, 1H), 8.30 (d, J=8 Hz, 2H), 8.88 (d, J=5 Hz, 1H). MS (EI) m/z 234/236 (M+, Cl pattern).

Reference Example 11h

By employing essentially the same procedure as used in reference example 11a, except using the product from reference example 97a, there is prepared 4-[2-oxo-pyrimidin- 4-yl]-benzoic acid. $^1$H NMR (DMSO) δ 7.77 (d, J=8 Hz, 2H), 7.97 (d, J=8 Hz, 1H), 8.70 (bs, 2H). MS (EI) m/z 216 (M)$^+$.

Reference Example 11i

By employing essentially the same procedure as used in reference example 11a, except using the product from reference example 97b, there is prepared Biphenyl-3,4'-dicarboxylic acid 3-Methyl ester. $^1$H NMR (DMSO) δ 3.90 (s, 3H), 7.69 (t, J=8 Hz, 2H), 7.86 (d, J=8 Hz, 2H), 8.0–8.11 (m, 4H), 8.25 (s, 1H). MS (EI) m/z 256 (M)$^+$.

Reference Example 11j

By employing essentially the same procedure as used in reference example 11a, except using the product from reference example 97c, there is prepared Biphenyl-2,4'-dicarboxylic acid 2-Methyl ester. $^1$H NMR (CDCl$_3$) δ 3.68 (s, 3H), 7.47–7.51 (m, 5H), 8.19 (d, J=8 Hz, 1H). MS (EI) m/z 256 (M)$^+$.

Reference Example 12a

4-[Pyridin-4-yl]-Benzaldehyde. To a cooled (−78° C.) solution of oxalyl chloride in CH$_2$Cl$_2$ (15 mL, 1M) is added, dropwise, DMSO (3 mL). The resulting solution is stirred for 5 minutes then a solution of 4-[pyridin-4-yl]-benzyl alcohol (2.80 g, 15 mmol) (reference example 13a) in CH$_2$Cl$_2$/DMSO (27 mL, 3:1 CH$_2$Cl$_2$/DMSO) is added dropwise. The resulting mixture is stirred 5 minutes then Et$_3$N added (15 mL, 108 mmol) in one portion. The cold bath is removed and stirring continued for 15 minutes. The reaction mixture is then diluted with ethyl acetate, washed with water and then brine, dried over MgSO$_4$ and concentrated. The crude, orange solid product is used without further purification.

Reference Example 12b

By employing essentially the same procedure as used in reference example 12a, except using the product from reference example 13b, there is prepared 4-[Pyridin-3-yl]-Benzaldehyde.

Reference Example 12c

By employing essentially the same procedure as used in reference example 12a, except using the product from reference example 13c, there is prepared 4-[Pyrimidin-5-yl]-Benzaldehyde.

Reference Example 12d

By employing essentially the same procedure as used in reference example 12a, except using the product from reference example 14a, there is prepared 4-[Pyridazin-3-yl]-Benzaldehyde.

Reference Example 12e

By employing essentially the same procedure as used in reference example 12a, except using the product from reference example 14b, there is prepared 4-[Pyridazin-4-yl]-Benzaldehyde.

Reference Example 12f

By employing essentially the same procedure as used in reference example 12a, except using the product from reference example 13d, there is prepared 4-(6-methoxy-pyridazin-3-yl)-benzaldehyde. $^1$H NMR (CDCl$_3$) δ 4.22 (s, 3H), 7.10 (d, J=9 Hz, 1H), 7.86 (d, J=9 Hz, 1H), 8.02 (d, J=8 Hz, 2H), 8.20 (d, J=8 Hz, 2H), 10.10 (s, 1H). MS (EI) m/z 214 (M$^+$).

Reference Example 12g

By employing essentially the same procedure as used in reference example 12a, except using the product from reference example 14c, there is prepared 4-[2-(2-chloro)-pyrimidin-4-yl]-benzaldehyde. $^1$H NMR (DMSO) δ 8.10 (d, J=8 Hz, 2H), 8.29 (d, J=5 Hz, 1H), 8.41 (d, J=8 Hz, 2H), 8.94 (d, J=5 Hz, 1H), 10.13 (s, 1H). MS (EI) m/z 218/220 (M+, Cl pattern).

Reference Example 13a

4-[Pyridin-4-yl]-Benzyl alcohol. To a cooled (−78° C.) solution of 4-bromo-benzyl-(t-butyidimethylsilyl)-ether (5.46 g, 18 mmol) (reference example 16) in THF (40 mL) is added, dropwise, n-BuLi (8.8 mL, 2.5M in hexanes). On complete addition, the resulting solution is stirred for 10 minutes then ZnCl$_2$ (40 mL, 0.5M in THF) is added. The cold bath is removed and stirring continued for 10 minutes. To this solution is added 4-bromo-pyridine* (approx. 2.2 mL, 22 mmol) in hexanes (25 mL) followed by (Ph$_3$P)$_4$Pd (900 mg, 0.77 mmol). The resulting mixture is heated to 60° C. at this temperature for 1 hour. The reaction mixture is allowed to cool to room temperature then diluted with ether, washed, sequentially, with 5% aqueous ammonium hydroxide solution and brine, dried over MgSO$_4$ and concentrated. The residue is taken up in THF (30 mL) and treated with n-Bu$_4$NF (25 mL, 1M in THF). The resulting solution is stirred for 25 minutes then diluted with ethyl acetate, washed with water and brine, dried over MgSO$_4$ and concentrated. The residue is triturated with ether, filtered and the solid dried under vacuum to give 2.8 g of the title compound as a tan solid.

*4-bromo-pyridine is obtained from its HCl salt by dissolving the salt in cold 1M NaOH (5% excess) then extracting with cold hexane. The hexane extract is dried over MgSO$_4$ and used without further manipulation.

Reference Example 13b

By employing essentially the same procedure as used in reference example 13a, except using 3-bromopyridine, there is prepared 4-[Pyridin-3-yl]-Benzyl alcohol. $^1$H NMR (DMSO) d 4.55 (d, J=6 Hz, 2H), 5.25 (t, J=6 Hz, 1H), 7.44 (d, J=8 Hz, 2H), 7.48 (dd, J=8, 5 Hz, 1H), 7.68 (d, J=8 Hz, 2H), 8.07 (dt, J=8, 2 Hz, 1H), 8.56 (dd, J=5, 2 Hz, 1H), 8.88 (d, J=2 Hz, 1H). MS (EI) m/z 185 (M)$^+$.

Reference Example 13c

By employing essentially the same procedure as used in reference example 13a, except using 5-bromopyrimidine, there is prepared 4-[Pyrimidin-5-yl]Benzyl Alcohol. $^1$H NMR (CDCl$_3$) d 2.61 (bs, 1H), 4.80 (d, J=7 Hz, 2H), 7.55 (m, 4H), 8.88 (s, 2H), 9.20 (s, 1H). MS (EI) m/z 186 (M)$^+$.

Reference Example 13d

By employing essentially the same procedure as used in reference example 13a, except using the product from reference example 41b, there is prepared 4-(6-methoxy-pyridazin-3-yl)-benzyl alcohol. $^1$H NMR (CDCl$_3$) δ 1.85 (bt, 1H), 4.19 (s, 3H), 4.78 (d, J=5 Hz, 2H), 7.06 (d, J=9 Hz, 1H), 7.50 (d, J=8 Hz, 2H), 7.78 (d, J=9 Hz, 1H), 8.01 (d, J=8 Hz, 2H). MS (EI) m/z 216 (M$^+$).

Reference Example 14a

4-[Pyridazin-3-yl]-Benzyl Alcohol. To a solution of 4-[pyridazin-3-yl]-benzyl-(t-butyidimethylsilyl) ether (2.71 g, 9 mmol) (reference example 15, less polar product) is added a solution of tetra-n-butylammonium fluoride in THF (12 mL, 1M). The resulting solution is stirred for 15 minutes then diluted with ethyl acetate. This solution is washed with water then brine. The aqueous washings are back extrated with 10% methanol in $CH_2Cl_2$. The combined organic extracts are dried over $MgSO_4$ then concentrated. The residue is purified by flash chromatography (eluting with ethyl acetate) to give 1.50 g of the title compound as a white solid. $^1$H NMR (CDCl$_3$) d 2.28 (t, J=5 Hz, 1H), 4.79 (d, J=5 Hz, 2H), 7.50 (m, 3H), 7.85 (dd, J=8, 1 Hz, 1H), 8.05 (d, J=8 Hz, 2H), 9.13 (dd, J=5, 1 Hz, 1) MS (EI) m/z 186 (M)$^+$.

Reference Example 14b

By employing essentially the same procedure as used in reference example 14a, except using the more polar product from reference example 15, there is prepared 4-[Pyridazin-4-yl]-Benzyl Alcohol. $^1$H NMR (CDCl$_3$) d 2.20 (t, J=6 Hz, 1H), 4.79 (d, J=6 Hz, 2H), 7.53 (d, J=8 Hz, 2H), 7.63 (m, 3H), 9.18 (d, J=4 Hz, 1H), 9.42 (bs, 1H). MS (EI) m/z 186 (M)$^+$.

Reference Example 14c

By employing essentially the same procedure as used in reference example 14a, except using the product from reference example 84, there is prepared 4-[2-(2-chloro)-pyrimidin-4-yl]-benzyl alcohol. $^1$H NMR (DMSO) d 4.57 (d, J=5 Hz, 2H), 5.34 (t, J=5 Hz, 1H), 7.49 (d, J=8 Hz, 2H), 8.14 (m, 3H), 8.79 (d, J=5 Hz, 1H). MS (EI) m/z 220/222 (M+, Cl pattern)

Reference Example 15

4-[Pyridazin-3-yl]-Benzyl-(t-Butyidimethylsilyl) Ether and 4-[Pyridazin-4-yl]-Benzyl-(t-Butyidimethylsilyl) Ether. To a solution cooled (−78° C.) of 4-Bromobenzyl(t-butyldimethylsilyl)-ether (9.03 g, 30 mmol) (reference example 16 in THF (60 mL) is added, dropwise, n-BuLi (12.6 mL, 2.5M in hexanes). The resulting solution is stirred for 5 minutes then pyridazine (2.25 mL, 31 mmol) is added in one portion. This solution is stirred for 20 minutes then aqueous HCl added (30 mL, 1M). The reaction mixture is diluted with ether, washed with brine dried over $MgSO_4$ and concentrated. The residue is taken up in acetone (45 mL) and this solution added to a solution of $KMnO_4$ in acetone (9.3 g, 60 mmol in approx. 200 mL). On complete addition, the brown colored mixture is stirred 5 minutes then filtered through celite. The mother liquor is concentrated and the residue purified by flash chromatography (eluting with 50% ethyl acetate in hexanes) to give 2.71 g of 4-[pyridazin-3-yl]-benzyl-(t-butyldimethylsilyl) ether: $^1$H NMR (CDCl$_3$) d 0.12 (s, 6H), 0.99 (s, 9H), 4.83 (s, 2H), 7.50 (d, J=8 Hz, 2H), 7.53 (dd, J=8, 5 Hz, 1H), 7.85 (dd, J=8, 1 Hz, 1H), 8.06 (d, J=8 Hz, 2H), 9.14 (dd, J=5, 1 Hz, 1H). MS (EI) m/z 301 (M+H)$^+$ and 2.0 g of 4-[pyridazin-4-yl]-benzyl-(t-butyidimethylsilyl) ether: $^1$H NMR (CDCl$_3$) d 0.11 (s, 6H), 0.96 (s, 9H), 4.80 (s, 2H), 7.47 (d, J=8 Hz, 2H), 7.63 (m, 3H), 9.20 (d, J=4 Hz, 1H), 9.45 (bs, 1H). MS (EI) m/z 301 (M+H)$^+$.

Reference Example 16

4-Bromobenzyl-(t-butyidimethylsilyl)-ether. To a cooled (0° C.) solution of 4-bromo-benzyl alcohol (3.74 g, 20 mmol) in ether (80 mL) is added 2,6-lutidine (2.6 mL, 22 mmol) followed by t-butyldimethylsilyl trifluoromethane-sulphonate (5.05 mL, 22 mmol). The resulting mixture is stirred for 40 minutes then diluted with ether, washed, sequentially, with water and brine, dried over $MgSO_4$ and concentrated. The residue is purified by flash chromatography (eluting with 5% ether in hexanes) to give 6.0 g of the title compound as an oil. $^1$H NMR (CDCl$_3$) d 0.09 (s, 6H), 0.93 (s, 9H), 4.68 (s, 2H), 7.18 (d, J=8 Hz, 2H), 7.44 (d, J=8 Hz, 2H). MS (EI) m/z 300 (M)$^+$.

Reference Example 17a

4-[pyridine-N-oxide-4-yl]-Benzoic Acid. Stirred 0.940 g Methyl 4-[pyridine-N-oxide-4-yl]-benzoate (reference example 18) (4.10 mmol) with 6 mL 1N NaOH and 20 mL 1:1 THF:CH$_3$OH. After 18 hours, added another 3 mL NaOH solution. After 24 more hours acidified with 1N HCl. Collected resulting white solid by filtration. Washed with H$_2$O; air dried. Used without further purification. MS(EI) m/z 215 (M$^+$), 171 (M-CO$_2$)$^+$.

Reference Example 17b

Using essentially the same procedure used to prepare reference example 17a except using methyl 4-(2-methoxy-pyrimidin-4-yl)-benzoate (reference example 19b) there is prepared 4-(2-methoxy-pyrimidin-4-yl)-benzoic acid. $^1$H NMR (DMSO) d 3.99 (s, 3H), 7.78 (d, J=5 Hz, 1H), 8.06 (d, J=8 Hz, 2H), 8.27 (d, J=8 Hz, 2H), 8.70 (d, J=5 Hz, 1H). MS (EI) m/z 230 (M+).

Reference Example 17c

Using essentially the same procedure used to prepare reference example 17a except using ethyl 4-(1-[2-Dimethylaminoethyl]-6-oxo-1,6-dihydropyridin-3-yl)benzoate (reference example 85a) there is prepared 4-(1-[2-Dimethylaminoethyl]-6-oxo-1,6-dihydropyridin-3-yl) benzoic acid. Purified by HPLC; isolated as the TFA salt. $^1$H NMR (D$_2$O): δ 2.86 (6H, s), 3.47 (2H, m), 4.34 (2H, m), 6.62 (1H, d, J=8.6 Hz), 7.50 (2H, d, J=8.4 Hz), 7.82–7.91 (4H, m). MS (ion spray) m/z 287 (M+H)$^+$.

Reference Example 17d

Using essentially the same procedure used to prepare reference example 17a except using ethyl 4-(1-Carbamoylmethyl-6-oxo-1,6-dihydropyridin-3-yl)benzoate (reference example 1av) there is prepared 4-(1-Carbamoylmethyl-6-oxo-1,6-dihydropyridin-3-yl)benzoic acid. MS (ion spray) m/z 273 (M+H)$^+$.

Reference Example 17e

Using essentially the same procedure used to prepare reference example 17a except using ethyl 4-(6-[2-Dimethylaminoethoxy]pyridin-3-yl)benzoate (reference example 85a) there is prepared 4-(6-[2-Dimethylaminoethoxy]pyridin-3-yl)benzoic acid. Purified by HPLC; isolated as the TFA salt. $^1$H NMR (D$_2$O): δ 2.84 (6H, s), 3.48 (2H, m), 4.44 (2H, m), 6.81 (1H, d, J=8.6 Hz), 7.50 (2H, d, J=8.2 Hz), 7.85 (2H, d, J=8.2 Hz), 7.88 (1H, m), 8.18 (1H, s). MS (ion spray) m/z 287 (M+H)$^+$.

Reference Example 17f

Using essentially the same procedure used to prepare reference example 17a except using 4-(2-oxo-hexahydro-pyrimidin-5-yl)-benzoic acid methyl ester as substrate (reference example 95) there is prepared 4-(2-oxo-hexahydro-pyrimidin-5-yl)-benzoic acid. $^1$H NMR (DMSO) δ 3.15 (m, 1H), 3.4 (m, 4H), 6.33 (bs, 2H), 7.45 (d, J=8 Hz, 2H), 7.90 (d, J=8 Hz, 2H).

Reference Example 17g

Using essentially the same procedure used to prepare reference example 17a except using 4-(1,3 dimethyl-2-oxo-hexahydro-pyrimidin-5-yl)-benzoic acid methyl ester as substrate (reference example 98) there is prepared 4-(1,3-dimethyl-2-oxo-hexahydro-pyrimidin-5-yl)-benzoic acid. MS (ion spray) m/z 249 (M+H)$^+$.

Reference Example 17h

Using essentially the same procedure used to prepare reference example 17a except using Biphenyl-3,4'-dicarboxylic acid 4'-{[2-(3-cyano-1H-indol-5-yl)-ethyl]-amide}3-methyl ester as substrate (reference example 1aac) there is prepared Biphenyl-3,4'-dicarboxylic acid 4'-{[2-(3-cyano-1H-indol-5-yl)-ethyl]-amide}. MS (CI) m/z 410 (M+H)$^+$.

Reference Example 17i

Using essentially the same procedure used to prepare reference example 17a except using Biphenyl-2,4'-dicarboxylic acid 4'-{[2-(3-cyano-1H-indol-5-yl)-ethyl]-amide}2-methyl ester as substrate (reference example 1aad) there is prepared Biphenyl-2,4'-dicarboxylic acid 4'-{[2-(3-Cyano-1H-indol-5-yl)-ethyl]-amide}. MS (ion spray) m/z 410 (M+H)$^+$.

Reference Example 17j

Using essentially the same procedure used to prepare reference example 17a except using methyl 4-[2-(acetylamino-methyl)-pyridin-4-yl]-benzoate as substrate (reference example 102b) there is prepared 4-[2-(acetylamino-methyl)-pyridin-4-yl]-benzoic acid. MS (ion spray) m/z 271 (M+H)$^+$.

Reference Example 17k

Using essentially the same procedure used to prepare reference example 17a except using 4-[[4-(4-methoxycarbonyl-phenyl)-pyridin-2-ylmethyl]-carbamoyl]-piperidine-1-carboxylic acid tert-butyl ester as substrate (reference example 102a) there is prepared 4-[[4-(4-carboxy-phenyl)-pyridin-2-ylmethyl]-carbamoyl]-piperidine-1-carboxylic acid tert-butyl ester. MS (ion spray) m/z 440 (M+H)$^+$.

Reference Example 17l

Using essentially the same procedure used to prepare reference example 17a, except using Ethyl 4-[1-(3-dimethylaminopropyl)-6-oxo-1,6-dihydropyridin-3-yl] benzoate (reference example 85c) as substrate, there is prepared 4-[1-(3-Dimethylaminopropyl)-6-oxo-1,6-dihydropyridin-3-yl]benzoic acid. MS (ion spray) m/z 301 (M+H)$^+$.

Reference Example 17m

Using essentially the same procedure used to prepare reference example 17a, except using Ethyl 4-[6-(3-dimethylaminopropoxy)pyridin-3-yl]benzoate (reference example 85c) as substrate there is prepared 4-[6-(3-Dimethylaminopropoxy)pyridin-3-yl]benzoic acid. MS (ion spray) m/z 301 (M+H)$^+$.

Reference Example 17n

Using essentially the same procedure used to prepare reference example 17a, except using Ethyl 4-{1-[(2-dimethylaminoethylcarbamoyl)methyl]-6-oxo-1,6-dihydropyridin-3-yl}benzoate (reference example 1aar) as substrate there is prepared 4-{1-[(2-dimethylaminoethylcarbamoyl)methyl]-6-oxo-1,6-dihydropyridin-3-yl}benzoic acid. MS (ion spray) m/z 344 (M+H)$^+$.

Reference Example 17o

Using essentially the same procedure used to prepare reference example 17a, except using methyl 4-(1-methyl-piperidin-4-yloxy)-benzoate (reference example 114d) as substrate there is prepared 4-(1-methyl-piperidin-4-yloxy)-benzoic acid.

Reference Example 17p

Using essentially the same procedure used to prepare reference example 17a, except using methyl 4-(1-methanesulphonyl-piperidin-4-yl)-benzoate (reference example 126) as substrate and purifying by reverse phase HPLC, there is prepared 4-(1-methanesulphonyl-piperidin-4-yl)-benzoic acid. $^1$H NMR (DMSO): d 7.88 (d, 2H), 7.40 (d, 2H), 3.68 (d, 2H), 2.91 (s, 3H), 2.70–2.85 (m, 3H), 1.84–1.93 (m, 2H), 1.68 (dq, 2H).

Reference Example 18

Methyl 4-[pyridine-N-oxide-4-yl]-benzoate. To a cooled (0° C.) solution of methyl 4-[pyridin-4-yl]-benzoate (2.1 g, 10 mmol) (reference example 19a) in $CH_2Cl_2$ (41 mL) is added m-CPBA (3.4 g, 50–60% technical grade, 10 mmol). The resulting solution is stirred for 1 hour then a further portion of m-CPBA added (1.7 g, 5 mmol). This solution is stirred for 1 hour (temperature held between 5–10° C.) then the reaction mixture poured directly onto a silica gel column. Elution with 10% MeOH/40% EtOAc/50% $CH_2Cl_2$ gave 2.0 g of the title compound as a tan solid. $^1$H NMR ($CDC_3OD$) d 3.94 (s, 3H), 7.90 (m, 4H), 8.14 (d, J=8.5 Hz, 2H), 8.39 (d, J=7 Hz, 2H). MS (EI) m/z 230 (M)$^+$.

Reference Example 19a

Methyl 4-[Pyridin-4-yl]-Benzoate. To a solution of 4-[pyridin-4-yl]-benzoic acid (2.0 g, 10 mmol) (reference example 11a) in methanol (30 mL) is added conc. $H_2SO_4$ (4 mL). The resulting solution is warmed to 60° C. and stirred at this temperature for 2.5 hours. The reaction mixture is then allowed to cool to room temperature then poured into ice. The pH of the resulting solution is adjusted to 7 using a 10 M solution of NaOH. The product is then extracted into ethyl acetate. This solution is washed with brine, dried over $MgSO_4$ and concentrated to give 2.1 g of the title compound as a white solid. $^1$H NMR ($CDCl_3$) d 3.94 (s, 3H), 7.50 (d, J=5 Hz, 2H), 7.69 (d, J=8 Hz, 2H), 8.13 (d, J=5 Hz, 2H) 8.68 (d, J=5 Hz, 2H). MS (EI) m/z 213 (M)$^+$.

Reference Example 19b

Using essentially the same procedure used to prepare reference example 19a except using 4-(2-chloro-pyrimidin-4-yl)-benzoic acid (reference example 11g) there is prepared methyl 4-(2-methoxy-pyrimidin-4-yl)-benzoate. $^1$H NMR ($CDCl_3$) ? 3.93 (s, 3H), 4.09 (s, 3H), 7.39 (d, J=5 Hz, 1H), 8.13 (d, J=8 Hz, 2H), 8.16 (d, J=8 Hz, 2H), 8.59 (d, J=5 Hz, 1H). MS (EI) m/z 244 (M+).

Reference Example 19c 4-(2-Oxo-pyrimidin-5-yl)-benzoic acid methyl ester. Using essentially the same procedure used to prepare reference example 19a except using 4-(2-Oxo-pyrimidin-5-yl)-benzoic acid (reference example 1h) as substrate. $^1$H NMR (CD$_3$OD)? 3.28 (m, 1H), 3.47 (d, J=7 Hz, 4H), 3.90 (s, 3H), 7.44 (d, J=8 Hz, 2H), 7.90 (d, J=8 Hz, 2H).

Reference Example 20

[3-(4-furan-2-yl-phenyl)-3-methyl-butyl]-carbamic acid tert-butyl ester. To a solution of 2-[4-(3-azido-1,1-dimethyl-propyl)-phenyl]-furan (1.06 g, 4.2 mmol) (reference example 21) in THF (14 mL) is added triphenylphosphine (1.21 g, 4.6 mmol) and the solution stirred for 5 hours then added H$_2$O (151 ul, 8.4 mmol) and stirred for 3 hours. To the solution is added di-tert-butyl dicarbonate (3.7 g, 16.8 mmol), stirred for 16 hours then concentrated. The residue is purified by flash chromatography (eluting with 15% ethyl acetate in hexanes) to give 1.17 g of title compound as a colorless oil. $^1$H NMR (CDCl$_3$) δ 1.34 (s, 6H), 1.39 (s, 9H), 1.83 (m, 2H), 2.92 (m, 2H), 4.27 (bs, 1H), 6.46 (m, 1H), 6.61 (d, J=3 Hz, 1H), 7.34 (d, J=9 Hz, 2H), 7.45 (d, J=2 Hz, 1H), 7.60 (d, J=9 Hz, 2H). MS (ion spray) m/z 330 (M+H)$^+$.

Reference Example 21

2-[4-(3-azido-1,1-dimethyl-propyl)-phenyl]-furan. To a cooled solution (0° C.) of 3-(4-furan-2-yl-phenyl)-3-methyl-butan-1-ol (1.2 g, 5.2 mmol) (reference example 22) in CH$_2$Cl$_2$ (17 mL) is added triethylamine (0.86 mL, 6.2 mmol), p-toluenesulfonyl chloride (1.18 g, 6.2 mmol) and 4-dimethylaminopyridine (305 mg, 2.5 mmol). The resulting solution is allowed to warm to 20° C. while stirring for 1.5 h then diluted with ethyl acetate, washed with water and brine, dried over MgSO$_4$ and concentrated. The residue is dissolved if DMF (17 mL), sodium azide (845 mg, 13 mmol) added and the mixture heated to 60° C. and stirred for 3 h. The mixture is cooled to 20° C., then diluted with ethyl acetate, washed with water and brine, dried over MgSO$_4$ and concentrated. The residue is purified by flash chromatography (eluting with 10% ethyl acetate in hexanes) to give 1.06 g of title compound as a colorless oil. $^1$H NMR (CDCl$_3$) δ 1.36 (s, 6H), 1.95 (t, J=8 Hz, 2H), 3.03 (t, J=8 Hz, 2H), 6.46 (m, 1H), 6.62 (m, 1H), 7.34 (d, J=8 Hz, 2H), 7.46 (d, J=2 Hz, 1H), 7.62 (d, J=8 Hz, 2H). MS (ion spray) m/z 256 (M+H)$^+$.

Reference Example 22

3-(4-furan-2-yl-phenyl)-3-methyl-butan-1-ol. To a cooled solution (0° C.) of 2-[4-(1,1-dimethyl-allyl)-phenyl]-furan (424 mg, 2 mmol) (reference example 51)in THF (4 mL) is added dropwise (1M)borane-THF complex (2.2 mL, 2.2 mmol) and the resulting mixture stirred for 1 hour. To the mixture is added 10% NaOH (1.5 mL) and 30 wt % H$_2$O$_2$ (1.5 mL) and stirred for 1 hour while allowing to warm to 20° C. The mixture is diluted with ether, washed with water and brine, dried over MgSO$_4$ and concentrated. The residue is purified by flash chromatography (eluting with 25% ethyl acetate in hexanes) to give 341 mg of the title compound. $^1$H NMR (CDCl$_3$) δ 1.34 (s, 6H), 1.40 (m, 1H), 1.94 (t, J=8 Hz, 2H), 3.48 (t, J=8 Hz, 2H), 6.45 (m, 1H), 6.60 (m, 1H), 7.35 (d, J=8 Hz, 2H), 7.44 (bs, 1H), 6.61 (d, J=8 Hz, 2H). MS (EI) m/z 230 (M+).

Reference Example 23

3-cyano-5-(2-[allyloxy-carbonyl-amino]-ethyl)indole. To a suspension of 5-(2-amino-ethyl)3-cyano-indole (reference example 2) (925 mg, 5 mmol) in CH$_2$Cl$_2$/THF (20 mL, 1/1) is added N,N-diisopropylethylamine (869 mL, 5 mmol) followed by allyl-1-benzotriazolyl carbonate (1.096 g, 5 mmol). The resulting mixture is stirred for 25 minutes then concentrated. The residue is purified by flash chromatography (eluting with 7% MeOH in CH$_2$Cl$_2$) to give 1.27 g of product as a white solid. $^1$H NMR (CDCl$_3$) d 2.92 (t, J=7 Hz, 2H), 3.50 (q, J=7 Hz, 2H), 4.53 (d, J=5 Hz, 2H), 4.79 (bs, 1H), 5.18 (d, J=10 Hz, 1H), 5.26 (d, J=17 Hz, 1H), 5.87 (m, 1H), 7.10 (dd, J=8,1 Hz, 1H), 7.34 (d, J=8 Hz, 1H), 7.54 (s, 1H), 7.67 (d, J=1 Hz, 1H), 9.08 (bs, 1H). MS (EI) m/z 269 (M+).

Reference Example 24a

6-Morpholin-4-yl-nicotinic acid. A mixture of 2.00 g (12.7 mmol) 6-chloronicotinic acid and 1.11 mL (12.7 mmol) morpholine is stirred for six hours at 120° C. After cooling, the reaction mixture is flash chromatographed (5:1, then 3:1 methylene chloride: ca 7N NH$_3$ in MeOH) to provide 0.419 g of product as a tan solid. Contaminated with both staring materials. Used without further purification. MS (ion spray) m/z 209 (M+H)$^+$.

Reference Example 24b 4-(5-2[-{3-Cyanoindol-5-yl}ethylcarbamoyl]pyridin-2-yl)piperazine-1-carboxylic acid ethyl ester. Prepared using essentially the same procedure as for reference example 24a except using N-(2-[3-Cyanoindol-5-yl]ethyl)-6-chloronicotinamide (reference example 1e). $^1$H NMR (5:1 CDCl$_3$:CD$_3$OD): δ 1.30 (3H, t, J=7.1 Hz), 3.04 (2H, t, J=7.2 Hz), 3.58–3.73 (10H, m), 4.17 (2H, q, J=7.1 Hz), 6.68 (1H, d, J=9.0 Hz), 7.20 (1H, d, J=8.3 Hz), 7.43 (1H, d, J=8.3 Hz), 7.58 (1H, s), 7.91 (1H, d, J=9.0 Hz), 7.98 (1H, s), 8.50 (1H, d, J=2.4 Hz). MS (ion spray) m/z 447 (M+H)$^+$.

Reference Example 24c 6-(2-Hydroxyethylamino)nicotinic acid. Prepared using essentially the same procedure as for reference example 24a except using 2-amino-ethanol. $^1$H NMR (CD$_3$OD): δ 3.47 (2H, m), 3.72 (2H, m), 6.53 (1H, d, J=9.3 Hz), 7.92 (1H, d, J=9.3 Hz), (1 H, s). MS (ion spray) m/z 183 (M+H)$^+$.

Reference Example 25a 2-(4-(carboxy)-phenyl)-2-methyl-propionamide. To a solution of 2-(4-(furan-2-yl)-phenyl)-2-methyl-propionamide (reference example 26) (124 mg, 0.5 mmol) in CH$_3$CN/CCl$_4$/H$_2$O (7 mL, 2/2/3) is added NaIO$_4$ (420 mg, 2 mmol) followed by RuCl$_3$ (H$_2$O)(3 mg). The resulting mixture is stirred vigorously for 1.5 h, then diluted with ethyl acetate, washed with water and brine, dried over MgSO$_4$ and concentrated to give 100 mg of the title compound as an orange solid. $^1$H NMR (CD$_3$OD) d 1.58 (s, 6H), 7.50 (d, J=8 Hz, 2H), 7.98 (d, J=8 Hz, 2H). MS (EI) m/z 208 (M+H).

Using essentially the same procedure except using the specified furan derivative, there is prepared Reference Example 25b N-(2-methoxy-ethyl)-2-(4-(carboxy)-phenyl)-2-methyl-propionamide. Using the product from reference example 27. $^1$H NMR (CD$_3$OD) d 1.58 (s, 6H), 3.29 (s, 3H), 3.36 (m, 4H), 6.24 (bs, 1H), 7.45 (m, 2H), 8.05 (m, 2H). MS (EI) m/z 266 (M+).

Reference Example 25c 4-(2-[N-t-Butoxycarbonyl-amino]-1,1-dimethyl-ethyl)-Benzoic Acid. Using the product from reference example 29.

$^1$H NMR (CDCl$_3$) d 1.30 (s, 6H), 1.38 (s, 9H), 3.26 (bs, 1H), 3.33 (d, J=6 Hz, 2H), 7.44 (d, J=8 Hz, 2H), 8.05 (d, J=8 Hz, 2H).

Reference Example 25d 4-(3-tert-butoxycarbonylamino-1,1-dimethyl-propyl)-benzoic acid. Using the product from reference example 20. $^1$H NMR (DMSO) δ 1.25 (s, 6H), 1.36 (s, 9H), 1.75 (m, 2H), 2.65 (m, 2H), 6.66 (bt, 1H), 7.47 (d, J=8 Hz, 2H), 7.88 (d, J=8 Hz, 2H), 12.79 (bs, 1H). MS (EI) m/z 308 (M+H)$^+$.

Reference Example 26

2-(4-(furan-2-yl)-phenyl)-2-methyl-propionamide. To a solution of 2-(4-(furan-2-yl)-phenyl)-2-methyl-propionic Acid (reference example 28) (115 mg, 0.5 mmol) in CH$_2$Cl$_2$ (3 mL) is added DMF (10 mL) followed by oxalyl chloride (0.3 mL, 2M in CH$_2$Cl$_2$). The resulting solution is stirred for 2.5 hours then concentrated. The residue is taken up in methanolic ammonia (7N) and stirred for 14.5 hours, then concentrated to give 124 mg of the title compound as a tan solid. $^1$H NMR (CDCl$_3$) d 1.58 (s, 6H), 5.2 (bs, 1H), 5.3 (bs, 1H), 6.45 (dd, J=3, 1 Hz, 1H), 6.63 (m, 1H), 7.39 (m, 2H), 7.45 (bs, 1H), 7.65 (m, 2H). MS (EI), m/z 229 (M+).

Reference Example 27

N-(2-methoxy-ethyl)-2-(4-(furan-2-yl)-phenyl)-2-methyl-propionamide. To a solution of 2-(4-(furan-2-yl)-phenyl)-2-methyl-propionic Acid (reference example 28) (344 mg, 1.5 mmol) in CH$_2$Cl$_2$ (4 mL) is added TBTU (528 mg, 1.65 mmol) followed by diisopropylethylamine (280 mL, 1.6 mmol). The resulting mixture is stirred for 2 h then a further portion of DIEA added (280 mL) along with 2-methoxy-ethylamine (225 mL, 2.6 mmol). The resulting solution is stirred for 90 minutes then concentrated. The residue is purified by flash chromatography (eluting with 10% CH$_2$Cl$_2$/50% ethyl acetate in hexanes) to give 380 mg of product as a white solid. $^1$H NMR (CD$_3$OD) d 1.58 (s, 6H), 3.24 (s, 3H), 3.36 (m, 4H), 5.58 (bs, 1H), 6.47 (dd, J=3, 2 Hz, 1H), 6.65 (d, J=3 Hz, 1H), 7.41 (m, 2H), 7.49 (d, J=2 Hz, 1H), 7.65 (m, 2H). MS (EI) m/z 287 (M+).

Reference Example 28

2-(4-(furan-2-yl)-phenyl)-2-methyl-propionic Acid. To a solution of 2-(4-(furan-2-yl)-phenyl)-2-methyl-propionic acid methyl ester (2.0 g, 8.2 mmol) (reference example 30a) in MeOH/THF (20 mL, 1/1) is added NaOH (2 mL, 6M). The resulting solution is stirred for 1 hour then heated to 65° C. and stirred at this temperature for 2 hours. The reaction mixture is then cooled and acidified (to pH 1) with hydrochloric acid (2 M). The resulting mixture is diluted with ether, washed with water and brine, dried over MgSO$_4$ and concentrated to give 1.78 g of the title compound as a solid. $^1$H NMR (CDCl$_3$) d 1.61 (s, 6H), 6.45 (dd, J 3, 2 Hz, 1H), 6.62 (d, J=3 Hz, 1H), 7.42 (m, 2H), 7.45 (d, J=2 Hz, 1H), 7.64 (m, 2H). MS (EI) m/z 230 (M+)

Reference Example 29

2-[4-(2-[N-t-Butoxycarbonyl-amino]-1,1-dimethyl-ethyl)-phenyl]-furan. To a cooled (0° C.) solution of lithium aluminum hydride (152 mg, 4 mmol) in THF (6 mL) is added 2-(4-(furan-2-yl)-phenyl)-2-methyl-propionitrile (422 mg, 2 mmol) (reference example 30b). On complete addition, the cold bath is removed and stirring continued for 3.5 hours. The resulting mixture is cooled to 0° C. then water (150 mL) NaOH (150 mL, 5M) and water (300 mL) added sequentially. The resulting slurry is diluted with ether then filtered through celite. The filtrate is concentrated then the residue dissolved in THF (5 mL). To this solution is added di-t-butyl-dicarbonate (480 mg, 2.2 mmol). The resulting solution is stirred for 1 hour, then concentrated the residue is purified by flash chromatography (eluting with 10% ethyl acetate in hexanes) to give 524 mg of product as an oil. $^1$H NMR (CDCl$_3$) d 1.31 (s, 6H), 1.39 (s, 9H), 3.31 (bd, J=6 Hz, 2H), 6.45 (dd, J=2, 1 Hz, 1H), 6.61 (d, J=2 Hz, 1H), 7.35 (d, J=8 Hz, 2H), 7.44 (d, J=1 Hz, 1H), 7.62 (d, J=8 Hz, 2H). MS (ion spray) m/z 316 (M+H)$^+$.

Reference Example 30a 2-(4-(furan-2-yl)-phenyl)-2-methyl-propionic acid methyl ester. To a cooled (0° C.) solution of furan (5.7 mL, 78 mmol) in TMEDA/THF (81.4 mL, 14/86) is added n-buLi (15 mL, 2.5 M in hexanes). The cold bath is removed and the resulting solution stirred for 45 minutes, then a solution of ZnCl$_2$ in THF added (40 mL, 0.5M). To this solution is added (Ph$_3$P)$_4$Pd (1.0 g, 0.86 mmol) and 2-(4-Bromo-phenyl)-2-methyl-propionic acid methyl ester (4.5 g, 17.5 mmol) (reference example 31 a). The resulting solution is warmed to 60° C. and stirred for 3 hours. The reaction mixture is then cooled, diluted with ether, washed with hydrochloric acid (2M), then brine, dried over MgSO$_4$ and concentrated. The residue is purified by flash chromatography (eluting with 5% ether in hexanes) to give 3.84 g of the title compound as a solid. $^1$H NMR (CDCl$_3$) d 1.60 (s, 6H), 3.67 (s, 3H), 6.45 (m, 1H), 6.63 (d, J=3 Hz, 1H), 7.35 (m, 2H), 7.46 (m, 1H), 7.65 (m, 2H). MS (EI) m/z 245 (M+H)$^+$.

Reference Example 30b 2,2-Dimethyl-(4-[Furan-2-yl]-Phenyl)-Acetonitrile. Using essentially the same procedure as in reference example 30a, except using 2-(4-Bromo-phenyl)-2-methyl-propionitrile (reference example 31b). $^1$H NMR (CDCl$_3$) d 1.74 (s, 6H), 6.47 (dd, J=2, 1 Hz, 1H), 6.66 (d, J=2 Hz, 1H), 7.47 (m, 3H), 7.68 (m, 2H),. MS (EI) m/z 211 (M)$^+$.

Reference Example 31a 2-(4-Bromo-phenyl)-2-methyl-propionic Acid Methyl ester. To a cooled (−20° C.) solution of 4-Bromo-phenyl-acetic acid methyl ester (9.1 g, 40 mmol) (reference example 32) in THF (80 mL) is added methyl iodide (5.6 mL, 90 mmol) followed by a solution of KOt-Bu in THF (88 mL, 1M). The resulting mixture is stirred for 1 hour then diluted with ether, washed with water, then brine, dried over MgSO$_4$ and concentrated to give 9.8 g of the title compound as an oil. $^1$H NMR (CDCl$_3$) d 1.55 (s, 6H), 3.63 (s, 3H), 7.2 (m, 2H), 7.43 (m, 2H).

Reference Example 31b 2-(4-bromo-phenyl)-2-methyl-propionitrile. Using essentially the same procedure as in reference example 31a, except using (4-Bromo-phenyl)-acetonitrile. $^1$H NMR (CDCl$_3$) d 1.70 (s, 6H), 7.34 (d, J=8 Hz, 2H), 7.50 (d, J=8 Hz, 2H). MS (EI) m/z 223, 225 Br pattern (M)$^+$ Reference Example 32

4-Bromo-phenyl-acetic acid methyl ester. To a solution of 4-Bromo-phenyl-acetic acid (8.6 g, 40 mmol) in DMF (80 mL) is added K$_2$CO$_3$ (6.16 g, 44 mmol) followed by methyl iodide (2.8 mL, 45 mmol). The resulting mixture is stirred for 2.5 hours, then diluted with ether, washed with water and brine, dried over MgSO$_4$ and concentrated to give 9.1 g of the title compound as an oil. This material is used without further purification. ¹H NMR (CDCl₃) d 3.58 (s, 2H), 3.69 (s, 3H), 7.13 (d, J=8 Hz, 2H), 7.43 (d, J=8 Hz, 2H). MS (EI) m/z 228/230 (M+) Br pattern.

Reference Example 33a

2-Methyl-4-(2-methoxy-pyridin-5-yl)-benzoic Acid. To a solution of Methyl 2-methyl-4-(2-methoxypyridin-5-yl)-benzoate (600 mg, 2.6 mmol) (reference example 34a) in THF/MeOH (8 mL, 1/1) is added NaOH (3 mL, 1M). The resulting mixture is stirred for 12 hours then acidified with hydrochloric acid (2M, to give pH 5). The mixture is diluted with ether then washed with brine, dried over MgSO₄ and concentrated. The residual solid is triturated with ether/hexane (1/20). The resulting product (500 mg) is used without further purification. ¹H NMR (CDCl₃) d 2.71 (s, 3H), 3.98 (s, 3H), 6.82 (d, J=8 Hz, 1H), 7.41 (m, 2H), 7.81 (dd, J=8, 2 Hz, 1H), 8.13 (d, J=8 Hz, 1H), 8.43 (d, J=2 Hz, 1H). MS (EI) m/z 243 (M+).

The following compounds are prepared using essentially the same procedure as described for reference example 33a except using the specified ester.

Reference Example 33b 4-(3,4-Dimethoxyphenyl)benzoic acid. Using Ethyl 4-(3,4-Dimethoxyphenyl)benzoate (reference example 34b).

Reference Example 33c 4-(6-methoxy-pyridin-3-yl)-benzoic acid. Using 4-(6-methoxy-pyridin-3-yl)-benzoic acid ethyl ester (reference example 34c). ¹H NMR (DMSO) δ 3.92 (s, 3H), 6.95 (d, J=9 Hz, 1H), 7.80 (d, J=8 Hz, 2H), 8.02 (d, J=8 Hz, 2H), 8.10 (dd, J=9, 2 Hz, 1H), 8.58 (d, J=2 Hz, 1H). MS (EI) m/z 229 (M+).

Reference Example 33d 3-chloro-4-(6-methoxy-pyridin-3-yl)-benzoic acid. Using 3-chloro-4-(6-methoxy-pyridin-3-yl)-benzoic acid methyl ester (reference example 38). ¹H NMR (DMSO) δ 3.92 (s, 3H), 6.96 (d, J=9 Hz, 1H), 7.60 (d, J=8 Hz, 1H), 7.88 (dd, J=9, 2 Hz, 1H), 7.96 (d, J=8 Hz, 1H), 8.04 (s, 1H), 8.29 (d, J=2 Hz, 1H). MS (EI) m/z 263/265 (M+, Cl).

Reference Example 33e 4-(2-[t-butyloxycarbonylamino-methyl]-pyridin-4-yl)-benzoic acid. Using the product from reference example 56 ¹H NMR (DMSO) δ 1.39 (s, 9H), 4.31 (d, J=6 Hz, 2H), 7.47 (bt, J=6 Hz, 1H), 7.65 (m, 2H), 7.86 (d, J=8 Hz, 2H), 8.07 (d, J=8 Hz, 2H), 8.60 (d, J=5 Hz, 1H). MS (ion spray) m/z 329 (M+H).

Reference Example 33f 4-(2-Carbamoyl-pyridin-4-yl)-benzoic acid. Using the product from reference example 58. ¹H NMR (DMSO) δ 7.74 (bs, 1H), 7.97 (m, 3H), 8.05 (d, J=8 Hz, 2H), 8.20 (bs, 1H), 8.34 (bs, 1H), 8.73 (d, J=5 Hz, 1H). MS (EI) m/z 242 M+.

Reference Example 33g 4-(2-[N,N-dimethylamino-methyl]-pyridin-4-yl)-benzoic acid. Using the product from reference example 59 and purifying by reverse phase HPLC (0.1% TFA/acetonitrile/water gradient) ¹H NMR (DMSO) δ 2.81 (s, 6H), 4.51 (s, 2H), 7.85 (d, J=5 Hz, 1H), 7.93 (s, 1H), 7.94 (d, J=8 Hz, 2H), 8.08 (d, J=8 Hz, 2H), 8.75 (d, J=5 Hz, 1H). MS (ion spray) m/z 257 (M+H).

Reference Example 34a

Methyl 2-methyl-4-(2-methoxy-pyridin-5-yl)-benzoate. To a cooled (−78° C.) solution of 2-methoxy-5-bromo-pyridine (1.88 g, 10 mmol) in THF (25 mL) is added, dropwise, n-BuLi (4.4 mL, 2.5M in hexanes). On complete addition, the resulting solution is stirred for 10 minutes then ZnCl₂ added (21 mL, 0.5M in THF). The cold bath is removed and stirring continued for 15 minutes. To this solution is added a solution comprised of 4-bromo-2-methyl-benzoic acid methyl ester (2.25 g, 9.8 mmol) and (Ph₃P)₄Pd (0.56 g, 0.48 mmol) in THF (5 mL). The resulting solution is warmed to 60° C. and stirred at this temperature for 2 h. The reaction mixture is allowed to cool, then diluted with ethyl acetate, washed with ammonium chloride solution (sat.) and brine, dried over MgSO₄ and concentrated. The residue is purified by flash chromatography (eluting with 10% ethyl acetate in hexanes) to give 626 mg of the title compounds an oil. ¹H NMR (CDCl₃) d 2.68 (s, 3H), 3.93 (s, 3H), 3.98 (s, 3H), 6.82 (d, J=9 Hz, 1H), 7.39 (m, 2H), 7.81 (d, J=9 Hz, 1H), 8.00 (d, J=9 Hz, 1H), 8.40 (d, J=2 Hz, 1H). MS (EI) m/z 257 (M+).

Using essentially the same procedure as in reference example 34a, except using commercially available 4-bromobenzoic acid ethyl ester and 3,4-dimethoxy-phenyl bromide (in place of 5-bromo-2-methoxy-pyridine) there is prepared:

Reference Example 34b

Ethyl 4-(3,4-Dimethoxyphenyl)benzoate.
¹H NMR(CDCl₃) δ 1.43 (3H, m), 3.92 (3H, m), 3.98 (3H, m), 6.95 (1H, m), 7.23 (1H, s), 7.20 (1H, m), 7.61 (2H, m), 8.12 (2H, m).

Using essentially the same procedure as in reference example 34a, except using 4-bromobenzoic acid ethyl ester there is prepared:

Reference Example 34c

Ethyl 4-(6-methoxypyrid-3-yl)benzoate. ¹H NMR (CDCl₃) δ 1.41 (3H, t, J=7.24 Hz), 3.99 (3H, s), 4.40 (2H, q, J=7.24 Hz), 8.63 (1H, d, J=8.63 Hz), 7.60 (2H, d, J=8.36 Hz), 7.83 (1H, dd, J₁=8.63 Hz, J₂=2.58 Hz), 8.12 (2H, d, J=8.36 Hz), 8.43 (1H, d, J=2.58 Hz). MS(EI) m/z 257 M³⁰.

Reference Example 35a 4-(1,2,4)Thiadiazol-5-ylbenzoic acid. A mixture of 0.500 g (2.17 mmol) 5-(p-trifluoromethylphenyl)-(1,2,4) thiadiazole in 5 mL concentrated sulfuric acid (Fisher) is heated to 150° C. for five hours and poured into ice water. A yellow precipitate is collected by filtration, washed with water, and dried to give 0.439 g of the product, as the sulfuric acid salt, as a white solid in 79.3% yield. Used without further purification. MS (EI) m/z 206 M⁺.

Reference Example 35b

Using essentially the same procedure except starting with 4-(3H-imidazol-4-yl)trifluoromethylbenzene (reference example 37) there is prepared: 4-(3H-imidazol-4-yl)-1benzenoic acid. Used further purification. MS(EI) m/z 188 (M⁺).

Reference Example 36a

N-[2-(3-Cyano-1H-indol-5-yl)-ethyl]-2-methyl-4-(6-oxo-1,6-dihydro-pyridin-5-yl)-benzamide. A mixture of N-[2-(3-

Cyano-1H-indol-5-yl)-ethyl]-4-(2-methoxy-pyridin-5-yl)-2-methyl-benzamide (146 mg, 0.35 mmol) (reference example 1n) and pyridinium hydrochloride (3 g) is heated to 160° C. and stirred at this temperature for 3 minutes. The liquid is then cooled and mixed with water. The resulting precipitated solid is filtered, washed with water (3×) then dried under vacuum to give 133 mg of th title compound as a solid. This material is used without further purification. MS (ion spray) m/z 397 (M+H).

Using esssentially the same procedure except using the specified methoxy-pyridine derivative, there is prepared:

Reference Example 36b

N-[2-(3-Cyano-1H-indol-5-yl)-ethyl]-4-(6-oxo-1,6-dihydro-pyridin-5-yl)-benzamide. Using the product from reference example 1p. MS (ion spray) m/z 383 (M+H).

Reference Example 36c

N-[2-(3-cyano-1H-indol-5-yl)-ethyl]-3-chloro-4-(6-oxo-1,6-dihydro-pyridin-3-yl)-benzamide. Using the product from reference example 1u. $^1$H NMR (DMSO) δ 2.97 (bt, 2H), 3.53 (m, 2H), 6.42 (d, J=9 Hz, 1H), 7.17 (d, J=9 Hz, 1H), 7.54 (m, 4H), 7.82 (d, J=8 Hz, 1H), 7.95 (m, 2H), 8.20 (m, 1H), 8.73 (bt, 1H), 8.88 (m, 1H), 12.15 (bs, 1H). MS (ion spray) m/z 417/419 (M+H)$^+$, Cl.

Reference Example 36d

N-[2-(3-cyano-1H-indol-5-yl)-ethyl]-4-(6-oxo-1,6-dihydro-pyridazin-3-yl)-benzamide. Using the product from reference example 1ak. $^1$H NMR (DMSO) δ 2.98 (t, J=7 Hz, 2H), 3.55 (m, 2H), 7.02 (d, J=10 Hz, 1H), 7.18 (d, J=7 Hz, 1H), 7.48 (m, 2H), 7.94 (m, 4H), 8.10 (d, J=10 Hz, 1H), 8.20 (d, J=3 Hz, 1H), 8.66 (bt, 1H), 12.11 (s, 1H), 13.29 (s, 1H). MS (ion spray) m/z 384 (M+H)$^+$.

Reference Example 36e 4-(6-oxo-1,6-dihydro-pyridazin-3-yl)-benzoic acid methyl ester. Using the product from reference example 63. $^1$H NMR (DMSO) δ 3.88 (s, 3H), 7.04 (d, J=10 Hz, 1H), 8.02 (d, J=8 Hz, 2H), 8.06 (d, J=8 Hz, 2H), 8.12 (d, J=10 Hz, 1H), 13.37 (bs, 1H). MS (EI) mtz 230 (M$^+$).

Reference Example 36f

Ethyl 4-(6-oxo-1,6-dihydropyridin-3-yl)benzoate. Using the product from reference example 34c $^1$H NMR (5:1 CDCl$_3$:CD$_3$OD): δ 1.41 (3H, t, J=7 Hz), 4.40 (2H, q, J=7 Hz), 6.70 (1H, d, J=10 Hz), 7.52 (2H, d, J=8 Hz), 7.63 (1H, d, J=3 Hz), 7.83 (1H, dd, J=3 Hz, 10 Hz), 8.09 (2H, d, J=8 Hz).

Reference Example 37

4-(3H-imidazol-4-yl)-trifluoromethylbenzene. To a solution of 5 g (24 mmol) 4-(trifluoromethyl)benzoyl chloride in 100 mL THF cooled to 0 C is added dropwise 72 mmol diazomethane in 200 mL ethyl ether. After 18 hours at 0° C., excess diazomethane is destroyed with acetic acid, and the solution is concentrated. To the resulting residue is added 100 mL THF and 40 mL 1M HCl in ethyl ether. After one hour the reaction is concentrated and then warmed in 25 mL MeOH, and this warm solution is added dropwise to a solution of 8.6 g (47 mmol) copper(II) acetate (Aldrich) in 5 mL 37% aqueous formaldehyde and 100 mL 28% ammonium hydroxide. The reaction is heated to 100 C for 30 minutes and allowed to cool overnight. The resulting solution is decanted away from a brown precipitate, and the precipitate is washed with water and taken up in 150 mL 1:1 EtOH: water. Hydrogen sulfide is bubbled through this solution to give a tan solid; the solution is stirred for two hours and concentrated. The residue is suspended in ethanol/water solution, filtered through Celite, and purified on HPLC to give 2.1 g of the product in 43% yield. MS(EI) m/z 212 (M$^+$).

Reference Example 38

3-chloro-4-(6-methoxy-pyridin-3-yl)-benzoic acid methyl ester. To a cooled solution (−78° C.) of 2-methoxy-5-bromopyridine (1.13 g, 6 mmol, reference example 41a) in THF (12 mL) is added over 10 min (2.5M)n-butyllithium (2.4 mL, 6 mmol) and the resulting solution stirred for 15 min. To this solution is added dropwise (0.5M)zinc chloride (12 mL, 6 mmol) and the temperature of this arylzinc bromide allowed to warm to 0° C. with stirring. To a cooled solution (0° C.), in a separate flask, of palladium bis (dibenzylideneacetone) (288 mg, 0.5 mmol) and 1,1'-bis (diphenylphosphino)ferrocene (276 mg, 0.5 mmol) in THF (2 mL) is added a solution of 3-chloro-4-trifluoromethanesulfonyloxy-benzoic acid methyl ester (1.59 g, 5 mmol) (reference example 39) in THF (2 mL) followed by the arylzinc bromide solution. The resulting solution is heated to 65° C. and stirred for 2.5 hours then cooled to 20° C., diluted with ether, washed with sat NH$_4$Cl soln and brine, dried over MgSO$_4$ and concentrated. The residue is purified by flash chromatography (eluting with 25% ether in hexanes) to give 428 mg of title compound as a yellow crystalline solid. $^1$H NMR(CDCl$_3$) δ 3.95 (s, 3H), 4.00 (s, 3H), 6.84 (d, J=9 Hz, 1H), 7.40 (d, J=8 Hz, 1H), 7.72 (dd, J=9, 2 Hz, 1H), 7.98 (dd, J=8, 2 Hz, 1H), 8.15 (s, 1H), 8.25 (d, J=2 Hz, 1H). MS (EI) m/z 277 (M+).

Reference Example 39

3-chloro-4-trifluoromethanesulfonyloxy-benzoic acid methyl ester. To a cooled mixture (−5° C.) of (60%) sodium hydride (1.1 g, 27.5 mmol) in THF (60 mL) is added dropwise a solution of 3-chloro-4-hydroxy-benzoic acid methyl ester (4.66 g, 25 mmol)(reference example 40) in THF (10 mL) and stirred mixture at 0° C. for 30 min. To this mixture is added a solution of N-phenyltrifluoromethanesulfonimide (13.4 g, 37.5 mmol) and 1,3-dimethyl-3,4,5,6-tetrahydro-2 (1H)pyrimidinone (20 mL) in THF (10 mL). The resulting mixture is allowed to warm to 20° C. and stirred for 1 hour, diluted with ether, washed with water and brine, dried over MgSO$_4$ and concentrated. The residue is purified by flash chromatography (eluting with 10% ether in hexanes) to give 6.86 g of title compound as a colorless oil. $^1$H NMR (CDCl$_3$) δ 3.96 (s, 3H), 7.44 (d, J=9 Hz, 1H); 8.02 (dd, J=9, 2 Hz, 1H), 8.21 (d, J=2 Hz, 1H). MS (EI) m/z 318/320 (M+, Cl).

Reference Example 40

3-chloro-4-hydroxy-benzoic acid methyl ester. To a solution of 3-chloro-4-hydroxy-benzoic acid hemihydrate (9.08 g, 50 mmol) in methanol (150 mL) is added slowly (conc) sulfuric acid (22.5 mL). The resulting solution is heated to 55° C. and stirred 2 hours then cooled to 20° C. Poured solution into ice and extracted with ether. The organic is washed with brine, dried over MgSO$_4$ and concentrated. The residue is purified by flash chromatography (eluting with 30% ethyl acetate in hexanes) to give 9.5 g of title compound as a white crystalline solid. $^1$H NMR (CDCl$_3$) δ 3.90 (s, 3H), 7.06 (d, J=9 Hz, 1H), 7.88 (dd, J=9, 2 Hz, 1H), 8.05 (d, J=2 Hz, 1H). MS (EI) m/z 186/188 (M+, Cl).

Reference Example 41a 2-methoxy-5-bromopyridine. To a solution of 2,5-dibromopyridine (20 g, 84 mmol) in DMSO (84 mL) is added (25 wt %) sodium methoxide (21.2 mL, 93 mmol). The resulting solution is heated to 80° C. and stirred for 45 min then cooled to 20° C., diluted with ether, washed with water and brine, dried over $MgSO_4$ and concentrated. The residue is purified by flash chromatography (eluting with 10% ether in hexanes) to give 14.6 g of title compound as a colorless oil. $^1$H NMR (CDCl$_3$) δ 3.90 (s, 3H), 6.66 (d, J=9 Hz, 1H), 7.63 (dd, J=9, 3 Hz, 1H), 8.20 (d, J=3 Hz, 1H). MS (EI) m/z 187/189 (M+, Br).

Reference Example 41b

Using essentially the same procedure used to prepare reference example 41a except using the product from reference example 60, there is prepared 3-bromo-6-methoxypyridazine. $^1$H NMR (CDCl$_3$) δ 4.11 (s, 3H), 6.87 (d, J=9 Hz, 1H), 7.48 (d, J=9 Hz, 1H). MS (ion spray) m/z 189/191 (M+H)$^+$, Br.

Reference Example 42a 4-(7H-pyrrolo[2,3-d]pyrimidin-6-yl)-benzoic acid. To a solution of 4-(7H-pyrrolo[2,3-d]pyrimidin-6-yl)-benzoic acid methyl ester (0.601 g, 2.4 mmol) (reference example 43a) in 1:1 THF-methanol (10 mL) is added NaOH (10N) (2.4 mL, 24 mmol) and 0.5 ml $H_2O$. The resulting solution is stirred for 1 hour then cooled to 0°–5° C. and adjusted to pH 3 with 2N HCl. The precipitated solid is filtered off, washed with a small volume of water and dried under high vacuum to give 0.355 g of title compound as a yellow solid. $^1$H NMR (DMSO) δ 7.59 (s, 1H), 8.10 (d, J=8 Hz, 2H), 8.20 (d, J=8 Hz, 2H), 9.22 (s, 1H), 9.50 (bs, 1H), 14.10 (bs, 1H). MS (EI) m/z 239 (M+).

Using essentially the same procedure as in reference example 42a except using the specified ester there is prepared.

Reference Example 42b 4-(1H-pyrrolo[3,2-c]pyridin-2-yl)-benzoic acid. Using the product from reference example 43b. $^1$H NMR (DMSO) δ 7.63 (s, 1H), 7.99 (d, J=6 Hz, 1H), 8.16 (m, 4H), 8.46 (d, J=6 Hz, 1H), 9.34 (s, 1H), 13.67 (bs, 1H). MS (EI) m/z 238 (M+).

Reference Example 42c 4-furo[3,2-c]pyridin-2-yl-benzoic acid. Using the product from reference example 43c. $^1$H NMR (DMSO) δ 7.89 (s, 1H), 8.05 (d, J=7 Hz, 1H), 8.12 (m, 4H), 8.68 (bd, 1H), 9.24 (bs, 1H), 13.20 (bs, 1H). MS (EI) m/z 239 (M+).

Reference Example 43a 4-(7H-pyrrolo[2,3-d]pyrimidin-6-yl)-benzoic acid methyl ester. To a solution of (5-iodo-pyrimidin-4-yl)carbamic acid tert-butyl ester (1.46 g, 4.55 mmol) (reference example 44a) in DMF (15 mL) is added 4-ethynyl-benzoic acid methyl ester (0.721 g, 4.5 mmol)(reference example 46), copper iodide 99.999% (21 mg, 0.112 mmol), bis(triphenylphosphine)palladium(II)chloride (158 mg, 0.225 mmol) and 1,8-diazabicyclo[5.4.0]undec-7-ene (1.5 mL, 10 mmol). The resulting solution is heated to 100° C. and stirred for 1 hour then cooled to 20° C. The solution is diluted with ethyl acetate, washed with water and brine, dried over $MgSO_4$ and concentrated. The residue is purified by flash chromatography (eluting with 50% ethyl acetate, 5% methanol in hexanes) to give 601 mg of title compound as a yellow crystalline solid. $^1$H NMR (DMSO) δ 3.89 (s, 3H), 7.24 (s, 1H), 8.06 (d, J=8 Hz, 2H), 8.14 (d, J=8 Hz, 2H), 8.81 (bs, 1H), 9.05 (bs, 1H), 12.79 (bs, 1H). MS (ion spray) m/z 254 (M+H)$^+$.

Using essentially the same procedure as in reference example 43a except using the specified aryl iodide there is prepared.

Reference Example 43b 4-(1H-pyrrolo[3,2-c]pyridin-2-yl)-benzoic acid methyl ester. Using the product from reference example 49. $^1$H NMR (CDCl$_3$) δ 1.34 (s, 9H), 3.96 (s, 3H), 6.69 (s, 1H), 7.51 (d, J=8 Hz, 2H), 8.08 (d, J=8 Hz, 1H), 8.11 (d, J=7 Hz, 2H), 8.51 (d, J=6 Hz, 1H), 8.90 (s, 1H). MS (EI) m/z 352 (M+).

Reference Example 43c 4-furo[3,2-c]pyridin-2-yl-benzoic acid methyl ester. Using the product from reference example 50. $^1$H NMR (CDCl$_3$) δ 3.96 (s, 3H), 7.20 (s, 1H), 7.49 (d, J=5 Hz, 1H), 7.94 (d, J=8 Hz, 2H), 8.14 (d, J=8 Hz, 2H), 8.53 (d, J=5 Hz, 1H), 8.97 (s, 1H). MS (EI) m/z 253 (M+).

Reference Example 44a (5-iodo-pyrimidin-4-yl)carbamic acid tert-butyl ester. To a mixture of 5-iodo-pyrimidin-4-yl amine (3.52 g, 15.9 mmol) (reference example 45) in THF (100 mL) is added pyridine (1.4 mL, 17.5 mmol) and di-tert-butyl dicarbonate (3.82 g, 17.5 mmol). The resulting mixture is heated to 50°–55° C. and stirred for 2.5 hours then cooled to room temp and concentrated. The residue is purified by flash chromatography (eluting with 20% ethyl acetate, 5% methanol in hexanes) to give 1.46 g of title compound as a pale yellow solid. $^1$H NMR (DMSO) δ 1.48 (s, 9H), 8.87 (s, 1H), 9.01 (s, 1H), 9.60 (bs, 1H). MS (EI) m/z 321 (M+).

Reference Example 44b

Using essentially the same procedure as in reference example 44a except using 4-amino-pyridine there is prepared pyridin-4-yl-carbamic acid tert-butyl ester. $^1$H NMR (CDCl$_3$) δ 1.52 (s, 9H), 6.82 (bs, 1H), 7.30 (d, J=7 Hz, 2H), 8.43 (d, J=7 Hz, 2H).

Reference Example 45

5-iodo-pyrimidin-4-yl amine. (Based on Brown, D. J.; J.S.C.I., 69, December, 1950, pp.353–356) To a solution of 4-aminopyrimidine (2.8 g, 29.4 mmol) in acetic acid (30 mL) is added ICI (3.03 mL, 60.4 mmol). The solution is heated to 100° C. and stirred for 3 hours then poured into $H_2O$ (140 mL). The mixture is decolorized with sodium bisulfite then cooled to 0°–5° C. and the pH adjusted to 6–7 with NaOH(s). The precipitated product is filtered off, washed with a small volume of $H_2O$ then dried under high vacuum to give 3.52 g of title compound as a white solid. $^1$H NMR (DMSO) δ 7.09 (bs, 2H), 8.30 (s, 1H), 8.45 (s, 1H). MS (EI) m/z 221 (M+H)$^+$.

Reference Example 46

4-ethynyl-benzoic acid methyl ester. To a solution of 4-trimethylsilanylethynyl-benzoic acid methyl ester (4.65 g, 20 mmol) (reference example 47) in THF (40 mL) is added (1M) tetrabutylammonium fluoride (3 mL, 30 mmol) and acetic acid (1.9 mL, 33 mmol). The resulting solution is stirred for 25 min, diluted with ethyl acetate, washed with water and brine, dried over MgSO$_4$ and concentrated. The residue is purified by flash chromatography (eluting with 10% ether, 10% dichloromethane in hexanes) to give 2.56 g of title compound as a pale yellow solid. $^1$H NMR (CDCl$_3$) δ 3.23 (s, 1H), 3.92 (s, 3H), 7.55 (d, J=8 Hz, 2H), 8.00 (d, J=8 Hz, 2H). MS (EI) m/z 160 (M+).

Reference Example 47

4-trimethylsilanylethynyl-benzoic acid methyl ester. To a cooled solution (–78° C.) of (trimethylsilyl)acetylene (4.2 mL, 30 mmol) in THF (25 mL) is added dropwise (2.5M) n-butyllithium (11.6 mL, 29 mmol) and stirred for 30 min followed by slow addition of (0.5M) zinc chloride (58 mL, 29 mmol). The resulting solution is allowed to warm to 20° C. followed by addition of 4-iodo-benzoic acid methyl ester (5.24 g, 20 mmol) (reference example 48) and tetrakis (triphenylphosphine)palladium(0) (1.16 g, 1 mmol) in THF (10 mL). The resulting mixture is heated to 55° C. and stirred for 2 hours then cooled to 20° C. The reaction mixture is diluted with ethyl acetate, washed with sat.NH$_4$Cl soln, water and brine, dried over MgSO$_4$ and concentrated to give 4.65 g of title compound. $^1$H NMR (CDCl$_3$) δ 0.26 (s, 2H), 3.91 (s, 3H), 7.52 (d, J=8 Hz, 2H), 7.97 (d, J=8 Hz, 2H). MS (EI) m/z 232 (M+).

Reference Example 48

4-iodo-benzoic acid methyl ester. To a solution of 4-iodobenzoic acid (9.92 g, 40 mmol) in DMF (80 mL) is added potassium carbonate (5.8 g, 42 mmol) and iodomethane (2.6 mL, 42 mmol). The resulting mixture is stirred for 17 hours, diluted with ethyl acetate, washed with water and brine, dried over MgSO$_4$ and concentrated. The crude solid is recrystallized in ethyl acetate/hexane to give 8.74 g of title compound. $^1$H NMR (CDCl$_3$) δ 3.91 (s, 3H), 7.74 (d, J=8 Hz, 2H), 7.80 (d, J=8 Hz, 2H). MS (EI) m/z 262 (M+).

Reference Example 49

(3-iodo-pyridin-4-yl)-carbamic acid tert-butyl ester. To a solution of pyridin-4-yl-carbamic acid tert-butyl ester (14.8 g, 76.3 mmol) (reference example 44b) in THF (300 mL) is added N,N,N',N'-tetramethylethylene-diamine (34.5 mL, 230 mmol) and the solution cooled to –78° C. To this solution is added slowly (2.5M) n-butyllithium (91.5 mL, 230 mmol), the reaction temperature allowed to rise to –20° C. and the resulting mixture stirred for 1.5 hours. The mixture is cooled to –78° C. and a solution of iodine (29.04 g, 114 mmol) in THF (60 mL) is added then stirred for 10 min. The mixture is warmed to 20° C., stirred 30 min then diluted with ethyl acetate, washed with water, sat. sodium thiosulfate and brine, dried over MgSO$_4$ and concentrated. The residue is purified by flash chromatography (eluting with 20% ethyl acetate in hexanes) to give 17.7 g of title compound as a light yellow crystalline solid. $^1$H NMR (CDCl$_3$) δ 1.54 (s, 9H), 7.03 (bs, 1H), 8.10 (d, J=6 Hz, 1H), 8.34 (d, J=6 Hz, 1H), 8.74 (s, 1H). MS (EI) m/z 320 (M+).

Reference Example 50

3-iodo-pyridin-4-ol. To a solution of 4-hydroxypyridine (12 g, 126 mmol) in H$_2$O (30 mL) is added sodium carbonate (11.32 g, 107 mmol) and the resulting mixture heated to reflux (100° C.) followed by the dropwise addition of a solution of potassium iodide (19.8 g, 119 mmol) and iodine (18 g, 71 mmol) in H$_2$O (50 mL). The resulting hot solution is adjusted to pH 6 using 2N HCl soln. and filtered hot through a cintered glass funnel. The filtrate is cooled and the precipitated product collected by filtration. The filtrate is heated to reflux and the above procedure repeated. The crude product is heated to reflux in 0.3M HCl soln. and filtered through a cintered glass funnel. The filtrate is kept near reflux while adjusting pH to 6 with 1N NaOH soln. then cooled to 5° C., the precipitate collected and dried under high vacuum giving 8 g of title compound as a yellow solid. $^1$H NMR (DMSO) δ 86.16 (d, J=7 Hz, 1H), 7.70 (d, J=7 Hz, 1H), 8.27 (s, 1H), 11.70 (bs, 1H). MS (EI) m/z221 (M+.).

Reference Example 51

2-[4-(1,1-dimethyl-allyl)-phenyl]-furan. To a cooled slurry (0° C.) of methyltriphenylphosphonium bromide (18.8 g, 52.6 mmol) in THF (60 mL) is added dropwise (1M)sodium bis(trimethylsilyl)amide (52.6 mL, 52.6 mmol) and the resulting mixture stirred for 30 min. To the mixture is added a solution of 2-(4-furan-2-yl-phenyl)-2-methyl-propionaldehyde (5.64 g, 26.3 mmol) (reference example 52) in THF (25 mL) and the resulting mixture stirred for 45 min. The mixture is diluted with ether, washed with water and brine, dried over MgSO$_4$ and concentrated. The residue is purified by flash chromatography (eluting with 10% ethyl acetate in hexanes) to give 6.2 g of title compound as a yellow oil. $^1$H NMR (CDCl$_3$) δ 1.41 (s, 6H), 5.03 (s, 1H), 5.08 (d, J=7 Hz, 1H), 6.03 (m, 1H), 6.45 (m, 1H), 6.60 (d, J=3 Hz, 1H), 7.36 (d, 8 Hz, 2H), 7.44 (s, 1H), 7.60 (d, J=8 Hz, 2H). MS (EI) m/z 212 (M+).

Reference Example 52

2-(4-furan-2-yl-phenyl)-2-methyl-propionaldehyde. To a solution of 2-(4-furan-2-yl-phenyl)-2-methyl-propan-1-ol (6.56 g, 30 mmol) (reference example 53) in CH$_2$Cl$_2$ (200 mL) is added Dess-Martin periodinane (22.5 g, 53 mmol) and the resulting mixture stirred for 45 min then concentrated. The residue is purified by flash chromatography (eluting with 10% ethyl acetate in hexanes) to give 5.64 g of title compound. $^1$H NMR (CDCl$_3$) δ 1.48 (s, 6H), 6.47 (m, 1H), 6.66 (d, J=3 Hz, 1H), 7.30 (d, J=8 Hz, 2H), 7.46 (s, 1H), 7.68 (d, J=8 Hz, 2H), 9.50 (s, 1H). MS (EI) m/z 214 (M+).

Reference Example 53

2-(4-furan-2-yl-phenyl)-2-methyl-propan-1-ol. To a cooled solution (0° C.) of (1M)lithium aluminum hydride (13.3 mL, 13.3 mmol) in THF (27 mL) is added a solution of 2-(4-furan-2-yl-phenyl)-2-propionic acid methyl ester (3.1 g, 12.7 mmol) (reference example 30a) in THF (11 mL). The resulting solution is stirred for 15 min then added slowly H$_2$O (0.5 mL), 15% NaOH (0.5 mL) and H$_2$O (1.5 mL). The resulting slurry is diluted with ether, filtered through a pad of celite and the filtrate concentrated to give 2.7 g of title compound as a white crystalline solid. $^1$H NMR (CDCl$_3$) δ 1.34 (s, 6H), 3.62 (m, 3H), 6.46 (m, 1H), 6.62 (d, J=3 Hz, 1H), 7.40 (d, J=8 Hz, 2H), 7.46 (bs, 1H), 7.64 (d, J=8 Hz, 2H). MS (EI) m/z 216 (M+).

Reference Example 54

A suspension of TFP resin (U.S. patent application Ser. No. 60/090,558) (1 g, 0.83 mmol/g) and. 4-t-butyl-benzoic acid (295 mg, 1.66 mmol in DMF (10 mL) is shaken for 10 minutes. then DMAP (20 mg, 0.16 mmol) in DMF (1 mL) added. To this mixture is added 1,3-diisopropylcarbodiimide (200 mL, 1.6 mmol). The resulting suspension is shaken for 2.5 hours then filtered and the solid washed, sequentially, with approximately 10 mL of each of $CH_2Cl_2$, DMF, THF, $CH_2Cl_2$. The resulting acylated resin is dried under vacuum and used without further processing.

A wide range of carboxylic acids can be activated using essentially the same procedure. A representative list of such carboxylic acids includes:

4-(4-carbamoyl-phenyl)-benzoic acid
4-(4-methoxy-phenyl)-benzoic acid
5-methoxy-indol-2-yl-carboxylic acid
6-chloro-benzothiophen-2-yl carboxylic acid
4-(4-benzyloxy-phenyl)-benzoic acid
4-chloro-benzoic acid
4-(methylsulphonyl)-benzoic acid
4-(aminosulphonyl)-benzoic acid Reference Example 55

N-(2-[3-Cyano-1-methylindol-5-yl]ethyl)-4-(6-methoxypyrid-3-yl)benzamide. A solution of 0.250 g (0.631 mmol) N-(2-[3-Cyano-indol-5-yl]ethyl)-4-(6-methoxypyrid-3-yl)benzamide (reference example 1p) in 5 mL DMF is added to a cooled (0° C.) solution of 0.0328 g (0.820 mmol) sodium hydride (60% dispersion in mineral oil) in 2 mL DMF. After ten minutes 0.043 mL (0.69 mmol) iodomethane is added, and the cooling bath removed. After 3 hours, the reaction is quenched with water, concentrated, and the resulting residue flash chromatographed (2:2:1 $CH_2Cl_2$:EtOAc:hexanes) to provide 0.167 g of the product as a white solid in 65% yield. $^1$H NMR ($CDCl_3$) δ 3.09 (2H, t, J=7 Hz), 3.80 (2H, m), 3.86 (3H, s), 3.99 (3H, s), 6.17 (1H, m, br), 6.83 (1H, d, J=8 Hz), 7.29 (1H, s), 7.37 (1H, d, J=8 Hz), 7.55–7.58 (3H, m), 7.64 (1H, s), 7.76–7.82 (3 H, m), 8.40 (1H, d, J=2 Hz). MS (ion spray) m/z 411 (M+H)$^+$.

Reference Example 56

Methyl 4-(2-[t-butyloxycarbonylamino-methyl]-pyridin-4-yl)-benzoate. To a solution of methyl 4-(2-cyano-pyridin-4-yl)-benzoate (1.15 g, 4.8 mmol) (reference example 57) in THF (20 mL) is added palladium on carbon (200 mg, 10% Pd by wt) followed by di-t-butyl-dicarbonate (1.12 g, 5.1 mmol). The resulting mixture is stirred under an atmosphere of hydrogen for 16 hours. Then purged with nitrogen, diluted with ethyl acetate and filtered through celite. The filtrate is concentrated under reduced pressure and the residue purified by flash chrmatography (eluting with 50% ethyl acetate in hexanes to give 534 mg of the title compound as an oil (32%). $^1$H NMR ($CDCl_3$) δ 1.47 (s, 9H), 3.96 (s, 3H), 4.51 (d, J=6 Hz, 2H), 7.41 (dd, J=5, 1.4 Hz, 1H), 7.50 (bs, 1H), 7.71 (d, J=8 Hz, 2H), 8.16 (d, J=8 Hz, 2H), 8.61 (d, J=5 Hz, 1H). MS (ion spray) m/z 343 (M+H).

Reference Example 57

Methyl 4 (2-cyano-pyridin-4-yl)-benzoate. To a solution of methyl 4-(pyridin-N-oxide-4-yl)-benzoate (1.15 g, 5 mmol) (reference example 18) in $CH_2Cl_2$ (10 mL) is added TMSCN (736 mL, 5.5 mmol) followed by N,N-diethyl carbamoyl chloride (742 mL, 5.8 mmol). The resulting solution is stirred for 116 hours then aqueous $K_2CO_3$ added (10 mL, 10%). The mixture is diluted with ethyl acetate, washed with brine, dried over $MgSO_4$ and concentrated to give 1.15 g of the title compound as a tan solid . This material is used without further purification. $^1$H NMR ($CDCl_3$) δ 3.86 (s, 3H), 8.05 (m, 2H), 8.08 (m, 2H), 8.12 (dd, J=5, 2 Hz, 1H), 8.49 (bs, 1H), 8.82 (d, J=5 Hz, 1H). MS (EI) m/z 238 M+.

Reference Example 58

Methyl 4-(2-carbamoyl-pyridin-4-yl)-benzoate. A solution of methyl 4-(2-cyano-pyridin-4-yl)-benzoate (400 mg, 1.68 mmol) (reference example 57) in 80% sulphuric acid (3 mL) is stirred at room temperature for 12 hours. The resulting solution is poured onto ice and the mixture brought to pH 8 with sat. sodium bicarbonate solution then extracted with ethyl acetate, washed with brine, dried over MgSO4 and concentrated. The residue is purified by flash chromatography (eluting with 40% ethyl acetate in chloroform) to give 340 mg of the title compound. $^1$H NMR ($CDCl_3$) δ 3.94 (s, 3H), 5.72 (bs, 1H), 7.67 (dd, J=5, 1 Hz, 1H), 7.75 (d, J=8 Hz, 2H), 7.9 (bs, 1H), 8.15 (d, J=8 Hz, 2H), 8.46 (bs, 1H), 8.63 (d, J=5 Hz, 1H). MS (EI) m/z 256.

Reference Example 59

Methyl 4-(2-[N,N-dimethylamino-methyl]-pyridin-4-yl)-benzoate. To a solution of Methyl 4-(2-[t-butyloxycarbonylamino-methyl]-pyridin-4-yl)-benzoate (reference example 56) (520 mg, 1.5 mmol) in $CH_2Cl_2$ (5 mL) is added TFA (1.5 mL) and 2 drops of water (approx. 100 mL). The resulting solution is stirred for 90 minutes, then concentrated under reduced pressure. The residue is dissolved in THF (4 mL) then $NaBH_4$ added (222 mg, 6 mmol) followed by paraformaldehyde (360 mg, 12 mmol). To this mixture is added TFA (4 mL) dropwise. The resulting mixture is stirred for 6 hours then concentrated. The residue is brought to pH 8 with aqueous NaOH (1M) and sat $NaHCO_3$. The mixture is then extracted with ethyl acetate then ethyl acetate methanol (9/1). The combined organic extracts are washed with brine dried over $MgSO_4$ and concentrated. The residue is purified by flash chromatography (eluting with 10% methanol in $CH_2Cl_2$) to give 329 mg of the title compound. $^1$H NMR ($CD_3OD$) δ 3.00 (s, 6H), 3.94 (s, 3H), 4.56 (s, 2H), 7.74 (d, J=5 Hz, 1H), 7.83 (s, 1H), 7.88 (d, J=8 Hz, 2H), 8.17 (d, J=8 Hz, 2H), 8.76 (d, J=5 Hz, 1H). MS (ion spray) m/z 271 (M+H).

Reference Example 60

3,6-dibromopyridazine. To a cooled solution (0° C.) of phosphorus tribromide (15.7 mL, 165 mmol) is added dropwise bromine (8.5 mL, 165 mmol). The resulting solid is allowed to stand for 10 min then quickly mixed thoroughly with a spatula. To the solid $PBr_5$ is added 3,6-dihydroxypyridazine (16.8 g, 150 mmol), the solids mixed thoroughly and the flask equipped with a condenser and drying tube. The mixture is heated to 100° C. for 3 hours then cooled to 20° C. The solids are transferred in small portions to a cooled (−5° C.) 2N $NH_4OH$ soln (200 mL). Collected solids by filtration and washed with cold (−5° C.) 1N NaOH (120 mL) then with $H_2O$ till neutral pH. Dissolved solids in ether, dried over $MgSO_4$, concentrated and dried under high vacuum to give 25.8 g of title compound as a pale yellow solid. $^1$H NMR (DMSO) δ 8.01 (s, 2H). MS (EI) m/z 236/238/240 (M$^+$), $Br_2$.

Reference Example 61a

4-[1-(2-dimethylamino-ethyl)-6-oxo-1,6-dihydro-pyridazin-3-yl]-benzoic acid. To a solution of 4-[1-(2-dimethylamino-ethyl)-6-oxo-1,6-dihydro-pyridazin-3-yl]-benzoic acid methyl ester (542 mg, 1.8 mmol, reference example 62a) in 1:1 THF/methanol (6 mL) is added 10N NaOH (1.8 mL, 18 mmol) followed by $H_2O$ (0.5 mL). The resulting solution is stirred for 1.5 hours then cooled to 0°–5° C., adjusted to pH 6 with 2N HCl and concentrated.

The residue is purified by reverse phase HPLC (eluting with 15%–40% acetonitrile(0.1%TFA)/H₂O(0.1%TFA) over 20 min) to give 487 mg of title compound. ¹H NMR (DMSO) δ 2.89 (s, 6H), 3.59 (m, 2H), 4.52 (bt, 2H), 7.14 (d, J=10 Hz, 1H), 8.04 (s, 4H), 8.16 (d, J=10 Hz, 1H), 9.63 (bs, 1H). MS (ion spray) m/z 288 (M+H)⁺.

Reference Example 61b

Using essentially the same procedure used to prepare reference example 61a except using the product from reference example 62b there is prepared 4-[1-(3-dimethylamino-propyl)-6-oxo-1,6-dihydro-pyridazin-3-yl]-benzoic acid. ¹H NMR (DMSO) δ 2.17 (m, 2H), 2.78 (s, 3H), 2.79 (s, 3H), 3.16 (m, 2H), 4.24 (bt, 2H), 7.14 (d, J=10 Hz, 1H), 8.05 (s, 4H), 8.16 (d, J=10 Hz, 1H), 9.61 (bs, 1H). MS (EI) m/z 302 (M+H)⁺.

Reference Example 62a

4-[1-(2-dimethylamino-ethyl)-6-oxo-1,6-dihydro-pyridazin-3-yl]-benzoic acid methyl ester. To DMSO (3.5 mL) is added 60% NaH dipersion in mineral oil (84 mg, 2.1 mmol) and the resulting mixture stirred for 5 min. To this solution is added 4-(6-oxo-1,6-dihydro-pyridazin-3-yl)-benzoic acid methyl ester (460 mg, 2 mmol reference example 36e) and the mixture stirred for 10 min (till homogeneous). In a separate flask containing DMSO (3.5 mL) is added 60% NaH (101 mg, 2.5 mmol) and stirred 5 min. To this solution is added 2-dimethylaminoethylchloride hydrochloride (346 mg, 2.4 mmol) and let stir for 5 min. This solution is transferred to the reaction solution, heated to 50° C., let stir for 2 hours. Cooled to 20° C., quenched with sat NH₄Cl soln (2 mL) and concentrated. The residue is purified by short path flash chromatography (eluting with 10% methanol in dichloromethane) to give 542 mg of title compound. ¹H NMR (CD₃OD) δ 2.35 (s, 6H), 2.88 (t, J=7 Hz, 2H), 3.93 (s, 3H), 4.42 (t, J=7 Hz, 2H), 7.08 (d, J=10 Hz, 1H), 8.06 (m, 5H). MS (EI) m/z 302 (M+H)⁺.

Reference Example 62b

Using essentially the same procedure used to prepare reference example 61a except using 3-(dimethyl-amino)-propylchloride hydrochloride, there is prepared 4-[1-(3-dimethylamino-propyl)-6-oxo-1,6-dihydro-pyridazin-3-yl]-benzoic acid methyl ester. ¹H NMR (CD₃OD) δ 2.07 (m, 2H), 2.25 (s, 6H), 2.45 (bt, 2H), 3.92 (s, 3H), 4.29 (bt, 2H), 7.07 (d, J=10 Hz, 1H), 8.04 (m, 5H). MS (ion spray) m/z 316 (M+H)⁺.

Reference Example 63

4-(6-methoxy-pyridazin-3-yl)-benzoic acid methyl ester. To a solution of 4-(6-methoxy-pyridazin-3-yl)-benzoic acid (5.02 g, 21.8 mmol) (reference example 11f) in methanol (75 mL) is added slowly conc. H₂SO₄ (3.75 mL). The resulting solution is heated to 50° C. and stirred for 1 hour. The solution is then concentrated to one third volume, cooled to 0°–5° C., adjusted to pH 6 with sat NaHCO₃ soln and extracted into ethyl acetate. The organic layer is washed with brine, dried over MgSO₄ and concentrated. The residue is purified by flash chromatography (eluting with 20% ethyl acetate in dichloromethane) to give 4.26 g of title compound as a white crystalline solid. ¹H NMR (DMSO) δ 3.90 (s, 3H), 4.10 (s, 3H), 7.38 (d, J=9 Hz, 1H), 8.10 (d, J=9 Hz, 2H), 8.25 (m, 3H). MS (EI) m/z 244 (M⁺).

Reference Example 64a

N-[2-(3-cyano-1H-indol-5-yl)-ethyl]-4-(6-oxo-piperidin-3-yl)benzamide. 4-(6-Oxo-piperidin-3-yl)-benzoic acid (190 mg, 0.87 mmol, reference example 65) and 5-(2-amino-ethyl)-1H-indole-3-carbonitrile (161 mg, 0.87 mmol, reference example 2) is dissolved in anhydrous DMF (3 mL). To this solution is added diisoproplyethylamine (330 µl, 1.9 mmol), followed by HBTU (330 mg, 0.87 mmol) and allowed to stir at room temperature overnight (16 hours). The product is isolated by Reverse-Phase chromatography of the crude reaction mixture (Dynamax C-18 60 A (5×30 cm), 50 ml/min, λ@ 220 nm, 10–70% B in 15 minutes, A: 0.1% TFA/water, B: 0.1% TFA/acetonitrile). ¹H NMR (300 MHz, DMSO) δ 1.94 (m, 2H), 2.26 (m, 2H), 2.92 (t, J=7.1, 2H), 3.19 (m, 1H), 3.48 (m, 2H), 3.46 (m, 2H), 7.13 (d, J=8.4, 1H), 7.15 (d, J=1.4, 2H), 7.36 (d, J=8.3, 2H), 7.43 (d, J=8.5, 1H), 7.46 (s, 1H), 7.55 (d, J=2.5, 1H), 7.73 (d, J=8.3, 2H), 8.17 (d, J=3.0, 1H), 8.47 (t, J=5.5, 1H). MS (Ion spray) m/z 387 (M+H)⁺.

Reference Example 64b

Using essentially the same procedure used to prepare reference example 64a except using the product from reference example 68 there is prepared N-Boc-3-cyano-5-{2-[4-(6-oxo-1,6-dihydro-pyridin-3-yl)-benzoylamino]-propyl}-indole. ¹H NMR (300 MHz, CDCl₃) d 8.11 (d, J=8.7 Hz, 1H), 8.09 (s, 1H), 7.79 (dd, J=9.4, 2.4 Hz, 1H), 7.76 (d, J=8.1 Hz, 2H), 7.65 (d, J=2.4 Hz, 1H), 7.56 (s, 1H), 7.47 (d, J=8.3 Hz, 2H), 7.36 (d, J=8.6 Hz, 1H), 6.71 (d, J=9.4 Hz, 1H), 6.02 (d, J=8.1 Hz, 1H), 4.57–4.47 (m, 1H), 3.13–2.96 (m, 2H), 1.68 (s, 9H), 1.27 (d, J=6.7 Hz, 3H); MS (ion spray) m/z 497 (M+H⁺).

Reference Example 64c

Using essentially the same procedure used to prepare reference example 64a except using the product from reference example 75 there is prepared tert-Butyl 4-{4-[2-(3-cyano-1H-indol-5-yl)ethylcarbamoyl]-phenyl}-3,6-dihydro-2H-pyridine-1-carboxylate. ¹H NMR (300 MHz, CDCl₃) d 8.92 (bs, 1H), 7.72–7.64 (m, 4H), 7.42–7.38 (m, 3H), 7.21 (d, J=6.9 Hz, 1H), 6.17 (bt, 1H), 6.09 (bs, 1H), 4.10–4.06 (m, 2H), 3.78 (dd, J=12.9, 6.7 Hz, 2H), 3.64 (t, J=5.7 Hz, 2H), 3.07 (t, J=6.8 Hz, 2H), 2.55–2.47 (m, 2H), 1.49 (s, 9H); MS (ion spray) m/z 471 (M+H⁺).

Reference Example 64d

Using essentially the same procedure used to prepare reference example 64a except using the product from reference example 81 there is prepared t-Butyl (3-{4-[2-(3-cyano-1H-indol-5-yl)ethylcarbamoyl]phenyl}-prop-2-ynyl) carbamate. ¹H NMR (300 MHz, CD₃OD) d 11.62 (bs, 1H), 8.56 (bs, 1H), 7.90 (d, 1H), 7.71 (m, 2H), 7.55 (s, 1H), 7.50–7.40 (m, 3H), 7.21 (d, 1H), 4.08 (s, 2H), 3.63 (m, 2H), 3.05 (t, 2H).

Reference Example 65

4-(6-Oxo-piperidin-3-yl)-benzoic acid. Ethyl 4-(6-oxo-piperidin-3-yl)-benzoate (320 mg, 1.30 mmol, reference example 66) is dissolved in MeOH (8 mL). To this solution is added 1 N NaOH (1.43 mL, 1.43 mmol) and the resulting solution stirred at room temperature for 1 hour. An additional portion of 1 N NaOH (2 mL) is added and the mixture allowed to stir at room temperature overnight (16 hours). 1 N HCl is added until pH 2–3 is reached. A precipitate formed and is filtered, washed with water and placed in a vacuum oven to dry overnight to afford the title compound (250 mg, 88%) as small white crystals (needles). ¹H NMR (300 MHz, DMSO) δ 1.94 (m, 2H), 2.23 (m, 2H), 3.06 (m, 1H), 3.23 (m, 2H), 7.42 (d, J=8.3, 2H), 7.57 (bs, 1H), 7.87 (d, J=8.1, 2H); MS (Ion spray) m/z 220 (M+H)+.

Reference Example 66

Ethyl 4-(6-oxo-piperidin-3-yl)-benzoate. Ethyl 4-(6-oxo-1,6-dihydro-pyridin-3-yl)-benzoate (450 mg, 1.8 mmol) (reference example 36f) is dissolved in HOAc (15 mL), and the the solution is degassed several times by alternating $N_2$/vacuum. 50 mg of $PtO_2$ is added and the mixture is degassed for several minutes before being placed under a $H_2$ atmosphere. The mixture is stirred at room temperature for 9 hours then degassed several times by alternating $N_2$/vacuum then filtered through a plug of celite. The plug is washed thoroughly with HOAc and the filtrate concentrated. The residue is chromatographed first on silica gel (3% MeOH/$CH_2Cl_2$), and then by Reverse-Phase HPLC to afford 330 mg of the title compound (72%) as a white solid. $^1$H NMR ($CDCl_3$) δ 1.39 (t, J=7 Hz, 3H), 2.12 (m, 2H), 2.56 (m, 2H), 3.13 (m, 1H), 3.41 (dd, J=11.3, 11.3, 1H), 3.53 (m, 1H), 4.37 (q, J=7, 2H), 6.78 (bs, 1H), 7.16 (d, J=8 Hz, 2H), 8.01 (d, J=8 Hz, 2H). MS (Ion spray) m/z 248 (M+H)+.

Reference Example 67a

Ethyl 4-(1-carboxymethyl-6-oxo-1,6-dihydropyridin-3-yl)benzoate. To a solution of ethyl 4-(1-tert-butoxycarbonylmethyl-6-oxo-1,6-dihydropyridin-3-yl) benzoate [1.03 g, 2.88 mmol, reference example 85b] in $CH_2Cl_2$ [10 ml] and $H_2O$ [0.125 ml] is added trifluoroacetic acid [2.5 ml]. After 18 hours removed solvent in vacuo and triturated the resulting solid with methylene chloride to give 0.815 g of the product as a white solid in 93.9% yield. $^1$H NMR (1:1 $CD_3OD:CDCl_3$): δ 1.43 (3H, t, J=7 Hz), 4.40 (2H, q, J=7 Hz), 4.81 (2H, s), 6.73 (1H, d, J=9 Hz), 7.60 (2H, d, J=8 Hz), 7.60 (1H, s), 7.88 (1H, d, J=9.0 Hz), 8.09 (2H, d, J=8 Hz). MS (ion spray) m/z 302 (M+H)+.

Reference Example 67b

Using essentially the same procedure used to prepare reference example 67a except using the product from reference example 64c there is prepared N-[2-(3-Cyano-1H-indol-5-yl)ethyl]-4-(1,2,3,6-tetrahydropyridin-4-yl) benzamide. $^1$H NMR (300 MHz, DMSO-$d_6$) d 12.11 (bs, 1H), 8.84 (bs, 2H), 8.57 (t, 1H), 8.19 (d, J=2.9 Hz, 1H), 7.82 (d, J=8.3 Hz, 2H), 7.55 (d, J=8.3 Hz, 2H), 7.47 (s, 1H), 7.46 (d, J=8.9 Hz, 1H), 7.16 (d, J=8.9 Hz, 1H), 6.31 (bs, 1H), 3.77 (bm, 2H), 3.55–3.47 (m, 2H), 3.36–3.29 (m, 2H), 2.94 (t, 2H), 2.69 (bm, 2H); MS (ion spray) m/z 371 (M+H+).

Reference Example 67c

3-Cyano-5-{2-[4-(6-oxo-1,6-dihydro-pyridin-3-yl)-benzoylamino]-propyl}-indole. Using essentially the same procedure used in reference example 67a except using the product from reference example 64b afforded the title compound. $^1$H NMR (300 MHz, DMSO-$d_6$) d 12.07 (bs, 1H), 8.30 (d, J=8.0 Hz, 1H), 8.17 (s, 1H), 7.88 (d, J=9.5 Hz, 1H), 7.83–7.80 (m, 3H), 7.62 (d, J=8.4 Hz, 2H), 7.50 (s, 1H), 7.42 (d, J=8.3 Hz, 1H), 7.17 (d, J=8.5 Hz, 1H), 6.43 (d, J=9.6 Hz, 1H), 4.26–4.17 (m, 1H), 3.02–2.82 (m, 2H), 1.16 (d, J=6.6 Hz, 3H); MS (ion spray) m/z 397 (M+H+).

Reference Example 68

N-Boc-5-(2-aminopropyl)-indole-3-carbonitrile. To a solution of N-Boc-5-(2-azidopropyl)-indole-3-carbonitrile (0.33 g, 0.97 mmol reference example 69) in tetrahydrofuran (5 mL) and a drop of water is added triphenylphosphine (1.1 g, 4.2 mmol). The reaction mixture is allowed to stir 3 days, and then concentrated and purified by column chromatography (silica, 3% to 5% MeOH/$CH_2Cl_2$) to provide 0.12 g of N-Boc-5-(2-aminopropyl)indole-3-carbonitrile: $^1$H NMR (300 MHz, DMSO-$d_6$) d 8.62 (s, 1H), 8.04 (d, J=8.6 Hz, 1H), 7.51 (s, 1H), 7.34 (d, J=8.7 Hz, 1H), 3.13–3.05 (m, 1H), 2.69 (d, J=6.6 Hz, 2H), 1.64 (s, 9H), 0.97 (d, J=6.2 Hz, 3H); MS (ion spray) m/z 300 (M+H+).

Reference Example 69

N-Boc-5-(2-azidopropyl)-indole-3-carbonitrile. N-Boc-5-(2-hydroxypropyl)-indole-3-carbonitrile (480 mg, 1.6 mmol, reference example 70) is dissolved in THF (10 mL) and cooled to 0° C. Triphenylphosphine (0.5 g, 2 mmol), diethylazodicarboxylate (0.3 mL, 2 mmol) and diphenylphosphorylazide (0.41 mL, 2 mmol) are added and the reaction stirred 14 hours. An additional portion (2 mmol) of each of the above reagents is added and the reaction stirred 6 hours. The resulting mixture n is partitioned between ethyl acetate and a saturated solution of sodium bicarbonate. The organic layer is separated, dried ($MgSO_4$), concentrated and purified by column chromatography (silica, 20% EtOAc/petroleum ether to EtOAc) to provide 0.33 g of N-Boc-5-(2-azidopropyl)-indole-3-carbonitrile: $^1$H NMR (300 MHz, $CDCl_3$) d 8.11 (d, J=8.2 Hz, 1H), 8.10 (s, 1H), 7.54 (d, J=1.0 Hz, 1H), 7.29 (dd, J=8.7, 1.6 Hz, 1H), 3.81–3.70 (m, 1H), 2.97–2.83 (m, 2H), 1.69 (s, 9H), 1.29 (d, J=6.5 Hz, 3H).

Reference Example 70

N-Boc-5-(2-hydroxypropyl)-indole-3-carbonitrile. A solution of N-Boc-5-(2-oxopropyl)-indole-3-carbonitrile (0.48 g, 1.6 mmol, reference example 71) in THF (15 mL) and ethanol (15 mL) is cooled to 0° C. and sodium borohydride (95 mg, 2.5 mmol) added in two portions over 15 minutes. After stirring an additional 15 minutes the reaction mixture is partitioned between ethyl acetate (150 mL) and a saturated aqueous ammonium chloride solution (50 mL). The organic layer is dried ($MgSO_4$) and concentrated to provide a semi-pure sample of N-Boc-5-(2-hydroxypropyl)-indole-3-carbonitrile which is used without further purification: $^1$H NMR (300 MHz, $CDCl_3$) d 8.10 (d, J=8.1 Hz, 1H), 8.09 (s, 1H), 7.56 (s, 1H), 7.30 (dd, J=8.7, 1.3 Hz, 1H), 4.16–4.04 (m, 1H), 3.7 (bs, 1H), 2.95–2.79 (m, 2H), 1.67 (s, 9H), 1.26 (d, J=6.4 Hz, 3H); MS (EI) m/z 300 (M+).

Reference Example 71

N-Boc-5-(2-oxopropyl)-indole-3-carbonitrile. A mixture of N-Boc-5-bromoindole-3-carbonitrile (1.08 g, 3.36 mmol, refererence example 72), tributyltin fluoride (2.1 g, 6.7 mmol), bis(tri-o-tolylphosphine) palladium dichloride (66 mg, 0.13 mmol), 2-trimethylsilyloxy-propene (1.1 mL, 6.7 mmol) and toluene (25 mL) is degassed and then heated in an 80° C. bath for 3 hours. Additional palladium catalyst (70 mg), 2-trimethylsilyloxy-propene (0.7 mL) and tributyltin fluoride (2.0 g) is added and the reaction is heated for an additional 1 hour. The reaction is cooled, and ether (25 mL) and 1N NaOH (25 mL) added followed by vigorous stirring for 10 minutes. The ether layer is separated, dried ($MgSO_4$), concentrated and purified by column chromatography (silica, $CH_2Cl_2$) to provide 0.48 g of N-Boc-5-(2-oxopropyl)-indole-3-carbonitrile: $^1$H NMR (300 MHz, DMSO-$d_6$) d 8.64 (s, 1H), 8.06 (d, J=8.6 Hz, 1H), 7.54 (s, 1H), 7.30 (d, J=8.6 Hz, 1H), 3.94 (s, 2H), 2.16 (s, 3H), 1.65 (s, 9H).); MS (EI) m/z 299 (M+H+).

Reference Example 72

N-Boc-5-bromoindole-3-carbonitrile. To a mixture of $CH_2Cl_2$ (20 mL) and acetone (5 mL) is added to 5-bromoindole-3-carbonitrile (1.23 g, 5.5 mmol, reference example 73) and di-t-butyidicarbonate (1.21 g, 5.5 mmol). N,N-Dimethylaminopyridine (24 mg, 0.2 mmol) is added and the reaction is stirred 1 hour. A precipitate formed which is filtered to provide 0.63 g of N-Boc-5-bromoindole-3-carbonitrile as a white solid. The filtrate is concentrated to provide 1.1 g of semi-pure product. The filtered product provided the following analytical data: $^1$H NMR (300 MHz, DMSO-d$_6$) d 8.73 (s, 1H), 8.07 (d, J=8.9 Hz, 1H), 7.90 (s, 1H), 7.66 (d, J=8.9 Hz, 1H), 1.64 (s, 9H).

Reference Example 73

5-Bromoindole-3-carbonitrile. Hydroxylamine hydrochloride (4.5 g, 66 mmol) is add to a mixture of 5-bromoindole-3-carbaldehyde (14.7 g, 66 mmol, reference example 74) and methanol (100 mL). After 1 hour toluene (80 mL) and THF (30 mL) are added and the reaction concentrated. Additional toluene (80 mL) is added and the reaction is azeotroped again. The mixture is dissolved in toluene (200 mL) and thionyl chloride (12 mL, 165 mmol) added causing a mild exotherm. The reaction is placed in a 70° C. bath and heated for 45 minutes. The reaction is then cooled and azeotroped with a mixture of CH$_2$Cl$_2$ and THF. The crude reaction mixture is dissolved in a mixture of methanol and CH$_2$Cl$_2$, adsorbed to silica gel and extracted with CH$_2$Cl$_2$ to provide 11.4 g of 5-bromoindole-3-carbonitrile. An analytically pure sample is obtained by recrystallization from toluene: (reddish needles) m.p. 189–191; $^1$H NMR (300 MHz, DMSO-d$_6$) d 12.38 (bs, 1H), 8.30 (d, J=3.0 Hz, 1H), 7.79 (d, J=1.5 Hz, 1H), 7.52 (d, J=8.6 Hz, 1H), 7.40 (dd, J=8.6, 1.6 Hz, 1H); MS (EI) m/z 220 (M$^+$, Br).

Reference Example 74

5-Bromoindole-3-carbaldehyde. Phosphorous oxychloride (10.5 mL, 112 mmol) is added slowly (over 10 min) to dimethylformamide (15 mL) with water bath cooling. To this solution is added a solution of 5-bromoindole (15 g, 93 mmol) in dimethylformamide (15 mL) over 15 minutes causing a slight exotherm. After 5 minutes the reaction is placed in an 80° C. bath and heated for 10 minutes. The reaction is cooled slightly and water (15 mL) added producing a vigorous exotherm. The reaction is heated in a bath temperature of 90° C. for 1.5 hours. The reaction is cooled and then added very slowly to 0.4 N NaOH (500 mL) forming a brown precipitate which is filtered, dissolved in EtOAc, dried (MgSO$_4$) and concentrated to yield a reddish solid. After sitting overnight the filtrate precipitated additional product which is collected and combined with the first batch to provide semi-pure aldehyde (15.3 g) which is used without further purification. $^1$H NMR (300 MHz, DMSO-d$_6$) d 12.30 (bs, 1H), 9.92 (s, 1H), 8.34 (d, J=3.0 Hz, 1H), 8.21 (s, 1H), 7.49 (d, J=8.6 Hz, 1H), 7.38 (dd, J=8.7, 1.8 Hz, 1H).

Reference Example 75 tert-Butyl 4-(4-Carboxyphenyl)-3,6-dihydro-2H-pyridine-1-carboxylate. To a solution of tert-butyl 1,2,3,6-tetrahydro-4-[(trifluoromethyl)sulfonyloxy]pyridine-1-carboxylate (2.63 g, 7.9 mmol, reference example 76) in dimethdxyethane (21 mL) is added 4-carboxybenzeneboronic acid (1.44 g, 8.7 mmol), 2M aqueous sodium carbonate (17.4 mL) and lithium chloride (0.99 g, 24 mmol). The mixture is degassed and then tetrakis(triphenylphosphine)palladium (450 mg, 0.4 mmol) added, the reaction is degassed again and then heated at reflux 6 h. The reaction is filtered and the solid washed with EtOAc. The organic phase is washed with 0.5 N HCl, dried (MgSO$_4$), concentrated and purified by column chromatography (silica, 3% MeOH/CH$_2$Cl$_{2/0.1}$%HOAc) providing a semi-purified product. This material is titurated with ether and a small amount of CH$_2$Cl$_2$ to provide 0.27 g of the title compound as a white solid: m.p. 200–209 (dec); $^1$H NMR (300 MHz, CDCl$_3$) d 8.07 (d, J=8.4 Hz, 2H), 7.47 (d, J=8.4 Hz, 2H), 6.20 (bs, 1H), 4.15–4.00 (m, 2H), 3.66 (t, J=5.6 Hz, 2H), 2.60–2.52 (m, 2H), 1.50 (s, 9H); MS (ion spray) m/z 304 (M+H$^+$).

Reference Example 76 tert-Butyl 1,2,3,6-Tetrahydro-4-[(trifluoromethyl)sulfonyloxy]pyridine-1-carboxylate. According to Wustrow and Wise, Synthesis 1991, 993. A solution of diisopropylamine (4.2 g, 29 mmol) in THF (9 mL) is cooled to −78° C. A solution of n-butyl lithium (11.2 mL, 2.5 M in hexanes) is added at −78° C. and the reaction warmed to 0° C. and then recooled to −78° C. A solution of tert-butyl 4-oxopiperidine-1-carboxylate (5.4 g, 27 mmol) in THF (15 mL) is added dropwise (5 min). After stirring an additional 25 minutes, a solution of N-phenyltrifluoromethanesulfonimide (10 g, 28 mmol) in THF (25 mL) is added and the reaction allowed to stir at room temperature 2 h. The reaction is concentrated, dissolved in CH$_2$Cl$_2$ and poured onto a dry pad of alumina (350 g). The product is eluted with 10% EtOAc/petroleum ether (1 L) and concentrated to provide 8 g of the title compound as a low melting solid: $^1$H NMR (300 MHz, CDCl$_3$) d 5.77 (bs, 1H), 4.06–4.04 (m, 2H), 3.63 (t, J=5.7 Hz, 2H), 2.46–2.40 (m, 2H), 1.48 (s, 9H).

Reference Example 77 t-Butyl 5-[2-[4-(3-t-butoxycarbonylaminoprop-1-ynyl)-benzoylamino]ethyl}-3-carbamimidoyl-indole-1-carboxylate. t-Butyl 5-[2-[4-(3-t-butoxycarbonylaminoprop-1-ynyl)-benzoylamino]ethyl}-3-thiocarbamoyl-indole-1-carboxylate (73 mg, 0.13 mmol, reference example 78) is dissolved in acetone (75 mL) and methyl iodide (5 mL) added. This mixture is heated to reflux. After 15 minutes, the solvent is removed in vacuo giving a yellow residue. MS (ion spray) m/e 591 (M+H$^+$). The residue (80 mg, 0.13 mmol) is dissolved in MeOH (15 mL) and ammonium acetate (0.5 g) added and this mixture heated at reflux for 20 minutes. The solvent is removed in vacuo and the residue partitioned between CH$_2$Cl$_2$ and water. The aqueous layer is extracted with CH$_2$Cl$_2$ and the combined organic layers washed with water, dried over magnesium sulfate and concentrated in vacuo. The crude product is purified by reverse phase HPLC eluting with 30–70%/15 minutes, giving 22 mg. MS (ion spray) m/z 560 (M+H$^+$).

Reference Example 78 t-Butyl 5-[2-[4-(3-t-butoxycarbonylaminoprop-1-ynyl)-benzoylamino]ethyl}-3-thiocarbamoyl-indole-1-carboxylate. t-Butyl 5-[2-[4-(3-t-butoxycarbonylaminoprop-1-ynyl)-benzoylamino]ethyl}-3-cyano-indole-1-carboxylate (80 mg, 0.15 mmol, reference example 79) is dissolved in pyridine (20 mL), triethylamine (2 mL) added. Hydrogen sulfide is bubbled into the reaction for 5 minutes. The reaction is then allowed to stand at R.T. overnight. The solvent is removed in vacuo and the residue is dissolved in CH$_2$Cl$_2$, washed with water and dried over magnesium sulfate. The solvent is removed in vacuo, giving 80 mg of residue which is used without further purification: $^1$H NMR (300 MHz, CDCl$_3$) d 8.61 (t, J=3.0 Hz, 2H), 8.24 (s, 1H), 8.12–8.06 (m, 2H), 7.71–7.59 (m, 2H), 7.39–7.20

(m, 3H), 6.41 (bs, 1H), 4.89 (bs, 1H), 4.14 (d, J=5.1 Hz, 2H), 3.78 (q, J=6.4 Hz, 2H), 3.05 (t, J=6.6 Hz, 2H), 1.66 (s, 9H), 1.46 (s, 91H).

Reference Example 79 t-Butyl 5-{2-[4-(3-t-butoxycarbonylaminoprop-1-ynyl)-benzoylamino]ethyl}-3-cyano-indole-1-carboxylate. To a suspension of t-Butyl (3-{4-[2-(3-cyano-1H-indol-5-yl) ethylcarbamoyl]phenyl}-prop-2-ynyl)carbamate (95 mg, 0.22 mmol, reference example 64d) in acetone (5 mL) is added di-t-butoxy-dicarbonate (47 mg, 0.22 mmol) and DMAP (0.9 mg, 8 mmol). Then pyridine (1 mL) is added and the mixture stirred at R.T. overnight. The solvent is removed in vacuo and the residue dissolved in $CH_2Cl_2$ and washed with water, then dried over magnesium sulfate and the solvent removed in vacuo, giving 88 mg of solid residue (75% yield). $^1$H NMR: (300 MHz, $CDCl_3$) d 8.63 (bs, 1H), 8.11 (d, J=9.7 Hz, 1H), 7.72–7.57 (m, 2H), 7.43 (d, J=8.4 Hz, 2H), 7.34–7.27 (m, 2H), 6.25 (bs, 1H), 4.84 (bs, 1H), 4.15 (d, J=5.2 Hz, 2H), 3.76 (q, J=6.6 Hz, 2H), 3.07 (t, J=6.9 Hz, 2H), 1.69 (s, 9H), 1.47 (s, 9H).

Reference Example 80

4-(3-t-Butoxycarbonylaminoprop-1-ynyl)benzoic acid. Methyl 4-(3-t-butoxycarbonylaminoprop-1-ynyl)benzoate (1.09 g, 38 mmol, reference example 81) is dissolved in MeOH (15 mL) and to this solution added NaOH (0.15 g, 38 mmol) dissolved in water (5 mL). This mixture is heated to reflux. After 5 hours, the solvent is removed in vacuo and $CH_2Cl_2$ and 1N HCl added to the residue. The organic layer is washed with 1N HCl, water and brine, then dried over magnesium sulfate. The solvent is removed in vacuo to give a white solid (0.60 g, 57% yield): $^1$H NMR (300 MHz, $CD_3OD$) d 7.86 (d, 2H), 7.39 (d, 2H), 3.98 (s, 2H), 1.38 (s, 9H).

Reference Example 81

Methyl 4-(3-t-butoxycarbonylaminoprop-1-ynyl) benzoate. Methyl-4-iodobenzoate (1.5 g, 5.7 mmol) and t-butyl prop-2-ynylcarbamate (0.89 g, 5.7 mmol, reference example 82) are dissolved in piperidine (12 mL) and this solution purged with nitrogen. Copper(I) iodide (22 mg, 0.11 mmol) and dichlorobis(triphenylphosphine) palladium (40 mg, 0.057 mmol) is added and the mixture is stirred at R.T. After 2 hours, the solvent is removed in vacuo and the residue added to $CH_2Cl_2$ and washed with 1N HCl, water and brine, then dried over magnesium sulfate. The solvent is removed in vacuo and the residue purified by flash chromatography, eluting with 20% ethyl acetate/hexane to provide the title compound as a white solid (1.1 g, 67% yield): $^1$H NMR (300 MHz, $CDCl_3$) d 7.98 (d, 2H), 7.48 (d, 2H), 4.79 (bs, 1H), 4.17 (d, 2H), 3.91 (s, 3H), 1.48 (s, 9H).

Reference Example 82 t-Butyl prop-2-ynylcarbamate. Propargylamine (10 g, 0.18 mol) is dissolved in $CH_2Cl_2$ (40 mL) and cooled in an ice bath. Di-t-butyl dicarbonate (40 g, 0.18 mol), dissolved in $CH_2Cl_2$ (60 mL), is added over 20 minutes. The cooling bath is removed and the reaction allowed to warm to R.T. and stirred overnight. The solvent is removed in vacuo and the residue used without further purification: $^1$H NMR (300 MHz, $CDCl_3$) d 4.75 (bs, 1H), 3.90 (d, 2H), 2.21 (t, 1H), 1.45 (s, 9H).

Reference Example 83

4-[2-(2-Dimethylamino-ethylamino)-pyrimidin-4-yl]-benzoic acid. To a solution of 4-[2-chloro-pyrimidin-4-yl]-benzoic acid (234 mg, 1 mmol, reference example 11 g) in DMSO (2 mL) is added 2-(N,N-dimethyl-amino)ethylamine (291 mL, 2 mmol). The resulting solution is heated to 85° C. and stirred at this temperature for 3.5 hours, then cooled and concentrated. The residue is purified by reverese phase HPLC to give 296 mg of the title compound as a TFA salt. $^1$H NMR ($CD_3OD$) d 2.97 (s, 6H), 3.45 (t, J=6 Hz, 2H), 3.88 (t, J=6 Hz, 2H), 7.31 (d, J=5 Hz, 1H), 8.13 (d, J=8 Hz, 2H), 8.20 (d, J=8 Hz, 2H), 8.44 (d, J=5 Hz, 1H). MS (ion spray) m/z 286 (M+).

Reference Example 84

4-[2-(2-Chloro)-pyrimidin-4-yl]-benzyl (t-butyidimethylsilyl) Ether. To a cooled (−78° C.) solution of 4-bromo-benzyl t-butyidimethylsilyl ether (3.0 g, 10 mmol, reference example 16) in THF (30 mL) is added, dropwise, n-buLi (4.08 mL, 2.5M in hexanes). The resulting solution is stirred for 10 minutes then a solution of 2-chloro-pyrimidine (1.14 g, 10 mmol) in THF (30 mL) added in one portion. This solution is warmed to −30° C. and stirred for 20 minutes then a solution comprised of acetic acid (600 mL, 10 mmol) and $H_2O$ (100 mL, 5.5 mmol) in THF (5 mL) added. The resulting mixture is warmed to 0° C. then DDQ (2.27 g, 10 mmol) in THF (10 mL) added. The cold bath is removed and stirring continued for 10 minutes. To this mixture is added NaOH (10 mL, 1M) then the mixture partitioned between ether and water. The ether fraction is washed with brine, dried over $MgSO_4$, and decolorized with activated charcoal, filtered through celite and the filtrate concentrated. The residue is purified by flash chromatography (eluting with 20% ethyl acetate in hexanes) to give 1.68 g of the title compound as an oil which crystallized on standing. $^1$H NMR ($CDCl_3$) d 0.04 (s, 6H), 0.84 (s, 9H), 4.70 (s, 2H), 7.45 (d, J=8 Hz, 2H), 7.53 (d, J=5 Hz, 1H), 7.96 (d, J=25 8 Hz, 2H), 8.50 (d, J=5 Hz, 1H). MS (ion spray) m/z 335 (M+H, Cl pattern).

Reference Example 85a

Ethyl 4-(1-[2-dimethylaminoethyl]-6-oxo-1,6-dihydropyridin-3-yl)benzoate and Ethyl 4-(6-[2-dimethyl-aminoethoxy]pyridin-3-yl)benzoate. To a cooled (0° C.) slurry of ethyl 4-(6-oxo-1,6-dihydropyridin-3-yl)benzoate [0.500 g, 2.06 mmol, reference example 36f] in THF:DMF [30 mL 5:1] is added 60% sodium hydride [0.247 g, 6.18 mmol]. After ten minutes added potassium iodide [2 mg] and 2-dimethylaminoethyl-chloride hydrochloride [Aldrich, 0.386 g, 2.68 mmol] and heated to 50° C. After twenty hours, quenched slowly with $H_2O$ [15 ml] and extracted with $CH_2Cl_2$. The organic extracts are combined and concentrated, then purified on an HPLC (40 to 60% AcCN in water with 0.1% TFA) to give ethyl 4-(1-[2-dimethylamino-ethyl]-6-oxo-1,6-dihydropyridin-3-yl) benzoate [0.337 g, 38.2% yield] as the TFA salt and ethyl 4-(6-[2-di-methylaminoethoxy]pyridin-3-yl)benzoate [0.110 g, 12.5%] yield as the TFA salt. For ethyl 4-(1-[2-dimethylaminoethyl]-6-oxo-1,6-dihydropyridin-3-yl) benzoate: $^1$H NMR ($CD_3OD$): δ 1.40 (3H, t, J=7.8 Hz), 3.03 (6H, s), 3.62 (2H, t, J=5.9 Hz), 4.38 (2H, q, J=7.8 Hz), 4.49 (2H, t, J=5.9 Hz), 6.72 (1H, d, J=9.2 Hz), 7.68 (2H, d, J=8.8 Hz), 7.98 (1H, dd, J=9.2 Hz, 3.0 Hz), 8.07 (2H, d, J=8.8 Hz), 8.13 (1H, d, J=3.0 Hz). MS (ion spray) m/z 315 (M+H)$^+$. For ethyl 4-(6-[2-dimethylaminoethoxy]pyridin-3-yl)benzoate: $^1$H NMR ($CD_3OD$): δ 1.41 (3H, t, J=8.1 Hz), 3.02 (6H, s), 3.64 (2H, t, J=6.1 Hz), 4.39 (2H, q, J=8.1 Hz), 4.74 (2H, t, J=6.1 Hz), 7.01 (1H, d, J=9.4 Hz), 7.73 (2H, d, J=8.8 Hz), 8.07 (1H, dd, J=9.4 Hz, 2.5 Hz), 8.10 (2H, d, J=8.8 Hz), 8.51 (1H, d, J=2.5 Hz). MS (ion spray) m/z 315 (M+H)$^+$.

Reference Example 85b

Using essentially the same conditions used to prepare reference example 85a except using t-butyl bromoacetate as the alkylating agent there is prepared Ethyl 4-(1-tert-butoxycarbonylmethyl-6-oxo-1,6-dihydropyridin-3-yl)benzoate. $^1$H NMR (CDCl$_3$): δ 1.41 (3H, t, J=7.3 Hz), 1.50 (9H, s), 4.40 (2H, q, J=7.3 Hz), 4.64 (2H, s), 6.70 (1H, d, J=9.5 Hz), 7.48 (2H, d, J=8.2 Hz), 7.50 (1H, s), 7.68 (1H, d, J=9.5 Hz), 8.08 (2H, d, J=8.2 Hz). MS (ion spray) m/z 358 (M+H)$^+$, 302 (M-tert-Bu)$^+$.

Reference Example 85c

Using essentially the same conditions used to prepare reference example 85a except using 3-dimethylaminopropyl chloride hydrochloride as the alkylating agent there is prepared Ethyl 4-[1-(3-dimethylaminopropyl)-6-oxo-1,6-dihydropyridin-3-yl]benzoate. MS (ion spray) m/z 329 (M+H)$^+$ and Ethyl 4-[6-(3-dimethylaminopropoxy)pyridin-3-yl]benzoate. MS (ion spray) m/z 329 (M+H)$^+$.

Reference Example 85d

Using essentially the same conditions used to prepare reference example 85a except using Allyl 4-(2-oxo-2H-pyridin-5-yl)benzoate (reference example 104) and t-butyl bromoacetate as substrates there is prepared Allyl 4-(1-[tert-butoxycarbonylmethyl]-2-oxo-2H-pyridin-5-yl)benzoate. MS (ion spray) m/z 370 (M+H)$^+$.

Reference Example 86a 4-(3-Amino-[1,2,4]triazin-6-yl)benzoic acid and 4-(3-Amino-[1,2,4]triazin-5-yl)benzoic acid. Aqueous NaOH (1N, 8.2 mL, 8.2 mmol) is added to a solution of a 2:1 mixture of the ethyl 4-(3-amino-[1,2,4]triazin-5-yl)benzoate and ethyl 4-(3-amino-[1,2,4]triazin-6-yl)benzoate (0.80 g, 3.3 mmol, reference example 87a) in MeOH (50 mL) and THF (100 mL). After stirring at ambient temperature for 18 hours, the reaction mixture is acidified to pH 4–5 with 2N HCl and partially evaporated. The resulting precipitate is collected, washed with H$_2$O and dried in vacuo to afford 4-(3-Amino-[1,2,4]triazin-6-yl)benzoic acid containing ~10% 4-(3-Amino-[1,2,4]triazin-5-yl)benzoic acid; yield 0.23 g (32%): $^1$H NMR (DMSO-d$_6$) d 8.10 (2H, d, J=7.3 Hz), 8.27 (2H, d, 7.3 Hz), 9.26 (1H, s); MS, m/z (isomeric mixture, ion spray) 235 [(M+18)+H]$^+$, 217 (M+H)$^+$. Further evaporation of the mother liquor and filtration of the precipitated solid gave 4-(3-Amino-[1,2,4]triazin-5-yl)benzoic acid. yield 0.40 g (56%): $^1$H NMR (DMSO-d$_6$) d 7.8–8.2 (4H, m), 8.95 (1H, s).

Reference Example 86b 4-(3-Oxo-2,3-dihydro-[1,2,4]triazin-6-yl)benzoic acid. Using the procedure of example 86a except substituting ethyl 4-(3-oxo-2,3-dihydro-[1,2,4]triazin-6-yl)-benzoate (reference example 87b) for a mixture of ethyl 4-(3-amino-[1,2,4]triazin-5-yl)benzoate and ethyl 4-(3-amino-[1,2,4]triazin-6-yl)benzoate afforded the title compound: $^1$H NMR (DMSO-d$_6$) d 3.90 [(0.2H, d, J=4.9 Hz), (hydrate)], 7.72 (0.80H, s), 8.05 (3.2H, s), 8.11 [(0.4H, d, J=7.7 Hz), (hydrate)], 8.32 [(0.4H, d, J=7.7 Hz), (hydrate)], 8.77 [(0.2H, s), (hydrate)].

Reference Example 86c 4-(5-Oxo-4,5-dihydro-[1,2,4]oxaidiazol-3-yl)-benzoic acid. Using the procedure of example 86a except using the product from reference example 89 afforded the title compound: $^1$H NMR (DMSO-d$_6$) d 7.93 (2H, d, J=7.3 Hz), 8.12 (2H, d, J=7.3 Hz).

Reference Example 87a

Ethyl 4-(3-amino-[1,2,4]triazin-5-yl)benzoate and ethyl 4-(3-amino-[1,2,4]triazin-6-yl)benzoate. Using the following modification of the procedure of Loev, B. and Goodman, M. M. (Tetrahedron Lett., 1968, 789) except substituting 4-carboethyoxy phenylglyoxal hydrate for glyoxal hydrate afforded approximately a 2:1 mixture of the ethyl 4-(3-amino-[1,2,4]triazin-5-yl)benzoate and ethyl 4-(3-amino-[1,2,4]triazin-6-yl)benzoate, respectively: Solid NaHCO$_3$ (0.79 g, 9.4 mmol) is added to a solution of aminoguanidine hydrochloride (1 g, 4.7 mol) in H$_2$O. The resulting solution is then added to a solution of 4-carboethyoxy phenylglyoxal hydrate (1 g, 4.7 mmol, reference example 88). The reaction mixture is stirred at ambient temperature for 72 hours and the precipitate collected, washed with H$_2$O and air-dried. The crude product is filtered through a pad of silica gel eluting with 4% CH$_2$Cl$_2$ in MeOH. Fractions containing only product are collected and the solvent removed under reduced pressure. The residue is triturated with ether to afford a 2:1 mixture of the title compounds ($^1$H NMR) as a white solid; yield 0.80 g (70%): $^1$H NMR (DMSO-d$_6$) d 1.35 (3H, t), 4.35 (1.34H, q), 4.37 (0.66H, q), 7.38 (0.33H, s), 7.56 (0.67H, s), 8.08 (1.34H, d), 8.13 (0.67H, d), 8.18 (1.34H, d), 8.32 (0.67H, d), 8.89 (0.67, s), 9.28 (0.33H, s); MS, m/z (EI) 244 (M$^+$).

Regiochemically pure ethyl 4-(3-amino-[1,2,4]triazin-5-yl)benzoate is also prepared by the procedure of Lalezari et al. (J. Het. Chem. 1969, 403) except substituting ethyl 4-acetyl benzoate for acetophenone facilitating identification of the structures of the respective regioisomers: $^1$H NMR (DMSO-d$_6$) d 1.35 (3H, t, J=7.1 Hz), 4.35 (2H, q, J=7.1 Hz), 7.56 (1H, s), 8.08 (2H, d, J=7.5 Hz), 8.18 (2H, d, J=7.5 Hz), 8.89 (1H, s); MS, m/z (ion spray) 263 [(M+18)+H]$^+$, 245 (M+H)$^+$.

Reference Example 87b

Ethyl 4-(3-oxo-2,3-dihydro-[1,2,4]triazin-6-yl)-benzoate. Using the procedure of reference example 87a except substituting semicarbazide hydrochloride for aminoguanidine hydrochloride afforded the title compound: $^1$H NMR (DMSO-d$_6$) d 1.33 (3H, t, J=4.6 Hz), 4.38 (2H, q, J=4.6 Hz), 7.74 (1H, s), 8.10 (4H, s), 11.12 (1H, s); MS, m/z (EI) 264 [(M+18)+H]$^+$, 246 (M+H)$^+$.

Reference Example 88

4-Carboethyoxy phenylglyoxal hydrate. The title compound is prepared using the following modification of an Org. Syn. preparation (vol. 2, 509) of phenylglyoxal and substituting ethyl 4-acetyl benzoate for acetophenone: Selenium dioxide (2.8 g, 0.026 mol) is added to a solution of ethyl 4-acetyl benzoate (5 g, 0.026 mol) in dioxane (30 mL) and water (1 mL). The reaction mixture is heated to reflux for 18 hours, cooled to ambient temperature and filtered through a pad of celite to remove the precipitated selenium. The filtrate is concentrated under reduced pressure and the residue is vacuum filtered through a pad of silica gel eluting successively with 33% and 50% hexanes in ethyl acetate to afford the title compound as a chromatographically pure yellow oil; yield 4.8 g (87%). A sample is further purified by trituation with ether to afford a white solid: $^1$H NMR (DMSO-d$_6$) d 1.32 (3H, t, J=6.3 Hz), 4.35 (2H, q, J=6.3 Hz), 5.67 (1H, t, J=5.9 Hz), 6.88 (2H, d, J=5.9 Hz), 8.08 (2H, d, J=7.1 Hz), 8.17 (2H, d, J=7.1 Hz).

Reference Example 89

Methyl 4-(5-oxo-4,5-dihydro-[1,2,4]oxaidiazol-3-yl)-benzoate. Ethyl chloroformate (0.23 mL, 0.26 g, 2 mmol) is added to a solution of 4-(carbomethoxy)benzaldehyde amidoxime (0.38 g, 2 mmol, reference example 90) in pyridine (10 mL) at ambient temperature. The reaction mixture is heated to reflux for 5 hours and the solvent evaporated. The residue is poured into $H_2O$ which is partially evaporated until a preciptate began to appear. The solids are collected, washed with $H_2O$, air-dried and dried in vacuo to afford the title compound as a white solid; yield 0.25 g (57%); $^1H$ NMR (CDCl$_3$/DMSO-d$_6$) d 3.95 (3H, s), 7.73 (2H, d, J=8.0 Hz), 8.13 (2H, d, J=8.0 Hz); MS, m/z(EI) 220 (M$^+$).

Reference Example 90

4-(Carbomethoxy)benzaldehyde amidoxime. Chlorine gas is bubbled through a solution of 4-(Carbomethoxy)benzaldehyde oxime (2.7 g, 0.015 mol, reference example 91) in CHCl$_3$ at 0° C. The reaction mixture turned green followed by a precipitate. Bubbling is continued until the reaction mixture became homogeneous at which time bubbling is ceased and the vessel sealed. After stirring for an additional ½ hour at ambient temperature, nitrogen is bubbled through the reaction mixture to remove excess chlorine. The solvent is evaporated and the residue is dissolved in EtOH (100 mL) to which NH$_3$ in MeOH (7M, 11 mL, 110 mmol) is added. After stirring for 1 hour at ambient temperature, the solvent is evaporated and the residue is vacuum filtered through a pad of silica gel eluting with 4% MeOH in CH$_2$Cl$_2$. Fractions containing only product are combined and concentrated. The residue is triturated with ether to afford the title compound as a white solid; yield 0.69 (24%): $^1H$ NMR (CDCl$_3$/DMSO-d$_6$) ? 3.92 (3H, s), 5.24 (2H, s), 7.77 (2H, d, J=9.1 Hz), 8.02 (2H, d, J=9.1 Hz), 9.68 (1H, s); MS, m/z(ion spray) 195 (M+H)$^+$.

Reference Example 91

4-(Carbomethoxy)benzaldehyde oxime. Sodium ethoxide (2.9 g, 0.43 mol) is added to a solution of hydroxylamine hydrochloride (3.3 g, 0.048 mol) in EtOH (100 mL). The mixture is filtered to remove the precipitated NaCl and 4-(carbomethoxy)benzaldehyde is added at ambient temperature. After stirring at this temperature for 18 hours, the solvent is evaporated and the residue is triturated with $H_2O$ and air-dried to afford the title compound as a white solid; yield 5.3 g (99%): MS (EI) m/z 180 (M+H)$^+$.

Reference Example 92a

4-[2-(morpholin-4yl-ethylamino)-pyrimidin-4-yl]-benzoic acid. To a solution of 4-[2-chloro-pyrimidin-4-yl]-benzoic acid (234 mg, 1 mmol, reference example 11g) in DMF (or DMSO) (3 mL) is added 2-(morpholin-4-yl)-ethyl amine (275 µL, 2.1 mmol). The resulting mixture was warmed to 80° C. and stirred for 4 h. The reaction mixture was then concentrated under a stream of nitrogen and the residue purified by reverse phase HPLC to give 166 mg of the title compound. $^1H$ NMR (DMSO-d$_6$) ? 3.18 (m, 2H), 3.40 (m, 2H), 3.50–3.80 (m, 6H), 3.97 (m, 2H) 7.33 (d, J=5 Hz, 1H), 7.53 (bt, 1H), 8.07 (d, J=8 Hz, 2H), 8.25 (d, J=8 Hz, 2H), 8.49 (d, J=5 Hz, 1H), 9.70 (bs, 1H). MS (ion spray) m/z 329 (M+H)$^+$.

The following compounds were prepared using essentially the same procedure employed in reference example 92a except using the cited amine instead of 2-(morpholin-4-yl)-ethyl amine.

Reference Example 92b

4-[2-(3-dimethylamino-propylamino)-pyrimidin-4-yl]-benzoic acid. Using 3-dimethylamino-propylamine. $^1H$ NMR (CD$_3$OD) ? 2.1 (m, 2H), 2.88 (s, 6H), 3.28 (t, J=7 Hz, 2H), 3.65 (bm, 2H), 7.33 (d, J=5 Hz, 1H), 8.15 (d, J=8 Hz, 2H), 8.24 (d, J=8 Hz, 2H), 8.40 (d, J=5 Hz, 1H). MS (ion spray) m/z 301 (M+H)$^+$.

Reference Example 92c

4-[2-(2-dimethylamino-ethyl-methyamino)-pyrimidin-4-yl]-benzoic acid. Using 2-(dimethylamino-ethyl)-methyamine. $^1H$ NMR (CD$_3$OD) ? 3.0 (s, 6H), 3.31 (s, 3H), 3.50 (t, J=7 Hz, 2H), 4.15 (t, J=7 Hz, 2H), 7.28 (d, J=5 Hz, 1H), 8.14 (d, J=8 Hz, 2H), 8.22 (d, J=8 Hz, 2H), 8.49 (d, J=5 Hz, 1H). MS (ion spray) m/z 301 (M+H)$^+$.

Reference Example 92d

2-[(4-{4-[2-(3-Cyano-1H-indol-5-yl)-ethylcarbamoyl]-phenyl}-pyrimidin-2-yl)-methyl-amino]-ethanesulfonic acid. Using 2-methylamino-ethyl sulphonic acid and N-[2-(3-Cyano-1H-indol-5-yl)-ethyl]-4-[2-chloro-pyrimidin-4-yl]-benzamide (reference example 1az) as substrates.

Reference Example 92e

N-[2-(3-Cyano-1H-indol-5-yl)-ethyl]-4-{2-[methyl-(2 (S),3 (R),4 (R),5 (R),6-pentahydroxy-hexyl)-amino]-pyrimidin-4-yl}-benzamide. Using N-methyl-(2 (S),3 (R),4 (R),5 (R),6-pentahydroxy-hexyl)-amine and N-[2-(3-Cyano-1H-indol-5-yl)-ethyl]-4-[2-chloro-pyrimidin-4-yl]-benzamide (reference example 1az) as substrates.

Reference Example 92f

N-[2-(3-Cyano-1H-indol-5-yl)-ethyl]-4-{2-[methyl-(2 (S),3 (R),4 (S),5 (R),6-pentahydroxy-hexyl)-amino]-pyrimidin-4-yl}-benzamide. Using N-methyl-(2 (S),3 (R),4 (S),5 (R),6-pentahydroxy-hexyl)-amine and N-[2-(3-Cyano-1H-indol-5-yl)-ethyl]-4-[2-chloro-pyrimidin-4-yl]-benzamide (reference example 1az) as substrates.

Reference Example 92g

N-[2-(3-cyano-1H-indol-5-yl)-ethyl]-4-[2-(2-hydroxy-1-hydroxymethyl-ethylamino)-pyrimidin-4-yl]-benzamide. Using 2-hydroxy-1-hydroxymethyl-ethylamine and N-[2-(3-Cyano-1H-indol-5-yl)-ethyl]-4-[2-chloro-pyrimidin-4-yl]-benzamide (reference example 1az) as substrates. MS (ion spray) m/z 457 (M+H)$^+$.

Reference Example 92h

2-[(4-{4-[2-(3-Cyano-1H-indol-5-yl)-ethylcarbamoyl]-phenyl}-pyrimidin-2-yl)-methyl-amino]-ethanesulfonic acid. Using 2-(N-methyl-amino)-ethanesulfonic acid and N-[2-(3-Cyano-1H-indol-5-yl)-ethyl]-4-[2-chloro-pyrimidin-4-yl]-benzamide (reference example 1az) as substrates.

Reference Example 92i

N-[2-(3-Cyano-1H-indol-5-yl)-ethyl]-4-[2-(3-imidazol-1-yl-propylamino)-pyrimidin-4-yl]-benzamide. Using 3-imidazol-1-yl-propylamine and N-[2-(3-Cyano-1H-indol-5-yl)-ethyl]-4-[2-chloro-pyrimidin-4-yl]-benzamide (reference example 1az) as substrates.

Reference Example 92j

N-[2-(3-Cyano-1H-indol-5-yl)-ethyl]-4-{2-[(2-diethylamino-ethyl)-methyl-amino]-pyrimidin-4-yl}- benzamide. Using 2-(diethylamino)-ethyl-methyl-amine and N-[2-(3-Cyano-1H-indol-5-yl)-ethyl]-4-[2-chloro-pyrimidin-4-yl]-benzamide (reference example 1az) as substrates.

Reference Example 92k

N-[2-(3-Cyano-1H-indol-5-yl)-ethyl]-4-[2-(2-diisopropylamino-ethylamino)-pyrimidin-4-yl]-benzamide. Using 2-(diisopropylamino)-ethylamine and N-[2-(3-Cyano-1H-indol-5-yl)-ethyl]-4-[2-chloro-pyrimidin-4-yl]-benzamide (reference example 1az) as substrates.

Reference Example 92l

N-[2-(3-Cyano-1H-indol-5-yl)-ethyl]-4-[2-(2-dibutylamino-ethylamino)-pyrimidin-4-yl]-benzamide. Using 2-(dibutylamino)-ethylamine and N-[2-(3-Cyano-1H-indol-5-yl)-ethyl]-4-[2-chloro-pyrimidin-4-yl]-benzamide (reference example 1az) as substrates.

Reference Example 92m

N-[2-(3-Cyano-1H-indol-5-yl)-ethyl]-4-[2-(3-morpholin-4-yl-propylamino)-pyrimidin-4-yl]-benzamide. Using 3-(morpholin-4-yl)-propylamine and N-[2-(3-Cyano-1H-indol-5-yl)-ethyl]-4-[2-chloro-pyrimidin-4-yl]-benzamide (reference example 1az) as substrates.

Reference Example 92n

N-[2-(3-Cyano-1H-indol-5-yl)-ethyl]-4-[2-(3-diethylamino-propylamino)-pyrimidin-4-yl]-benzamide. Using 3-(diethylamino)-propylamine and N-[2-(3-Cyano-1H-indol-5-yl)-ethyl]-4-[2-chloro-pyrimidin-4-yl]-benzamide (reference example 1az) as substrates.

Reference Example 92p

N-[2-(3-Cyano-1H-indol-5-yl)-ethyl]-4-[2-(3-piperidin-1-yl-propylamino)-pyrimidin-4-yl]-benzamide. Using 3-(piperidin-1-yl)-propylamine and N-[2-(3-Cyano-1H-indol-5-yl)-ethyl]-4-[2-chloro-pyrimidin-4-yl]-benzamide (reference example 1az) as substrates.

Reference Example 92q

N-[2-(3-Cyano-1H-indol-5-yl)-ethyl]-4-(2-{[2-(ethyl-methyl-amino)-ethyl]-methyl-amino}-pyrimiidin-4-yl)-benzamide. Using [2-(ethyl-methyl-amino)-ethyl]-methyl-amine and N-[2-(3-Cyano-1H-indol-5-yl)-ethyl]-4-[2-chloro-pyrimidin-4-yl]-benzamide (reference example 1az) as substrates.

Reference Example 92r

N-[2-(3-Cyano-1H-indol-5-yl)-ethyl]-4-[2-(5-dimethylamino-pentylamino)-pyrimidin-4-yl]-benzamide. Using 5-dimethylamino-pentylamine (reference example 93a) and and N-[2-(3-Cyano-1H-indol-5-yl)-ethyl]-4-[2-chloro-pyrimidin-4-yl]-benzamide (reference example 1az) as substrates. MS (ion spray) m/z 496 (M+H)$^+$.

Reference Example 92s

N-[2-(3-Cyano-1H-indol-5-yl)-ethyl]-4-[2-(5-morpholin-4-yl-pentylamino)-pyrimidin-4-yl]-benzamide. Using 5-(morpholin-4-yl)-pentylamine (reference example 93b) and and N-[2-(3-Cyano-1H-indol-5-yl)-ethyl]-4-[2-chloro-pyrimidin-4-yl]-benzamide (reference example 1az) as substrates. MS (ion spray) m/z 538 (M+H)$^+$.

Reference Example 92t

N-[2-(3-Cyano-1H-indol-5-yl)-ethyl]-4-[2-(5-piperidin-1-yl-pentylamino)-pyrimidin-4-yl]-benzamide. Using 5-(piperidin-1-yl)-pentylamine (reference example 93c) and and N-[2-(3-Cyano-1H-indol-5-yl)-ethyl]-4-[2-chloro-pyrimidin-4-yl]-benzamide (reference example 1az) as substrates. MS (ion spray) m/z 536 (M+H)$^+$.

Reference Example 92u

N-[2-(3-Cyano-1H-indol-5-yl)-ethyl]-4-[2-(5-pyrrolidin-1-yl-pentylamino)-pyrimidin-4-yl]-benzamide. Using 5-(pyrrolidin-1-yl)-pentylamine (reference example 93d) and and N-[2-(3-Cyano-1H-indol-5-yl)-ethyl]-4-[2-chloro-pyrimidin-4-yl]-benzamide (reference example 1az) as substrates. MS (ion spray) m/z 522 (M+H)$^+$.

Reference Example 92v

N-[2-(3-Cyano-1H-indol-5-yl)ethyl]-4-[2-(4-methylpiperazin-1-yl)pyrimidin-4-yl]benzamide. Using N-methyl-piperazine and N-[2-(3-Cyano-1H-indol-5-yl)-ethyl]-4-[2-chloro-pyrimidin-4-yl]-benzamide (reference example 1az) as substrates. MS (ion spray) m/z 466 (M+H)$^+$.

Reference Example 92w

4-[(4-{4-[2-(3-Cyano-1H-indol-5-yl)ethylcarbamoyl]phenyl}pyrimidin-2-yl)methylamino]-butyric acid. Using 4-(methylamino)-butyric acid and N-[2-(3-Cyano-1H-indol-5-yl)-ethyl]-4-[2-chloro-pyrimidin-4-yl]-benzamide (reference example 1az) as substrates. MS (ion spray) m/z 483 (M+H)$^+$.

Reference Example 92x

N-[2-(3-Cyano-1H-indol-5-y)-ethyl]-4-[2-(2,2,2-trifluoroethoxy)pyrimidin-4-yl]benzamide. Using trifluoroethanol and N-[2-(3-Cyano-1H-indol-5-yl)-ethyl]-4-[2-chloro-pyrimidin-4-yl]-benzamide (reference example 1az) as substrates. MS (ion spray) m/z 466 (M+H)$^+$.

Reference Example 92y

N-[2-(3-Cyano-1H-indol-5-yl)-ethyl]-4-(2-pyrrolidin-1-ylpyrimidin-4-yl)benzamide. Using pyrrolidine and N-[2-(3-Cyano-1H-indol-5-yl)-ethyl]-4-[2-chloro-pyrimidin-4-yl]-benzamide (reference example 1az) as substrates. MS (ion spray) m/z 437 (M+H)$^+$.

Reference Example 92z

N-[2-(3-Cyano-1H-indol-5-yl)-ethyl]-4-[2-(2-hydroxymethylpyrrolidin-1-yl)-pyrimidin-4-yl]benzamide. Using 2-(hydroxymethyl)-pyrrolidine and N-[2-(3-Cyano-1H-indol-5-yl)-ethyl]-4-[2-chloro-pyrimidin-4-yl]-benzamide (reference example 1az) as substrates. MS (ion spray) m/z 467 (M+H)$^+$.

Reference Example 92aa

N-[2-(3-Cyano-1H-indol-5-y)-ethyl]-4-[2-(carbamoylmethyl-N-methylamino)-pyrimidin-4-yl]benzamide. Using N-methyl glycine amide and N-[2-(3-Cyano-1H-indol-5-yl)-ethyl]-4-[2-chloro-pyrimidin-4-yl]-benzamide (reference example 1az) as substrates. MS (ion spray) m/z 454 (M+H)$^+$.

Reference Example 92ab

N-[2-(3-Cyano-1H-indol-5-yl)ethyl]-4-[2-(6-pyrrolidin-1-ylhexylamino)pyrimidin-4-yl]benzamide. Using 6-pyrrolidin-1-ylhexylamine (reference example 93e) and N-[2-(3-Cyano-1H-indol-5-yl)-ethyl]-4-[2-chloro-pyrimidin-4-yl]-benzamide (reference example 1az) as substrates. MS (ion spray) m/z 536 (M+H)+.

Reference Example 92ac

N-[2-(3-Cyano-1H-indol-5-yl)ethyl]-4-[2-(6-piperidin-1-ylhexylamino)pyrimidin-4-yl]benzamide. Using 6-piperidin-1-ylhexylamine (reference example 93f) and N-[2-(3-Cyano-1H-indol-5-yl)-ethyl]-4-[2-chloro-pyrimidin-4-yl]-benzamide (reference example 1az) as substrates. MS (ion spray) m/z 550 (M+H)+.

Reference Example 92ad

N-[2-(3-Cyano-1H-indol-5-yl)ethyl]-4-[2-(4-piperidin-1-ylbutylamino)pyrimidin-4-yl]benzamide. Using 4-piperidin-1-ylbutylamine (reference example 93 g) and N-[2-(3-Cyano-1H-indol-5-yl)-ethyl]-4-[2-chloro-pyrimidin-4-yl]-benzamide (reference example 1az) as substrates. MS (ion spray) m/z 522 (M+H)+.

Reference Example 92ae

N-[2-(3-Cyano-1H-indol-5-yl)ethyl]-4-[2-(4-diethylaminobutylamino)pyrimidin-4-yl]benzamide. Using 4-diethylaminobutylamine (reference example 93h) and N-[2-(3-Cyano-1H-indol-5-yl)-ethyl]-4-[2-chloro-pyrimidin-4-yl]-benzamide (reference example 1az) as substrates. MS (ion spray) m/z 510 (M+H)+.

Reference Example 92af

N-[2-(3-Cyano-1H-indol-5-yl)ethyl]-4-[2-(6-morpholin-4-ylhexylamino)pyrimidin-4-yl]benzamide. Using 6-morpholin-4-ylhexylamine (reference example 93i) and N-[2-(3-Cyano-1H-indol-5-yl)-ethyl]-4-[2-chloro-pyrimidin-4-yl]-benzamide (reference example 1az) as substrates MS (ion spray) m/z 552 (M+H)+.

Reference Example 92ag

N-[2-(3-Cyano-1H-indol-5-yl)ethyl]-4-[2-(6-dimethylaminohexylamino)pyrimidin-4-yl]benzamide. Using 6-(dimethylamino)-hexylamine and N-[2-(3-Cyano-1H-indol-5-yl)-ethyl]-4-[2-chloro-pyrimidin-4-yl]-benzamide (reference example 1az) as substrates. MS (ion spray) m/z 510 (M+H)+.

Reference Example 92ah

N-[2-(3-Cyano-1H-indol-5-yl)ethyl]-4-[2-(4-dimethylaminobutylamino)pyrimidin-4-ylbenzamide Using 4-(dimethylamino)-butylamine and N-[2-(3-Cyano-1H-indol-5-yl)-ethyl]-4-[2-chloro-pyrimidin-4-yl]-benzamide (reference example 1az) as substrates. MS (ion spray) m/z 482 (M+H)+.

Reference Example 92ai

4-[2-(Bicyclo[2.2.1]hept-2-ylamino)pyrimidin-4-yl]-N-[2-(3-cyano-1H-indol-5-yl)ethyl]benzamide. Using Bicyclo[2.2.1]hept-2-ylamine and N-[2-(3-Cyano-1H-indol-5-yl)-ethyl]-4-[2-chloro-pyrimidin-4-yl]-benzamide (reference example 1az) as substrates. MS (ion spray) m/z 477 (M+H)+.

Reference Example 92aj 1-(4-{4-[2-(3-Cyano-1H-indol-5-yl)ethylcarbamoyl] phenyl}pyrimidin-2-yl)pyrrolidine-2-carboxylic acid amide. Using pyrrolidine-2-carboxylic acid amide. and N-[2-(3-Cyano-1H-indol-5-yl)-ethyl]-4-[2-chloro-pyrimidin-4-yl]-benzamide (reference example 1az) as substrates. MS (ion spray) m/z 480 (M+H)+.

Reference Example 92ak

N-[2-(3-Cyano-1H-indol-5-yl)ethyl]-4-{2-[(2-hydroxy-ethyl)-N-methylamino]pyrimidin-4-yl}benzamide. Using (2-hydroxy-ethyl)-N-methylamine and N-[2-(3-Cyano-1H-indol-5-yl)-ethyl]-4-[2-chloro-pyrimidin-4-yl]-benzamide (reference example 1az) as substrates. MS (ion spray) m/z 441 (M+H)+.

Reference Example 92al

N-[2-(3-cyano-1H-indol-5-yl)-ethyl]-4-(2-morpholin-4-yl-pyrimidin-4-yl)-benzamide. Using morpholine and N-[2-(3-Cyano-1H-indol-5-yl)-ethyl]-4-[2-chloro-pyrimidin-4-yl]-benzamide (reference example 1az) as substrates. $^1$H NMR (DMSO) δ 2.98 (bt, 2H, J=7 Hz); 3.56 (m, 2H); 3.70 (bs, 4H); 3.79 (bs, 4H); 7.18 (d, 1H, J=9 Hz); 7.32 (d, 1H, J=5 Hz); 7.49 (m, 2H); 7.94 (d, 2H, J=8 Hz); 8.22 (m, 3H); 8.50 (d, 1H, J=5 Hz); 8.74 (bt, 1H); 12.20 (bs, 1H). MS (ion spray) m/z 453 (M+H)+.

Reference Example 92am

N-[2-(3-cyano-1H-indol-5-yl)-ethyl]-4-[2-(cyclopropylmethyl-amino)-pyrimidin-4-yl]-benzamide. Using cyclopropylmethyl-amine and N-[2-(3-Cyano-1H-indol-5-yl)-ethyl]-4-[2-chloro-pyrimidin-4-yl]-benzamide (reference example 1az) as substrates. $^1$H NMR (DMSO) δ 0.26 (m, 2H); 0.44 (m, 2H); 3.00 (bt, 2H, J=7 Hz); 3.25 (bs, 2H); 3.56 (m, 2H); 7.20 (m, 2H); 7.36 (bt, 1H); 7.50 (m, 2H); 7.94 (d, 2H, J=8 Hz); 8.29 (m, 3H); 8.38 (d, 1H, J=5 Hz); 8.69 (bt, 1H); 12.15 (bs, 1H). MS (ion spray) m/z 437 (M+H)+.

Reference Example 92an

N-[2-(3-cyano-1H-indol-5-yl)-ethyl]-4-[2-[(2-methoxy-ethyl)-methyl-amino]-pyrimidin-4-yl]-benzamide. Using (2-methoxy-ethyl)-methyl-amine and N-[2-(3-Cyano-1H-indol-5-yl)-ethyl]-4-[2-chloro-pyrimidin-4-yl]-benzamide (reference example 1az) as substrates. $^1$H NMR (DMSO) δ 2.98 (t, 2H, J=7 Hz); 3.22 (s, 3H); 3.28 (s, 3H); 3.58 (m, 4H); 3.85 (m, 2H); 7.21 (m, 2H); 7.50 (m,2H); 7.93 (d, 2H, J=9 Hz); 8.20 (m, 3H); 8.45 (d, 1H, J=5 Hz); 8.69 (bt, 1H); 12.13 (bs, 1H). MS (ion spray) m/z 455 (M+H)+.

Reference Example 92ap

N-[2-(3-cyano-1H-indol-5-y)-ethyl]-4-[2-(3-hydroxy-propylamino)-pyrimidin-4-yl]-benzamide. Using 3-hydroxy-propylamine and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.73 (t, 2H, J=7 Hz); 2.98 (t, 2H, J=7 Hz); 3.40 (m, 2H); 4.48 (bs, 1H); 7.20 (m, 3H); 7.48 (m, 2H); 7.92 (d, 2H, J=8 Hz); 8.18 (m, 3H); 8.37 (bd, 1H, J=5 Hz); 8.68 (bt, 1H); 12.12 (bs, 1H). MS (ion spray) m/z 441 (M+H)+.

Reference Example 92aq

N-[2-(3-cyano-1H-indol-5-yl)-ethyl]-4-[2-(2-hydroxy-ethyl)-propyl-amino]-pyrimidin-4-yl]-benzamide. Using (2-hydroxy-ethyl)-propyl-amine and N-[2-(3-Cyano-1H-indol-5-yl)-ethyl]-4-[2-chloro-pyrimidin-4-yl]-benzamide (reference example 1az) as substrates. $^1$H NMR (DMSO) δ

0.90 (t, 3H, J=7 Hz); 1.63 (bd, 2H); 2.98 (t, 2H, J=7 Hz); 3.63 (m, 8H); 4.73 (t, 1 H, J=5 Hz); 7.19 (m, 2H); 7.48 (m, 2H); 7.92 (d, 2H, J=8 Hz); 8.19 (m, 3H); 8.43 (d, 1H, J=5 Hz); 8.67 (bt, 1H); 12.11 (bs, 1H). MS (ion spray) m/z 469 (M+H)$^+$.

Reference Example 92ar

N-[2-(3-cyano-1H-indol-5-yl)-ethyl]-4-(2-piperidin-1-yl-pyrimidin-4-yl)-benzamide. Using piperidine and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.6 (m, 6H); 2.98 (m, 2H); 3.55 (m, 2H); 3.84 (m, 4H); 7.19 (m, 2H); 7.49 (m, 2H); 7.93 (d, 2H, J=8 Hz); 8.20 (m, 31H); 8.44 (d, 1H, J=5 Hz); 8.69 (bt, 1H); 12.14 (bs, 1H). MS (ion spray) m/z 451 (M+H)$^+$.

Reference Example 92as

N-[2-(3-cyano-1H-indol-5-y)-ethyl]-4-[2-(ethyl-methyl-amino)-pyrimidin-4-yl]-benzamide. Using ethylmethylamine and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.15 (t, 3H, J=7 Hz); 2.99 (bt, 2H); 3.17 (s, 3H); 3.56 (m, 2H); 3.73 (m, 2H); 7.20 (m, 2H); 7.50 (m, 2H); 7.94 (d, 2H, J=7 Hz); 8.20 (m, 3H); 8.44 (d, 1H, J=5 Hz); 8.69 (bs, 1H); 12.14 (bs, 1H). MS (ion spray) m/z 425 (M+H)$^+$.

Reference Example 92at

N-[2-(3-cyano-1H-indol-5-yl)-ethyl]-4-[2-(4-hydroxy-piperidin-1-yl)-pyrimidin-4-yl]-benzamide. Using 4-hydroxy-piperidine and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.36 (m, 2H); 1.82 (m, 2H); 2.98 (t, 2H, J=7 Hz); 3.34 (m, 2H); 3.55 (m, 2H); 3.76 (bs, 1H); 4.39 (bd, 2H); 4.75 (bs, 1H); 7.20 (m, 2H); 7.48 (m, 2H); 7.92 (d, 2H, J=9 Hz); 8.20 (m, 3H); 8.45 (d, 1H, J=5 Hz); 8.67 (bt, 1H); 12.12 (bs, 1H). MS (ion spray) m/z 467 (M+H)$^+$.

Reference Example 92au

N-[2-(3-cyano-1H-indol-5-yl)-ethyl]-4-[2-(2,3-dihydroxy-propylamino)-pyrimidin-4-yl]-benzamide. Using 2,3-dihydroxy-propylamine and N-[2-(3-Cyano-1H-indol-5-yl)-ethyl]-4-[2-chloro-pyrimidin-4-yl]-benzamide (reference example 1az) as substrates. MS (ion spray) m/z 457 (M+H)$^+$.

Reference Example 92av

N-[2-(3-cyano-1H-indol-5-yl)-ethyl]-4-[2-[(2,3-dihydroxy-propyl)-methyl-amino]-pyrimidin-4-yl]-benzamide. Using 2,3-dihydroxy-propyl-methylamine and N-[2-(3-Cyano-1H-indol-5-yl)-ethyl]-4-[2-chloro-pyrimidin-4-yl]-benzamide (reference example 1az) as substrates. MS (ion spray) m/z 471 (M+H)$^+$.

Reference Example 92aw

N-[2-(3-cyano-1H-indol-5-yl)-ethyl]-4-[2-((s)-2-methoxymethyl-pyrrolidin-1-yl)-pyrimidin-4-yl]-benzamide. Using (s)-2-methoxymethyl-pyrrolidine and N-[2-(3-Cyano-1H-indol-5-yl)-ethyl]-4-[2-chloro-pyrimidin-4-yl]-benzamide (reference example 1az) as substrates. MS (ion spray) m/z 481 (M+H)$^+$.

Reference Example 92ax

4-[4-[4-[2-(3-cyano-1H-indol-5-yl)-ethylcarbamoyl]-phenyl]-pyrimidin-2-yl]-piperazine-1-carboxylic acid tert-butyl ester. Using piperazine-1-carboxylic acid tert-butyl ester and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.44 (s, 9H); 2.98 (t, 2H, J=7 Hz); 3.45 (bs, 4H); 3.56 (m, 2H); 3.83 (bs, 4H); 7.18 (d, 1H, J=8 Hz); 7.31 (d, 1H, J=5 Hz); 7.48 (d, 1H, J=8 Hz); 7.51 (s, 1H); 7.94 (d, 2H, J=8 Hz); 8.22 (m, 3H); 8.49 (d, 1H, J=5 Hz); 8.70 (bt, 1H); 12.12 (bs, 1H). MS (ion spray) m/z 552 (M+H)$^+$.

Reference Example 92ay

N-[2-(3-cyano-1H-indol-5-yl)-ethyl]-4-[2-[2-(2-oxo-imidazolidin-1-yl)-ethylamino]-pyrimidin-4-yl]-benzamide. Using 2-(2-oxo-imidazolidin-1-yl)-ethylamine and N-[2-(3-Cyano-1H-indol-5-yl)-ethyl]-4-[2-chloro-pyrimidin-4-yl]-benzamide (reference example 1az) as substrates. $^1$H NMR (DMSO) δ 2.96 (bt, 2H); 3.24 (m, 4H); 3.47 (m, 6H); 6.26 (s, 1H); 7.18 (m, 2H); 7.27 (bt, 1H, J=5 Hz); 7.48 (m, 2H); 7.91 (d, 2H, J=9 Hz); 8.19 (m, 3H); 8.36 (bd, 1H); 8.67 (t, 1H, J=5 Hz); 12.10 (bs, 1H). MS (ion spray) m/z 495 (M+H)$^+$.

Reference Example 92az

N-[2-(3-cyano-1H-indol-5-yl)-ethyl]-4-[2-(3-methoxy-propylamino)-pyrimidin-4-yl]-benzamide. Using 3-methoxy-propylamine and N-[2-(3-Cyano-1H-indol-5-yl)-ethyl]-4-[2-chloro-pyrimidin-4-yl]-benzamide (reference example 1az) as substrates. $^1$H NMR (DMSO) δ 1.81 (m, 2H); 2.98 (m, 2H); 3.24 (s, 3H); 3.41 (m, 4H); 3.56 (m, 2H); 7.19 (m, 2H); 7.28 (bs, 1H); 7.50 (m, 2H); 7.92 (m, 2H); 8.18 (m, 3H); 8.38 (bs, 1H); 8.68 (bs, 1H); 12.13 (bs, 1H). MS (ion spray) m/z 455 (M+H)$^+$.

Reference Example 92aaa

N-[2-(3-cyano-1H-indol-5-yl)-ethyl]-4-[2-(2-hydroxy-ethylamino)-pyrimidin-4-y]-benzamide. Using 2-hydroxy-ethylamine and N-[2-(3-Cyano-1H-indol-5-yl)-ethyl]-4-[2-chloro-pyrimidin-4-yl]-benzamide (reference example 1az) as substrates. $^1$H NMR (DMSO) δ 2.98 (t, 2H, J=7 Hz); 3.44 (bs, 2H); 3.55 (m, 4H); 4.70 (t, 1H, J=6 Hz); 7.17 (m, 3H); 7.48 (m, 2H); 7.92 (d, 2H, J=9 Hz); 8.18 (m, 3H); 8.38 (d, 1H, J=5 Hz); 8.68 (bt, 1H); 12.12 (bs, 1H). MS (ion spray) m/z 427 (M+H)$^+$.

Reference Example 92aab 4-(2-dimethylamino-pyrimidin-4-yl)-benzoic acid. Using dimethylamine and 4-[2-chloro-pyrimidin-4-yl]-benzoic acid as substrates. MS (ion spray) m/z 244 (M+H)$^+$.

Reference Example 93a

5-Dimethylamino-pentylamine. To a cooled (0° C.) solution of lithium aluminum hydride (8 ml, 0.5M in ether) is added, slowly, a solution of 5-(dimethylamino)-pentanenitrile (126 mg, 1 mmol, reference example 94a) in ether (1 mL). On complete addition, the cold bath is removed and stirring continued for 2 h. The reaction mixture is then cooled to 0° C. and quenched by dropwise addition of water (160 mL), sodium hydroxide solution (160 mL, 5M), then a further portion of water (160 mL). The resulting mixture is filtered through celite and the filtrate concentrated under reduced pressure to give an oil which is used without further purification.

The following compounds are prepared using essentially the same procedure as used in reference example 93a, except using the cited nitrile in place of 5-(dimethylamino)-pentanenitrile.

Reference Example 93b 5-(morpholin-4-yl)-pentylamine. Using 5-(morpholino-4-yl)-pentanenitrile (reference example 94b) as substrate.

Reference Example 93c 5-(piperidin-1-yl)-pentylamine. Using 5-(piperidin-1-yl)-pentanenitrile (reference example 94c) as substrate.

Reference Example 93d 5-(pyrrolidin-1-yl)-pentylamine. Using 5-(pyrrolidin-1-yl)-pentanenitrile (reference example 94d) as substrate.

Reference Example 93e

6-Pyrrolidin-1-ylhexylamine. Using 6-Pyrrolidin-1-ylhexanenitrile (reference example 94e) as substrate. MS (ion spray) m/z 171 (M+H)$^+$.

Reference Example 93f 6-piperidin-1-ylhexylamine. Using 6-Piperidin-1-ylhexanenitrile (reference example 94f) as substrate. MS (ion spray) m/z 185 (M+H)$^+$.

Reference Example 93g 4-piperidin-1-ylbutylamine. Using 4-Piperidin-1-ylbutanenitrile (reference example 94 g) as substrate. MS (ion spray) m/z 157 (M+H)$^+$.

Reference Example 93h 4-(diethylamino)-butylamine. Using 4-(diethylamino)-butanenitrile (reference example 94h) as substrate. MS (ion spray) m/z 145 (M+H)$^+$.

Reference Example 93i 6-morpholin-4-ylhexylamine. Using 6-morpholin-4-ylhexanenitrile (reference example 94i) as substrate. MS (ion spray) m/z 187 (M+H)$^+$.

Reference Example 94a 5-(dimethylamino)-pentanenitrile. A mixture of dimethylamine (4 mL, 40% in water) and 5-bromo-pentanenitrile (2.3 mL, 20 mmol) is stirred for 24 h. The resulting reaction mixture is diluted with sodium hydroxide solution (10 mL, 5M) and extracted with ether. The ether extract is dried over $K_2CO_3$ and concentrated under reduced pressure to give an oil (1.5 g) which is used without further purification.

The following compounds are prepared using essentially the same procedure as used in reference example 94a, except using a solution of the cited amine (2 eq.) in benzene (4 mL) in place of dimethylamine in water.

Reference Example 94b 5-(morpholino-4-yl)-pentanenitrile. Using morpholine as substrate gives 3.5 g of oil.

Reference Example 94c.

5-(Piperidin-1-yl)-pentanenitrile. Using piperidine as substrate gives 3.29 g of oil.

Reference Example 94d 5-(pyrrolidin-1-yl)-pentanenitrile. Using pyrrolidine as substrate gives 3.32 g of oil.

Reference Example 94e.

6-Pyrrolidino-hexanenitrile. Using pyrrolidine and 6-chloro-hexanenitrile as substrates. MS (ion spray) m/z 167 (M+H)$^+$.

Reference Example 94f

6-Piperidin-1-ylhexanenitrile. Using piperidine and 6-chloro-hexanenitrile as substrates. MS (ion spray) m/z 181 (M+H)$^+$.

Reference Example 94g

4-Piperidin-1-ylbutanenitrile. Using piperidine and 4-chloro-butanenitrile as substrates. MS (ion spray) m/z 153.

Reference Example 94h 4 (diethylamino)-butanenitrile. Using diethylamine and 4-chloro-butanenitrile as substrates. MS (ion spray) m/z 141.

Reference Example 94i 6-morpholin-4-ylhexanenitrile. Using morpholine and 6-chloro-hexanenitrile as substrates. MS (ion spray) m/z 183.

Reference Example 95

4-(2-oxo-hexahydro-pyrimidin-5-yl)-benzoic acid methyl ester.

To a solution of 4-(2-oxo-pyrimidin-5-yl)-benzoic acid methyl ester (761 mg, 3.3 mmol, reference example 19c) in DMF (20 mL) and methanol (5 mL) was added Pd on carbon (250 mg, 10% w/w). The resulting mixtured was stirred under an atmosphere of hydrogen gas for 3 h. This mixture is purged with nitrogen gas then filtered through celite. The filtrate is concentrated and the residue purified by flash chromatography (eluting with 5% methanol in dichloromethane) to give the title compound (421 mg) as a white solid. $^1$H NMR (CD$_3$OD) ? 3.28 (m, 1H), 3.47 (d, J=7 Hz, 4H), 3.90 (s, 3H), 7.44 (d, J=8 Hz, 2H), 7.90 (d, J=8 Hz, 2H).

Reference Example 96

4-(2-oxo-pyrimidin-5-yl)-benzaldehyde. To a solution of 4-(2-[t-butyldiphenylsilyloxy]-pyrimidin-5-yl)-benzaldehyde dimethyl ketal (2.28 g, 4.7 mmol reference example 97a) in THF (10 mL) is added hydrochloric acid (10 mL, 2M). The resulting mixture is stirred for 1 h. This mixture is concentrated to about half its original volume under reduced pressure. The solid is filtered then washed with water and ether to give the title compound (1.1 g) as a white solid. $^1$H NMR (DMSO) δ 7.88 (d, J=8 Hz, 2H), 7.95 (d, J=8 Hz, 2H), 8.79 (s, 2H), 9.99 (s, 1H).

Reference Example 97a 4-(2-[t-butyldiphenylsilyloxy]-pyrimidin-5-yl)-benzaldehyde dimethyl ketal. To a cooled (−78° C.) solution of 4-bromo-benzaldehyde dimethyl ketal (2.31 g 10 mmol) in THF (30 mL) is added, dropwise, n-butyl lithium (4.4 mL, 2.5 M in hexanes). On complete addition, the reaction mixture is stirred for 5 min then ZnCl$_2$ solution (20 mL, 0.5M in THF) is added. The cold bath is removed and stirring continued for 5 min. then a solution comprising of 5-bromo-(2-[t-butyldiphenylsilyloxy]-pyrimidine (4.13 g, 10 mmol) and (Ph$_3$P)$_4$Pd (1.1 g, 1 mmol) in THF (20 mL) is added. This mixture is warmewd to 60° C. and stirred at this temperature for 2 h. The resulting solution is cooled to room temperature, diluted with ether, washed, sequentially, with 5% aqueous ammonia solution, water and brine, dried over MgSO$_4$ and concentrated. The residue is purified by flash chromatography (eluting with 10% ethyl acetate, 10% dichloromethane in hexanes) to give 2.28 g of the title compound as an oil. $^1$H NMR (CDCl$_3$) δ 1.18 (s, 9H), 3.35 (s, 6H), 5.44 (s, 1H), 7.38 (m, 6H), 7.44 (d, J=8 Hz, 2H), 7.53 (d, J=8 Hz, 2H), 7.8 (m, 4H), 8.59 (s, 2H).

Reference Example 97b 4-(3-Methoxycarbonyl-phenyl)-Benzaldehyde. Using essentially the same procedure used in reference example 97a except using methyl 3-bromo-benzoate as substrate in place of 5-bromo-(2-[t-butyldiphenylsilyloxy]-pyrimidine and using the following modified workup: On cooling to room temperature, the reaction mixture is diluted with ethyl acetate and washed with hydrochloric acid (2M) then brine, dried over MgSO$_4$ and concentrated. The residue is purified by flash chromatography (eluting with 20% ethyl acetate/5% dichloromethane in hexanes) to give the title compound as a yellow solid. MS (EI) m/z 240 (M)$^+$.

Reference Example 97c 4-(2-Methoxycarbonyl-phenyl)-Benzaldehyde. Using essentially the same procedure used in reference example 97b except using methyl 2-iodo-benzoate as substrate in place of methyl 3-bromo-benzoate. MS (EI) m/z 240 (M)$^+$.

Reference Example 98

4-(1,3-Dimethyl-2-oxo-hexahydro-pyrimidin-5-yl)-benzoic acid methyl ester. To a cooled (0° C.) suspension of sodium hydride dispersion (60% in mineral oil (88 mg, 2.2 mmol) in THF (3 mL) is added a solution comprising of 4-(2-oxo-hexahydro-pyrimidin-5-yl)-benzoic acid methyl ester (236 mg, 1 mmol, reference example 95) and methyl iodide (300 µL, 5 mmol) in DMF (4 mL). The resulting mixture is stirred for 16 h. then quenched with water, diluted with ethyl acetate, washed with water and brine, dried over MgSO$_4$ and concentrated to give the title compound (255 mg) as a tan solid. $^1$H NMR (CDCl$_3$) δ 2.98 (s, 6H), 3.37–3.53 (m, 5H), 3.93 (s, 3H), 7.32 (d, J=8 Hz, 2H), 8.01 (d, J=8 Hz, 2H). MS (ion spray) m/z 263 (M+H)$^+$.

Reference Example 99a

Biphenyl-3,4'-dicarboxylic acid 4'-{[2-(3-Cyano-1H-indol-5-yl)-ethyl]-amide} 3-[(2-methoxy-ethyl)-amide]. To a solution of Biphenyl-3,4'-dicarboxylic acid 4'-{[2-(3-cyano-1H-indol-5-ylfiethyl]-amide} (102 mg, 0.25 mmol, reference example 17h) in dichloromethane/DMF (3:1, 1 mL total volume) is added TBTU (88 mg, 0.27 mmol) and diisopropylethylamine (48 mL, 0.28 mmol). The resulting solution is stirred for 2 min. then a further portion of diisopropylethylamine (48 mL) and 2-methoxy-ethylamine (44 mL) is added. This solution is stirred for 35 min. then concentrated under reduced pressure. The residue is suspended in dichloromethane and filtered. The solid is washed with dichloromethane/methanol (3:1) then dried under vacuum to give 121 mg of the title compound. MS (ion spray) m/z 467 (M+H)$^+$.

Reference Example 99b

3'-(Morpholine-4-carbonyl)-biphenyl-4-carboxylic acid [2-(3-cyano-1H-indol-5-yl)-ethyl]-amide. Using essentially the same procedure used in reference example 99a, except using morpholine as substrate in place of 2-methoxy-ethylamine. MS (ion spray) m/z 479 (M+H)$^+$.

Reference Example 99c

Biphenyl-3,4'-dicarboxylic acid 4'-{[2-(3-cyano-1H-indol-5-yl)-ethyl]-amide} 3-[(2-morpholin-4-yl-ethyl)-amide]. Using essentially the same procedure used in reference example 99a, except using 2-(morpholin-4-yl)-ethylamine as substrate in place of 2-methoxy-ethylamine. MS (ion spray) m/z 522 (M+H)$^+$.

Reference Example 99d

Biphenyl-2,4'-dicarboxylic acid 4'-{[2-(3-cyano-1H-indol-5-yl)-ethyl]-amide} 2-[(3-diethylamino-propyl)-amide]. Using essentially the same procedure used in reference example 99a, except using 3-(diethylamino) propylamine and Biphenyl-2,4'-dicarboxylic acid 4'-{[2-(3-cyano-1H-indol-5-yl)-ethyl]-amide} (reference example 17i) as substrates. MS (ion spray) m/z 522 (M+H)$^+$.

Reference Example 99e

Biphenyl-2,4'-dicarboxylic acid 4'-{[2-(3-cyano-1H-indol-5-yl)-ethyl]-amide} 2-[(3-morpholin-4-yl-propyl)-amide]. Using essentially the same procedure used in reference example 99a, except using 3-(morpholin-4-ylpropylamine and Biphenyl-2,4'-dicarboxylic acid 4'-{[2-(3-cyano-1H-indol-5-yl)-ethyl]-amide} (reference example 17i) as substrates. MS (ion spray) m/z 536 (M+H)$^+$.

Reference Example 99f

Biphenyl-2,4'-dicarboxylic acid 4'-{[2-(3-cyano-1H-indol-5-yl)-ethyl]-amide} 2-[(3-piperidin-1-yl-propyl)-amide]. Using essentially the same procedure used in reference example 99a, except using 3-(piperidin-1-yl)-propylamine and Biphenyl-2,4'-dicarboxylic acid 4'-{[2-(3-cyano-1H-indol-5-yl)-ethyl]-amide} (reference example 17i) as substrates. MS (ion spray) m/z 534 (M+H)$^+$.

Reference Example 99 g

Biphenyl-2,4'-dicarboxylic acid 4'-{[2-(3-cyano-1H-indol-5-yl)-ethyl]-amide} 2-[(4-dimethylamino-butyl)-amide]. Using essentially the same procedure used in reference example 99a, except using 4-(dimethylamino)-butylamine and Biphenyl-2,4'-dicarboxylic acid 4'-{[2-(3-cyano-1H-indol-5-yl)-ethyl]-amide} (reference example 17i) as substrates. MS (ion spray) m/z 508 (M+H)$^+$.

Reference Example 99h

Biphenyl-2,4'-dicarboxylic acid 4'-{[2-(3-cyano-1H-indol-5-yl)-ethyl]-amide} 2-[(2,3-dihydroxy-propyl)-methyl-amide]. Using essentially the same procedure used in reference example 99a, except using (2,3-dihydroxy-propyl)-methyl-amine and Biphenyl-2,4'-dicarboxylic acid 4'-{[2-(3-cyano-1H-indol-5-yl)-ethyl]-amide} (reference example 17i) as substrates. MS (ion spray) m/z 497 (M+H)$^+$.

Reference Example 99i

Biphenyl-2,4'-dicarboxylic acid 4'-{[2-(3-cyano-1H-indol-5-yl)-ethyl]-amide} 2-[(2,3-dihydroxy-propyl)-amide]. Using essentially the same procedure used in reference example 99a, except using 2,3-dihydroxy-propyl-amine and Biphenyl-2,4'-dicarboxylic acid 4'-{[2-(3-cyano-1H-indol-5-yl)-ethyl]-amide} (reference example 17i) as substrates. MS (ion spray) m/z 497 (M+H)$^+$.

Reference Example 100a

N-[2-(3-Cyano-1H-indol-5-yl)-ethyl]-4-[2-(2-methoxyethoxy)-pyrimidin-4-yl]benzamide. To a solution of 2-methoxyethanol (0.118 mL, 1.50 mmoles) in DMSO (5 mL) was added sodium hydride (Aldrich, 60% dispersion, 0.0720 g, 1.80 mmoles), followed by stirring until $H_2$ evolution ceased (15 minutes). One milliliter of this alkoxide stock solution was added to N-[2-(3-Cyano-1H-indol-5-yl)-ethyl]-4-[2-chloropyrimidin-4-yl]benzamide (0.147 g, 0.249 mmoles, reference example 1az), followed by heating (60° C.). After two hours, another 0.5 mL of the alkoxide stock solution was added. After two more hours, the reaction was quenched with water (40 mL) and the resulting precipitate collected by filtration. The precipitate was washed with water and $CH_2Cl_2$ and dried under vacuum to give the product as a white solid. MS (ion spray) m/z 442 (M+H)+.

The following compounds were prepared using essentially the same procedure used in reference example 100a except using the cited alcohol in place of 2-methoxyethanol.

Reference Example 100b

N[2-(3-Cyano-1H-indol-5-yl)ethyl]-4-[2-(1-carbamoylethoxy)pyrimidin-4-yl]benzamide. Using 2-hydroxy-propionamide as substrate. MS (ion spray) m/z 455 (M+H)+.

Reference Example 100c

N[2-(3-Cyano-1H-indol-5-yl)ethyl-4-[2-(6-dimethylaminohexyloxy)pyrimidin-4-yl]benzamide. Using 6-dimethylaminohexanol as substrate. MS (ion spray) m/z 511 (M+H)+.

Reference Example 100d

N[2-(3-Cyano-1H-indol-5-yl)ethyl]-4-[2-(2-oxopiperidin-3-yloxy)pyrimidin-4-yl]benzamide. Using 2-hydroxy-valerolactam as substrate. MS (ion spray) m/z 481 (M+H)+.

Reference Example 100e

N[2-(3-Cyano-1H-indol-5-yl)ethyl]-4-[2-(2-pyrrolidin-1-yl-ethoxy)pyrimidin-4-yl]benzamide. Using 2-(pyrrolidin-1-yl)-ethanol as substrate. MS (ion spray) m/z 481 (M+H)+.

Reference Example 100f

N[2-(3-Cyano-1H-indol-5-yl)ethyl]-4-[2-(2-dimethylaminoethoxy)pyrimidin-4-y]benzamide. Using 2-(dimethylamino)-ethanol as substrate. MS (ion spray) m/z 455 (M+H)+.

Reference Example 101a 4-(3-[2-Dimethylaminoethoxy]phenyl)benzoic acid. Stirred a solution of 3-(2-Dimethylaminoethoxy)phenyl iodide (0.495 g, 1.70 mmoles), 4-carboxybenzeneboronic acid (Lancaster, 0.282 g, 1.70 mmoles), and sodium carbonate (0.360 g, 3.40 mmoles) in 1:1 $H_2O$: AcCN (20 mL) under vacuum for five minutes, followed by the addition of tetrakis (triphenylphosphine)palladium (0) (0.170g). The reaction mixture was heated (90° C.) for three hours, and the catalyst was filtered off through Celite. The effluent was concentrated slightly to remove the AcCN, and the resulting aqueous solution was acidified with 2N HCl and purified on an HPLC to yield 0.462 g of the title compound as the TFA salt. MS (ion spray) m/z 286 (M+H)+.

The following compounds were prepared using essentially the same procedure used in reference example 101a except using the specified aryl halide in place of 3-(2-dimethylaminoethoxy)phenyliodide.

Reference Example 101b 4-(1-Oxypyridin-2-yl)benzoic acid. Using 2-bromo-pyridine-N-oxide. MS (ion spray) m/z 216 (M+H)+.

Reference Example 101c 4-(2-[2-Dimethylaminoethoxy]phenyl)benzoic acid. Using 2-(2-Dimethylaminoethoxy)phenyl-iodide as substrate. MS (ion spray) m/z 286 (M+H)+.

Reference Example 101d 4-(2-[3-Dimethylaminopropoxy]phenyl)benzoic acid. Using 2-[3-Dimethylaminopropoxy]phenyl iodide as substrate. MS (ion spray) m/z 300 (M+H)+.

Reference Example 101e 4-(3-[3-Dimethylaminopropoxy]phenyl)benzoic acid. Using 3-[3-Dimethylaminopropoxy]phenyl iodide as substrate. MS (ion spray) m/z 300 (M+H)+.

Reference Example 101f 4-(1-Oxypyridin-3-yl)benzoic acid. Using 3-bromo-pyridine-N-oxide as substrate.

Reference Example 102a

4-[[4-(4-methoxycarbonyl-phenyl)-pyridin-2-ylmethyl]-carbamoyl]-piperidine-1-carboxylic acid tert-butyl ester. To a solution of piperidine-1,4-dicarboxylic acid mono-tert-butyl ester (275 mg, 1.2 mmol) in $CH_2Cl_2$ (2 ml) was added diisopropylethylamine (0.23 ml, 1.32 mmol). The resulting solution was stirred for 5 minutes then TBTU (337 mg, 1.26 mmol) was added and stirred for 20 minutes. To the reaction mixture was added a solution of 4-(2-aminomethyl-pyridin-4-yl)-benzoic acid methyl ester trifluoroacetic acid salt (356 mg, 1 mmol, reference example 103a) and diisopropylethylamine (0.192 ml, 1.1 mmol) in $CH_2Cl_2$ (2 ml). The reaction mixture was stirred 45 minutes then concentrated under reduced pressure. The residue was purified by flash chromatography (eluting with 40% ethyl acetate/10% methanol/hexanes) to give 455 mg of product as a white foam. MS (ion spray) m/z 454 (M+H)+.

Reference Example 102b

Using essentially the same procedure used to prepare reference example 102a except using acetic acid as substrate in place of piperidine-1,4-dicarboxylic acid mono-tert-butyl ester, there is prepared 4-[2-(acetylamino-methyl)-pyridin-4-yl]-benzoic acid methyl ester. MS (ion spray) m/z 285 (M+H)+.

Reference Example 103a 4-(2-aminomethyl-pyridin-4-yl)-benzoic acid methyl ester trifluoroacetic acid salt. To a solution of 4-[2-(tert-butoxycarbonylamino-methyl)-pyridin-4-yl]-benzoic acid methyl ester (1.96 g, 5.72 mmol, reference example 56) in $CH_2Cl_2$ (19 ml) was added TFA (6 ml). The reaction solution was stirred 3 hrs then concentrated under reduced pressure. The residue was purified by trituration with ether. The solids were collected by filtration, washed with ether and dried under vacuum to give 1.68 g of product. MS (EI) m/z 243 (M+H)+.

Reference Example 103b

Ethyl 4-(1-[carboxymethyl]-6-oxo-1,6-dihydropyridin-3-yl)benzoate. Prepared using essentially the same procedure used to prepare reference example 103a except using Ethyl 4-{1-[(tert-butoxycarbonyl)methyl]-6-oxo-1,6-dihydropyridin-3-yl}benzoate (reference example 85b). MS (ion spray) m/z 302 (M+H)$^+$.

Reference Example 104

Allyl 4-(2-oxo-2H-pyridin-5-yl)benzoate. To a solution of ethyl 4-(2-oxo-2H-pyridin-5-yl)benzoate (1.24 g, 5.10 mmoles, reference example 36f) in allyl alcohol (50 mL) was added titanium (IV) isopropoxide. The resulting mixture was heated to 70° C. for seven hours at which point more titanium (IV) isopropoxide (3 mL) was added. After 18 hours the heat was removed and 1N HCl solution (50 mL) was added followed by extraction with $CH_2Cl_2$ (200 mL). The organic layer was isolated and concentrated to give the title compound in quantitative yield. MS (ion spray) m/z 256 (M+H)$^+$.

Reference Example 105

4-[2-amino-1,1-dimethyl-ethyl]-N-[2-(3-cyano-1H-indol-5-yl)-ethyl]-benzamide. To a solution of (2-[4-[2-(3-cyano-1H-indol-5-yl)-ethylcarbamoyl]-phenyl]-2-methyl-propyl)-carbamic acid tert-butyl ester (1.16 g, 2.5 mmol) (prepared using the procedure of reference example 1w) in $CH_2Cl_2$ (8 ml) was added TFA (1.6 ml) and the reaction stirred 2 hrs. Water (50 µL) was add-ed and the reaction concentrated under reduced pressure. The residue was purified by flash chromatography (eluting with 10% 7M $NH_3$ in $CH_3OH/CH_2Cl_2$) to give 808 mg of product. MS (ion spray) m/z 361 (M+H)$^+$.

Reference Example 106

N[2-(3-cyano-1H-indol-5-yl)-ethyl]-4-(2-methanesulfonylamino-1,1-dimethyl-ethyl)-benzamide. To a solution of 4-[2-amino-1,1-dimethyl-ethyl]-N-[2-(3-cyano-1H-indol-5-yl)-ethyl]-benzamide (97 mg, 0.27 mmol) (reference example 105) in $CH_2Cl_2$ (1 ml) was added pyridine (24 µL, 0.30 mmol) and methanesulfonyl chloride (23 µL, 0.30 mmol). The reaction was stirred for 5 min then concentrated under reduced pressure. The residue was purified by flash chromatography (eluting with 8% 7M $NH_3$ in $CH_3OH/CH_2Cl_2$ to give 95 mg of product. MS (ion spray) m/z 439 (M+H)$^+$.

Reference Example 107a

N[2-(3-Cyano-1H-indol-5-yl)-ethyl]-4-(1,1-dimethyl-2-ureido-ethyl)-benzamide. To a solution of 4-[2-amino-1,1-dimethyl-ethyl]-N-[2-(3-cyano-1H-indol-5-yl)-ethyl]-benzamide (90 mg, 0.25 mmol) (reference example 105) in 1,4-dioxane (1 ml) was added trimethylsilyl isocyanate (68 µL, 0.50 mmol). The resulting mixture is stirred for 16 h. The precipitated solids are collected by vacuum filtration, washed with a small volume of $CH_2Cl_2$ and dried under high vacuum to give 99 mg of product. MS (ion spray) m/z 404 (M+H)$^+$.

Reference Example 107b

N[2-(3-Cyano-1H-indol-5-yl)-ethyl]-4-[2-(3-ethyl-ureido)-1,1-dimethyl-ethyl]-benzamide. Prepared using essentially the same procedure used in reference example 107a except using ethyl isocyanate as substrate. MS (ion spray) m/z 432 (M+H)$^+$.

Reference Example 107c 4-(1-carbamoyl-piperidin-4-yl)-benzoic acid Prepared using essentially the same procedure used in reference example 107a except using 4-(piperidin-4-yl)-benzoic acid (reference example 109) as substrate.

Reference Example 108

4-(2-dimethylamino-3,4,5,6-tetrahydro-pyrimidin-4-yl)-benzoic acid. To a solution of 4-(2-dimethylamino-pyrimidin-4-yl)-benzoic acid (275 mg, 1.13 mmol reference example 92aab) in $H_2O$ (13 ml) was added conc HCl (212 µL, 2.54 mmol) followed by 10% palladium on carbon (366 mg). The resulting mixture was stirred under $H_2$ for 2.5 hrs. The mixture was filtered through a celite pad to remove the catalyst, using $CH_2Cl_2$ as a wash. The filtrate was concentrated under reduced pressure to give 260 mg of product as the HCl salt. MS (ion spray) m/z 248 (M+H)$^+$.

Reference Example 109

4-(Piperidin-4-yl)-benzoic acid. To the sodium salt of 4-pyridine benzoic acid (500 mg, 2.25 mmol) suspended in 20% AcOH/MeOH (20 ml) was added $PtO_2$ (250 mg) and the mixture was hydrogenated at 50 psi with agitation (Parr) for 4 h. The solution was filtered through celite, washed with MeOH (3×5 ml), evaporated with hexane (4×) to azeotrope the acetic acid. TLC of the crude ($EtOH/H_2O/NH_4OH$ 10:1:1) shows no starting material, but did show 2 more polar spots. After evaporation from hexane, the white solid (596 mg crude, still with residual HOAc) was dried in a vacuum overnight, and used without further purification in subsequent steps. MS m/z [M+H]$^+$.

Reference Example 110

Preparation of 4-(1-acetyl-piperidin-4-yl)-benzoic acid. To a solution of 4-piperidin-4-yl)-benzoic acid (102 mg, 0.5 mmol, reference example 109) dissolved in pyridine (2 mL) was added acetic anhydride (255 mg, 2.5 mmol) and the reaction stirred overnight at room temperature. The reaction was concentrated in vacuo and residual pyridine partially removed by azeotroping with dichloromethane/methanol 1:1. The crude product was then washed with dichlormethane and the solvent decanted to yield a white solid residue (61 mg, 49%) 4-(1-acetyl-piperidin-4-yl)-benzoic acid. $^1$H NMR ($CD_3OD$): δ 7.89 (d, 2H); 7.27 (d, 2H); 4.65 (d, 1H); 4.03 (d, 1H); 3.21 (dt, 2H); 2.68–2.88 (m, 2H); 1.93 (s, 3H); 1.85–2.04 (m, 2H); 1.50–1.75 (m, 3H). MS m/z 248 (M+H)+.

Reference Example 111

4-(1-methyl-piperdin-4-yl)-benzoic acid. 4-piperidin-4yl-benzoic acid (110 mg, 0.54 mmol, reference example 109) was added to paraformaldehyde (180 mg, 6 mmol) in MeOH (10 mL) and $NaCNBH_3$ (120 mg, 1.94 mmol). The reaction was stirred at room temperature for 4 days, at which time HPLC shows no remaining starting material. The solution was acidified to pH 2 with concentrated HCl, evaporated, dissolved in water (20 mL), and extracted with ether (3×20 mL). Then the solution was brought to pH 12 with KOH pellets, extracted with dichloromethane (3×20 mL) and finally brought to pH5 with acetic acid. The mixture was lyophilized and the solid was extracted with MeOH (3×15 mL). The combined methanol extracts were evaporated and the residue chromatographed (reverse-phase HPLC, C18 column, 10–100% $CH_3CN/water$) to yield, after lyophilization, 72 mg of the desired product (61%). $^1$H NMR (CD$_3$OD): δ 7.98 (d, 2H), 7.38 (d, 2H), 3.60 (m, 2H), 3.18 (t, 2H), 2.94 (s, 3H), 2.85–2.95 (m, 2H), 2.08–2.18 (m, 2H), 1.90–2.02 (m, 2H). MS (ion spray) m/z 220 (M+H$^+$). >98% pure by analytical HPLC.

Reference Example 112

4-(1-oxo-1-methyl-piperidin-4-yl)-benzoic acid. 4-(1-methyl-piperidin-4-yl)-benzoic acid (47 mg, 0.21 mmol, reference example 111) dissolved in CHCl$_3$ (3 mL) was added to mCPBA (60 mg). After 3 h, HPLC showed only 1 peak (9 min), which was different from the starting material. The solvent was evaporated and the crude product was partially purified by reverse-phase HPLC (C-18 column, 10–100% CH$_3$CN/water) to yield the product 4-(1-oxo-1-methyl-piperidin-4-yl)-benzoic acid. (28 mg, 56%) as a solid. $^1$H NMR (CD$_3$OD): δ 7.98 (d, 2H), 7.42 (d, 2H), 3.72–3.88 (m, 4H), 3.58 (s, 3H), 2.91–3.02 (m, 2H), 2.28–2.42 (m, 2H), 2.01–2.07 (m, 2H). MS (ion spray) m/z 236 [M+H]$^+$. >92% pure by analytical HPLC.

Reference Example 113a 4-(4-Dimethylamino-piperidin-1-yl)-benzoic acid. 280 mg (1.22 mmol) of 4-(4-dimethylamino-piperidin-1-yl)-benzonitrile (reference example 114a) was dissolved in 2 ml of acetic acid, 4 ml of 6 N HCl was added and the mixture stirred with reflux for 16 h. After cooling 20 ml of water was added and extracted with DCM (3×). The pH of the aqueous phase was adjusted to 5 with KOH pellets, white solid precipitated which was filtered off, washed and dried to give 257 mg of the title compound (85% yield). $^1$H NMR (CDCl$_3$): δ 7.88 (dd, 2H), 6.98 (dd, 2H), 4.09 (d, 2H), 3.42 (m, 1H), 3.29 (t, 2H), 2.90 (s, 6H), 2.89–2.96 (m, 2H), 2.18 (m, 2H), 1.80 (dq, 2H). MS (ion spray) m/z 249 (M+H)+. 90% pure by analytical HPLC.

Reference Example 113b 4-(4-Amino-piperidin-1-yl)-benzoic acid. Prepared using essentially the same procedure used in reference example 114a except using 4-(4-Amino-piperidin-1-yl)-benzonitrile (reference example 114b) as substrate. MS (ion spray) m/z 221 (M+H)+.

Reference Example 113c

4-[4-(2-dimethylamino-ethyl-amino)-piperidin-1-yl]-benzoic acid. Prepared using essentially the same procedure used in reference example 114a except using 4-[4-(2-dimethylamino-ethyl-amino)-piperidin-1-yl]-benzonitrile (reference example 114c) as substrate. MS (ion spray) m/z 292 (M+H)+.

Reference Example 113d 4-(4-hydroxy-piperidin-1-yl)-benzoic acid Prepared using essentially the same procedure used in reference example 114a except using 4-[4-(hydroxy)-piperidin-1-yl]-benzonitrile (reference example 122). MS (EI) m/z 221 (M$^+$).

Reference Example 114a 4-(4-Dimethylamino-piperidin-1-yl)-benzonitrile. A mixture of 4-(4-oxo-piperidin-1-yl)-benzonitrile (100 mg, 0.5 mmol, reference example 116) dimethylamine hydrochloride (408 mg, 5 mmol) and NaCNBH$_3$ (25 mg, 0.4 mmol) was dissolved in MeOH (7 mL) and stirred at room temperature overnight. After 24 h, additional NaCNBH$_3$ (24 mg, 0.38 mmol) was added and the mixture was stirred overnight at room temperature. The pH of the mixture was adjusted to pH 2 with concentrated HCl and extracted with Et$_2$O (3×). The aqueous phase was adjusted to pH 10 with KOH pellets, and extracted (3×) with Et$_2$O. The latter combined organic phases were washed with brine, dried with Na$_2$SO$_4$, filtered and evaporated. The crude material was taken into the next step without further purification. $^1$H NMR (CDCl$_3$): δ 7.44 (d, 2H), 6.83 (d, 2H), 3.86 (m, 2H), 2.86 (dt, 2H), 2.32–2.38 (m, 1H), 2.28 (s, 6H), 1.92 m(m, 2H), 1.54 (dq, 2H). MS (EI) m/z 229 (M+H)+.

Reference Example 114b 4-(4-Amino-piperidin-1-yl)-benzonitrile. Prepared using essentially the same procedure used in reference example 114a except using NH$_4$OAc as substrate in place of dimethylamine hydrochloride. $^1$H NMR (CDCl$_3$): δ 7.45 (d, 2H), 6.84 (d, 2H), 3.80 (d, 3H), 2.92 (m, 2H), 1.92 (d, 2H), 1.28–1.46 (m, 2H). MS (ion spray) m/z 202 (M+H)+.

Reference Example 114c

4-[4-(2-dimethylamino-ethyl-amino)-piperidin-1-yl]-benzonitrile. Prepared using essentially the same procedure used in reference example 114a except using N,N-dimethylethylene diamine as substrate in place of dimethylamine hydrochloride. $^1$H NMR (CDCl$_3$): d 7.45 (d, 2H), 6.84 (d, 2H), 3.27 (m, 1H), 2.94 (t, 2H), 2.73 (m, 2H), 2.39 (t, 2H), 2.21 (s, 6H), 1.94 (dd, 2H), 1.62 (brs, 2H), 1.43 (q, 2H). MS (ion spray) m/z 273 (M+H)+.

Reference Example 114d

Methyl 4-(1-methyl-piperidin-4-yloxy)-benzoate. Prepared using essentially the same procedure used in reference example 114a except using formaldehyde and Methyl 4-(piperidin-4-yloxy)-benzoate (reference example 123) as substrates. $^1$H NMR (CDCl$_3$): d 8.01 (d, 2H), 6.91 (d, 2H), 4.80 (s, 1H), 3.89 (s, 3H), 3.35 (brd, 2H), 3.13 (q, 2H), 2.80 (d, 3H), 2.65 (t, 2H), 2.18 (d, 2H). MS (ion spray) m/z 250 (M+H)+.

Reference Example 115

4-(4-[tert-butoxycarbonylamino]-piperidin-1-yl)-benzoic acid. To a solution of of 4-(4-amino piperidin-1-yl)-benzoic acid (242 mg, 1.1 mmol, reference example 113b) dissolved in 5 ml of dichloromethane is added 300 mg of triethylamine and 305 mg (1.4 mmol) of Boc$_2$O. The resulting mixture is stirred at room temperature for 16 h. Solvent is evaporated and the mixture separated by chromatography on silica with DCM/MeOH (10%) to give 214 mg of the title compound. $^1$H NMR (CD$_3$OD): δ 7.85 (d, 2H), 6.94 (d, 2H), 3.85 (m, 2H), 3.65 (m, 1H), 2.93 (m, 2H), 1.91 (m, 2H), 1.49 (s, 9H), 1.32–1.40 (m, 2H). MS (EI) m/z 320 (M+).

Reference Example 116

4-(4-oxo-piperidin-1-yl)-benzonitrile. To 4-(1,4-dioxa-8-aza-spiro[4.5]dec-8-yl)-benzonitrile (460 mg, 1.88 mmol, reference example 117) dissolved in THF (2 mL) was added 10% H$_2$SO$_4$ (4 mL) and the reaction was stirred for 24 h at room temperature. TLC (40% EtOAc in hexanes) shows a small amount of starting material, but mainly a more polar product. The reaction was diluted with water, extracted with dichloromethane (3×), washed with saturated aqueous NaCl solution, dried with Na$_2$SO$_4$, filtered and evaporated. The crude product was chromatographed on silica gel (20–40% EtOAc in hexanes) to afford the title compound (315 mg, 84%). ¹H NMR (CDCl₃): δ 7.52 (d, 2H), 6.88 (d, 2H), 3.72 (t, 4H), 2.57 (t, 4H). MS (ion spray) m/z 200 (M+).

Reference Example 117

4-(1,4-dioxa-8-aza-spiro[4.5]dec-8-yl)-benzonitrile. A mixture of 4-fluorobenzonitrile (2.49 g, 20.57 mmol (14.73 g, 103 mmol) 1,4-dioxa-8-azaspiro[4.5]decane and K₂CO₃ (4.14 g, 30 mmol) in dioxane (40 mL) was refluxed for 65 h. The reaction was filtered and the solvent was evaporated. Chromatography on silica gel (10–30% EtOAc in hexanes) provided the desired alkylated product 1,4-dioxa-8-azaspiro [4.5]decane (3.9 g, 79%). ¹H NMR (CDCl₃): δ 7.47 (d, 2H), 6.86 (d, 2H), 3.98 (s, 4H), 3.48 (t, 4H), 1.78 (t, 4H). MS (ion spray) m/z 245 (M+H)+.

Reference Example 118

4-(1-oxy-pyridin-4-yloxy)-benzoic acid. 246 mg (1 mol) of methyl 4-(1-oxy-pyridin-4-yloxy)-benzoate (reference example 119) was dissolved in 6 ml of ethanol, 4 ml of 1N NaOH is added and refluxed for 3 h. The mixture was neutralized with conc. HCl, evaporated and purified by preparative HPLC ¹H NMR (CDCl₃): δ 8.51 (d, 1H); 7.86 (d, 2H); 7.33 (d, 2H); 6.80 (d, 2H). MS (ion spray) m/z 232 (M+H)+.

Reference Example 119

Methyl 4-(1-oxy-pyridin-4-yloxy)-benzoate 304 mg (2 mol) of 4-hydroxy benzoic acid methyl ester, 280 mg (2 mmol) of 4-nitro pyridine oxide (2 mol) and 420 mg (3 mol) of K₂CO₃ were dissolved in 5 ml of dry DMF and stirred for 2 h at 110° C. Cooled mixture was poured into brine and extracted with EtOAc (3×), washed with brine, dried with Na₂SO₄ and evaporated to give 246 mg of the title compound. ¹H NMR (CDCl₃): d 8.18 (d, 2H); 8.10 (d, 2H); 7.89 (d, 1H); 7.12 (d, 1H); 6.93 (d, 1H); 6.88 (d, 1H); 3.92 (s, 3H). MS (EI) m/z 245 (M+H)+.

Reference Example 120

4-[4-(2-dimethylamino-ethyl-tert-butyloxycarbonyl-amino)-piperidin-1-yl]-benzoic Acid. 140 mg (0.48 mmol) of the 4-[4-(2-dimethylamino-ethyl-amino)-piperidin-1-yl]-benzoic acid (reference example 113c) were dissolved in 8 ml of THF, 655 mg (3 mol) of Boc₂O was added and stirred 3 days at room temperature. The mixture was diluted with water and extracted with DCM (3×); the combined extracts were washed with brine, dried over Na₂SO₄, filtered and evaporated. The resulting solid was washed with DCM/ether and dried to give 114 mg (61%) of the title compound. ¹H NMR (CDCl₃): d 7.84 (m, 2H), 6.79 (d, 1H), 3.95 (m, H), 3.70 (m, 4H), 3.18 (m, 2H), 2.84 (s, 3H), 2.79 (s, 3H), 2.70 (t, 1H), 1.88 (m, 2H), 1.76 (m, 2H), 1.57 (s, 3H), 1.44 (s, 6H). MS (ion spray) m/z 392 (M+H)+.

Reference Example 121

4-(4-Methoxy-piperidin-1-yl)-Benzoic Acid. 170 mg (0.77 mmol) of 4-(4-hydroxy-piperidin-1-yl)-benzoic acid (reference example 113d) were dissolved in 3 ml of THF and 3 ml of DMSO, 120 mg (1.1 equiv) of methyl iodide and 68 mg (1.69 mmol) of NaH were added and stirred 16 h at room temperature. The mixture was poured into brine and extracted with DCM (3×) aqueous phase acidified with HCl to pH 1 and extracted again with DCM (3×). The combined organic extracts were washed with brine, dried with Na₂SO₄, filtered and evaporated. TLC (DCM/MeOH 10%) showed a mixture of the starting material (Rf~0.5) and a new product with Rf~0.6. The two were separated by chromatography on silica with DCM/MeOH (0–10%) as a mobile phase to give 60 mg of the title compound. ¹H NMR (CDCl₃): d 7.95 (d, 2H), 6.87 (d, 2H), 3.68 (m, 2H), 3.63 (m, 1H), 3.38 (s, 3H), 3.14 (m, 2H), 1.98 (m, 2H), 1.68 (m, 2H). MS (ion spray) m/z 236 (M+H)+.

Reference Example 122

4-(4-hydroxy-piperidin-1-yl)-benzonitrile. 240 mg (1.2 mmol) of 4-(4-oxo-piperidin-1-yl)-benzonitrile (reference example 116) was dissolved in 5 ml of methanol, 23 mg (0.6 mmol) of NaBH₄ was added and stirred 3 h at room temperature. A few drops of water were added, methanol evaporated then 20 ml of water were added and extracted with DCM (3×), dried with Na₂SO₄, filtered and evaporated to give 230 mg (95% yield) of the title compound. ¹H NMR (CDCl₃): d 7.47 (d, 2H), 6.85 (d, 2H), 3.93 (bs, H), 3.70 (m, 2H), 3.11 (m, 2H), 1.95 (m, 2H), 1.62 (m, 2H). MS (ion spray) m/z 202 (M+H)+.

Reference Example 123

Methyl 4-(piperidin-4-yl-oxy)-benzoate. 266 mg (0.79 mmol) of methyl 4-(N-BOC-piperidin-4-yl-oxy)-benzoate (reference Example 124) was dissolved in 4 ml of DCM to which 4 ml of TFA was added and stirred 1 h at room temperature. The mixture was evaporated to dryness and purified by preparative HPLC with the mobile phase water/acetonitrile/0.1% TFA to give 217 mg of the TFA salt of the title compound. ¹H NMR (CD₃OD): d 7.97 (d, 2H), 7.06 (d, 2H), 4.78–4.85 (m, 1H), 3.86 (s, 3H), 3.19–3.44 (m, 4H), 2.14–2.23 (m, 2H), 2.00–2.08 (m, 2H). MS (ion spray) m/z 236 (M+H)+.

Reference Example 124

Methyl 4-(N-BOC-piperidin-4-yl-oxy)-benzoate. 656 mg (2.5 mmol) of triphenylphosphine and 304 mg (2 mmol) of 4-hydroxy methyl benzoate were dissolved in 3 ml of dry THF at 0° C. and a solution of 402 mg (2 mmol) of N-Boc 4-piperidinol and 418 mg (2.4 mmol) of diethylazodicarboxylate in 4 ml of dry THF were added dropwise over 5 min. The mixture was stirred at 0° C. for 2 h and then allowed to warm to room temperature and stirred for 3 days.The mixture was separated by chromatography on silica with a gradient of hexane/EtOAc (5–20%) to give 266 mg (40% yield) of the title compound. ¹H NMR (CDCl₃): 7.96 (d, 2H), 6.90 (d, 2H), 4.52–4.56 (m, 1H), 3.87 (s, 3H), 3.65–3.72 (m, 2H), 3.31–3.39 (m, 2H), 1.83–1.97 (m, 2H), 1.70–1.82 (m, 2H), 1.45 (s, 9H). MS (EI) m/z 184.

Reference Example 125

4-(4-Acetylamino-piperidin-1-yl)N-[2-(3-Cyano-1H-indol-5-yl)-ethyl]-benzamide. 40 mg (0.09 mmol) of 4-(4-amino-piperidin-1-yl)-N-[2-(3-Cyano-1H-indol-5-yl)-ethyl]-benzamide. (reference Example 1aav). was dissolved in 2 ml of pyridine, 22 mg (0.22 mmol) of acetic anhydride was added and stirred at room temperature for 16 h. The reaction mixture was evaporated to dryness. MS (CI) 430 (M+H)⁺.

Reference Example 126

Methyl 4-(1-methanesulphonyl-piperidin-4-yl) Benzoate. 87 mg (0.40 mmol) of Methyl 4-(piperidin-4-yl) Benzoate (reference Example 127) was dissolved in 3 ml of DCM, cooled to 0° C. and 55 mg (0.48 mmol) of methanesulfonyl chloride added and stirred for 1 h. The mixture was poured into water, extracted with DCM (3×), washed with dilute NaHCO$_3$, dried with Na$_2$SO$_4$, filtered and evaporated. The crude was purified by chromatography on silica with hexane/EtOAc as the mobile phase to give 81 mg (61% yield) of the title compound. $^1$H NMR (CDCl$_3$): δ 7.98 (d, 2H), 7.26 (d, 2H), 3.93 (m, 2H), 3.90 (s, 3H), 2.81 (s, 3H), 2.63–2.78 (m, 3H), 1.76–1.96 (m, 4H). MS (ion spray) m/z 298 (M+H)$^+$.

Reference Example 127

Methyl 4-(piperidin-4-yl) Benzoate. 160 mg (0.78 mmol) of 4-(piperidine-4-yl) benzoic acid (reference example 109) was dissolved in 2 ml of MeOH. 0.5 ml of conc. H$_2$SO4 was added dropwise and the mixture was refluxed for 2 h. It was cooled, diluted with water, pH adjusted to 12 with KOH pellets and extracted with DCM (3×). The aqueous phase was purified by preparative HPLC with a 10–100% gradient of water/acetonitrile/0.1% TFA to give 87 mg of the title compound. MS (ion spray) m/z 220 (M+H)$^+$.

The molecules described herein inhibit blood coagulation by virtue of their ability to inhibit the penultimate enzyme in the coagulation cascade, Factor Xa, rather than thrombin. Both free Factor Xa and Factor Xa assembled in the prothrombinase complex (Factor Xa, Factor Va, calcium and phospholipid) are inhibited. Factor Xa inhibition is obtained by direct complex formation between the inhibitor and the enzyme and is therefore independent of the plasma co-factor antithrombin III. Effective Factor Xa inhibition is achieved by administering the compounds either by oral administration, continuous intravenous infusion, bolus intravenous administration or any other parenteral route such that it achieves the desired effect of preventing the Factor Xa induced formation of thrombin from prothrombin.

Anticoagulant therapy is indicated for the treatment and prophylaxis of a variety of physiological thrombotic conditions of both the venous and arterial vasculature. In the arterial system, abnormal thrombus formation is primarily associated with arteries of the coronary, cerebral and peripheral vasculature. The diseases associated with thrombotic occlusion of these vessels principally include acute myocardial infarction (AMI), unstable angina, thromboembolism, acute vessel closure associated with thrombolytic therapy and percutaneous transluminal coronary angioplasty (PTCA), transient ischemic attacks, stroke, intermittent claudication and bypass grafting of the coronary (CABG) or peripheral arteries. Chronic anticoagulant therapy may also be beneficial in preventing the vessel luminal narrowing (restenosis) that often occurs following PTCA and CABG, and in the maintenance of vascular access patency in long-term hemodialysis patients. With respect to the venous vasculature, pathologic thrombus formation frequently occurs in the veins of the lower extremities following abdominal, knee and hip surgery (deep vein thrombosis, DVT). DVT further predisposes the patient to a higher risk of pulmonary thromboembolism. A systemic, disseminated intravascular coagulopathy (DIC) commonly occurs in both vascular systems during septic shock, certain viral infections and cancer. This condition is characterized by a rapid consumption of coagulation factors and their plasma inhibitors resulting in the formation of life-threatening thrombin throughout the microvasculature of several organ systems. The indications discussed above include some, but not all, of the possible clinical situations where anticoagulant therapy is warranted. Those experienced in this field are well aware of the circumstances requiring either acute or chronic prophylactic anticoagulant therapy.

In addition to their use in anticoagulant therapy, Factor Xa inhibitors may find utility in the treatment or prevention of other diseases in which the generation of thrombin has been implicated as playing a physiologic role. For example, thrombin has been proposed to contribute to the morbidity and mortality of such chronic and degenerative diseases as arthritis, cancer, atherosclerosis and Alzheimer's disease by virtue of its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF and DNA syntheses. Inhibition of Factor Xa will effectively block thrombin generation and therefore neutralize any physiologic effects of thrombin on various cell types.

Accordingly, the invention provides a method of inhibiting Factor Xa comprising contacting a Factor Xa inhibitory amount of a compound of formula I with a composition containing Factor Xa. According to a further feature of the invention there is provided a method of inhibiting the formation of thrombin comprising contacting Factor Xa inhibitory amount of a compound of formula I with a composition containing Factor Xa.

According to a further feature of the invention there is provided a method for the treatment of a human or animal patient suffering from, or subject to, conditions which can be ameliorated by the administration of an inhibitor of Factor Xa, for example conditions as hereinbefore described, which comprises the administration to the patient of an effective amount of compound of formula I or a composition containing a compound of formula I. "Effective amount" is meant to describe an amount of compound of the present invention effective in inhibiting Factor Xa and thus producing the desired therapeutic effect.

The present invention also includes within its scope pharmaceutical formulations which comprise at least one of the compounds of Formula I in association with a pharmaceutically acceptable carrier or coating.

In practice, compounds of the present invention may generally be administered parenterally, intravenously, subcutaneously, intramuscularly, colonically, nasally, intraperitoneally, rectally or orally.

The products according to the invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, and stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilized by heating, irradiation or microfiltration.

Suitable compositions containing the compounds of the invention may be prepared by conventional means. For example, compounds of the invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula I.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100, preferably about 0.01 to about 10, mg/kg body weight per day by inhalation, from about 0.01 to about 100, preferably 0.1 to 70, more especially 0.5 to 10, mg/kg body weight per day by oral administration, and from about 0.01 to about 50, preferably 0.01 to 10, mg/kg body weight per day by intravenous administration. In each particular case, the doses will be determined in accordance with the factors distinctive to the subject to be treated, such as age, weight, general state of health and other characteristics which can influence the efficacy of the medicinal product.

The products according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. For other patients, it will be necessary to prescribe not more than one or two doses per day.

The compounds of formula (I) may be used alone or in combination with other diagnostic, cardioprotective agents, direct thrombin inhibitors, anticoagulants, antiplatelet or fibrinolytic agents. Often patients are concurrently treated prior, during and after interventional procedures with agents of these classes either in order to safely perform the interventional procedure or to prevent deleterious effects of thrombus formation. Some examples of classes of agents which may be used in combination with a compound of formula (I) are selected from: anti-coagulants such as Factor Xa inhibitors, Factor VIIa inhibitors, warfarin or heparin; synthetic pentasaccharides; anti-platelet agents such as aspirin, piroxicam or ticlopidine; direct thrombin inhibitors (e.g. boroarginine derivatives, hirudin or argatroban (Novastan®)); fibrinogen receptor antagonists; statins/fibrates; or fibrinolytic agents (thrombolytic agents) such as tissue plasminogen activator, anistreplase (Eminase®), urokinase or streptokinase; or combinations thereof.

The term cardioprotective agents as used herein, denotes agents that act to protect myocardium during ischemia. These cardioprotective agents include, but are nor limited to, adenosine agonists, β-blockers and Na/H exchange inhibitors. Adendosine agonists include those compounds disclosed in Spada et al., U.S. Pat. No. 5,364,862 and Spada et al., U.S. Pat. No. 5,736,554, the disclosures of which are hereby incorporated herein by reference. An example of an adenosine agonists is AMP 579 (Phone-Poulenc Rorer). An example of a Na/H exchange inhibitor is Cariporide (HOE 642).

The term anti-coagulant agents as used herein, denotes agents that inhibit blood coagulation. Such agents include warfarin (Coumadin®) and heparin.

The term anti-platelet agents as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam (Feldane®), including pharmaceutically acceptable salts or prodrugs thereof. Other suitable anti-platelet agents include ticlopidine (Ticlid), thromboxane-A2-receptor antagonists and thromboxane-A2-synthetase inhibitors, as well as pharmaceutically acceptable salts or prodrugs thereof.

The phrase direct thrombin inhibitors (i.e. Factor IIa inhibitors), as used herein, denotes inhibitors of the serine protease thrombin. By inhibiting thrombin directly, the inhibition of the cleavage of fibrinogen to fibrin, activation of Factor XIIIa, activation of platelets, and feedback of thrombin to the coagulation cascade to generate more thrombin, occurs. Such direct inhibitors include boroarginine derivatives and boropeptides, hirudin and argatroban (Novastan®), including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The phrase fibrinolytic agents (or thrombolytics or fibrinolytics), as used herein, denotes agents that lyse blood clots. Such agents include tissue plasminogen activator, anistreplase (Eminase®), urokinase or streptokinase, including pharmaceutically acceptable salts or prodrugs thereof. Tissue plasminogen activator (tPA) is commercially available from Genentech Inc., South San Francisco, Calif. The term urokinase, as used herein, is intended to denote both dual and single chain urokinase, the latter also being referred to herein as prourokinase.

The compounds described herein may be administered to treat thrombotic complications in a variety of animals such as primates including humans. Inhibition of factor Xa is useful not only in the anticoagulant therapy of individuals having thrombotic conditions but is useful whenever inhibition of blood coagulation is required such as to prevent coagulation of stored whole blood and to prevent coagulation in other biological samples for testing or storage. Thus, any inhibitor of Factor Xa activity can be added to or contacted with any medium containing or suspected of containing Factor Xa and in which it is desired that blood coagulation be inhibited.

The compounds of the present invention may be used in combination with any antihypertensive agent or cholesterol or lipid regulating agent, or concurrently with agents used in the treatment of restenosis, atherosclerosis or high blood pressure. Some examples of agents that are useful in combination with a compound according to the invention in the treatment of high blood pressure include compounds of the following classes: beta-blockers, ACE inhibitors, calcium channel antagonists and alpha-receptor antagonists. Some examples of agents that are useful in combination with a compound according to the invention in the treatment of elevated cholesterol levels or disregulated lipid levels include compounds known to be HMGCoA reductase inhibitors, compounds of the fibrate class.

It is understood that the present invention includes combinations of compounds of the present invention with one or more of the aforementioned therapeutic class agents Compounds within the scope of the present invention exhibit marked pharmacological activities according to tests described in the literature and below which tests results are believed to correlate to pharmacological activity in humans and other mammals.

Enzyme Assays:

The ability of the compounds of the present invention to act as inhibitors of Factor Xa, thrombin, trypsin, tissue-plasminogen activator (t-PA), urokinase-plasminogen activator (u-PA), plasmin and activated protein C is evaluated by determining the concentration of inhibitor which resulted in a 50% loss in enzyme activity (IC50) using purified enzymes.

All enzyme assays are carried out at room temperature in 96-well microtiter plates using a final enzyme concentration of 1 nM. The concentrations of Factor Xa and thrombin are determined by active site titration and the concentrations of all other enzymes are based on the protein concentration supplied by the manufacturer. Compounds according to the invention are dissolved in DMSO, diluted with their respective buffers and assayed at a maximal final DMSO concentration of 1.25%. Compound dilutions are added to wells containing buffer and enzyme and pre-equilibrated for between 5 and 30 minutes. The enzyme reactions are initiated by the addition of substrate and the color developed from the hydrolysis of the peptide-p-nitroanilide substrates is monitored continuously for 5 minutes at 405 nm on a Vmax microplate reader (Molecular Devices). Under these conditions, less than 10% of the substrate is utilized in all assays. The initial velocities measured are used to calculate the amount of inhibitor which resulted in a 50% reduction of the control velocity ($IC_{50}$). The apparent Ki values are then determined according to the Cheng-Prusoff equation (IC50= Ki [1+[S]/Km]) assuming competitive inhibition kinetics.

An additional in vitro assay may be used to evaluate the potency of compounds according to the invention in normal human plasma. The activated partial thromboplastin time is a plasma-based clotting assay that relies on the in situ generation of Factor Xa, its assembly into the prothrombinase complex and the subsequent generation of thrombin and fibrin which ultimately yields the formation of a clot as the assay endpoint. This assay is currently used clinically to monitor the ex vivo effects of the commonly used anticoagulant drug heparin as well as direct acting antithrombin agents undergoing clinical evaluation. Therefore, activity in this in vitro assay is considered as a surrogate marker for in vivo anticoagulant activity.

Human Plasma Based Clotting Assay

Activated partial thromboplastin clotting times are determined in duplicate on a MLA Electra 800 instrument. A volume of 100 µl of citrated normal human pooled plasma (George King Biomedical) is added to a cuvette containing 100 µl of a compound according to the invention in Tris/NaCl buffer (pH 7.5) and placed in the instrument. Following a 3 minute warming period the instrument automatically adds 100 µl of activated cephaloplastin reagent (Actin, Dade) followed by 100 µl of 0.035 M $CaCl_2$ to initiate the clotting reaction. Clot formation is determined spectrophotometrically and measured in seconds. Compound potency is quantitated as the concentration required to double a control clotting time measured with human plasma in the absence of the compound according to the invention.

Compounds according to the invention may also be evaluated for their in vivo antithrombotic efficacy in two well established animal experimental models of acute vascular thrombosis. A rabbit model of jugular vein thrombosis and a rat model of carotid artery thrombosis are used to demonstrate the antithrombotic activity of these compounds in distinct animal model paradigms of human venous thrombosis and arterial thrombosis, respectively.

Experimental In Vivo Rabbit Venous Thrombosis Model

This is a well characterized model of fibrin rich venous thrombosis that is validated in the literature and shown to be sensitive to several anticoagulant drugs including heparin (Antithrombotic Effect of Recombinant Truncated Tissue Factor Pathway Inhibitor (TFPI 1-161) in Experimental Venous Thrombosis—a Comparison with Low Molecular Weight Heparin, J. Holst, B. Lindblad, D. Bergqvist, O. Nordfang, P. B. Ostergaard, J. G. L. Petersen, G. Nielsen and U. Hedner. *Thrombosis and Haemostasis*, 71, 214–219 (1994). The purpose of utilizing this model is to evaluate the ability of compounds to prevent the formation of venous thrombi (clots) in vivo generated at a site of injury and partial stasis in the jugular vein.

Male and female New Zealand white rabbits weighing 1.5–2 kg are anesthetized with 35 mg/kg of ketamine and 5 mg/kg xylazine in a volume of 1 mL/kg (i.m.). The right jugular vein is cannulated for infusion of anesthetic (ketamine/xylazine 17/2.5 mg/kg/hr at a rate of approximately 0.5 mL/hr) and administration of test substances. The right carotid artery is cannulated for recording arterial blood pressure and collecting blood samples. Body temperature is maintained at 39° C. with a GAYMAR T-PUMP. The left external jugular vein is isolated and all side branches along an exposed 2–3 cm of vessel are tied off. The internal jugular vein is cannulated, just above the bifurcation of the common jugular, and the tip of the cannula is advanced just proximal to the common jugular vein. A 1 cm segment of the vein is isolated with non-traumatic vascular clamps and a relative stenosis is formed by tying a ligature around the vein with an 18 G needle just below the distal most clamp. This creates a region of reduced flow and partial stasis at the injury site. The isolated segment is gently rinsed with saline 2–3 times via the cannula in the internal jugular. Thereafter the isolated segment is filled with 0.5 mL of 0.5% polyoxyethylene ether (W-1) for 5 minutes. W-1 is a detergent which disrupts the endothelial cell lining of the segment, thus providing a thrombogenic surface for initiating clot formation. After 5 minutes the W-1 is withdrawn from the segment, and the segment is again gently rinsed with saline 2–3 times. The vascular clamps are then removed, restoring blood flow through this portion of the vessel. Clot formation is allowed to form and grow for 30 minutes after which the vein is cut just below the stenotic ligature and inspected for blood flow (the absence of blood flow is recorded as complete occlusion). The entire isolated segment of vein is then ligated and the formed clot is removed and weighed (wet weight). The effect of test agents on final clot weights is used as the primary end point. Animals are maintained for an additional thirty minutes to obtain a final pharmacodynamic measure of anticoagulation. Drug administration is initiated 15 minutes prior to vascular injury with W-1 and continued through the period of clot formation and maturation. Three blood samples (3 mL ea.) are obtained for evaluation of hemostatic parameters: one just prior to administration of W-1; a second 30 minutes after removal of the vascular clamps and a third at the termination of the experiment. Antithrombotic efficacy is expressed as a reduction in the final clot weight in preparations treated with a compound according to the invention relative to vehicle treated control animals.

Experimental In Vivo Rat Arterial Thrombosis Model

The antithrombotic efficacy of Factor Xa inhibitors against platelet-rich arterial thrombosis may be evaluated using a well characterized rat carotid artery $FeCl_2$-induced thrombosis model (Superior Activity of a Thromboxane Receptor Antagonist as Compared with Aspirin in Rat Models of Arterial and Venous Thrombosis, W. A. Schumacher, C. L. Heran, T. E. Steinbacher, S. Youssef and M. L. Ogletree. *Journal of Cardiovascular Pharmacology*, 22, 526–533 (1993); Rat Model of Arterial Thrombosis Induced by Ferric Chloride, K. D. Kurtz, B. W. Main, and G. E. Sandusky. *Thrombosis Research*, 60, 269–280 (1990); The Effect of Thrombin Inhibition in a Rat Arterial Thrombosis Model, R. J. Broersma, L. W. Kutcher and E. F. Heminger. *Thrombosis Research*, 64, 405–412 (1991). This model is widely used to evaluate the antithrombotic potential of a variety of agents including heparin and the direct acting thrombin inhibitors.

Sprague Dawley rats weighing 375–450 g are anesthetized with sodium pentobarbital (50 mg/kg i.p.). Upon reaching an acceptable level of anesthesia, the ventral surface of the neck is shaved and prepared for aseptic surgery. Electrocardiogram electrodes are connected and lead 11 is monitored throughout the experiment. The right femoral vein and artery are cannulated with PE-50 tubing for administration of a compound according to the invention and for obtaining blood samples and monitoring blood pressure, respectively. A midline incision is made in the ventral surface of the neck. The trachea is exposed and intubated with PE-240 tubing to ensure airway patency. The right carotid artery is isolated and two 4–0 silk sutures are placed around the vessel to facilitate instrumentation. An electromagnetic flow probe (0.95–1 mm lumen) is placed around the vessel to measure blood flow. Distal to the probe a 4×4 mm strip of parafilm is placed under the vessel to isolate it from the surrounding muscle bed. After baseline flow measurements are made, a 2×5 mm strip of filter paper previously saturated in 35% $FeCl_2$ is placed on top of the vessel downstream from the probe for ten minutes and then removed. The $FeCl_2$ is thought to diffuse into the underlying segment of artery and cause deendothelialization resulting in acute thrombus formation. Following application of the $FeCl_2$-soaked filter paper, blood pressure, carotid artery blood flow and heart rate are monitored for an observation period of 60 minutes. Following occlusion of the vessel (defined as the attainment of zero blood flow), or 60 minutes after filter paper application if patency is maintained, the artery is ligated proximal and distal to the area of injury and the vessel is excised. The thrombus is removed and weighed immediately and recorded as the primary end point of the study.

Following surgical instrumentation a control blood sample (B1) is drawn. All blood samples are collected from the arterial catheter and mixed with sodium citrate to prevent clotting. After each blood sample, the catheter is flushed with 0.5 mL of 0.9% saline. A compound according to the invention is administered intravenously (i.v.) starting 5 minutes prior to $FeCl_2$ application. The time between $FeCl_2$ application and the time at which carotid blood flow reached zero is recorded as time to occlusion (TTO). For vessels that did not occlude within 60 minutes, TTO is assigned a value of 60 minutes. Five minutes after application of $FeCl_2$, a second blood sample is drawn (B2). After 10 minutes of $FeCl_2$ exposure, the filter paper is removed from the vessel and the animal is monitored for the remainder of the experiment. Upon reaching zero blood flow blood a third blood sample is drawn (B3) and the clot is removed and weighed. Template bleeding time measurements are performed on the forelimb toe pads at the same time that blood samples are obtained. Coagulation profiles consisting of activated partial thromboplastin time (APTT) and prothrombin time (PT) are performed on all blood samples. In some instances a compound according to the invention may be administered orally. Rats are restrained manually using standard techniques and compounds are administered by intragastric gavage using a 18 gauge curved dosing needle (volume of 5 mL/kg). Fifteen minutes after intragastric dosing, the animal is anesthetized and instrumented as described previously. Experiments are then performed according to the protocol described above.

The present invention may be embodied in other specific forms without departing from the spirit or essential attributes thereof.

What is claimed is:

1. A compound of formula I:

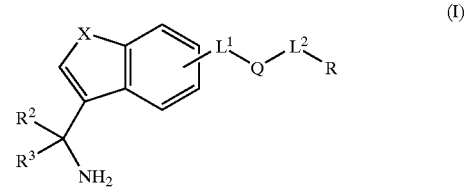

wherein
  X is $NR^1$;
  R is hydrogen, cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused hieterocyclylaryl, fused heterocyclenylaryl, heteroaryl, fused cycloalkylheteroaryl, fused cycloalkenylheteroaryl, fused heterocyclenylheteroaryl or fused heterocyclylheteroaryl, provided that where $L^2$ is a chemical bond then Q is attached to R through a carbon atom thereof or where R is hydrogen then $L^2$ is not a chemical bond;

$R^1$ is hydrogen, alkyl, aralkyl, heteroaralkyl, acyl, aroyl, heteroaroyl, alkoxycarbonyl, aryloxycarbonyl or heteroaryloxycarbonyl;

$R^2$ and $R^3$ are hydrogen, or taken together are =$NR^4$;

$R^4$ is hydrogen, $R^5O_2C$—, $R^5O$—, HO—, cyano, $R^5CO$—, HCO—, lower alkyl, nitro, or $R^6R^7N$—;

$R^5$ is alkyl, aryl, heteroaryl, aralkyl, or heteroaralkyl;

$R^6$ and $R^7$ are independently hydrogen or alkyl;

$L^1$ is alkylene, alkenylene or alkynylene;

$L^2$ is a chemical bond, alkylene, alkenylene or alkynylene;

Q is —$NR^{8'}$—, —O—, —C(O)—, —C(O)—O—, —O—C(O)—, —$NR^{8'}C(X^1)$—, —$C(X^1)NR^{8'}$—, —$NR^8C(X^1)O$—, —$OC(X^1)NR^8$—, —$NR^8C(X^1)NR^8$—, —$NR^8C(X^1)NR^8$—, —$S(O)_n$—, —$NR^8SO_2$— or —$SO_2NR^8$—, provided that a nitrogen atom or oxygen atom of Q is not directly bonded to a carbon atom of $L^1$ or $L^2$ having a double bond or triple bond, or Q-$L^2$—R is cycloalkyl, cycloalkenyl, heterocyclyl, heterocyclenyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl or fused heterocyclylheteroaryl, provided that a nitrogen atom or oxygen atom of Q is not directly bonded to a carbon atom of $L^1$ having a double bond or triple bond;

$X^1$ is O or S;

$R^{8'}$ is hydrogen, alkyl, aralkyl, heteroaralkyl, acyl, aroyl, heteroaroyl or alkoxycarbonyl;

$R^8$ is hydrogen, alkyl, aralkyl, heteroaralkyl, acyl, aroyl or heteroaroyl; and n is 0, 1 or 2, or an oxide thereof, a pharmaceutically acceptable salt thereof, a solvate thereof, or prodrug thereof.

2. The compound of claim 1 wherein R is aryl, heteroaryl or heterocyclyl.

3. The compound of claim 1 wherein R is substituted phenyl.

4. The compound of claim 1 wherein R is (phenyl substituted phenyl), (heteroaryl substituted phenyl), (phenyl substituted heteroaryl), (heteroaryl substituted heteroaryl), (phenyl substituted cyclyoalkyl), (heteroaryl substituted cyclyoalkyl), (cyclyoalkyl substituted heteroaryl), (cyclyoalkyl substituted phenyl), (cyclyoalkyl substituted cyclyoalkyl), (phenyl substituted cyclyoalkenyl), (heteroaryl substituted cyclyoalkenyl), (cyclyoalkenyl substituted heteroaryl), (cyclyoalkenyl substituted phenyl), (cyclyoalkenyl substituted cyclyoalkeny), (phenyl substituted heterocyclyl), (heteroaryl substituted heterocyclyl), (cyclyoalkyl substituted heterocyclyl), (heterocyclyl substituted phenyl), (heterocyclyl substituted heterocyclyl), (phenyl substituted heterocyclenyl), (heteroaryl substituted heterocyclenyl), (cyclyoalkenyl substituted heterocycleryl), (heterocyclenyl substituted phenyl), or (heterocyclenyl substituted heterocyclenyl).

5. The compound of claim 1 wherein R is (phenyl substituted phenyl), (heteroaryl substituted phenyl), (phenyl substituted heteroaryl), (heteroaryl substituted heteroaryl), (phenyl substituted heterocyclyl), (heteroaryl substituted heterocyclyl), (cyclyoalkyl substituted heterocyclyl), (heterocyclyl substituted phenyl), (heterocyclyl substituted heterocyclyl), (phenyl substituted heterocyclenyl), (heteroaryl substituted heterocyclenyl), (cyclyoalkenyl substituted heterocyclenyl), (heterocyclenyl substituted phenyl), or (heterocyclenyl substituted heterocyclenyl).

6. The compound of claim 1 wherein R is (phenyl substituted heteroaryl), (phenyl substituted heterocyclyl), or (phenyl substituted heterocyclenyl).

7. The compound of claim 1 wherein R is (phenyl substituted heteroaryl), (phenyl substituted heterocyclyl), or (phenyl substituted heterocyclenyl); $L^2$ is bonded to said phenyl in the 1-position of the phenyl moiety and said heterocyclyl, heterocyclenyl, or heteroaryl, is bonded to said phenyl in the 4-position of the phenyl moiety.

8. The compound of claim 1 wherein $R^1$ is hydrogen.

9. The compound of claim 1 wherein $R^8$ is hydrogen.

10. The compound of claim 1 wherein $R^1$ and $R^2$ taken together are =$NR^4$.

11. The compound of claim 1 wherein $R^4$ is hydrogen.

12. The compound of claim 1 wherein $R^5$ is alkyl.

13. The compound of claim 8 wherein $R^5$ is methyl.

14. The compound of claim 13 wherein $L^2$ is a chemical bond.

15. The compound of claim 1 wherein $R^6$ and $R^7$ are hydrogen.

16. The compound of claim 1 wherein L is alkylene.

17. The compound of claim 1 wherein $L^1$ is ethylene.

18. The compound of claim 1 wherein $L^1$ is bonded to the 5-position of the moiety.

19. The compound of claim 1 wherein $L^2$ is a chemical bond or alkylene.

20. The compound of claim 1 wherein $X^1$ is O.

21. The compound of claim 1 wherein Q is —$NR^8CO$—, —$CONR^8$—, —$NR^1SO_2$— or —$SO_2NR^8$—.

22. The compound of claim 1 wherein Q is —$NR^8CO$—.

23. The compound of claim 1 wherein $R^8$ and $R^{8'}$ are hydrogen.

24. The compound of claim 1 wherein n is 2.

25. The compound of claim 1 wherein $L^1$ is bonded to the 5-position of the moiety; and R is (phenyl substituted pyridinonyl), (phenyl substituted pyrrolopyrimidinyl), (phenyl substituted pyridazinyl), (phenyl substituted pyridazinonyl), (phenyl substituted pyridyl), or (phenyl substituted pyrimidinyl).

26. The compound of claim 1 wherein R is (phenyl substituted pyrimidinyl), said pyrimidinyl is substituted with at least one ring system substituent selected from the group consisting of alkoxy, $Y^1Y^2N$-alkyl-, $Y^1Y^2N$—, azaheterocyclyl, $Y^1Y^2NCO$-alkylene-O—, azaheterocyclyl-alkylene-O—, and $Y^1Y^2N$-alkylene-O—; wherein $Y^1$ and $Y^2$ are independently hydrogen, alkyl, alkoxyalkyl, hydroxyalkyl, cycloalkyl, cycloalkylalkyl, $Y^1Y^2N$-alkyl, aryl, aralkyl, heteroaralkyl, heterocyclylalkyl, heterocyclenylalkyl, or sulfo-alkyl-; or when $Y^1$ is H—CO—, alkyl-CO—, aryl-CO—, or heterocyclyl-CO—, then $Y^2$ is hydrogen, alkyl, aryl, or aralkyl.

27. A compound according to claim 1 which is selected from the group consisting of N-(2-[3-Carbamimidoyl-5-indolyl]ethyl)-4-pyrid-3-ylbenzamide;

N-(2-[3-Carbamimidoyl-5-indolyl]ethyl)-4-(pyrimidin-5-yl)-benzamide);

5-(Pyrid-2-yl)-thiophene-2-carboxylic acid 2-(3-Carbamimidoyl-5-indolyl)ethyl amide;

N-(2-[3-Carbamimidoylindol-5-yl]ethyl)-6-morpholin-4-ylnicotinamide4-(5-2[-{3-Carbamimidoylindol-5-yl}ethylcarbamoyl]pyridin-2-yl)piperazine-1-carboxylic acid ethyl ester;

N-(2-[3-Carbamimidoylindol-5-yl]ethyl)-6-imidazol-1-ylnicotinamide;

N-(2-[3-Carbamimidoylindol-5-yl]ethyl)-4-imidazol-1-ylbenzamide;

N-(2-[3-Carbamimidoylindol-5-yl]ethyl)-4-(3H-imidazol-4-yl)benzamide;

N-(2-[3-Carbamimidoylindol-5-yl]ethyl)-4-(1,2,4)thiadiazol-5-ylbenzamide;

N-[2-(3-Carbamimidoyl-1H-indol-5-yl)-ethyl]-4-(1-carbamoyl-1-methyl-ethyl-benzamide;

N-[2-(3-Carbamimidoyl-1H-indol-5-yl)-ethyl]-4-(1-[N-(2-methoxyethyl)]-carbamoyl-1-methyl-ethyl-benzamide;

N-[2-(3-Carbamimidoyl-1H-indol-5-yl)-ethyl]-4-(t-butyl)-benzamide;

N-[2-(3-Carbamimidoyl-1H-indol-5-yl)-ethyl]-4-(pyridazin-4-yl)-benzamide;

N-[2-(3-Carbamimidoyl-1H-indol-5-yl)-ethyl]-2-methyl-4-(6-oxo-1,6-dihydro-pyridin-3-yl)-benzamide 3',4'-Dimethoxybiphenyl-4-carboxylic acid (2-[3-Carbamimidoylindol-5-yl]ethyl)amide;

N-(2-[3-Carbamimidoylindol-5-yl]ethyl)-4-(6-methoxypyrid-3-yl)benzamide;

N-(2-[3-Carbamimidoylindol-5-yl]ethyl)-4-(1-oxy-pyrid-4-yl)benzamide;

N-[2-(3-Carbamimidoyl-1H-indol-5-yl)-ethyl]-4-(7H-pyrrolo[2,3-d]pyrimidin-6-yl)benzamide;

N-[2-(3-Carbamimidoyl-1H-indol-5-yl)-ethyl]-4-(1H-pyrrolo[3,2-c]pyridin-2-yl)-benzamide;

N-[2-(3-Carbamimidoyl-1H-indol-5-yl)-ethyl]-4-furo[3,2-c]pyridin-2-yl-benzamide;

N-[2-(3-Carbamimidoyl-1H-indol-5-yl)-ethyl]-3-chloro-4-(6-oxo-1,6-dihydro-pyridin-3-yl)-benzamide;

N-(2-[3-Carbamimidoyl-1H-indol-5-yl]ethyl)-4-(6-oxo-1,6-dihydro-pyrid-3-yl)benzamide;

4-(3-Amino-1,1-dimethyl-propyl)-N-[2-(3-Carbamimidoyl-1H-indol-5-yl)-ethyl]-benzamide;

N-[2-(3-Carbamimidoyl-1H-indol-5-yl)-ethyl]-2-(4-chloro-phenyl)-acetamide;

5-chloro-thiophene-2-carboxylic acid [2-(3-Carbamimidoyl-1H-indol-5-yl)-ethyl]-amide;

N-(2-[3-Carbamimidoylindol-5-yl]ethyl)-6-(2-hydroxyethylamino)nicotinamide;

N-(2-[3-Carbamimidoylindol-5-yl]ethyl)-6-(1,2,4)-triazol-1-ylnicotinamide;

N-(2-[3-Carbamimidoylindol-5-yl]ethyl)-6-pyrrol-1-ylnicotinamide;

N-(2-[3-Carbamimidoylindol-5-yl]ethyl)-6-pyrazol-1-ylnicotinamide;

N-(2-[3-Carbamimidoyl-1-methylindol-5-yl]ethyl)-4-(6-methoxypyrid-3-yl)benzamide;

N-[2-(3-Carbamimidoyl-1H-indol-5-yl)ethyl]-3-chlorobenzamide;

N-[2-(3-Carbamimidoyl-1H-indol-5-yl)-ethyl]-2-(3-chloro-phenyl)-acetamide;

4-(2-Aminomethyl-pyridin-4-yl)-N-[2-(3-Carbamimidoyl-1H-indol-5-yl)-ethyl]-benzamide;

4-{4-[2-(3-Carbamimidoy-1H-indol-5-yl)-ethylcarbamoyl]-phenyl-pyridine-2-carboxylic acid amide;

N-[2-(3-Carbamimidoy-1H-indol-5-yl)-ethyl]-4-(2-(N,N-dimethylaminomethyl)-pyridin-4-yl)benzamide);

N-[2-(3-Carbamimidoyl-1H-indol-5-yl)-ethyl]-4-(6-oxo-1,6-dihydro-pyridazin-3-yl)-benzamide;

N-[2-(3-Carbamimidoyl-1H-indol-5-yl)-ethyl]-4-(6-methoxy-pyridazin-3-yl)-benzamide;

N-[2-(3-Carbamimidoyl-1H-indol-5-yl)-ethyl]-4-[1-(2-dimethylamino-ethyl)-6-oxo-1,6-dihydro-pyridazin-3-yl]-benzamide;

N-[2-(3-Carbamimidoyl-1H-indol-5-yl)-ethyl]-4-[1-(3-dimethylamino-propyl)-6-oxo-1,6-dihydro-pyridazin-3-yl]-benzamide;

N-[2-(3-Carbamimidoyl-1H-indol-5-yl)-ethyl]-4-[2-(2-dimethylamino-ethylamino)-pyrimidin-4-yl]-benzamide;

N-[2-(3-Carbamimidoyl-1H-indol-5-yl)-ethyl]-4-[2-methoxy-pyrimidin-4-yl]-benzamide;

N-(2-[3-Carbamimidoylindol-5-yl]ethyl)-4-(1-[2-dimethylaminoethyl]-6-oxo-1,6-dihydropyridin-3-yl)benzamide;

N-(2-[3-Carbamimidoylindol-5-yl]ethyl)-4-(1-carbamoylmethyl-6-oxo-1,6-dihydropyridin-3-yl)benzamide;

4-(3-Amino-[1,2,4]triazin-6-yl)-N-[2-(3-Carbamimidoyl-1H-indol-5-yl)-ethyl]-benzamide;

4-(3-Amino-[1,2,4]triazin-5-yl)-N-[2-(3-Carbamimidoyl-1H-indol-5-yl)-ethyl]-benzamide;

N-[2-(3-Carbamimidoyl-1H-indol-5-yl)-ethyl]-4-(3-oxo-2,3-dihydro-[1,2,4]triazin-6-yl)-benzamide;

N-[2-(3-Carbamimidoyl-1H-indol-5yl)ethyl]-4-(5-oxo-4,5-dihydro-[1,2,4]oxadiazol-3-yl)-benzamide N-[2-(3-Carbamimidoyl-1H-indol-5-yl)ethyl]-4-(6-oxo-piperidin-3-yl)-benzamide;

N-[2-(3-Carbamimidoyl-1H-indol-5-yl)-ethyl]-4-[2-(morpholin-4yl-ethylamino)-pyrimidin-4-yl]-benzamide;

N-[2-(3-Carbamimidoyl-1H-indol-5-yl)-ethyl]-4-[2-(3-dimethylamino-propylamino)-pyrimidin-4-yl]-benzamide;

N-[2-(3-Carbamimidoyl-1H-indol-5-yl)-ethyl]-4-[2-([2-dimethylamino-ethyl]-methyl-amino)-pyrimidin-4-yl]-benzamide;

2-[(4-{4-[2-(3-Carbamimidoyl-1H-indol-5-yl)-ethylcarbamoyl]-phenyl}-pyrimidin-2-yl)-methyl-amino]-ethanesulfonic acid;

N-[2-(3-Carbamimidoyl-1H-indol-5-yl)-ethyl]-4-{2-[methyl-(2 (S),3 (R),4 (R),5 (R),6-pentahydroxy-hexyl)-amino]-pyrimidin-4-yl}-benzamide N-[2-(3-Carbamimidoyl-1H-indol-5-yl)-ethyl]-4-{2-[methyl-(2 (S),3 (R),4 (S),5 (R),6-pentahydroxy-hexyl)-amino]-pyrimidin-4-yl}-benzamide;

N-[2-(3-Carbamimidoyl-1H-indol-5-yl)-ethyl]-4-[2-(2-hydroxy-1-hydroxymethyl-ethylamino)-pyrimidin-4-yl]-benzamide;

2-[(4-{4-[2-(3-Carbamimidoyl-1H-indol-5-yl)-ethylcarbamoyl]-phenyl}-pyrimidin-2-yl)-methyl-amino]-ethanesulfonic acid;

N-[2-(3-Carbamimidoyl-1H-indol-5-yl)-ethyl]-4-[2-(3-imidazol-1-yl-propylamino)-pyrimidin-4-yl]-benzamide;

N-[2-(3-Carbamimidoyl-1H-indol-5-yl)-ethyl]-4-{2-[(2-diethylamino-ethyl)methyl-amino]-pyrimidin-4-yl}-benzamide;

N-[2-(3-Carbamimidoyl-1H-indol-5-yl)-ethyl]-4-[2-(2-diisopropylamino-ethylamino)-pyrimidin-4-yl]-benzamide;

N-[2-(3-Carbamimidoyl-1H-indol-5-yl)ethyl]-4-[2-(2-dibutylamino-ethylamino)-pyrimidin-4-yl]-benzamide;

N-[2-(3-Carbamimidoyl-1H-indol-5-yl)-ethyl]-4-[2-(3-morpholin-4-yl-propylamino)-pyrimidin-4-yl]-benzamide;

N-[2-(3-Carbamimidoyl-1H-indol-5-yl)-ethyl]-4-[2-(3-diethylamino-propylamino)-pyrimidin-4-yl]-benzamide;

N-[2-(3-Carbamimidoyl-1H-indol-5-yl)-ethyl]-4-[2-(3-piperidin-1-yl-propylamino)-pyrimidin-4-yl]-benzamide;

N-[2-(3-Carbamimidoyl-1H-indol-5-yl)-ethyl]-4-(2-{[2-(ethyl-methyl-amino)-ethyl]-methyl-amino}-pyrimidin-4-yl)-benzamide;

N-[2-(3-Carbamimidoyl-1H-indol-5-yl)-ethyl]-4-[2-(5-dimethylamino-pentylamino)-pyrimidin-4-yl]-benzamide;

N-[2-(3-Carbamimidoyl-1H-indol-5-yl)-ethyl]-4-[2-(5-morpholin-4-yl-pentylamino)-pyrimidin-4-yl]-benzamide;

N-[2-(3-Carbamimidoyl-1H-indol-5-yl)-ethyl]-4-[2-(5-piperidin-1-yl-pentylamino)-pyrimidin-4-yl]-benzamide;

N-[2-(3-Carbamimidoyl-1H-indol-5-yl)-ethyl]-4-[2-(5-pyrrolidin-1-yl-pentylamino)-pyrimidin-4-yl]-benzamide;

N-[2-(3-Carbamimidoyl-1H-indol-5-yl)-ethyl]-4-(2-oxo-hexahydro-pyrimidin-5-yl)-benzamide;

N-[2-(3-Carbamimidoyl-1H-indol-5-yl)-ethyl]-4-(1,3-dimethyl-2-oxo-hexahydro-pyrimidin-5-yl) benzamide;

Biphenyl-3,4'-dicarboxylic acid 4'-{[2-(3-Carbamimidoyl-1H-indol-5-yl)-ethyl]-amide} 3-[(2-methoxy-ethyl)-amide];

3'-(Morpholine-4-carbonyl)-biphenyl-4-carboxylic acid [2-(3-Carbamimidoyl-1H-indol-5-yl)-ethyl]-amide;

Biphenyl-3,4'-dicarboxylic acid 4'-{[2-(3-Carbamimidoyl-1H-indol-5-yl)-ethyl]-amide} 3-[(2-morpholin-4-yl-ethyl)-amide];

Biphenyl-2,4'-dicarboxylic acid 4'-{[2-(3-Carbamimidoyl-1H-indol-5-yl)-ethyl]-amide} 2-[(3-diethylamino-propyl)-amide];

Biphenyl-2,4'-dicarboxylic acid 4'-{[2-(3-Carbamimidoyl-1H-indol-5-yl)-ethyl]-amide} 2-[(3-morpholin-4-yl-propyl)-amide];

Biphenyl-2,4'-dicarboxylic acid 4'-{[2-(3-Carbamimidoyl-1H-indol-5-yl)-ethyl]-amide} 2-[(3-piperidin-1-yl-propyl)amide];

Biphenyl-2,4'-dicarboxylic acid 4'-{[2-(3-Carbamimidoyl-1H-indol-5-yl)-ethyl]-amide} 2-[(4-dimethylamino-butyl)-amide];

Biphenyl-2,4'-dicarboxylic acid 4'-{[2-(3-Carbamimidoyl-1H-indol-5-yl)-ethyl]-amide} 2-[(2,3-dihydroxy-propyl)-methyl-amide];

Biphenyl-2,4'-dicarboxylic acid 4'-{[2-(3-Carbamimidoyl-1H-indol-5-yl)-ethyl]-amide} 2-[(2,3-dihydroxy-propyl)-amide];

N-[2-(3-Carbamimidoyl-1H-indol-5-yl)ethyl]-4-[2-(4-methylpiperazin-1-yl)pyrimidin-4-yl]benzamide;

4-[(4-{4-[2-(3-Carbamimidoyl-1H-indol-5-yl)ethylcarbamoyl]phenyl}pyrimidin-2-yl)methylamino]butyric acid;

N-[2-(3-Carbamimidoyl-1H-indol-5-yl)ethyl]-4-[2-(2,2,2-trifluoroethoxy)pyrimidin-4-yl]benzamide;

N-[2-(3-Carbamimidoyl-1H-indol-5-yl)-ethyl]-4-(2-pyrrolidin-1-ylpyrimidin-4-yl)benzamide;

N-[2-(3-Carbamimidoyl-1H-indol-5-yl)-ethyl]-4-[2-(2-hydroxymethylpyrrolidin-1-yl)-pyrimidin-4-yl] benzamide;

N-[2-(3-Carbamimidoyl-1H-indol-5-yl)-ethyl]-4-[2-(carbamoylmethyl-N-methylamino)-pyrimidin-4-yl] benzamide;

N-[2-(3-Carbamimidoyl-1H-indol-5-yl)-ethyl]-4-[2-(6-pyrrolidin-1-yl-hexylamino)pyrimidin-4-yl] benzamide;

N-[2-(3-Carbamimidoyl-1H-indol-5-yl)ethyl]-4-[2-(6-piperidin-1-ylhexylamino)pyrimidin-4-yl]benzamide;

N-[2-(3-Carbamimidoyl-1H-indol-5-yl)ethyl]-4-[2-(4-piperidin-1-ylbutylamino)pyrimidin-4-yl]benzamide;

N-[2-(3-Carbamimidoyl-1H-indol-5-yl)ethyl]-4-[2-(4-diethylaminobutylamino)pyrimidin-4-yl]benzamide;

N-[2-(3-Carbamimidoyl-1H-indol-5-yl)ethyl]-4-[2-(6-morpholin-4-ylhexylamino)pyrimidin-4-yl]benzamide;

N-[2-(3-Carbamimidoyl-1H-indol-5-yl)ethyl]-4-[2-(6-dimethylaminohexylamino)pyrimidin-4-yl]benzamide;

N-[2-(3-Carbamimidoyl-1H-indol-5-yl)ethyl]-4-[2-(4-dimethylaminobutylamino)pyrimidin-4-yl]benzamide;

4-[2-(Bicyclo[2;2;1]hept-2-ylamino)pyrimidin-4-yl]-N-[2-(3-Carbamimidoyl-1H-indol-5-yl)ethyl]benzamide;

1-(4-{4-[2-(3-Carbamimidoyl-1H-indol-5-yl)ethylcarbamoyl]phenyl}pyrimidin-2-yl)pyrrolidine-2-carboxylic acid amide;

N-[2-(3-Carbamimidoyl-1H-indol-5-yl)ethyl]-4-{2-[(2-hydroxy-ethyl)-N-methylamino]pyrimidin-4-yl}benzamide;

N-[2-(3-Carbamimidoyl-1H-indol-5-yl)-ethyl]-4-(2-morpholin-4-yl-pyrimidin-4-yl)-benzamide;

N-[2-(3-Carbamimidoyl-1H-indol-5-yl)-ethyl]-4-[2-(cyclopropylmethyl-amino)-pyrimidin-4-yl]-benzamide;

N-[2-(Carbamimidoyl-1H-indol-5-yl)-ethyl]-4-[2-[(2-methoxy-ethyl)-methyl-amino]-pyrimidin-4-yl]-benzamide;
N-[2-(3-Carbamimidoyl-1H-indol-5-yl)-ethyl]-4-[2-(3-hydroxy-propylamino)-pyrimidin-4-yl]-benzamide;
N-[2-(3-Carbamimidoyl-1H-indol-5-yl)-ethyl]-4-[(2-hydroxy-ethyl)-propyl-amino]-pyrimidin-4-yl]-benzamide;
N-[2-(3-Carbamimidoyl-1H-indole-5yl)-ethyl]-4-(2-piperidin-1-yl-pyrimidin-4-yl)-benzamide;
N-[2-(3-Carbamimidoyl-1H-indol-5-yl)-ethyl]-4-[2-(ethyl-methyl-amino)-pyrimidin-4-yl]-benzamide;
N-[2-(3-Carbamimidoyl-1H-indol-5-yl)-ethyl]-4-[2-(4-hydroxy-piperidin-1-yl)-pyrimidin-4-yl]-benzamide;
N-[2-(3-Carbamimidoyl-1H-indol-5-yl)-ethyl]-4-[2-(2,3-dihydroxy-propylamino)-pyrimidin-4-y]-benzamide;
N-[2-(3-Carbamimidoyl-1H-indol-5-yl)-ethyl]-4-[2-[(2,3-dihydroxy-propyl)-methyl-amino]-pyrimidin-4-yl]-benzamide;
N-[2-(3-Carbamimidoyl-1H-indol-5-yl)-ethyl]-4-[2-((s)-2-methoxymethyl-pyrrolidin-1-yl)-pyrimidin-4-yl]-benzamide;
N-[2-(3-Carbamimidoyl-1H-indol-5-yl)-ethyl]-4-(2-piperazin-1-yl-pyrimidin-4-yl)-benzamide;
N-[2-(3-Carbamimidoyl-1H-indol-5-yl)-4-[2-[2-(2-oxo-imidazolidin-1-yl)-ethylamino]-pyrimidin-4-yl]-benzamide;
N-[2-(3-Carbamimidoyl-1H-indol-5-yl)-ethyl]-4-[2-(3-methoxy-propylamino)-pyrimidin-4-yl]-benzamide;
4-[2-(3-Carbamimidoyl-1H-indol-5-yl)-ethyl]-4-[2-(2-hydroxy-ethylamino)-pyrimidin-4-yl]-benzamide;
N-[2-(3-Carbamimidoyl-1H-indol-5-yl)-ethyl]-4-[2-(2-methoxyethoxy)-pyrimidin-4-yl]benzamide;
N-[2-(3-Carbamimidoyl-1H-indol-5-yl)ethyl]-4-[2-(1-Carbamoylethoxy)pyrimidin-4-yl]benzamide;
N-[2-(3-Carbamimidoyl-1H-indol-5-yl)ethyl]-4-[2-(6-dimetyainoheyloxy)pyrimidin-4-yl]benzamide;
N-[2-(3-Carbamimidoyl-1H-indol-5-yl)ethyl]-4-[2-(2-pyrrolidin-1-yl-ethoxy)pyrimidin-4-yl]benzamide;
N-[2-(3-Carbamimidoyl-1H-indol-5-yl)ethyl]-4-[2-(2-dimethylaminoethoxy)pyrimidin-4-yl]benzamide;
3'-(2-Dimethylaminoethoxy)biphenyl-4-carboxylic acid [2-(3-Carbamimidoyl-1H-indol-5-yl)ethyl]amide;
N-[2-(3-Carbamimidoyl-1H-indol-5-yl)ethyl]-4-(1-oxypyridin-2-yl)benzamide;
2'-(2-Dimethylaminoethoxy)biphenyl-4-carboxylic acid [2-(3-Carbamimidoyl-1H-indol-5-yl)ethyl]amide;
2'-(3-Dimethylaminopropoxy)biphenyl-4-carboxylic acid [2-(3-Carbamimidoyl-1H-indol-5-yl)ethyl]amide;
3'-(3-Dimethylaminopropoxy)biphenyl-4-carboxylic acid [2-(3-Carbamimidoyl-1H-indol-5-yl)ethyl]amide;
N-[2-(3-Carbamimidoyl-1H-indol-5-yl)-ethyl]-4-(1-oxo-pyridin-3-yl)-benzamide;
4-[2-(acetylamino-methyl)-pyridin-4-yl]-N-[2-(3-Carbamimidoyl-1H-indol-5-yl)ethyl]-benzamide;
Piperidine-4-carboxylic acid (4-[4-[2-(3-Carbamimidoyl-1H-indol-5-yl)-ethylcarbamoyl]-phenyl-]-pyridin-2-ylmethyl)-amide;
N-[2-(3-Carbamimidoyl-1H-indol-5-yl)ethyl]-4-[]-(3-dimethylaminopropyl)-6-oxo-1,6-dihydropyridin-3-yl]benzamide;
N-[2-(3-Carbamimidoyl-1H-indol-5-yl)ethyl]-4-[6-(3-dimethylaminopropoxy)pyridin-3-yl]benzamide;
(5-{4-[2-(3-Carbamimidoyl-1H-indol-5-yl)ethylcarbamoyl]phenyl}-2-oxo-2H-pyridin-1-yl)acetamide;
N-[2-(3-Carbamimidoyl-1H-indol-5-yl)-ethyl]-4-{1-[(2-dimethylaminoethylcarbamoyl)methyl]-6-oxo-1,6-dihydropyridin-3-yl}benzamide;
N-[2-(3-Carbamimidoyl-1H-indol-5-yl)-ethyl]-4-(4-dimethylamino-piperidin-1-yl)-benzamide;
N-[2-(3-Carbamimidoyl-1H-indol-5-y)-ethyl]-4-[4-(2-dimethylamino-ethylamino)-piperidin-1-yl-]benzamide;
4-(4-Amino-piperidin-1-yl)-N-[2-(3-Carbamimidoyl-1H-indol-5-yl)-ethyl]-benzamide;
N-[2-(3-Carbamimidoyl-1H-indol-5-yl)-ethyl]-4-(4-methoxy-piperidin-1-yl)-benzamide;
4-(4-Acetylamino-piperidin-1-yl)-N-[2-(3-Carbamimidoyl-1H-indol-5-yl)-ethyl]-benzamide;
4-(1-Acetyl-piperidin-4-yl)-N-[2-(3-Carbamimidoyl-1H-indol-5-yl)-ethyl]-benzamide;
4-{4-[2-(3-Carbamimidoyl-1H-indol-5-yl)-ethylcarbamoyl]-phenyl}-piperidine-1-carboxylic acid amide;
N-[2-(3-Carbamimidoyl-1H-indol-5-yl)-ethyl]-4-(1-methyl-1-oxy-piperidin-4-yl)-benzamide;
N-[2-(3-Carbamimidoyl-1H-indol-5-yl)-ethyl]-4-(1-methyl-piperidin-4-yl)-benzamide;
N-[2-(3-Carbamimidoyl-1H-indol-5-yl)-ethyl]-4-(1-methanesulfonyl-piperidin-4-yl)-benzamide;
4-(2-Acetylamino-1,1-dimethyl-ethyl)-N-[2-(3-Carbamimidoyl-1H-indol-5-yl)-ethyl]-benzamide;
N-[2-(3-Carbamimidoyl-1H-indol-5-yl)-ethyl]-4-(2-methanesulfonylamino-1,1-dimethyl-ethyl)-benzamide;
Piperidine-4-carboxylic acid (2-{4-[2-(3-Carbamimidoyl-1H-indol-5-yl)-ethylcarbamoyl]-phenyl}-2-methyl-propyl)-amide;
N-[2-(3-Carbamimidoyl-1H-indol-5-yl)-ethyl]-4-(1,1-dimethyl-2-ureido-ethyl)-benzamide;
N-[2-(3-Carbamimidoyl-1H-indol-5-yl)-ethyl]-4-[2-(3-ethyl-ureido)-1,1-dimethyl-ethyl]-benzamide;
N-[2-(3-Carbamimidoyl-1H-indol-5-yl)-ethyl]-4-(2-dimethylamino-3,4,5,6-tetrahydro-pyrimidin-4-y)-benzamide;
N-[2-(3-Carbamimidoyl-1H-indol-5-yl)-ethyl]-4-(1-oxy-pyridin-4-yloxy)-benzamide;
N-[2-(3-Carbamimidoyl-1H-indol-5-yl)-ethyl]-4-(1-methyl-piperidin-4-yloxy)-benzamide;
N-[2-(3-Carbamimidoyl-1H-indol-5-yl)ethyl]-4-(1,2,3,6-tetrahydropyridin-4-yl)-benzamide;
N-[2-(3-Carbamimidoyl-1H-indol-5-yl)ethyl]-4-piperidin-4-yl-benzamide;
4-(2-Amino-1,1-dimethylethyl)-N-(2-[3-Carbamimidoylindol-5-yl]ethyl)benzamide;
N-(2-[3-Carbamimidoylindol-5-yl]ethyl)-4-(6-[2-dimethylaminoethoxy]pyridin-3-yl)benzamide;
N-(2-[3-Carbamimidoylindol-5-yl]ethyl)-4-pyrid-4-ylbenzamide;
N-(2-[3-Carbamimidoyl indol-5-yl]ethyl)-4-(4-carbamoyl-phenyl)-benzamide;
N-(2-[3-Carbamimidoylindol-5-yl]ethyl)-4-(4-methoxyphenyl)-benzamide;
N-(2-[3-Carbamimidoylindol-5-yl]ethyl)-(5-methoxy-indol-2-yl)-carboxamide;

N-(2-[3-Carbamimidoylindol-5-yl]ethyl)-(6-chloro-benzothiophen-2-yl)-carboxamide;

N-(2-[3-Carbamimidoylindol-5-yl]ethyl)-4-(4-benzyloxy-phenyl)-benzamide;

N-(2-[3-Carbamimidoylindol-5-yl]ethyl)-4-chloro-benzamide;

N-(2-[3-Carbamimidoylindol-5-yl]ethyl)-4-(methylsulphonyl)-benzamide;

N-(2-[3-Carbamimidoyl indol-5-yl]ethyl)-4-(amino-sulphonyl)-benzamide;

4-(3-Aminoprop-1-ynyl)-N-[2-(3-Carbamimidoyl-1H-indol-5-yl)-ethyl]-benzamide;

5-{4-[2-(3-Carbamimidoyl-1H-indol-5-yl)ethylcarbamoyl]phenyl}-2-oxo-2H-pyridin-1-yl)acetic acid; and 3-Carbamimidoyl-5-{2-[4-(6-oxo-1,6-dihydro-pyridin-3-yl)-benzoylamino]-propyl}-indole.

28. A compound according to claim 27 which is selected from the group consisting of N-[2-(3-Carbamimidoyl-1H-indol-5-yl)-ethyl]-4-(pyridazin-4-yl)-benzamide;

N-[2-(3-Carbamimidoyl-1H-indol-5-yl)-ethyl]-2-methyl-4-(6-oxo-1,6-dihydro-pyridin-3-yl)-benzamide;

N-(2-[3-Carbamimidoylindol-5-yl]ethyl)-4-(6-methoxypyrid-3-yl)benzamide;

N-(2-[3-Carbamimidoylindol-5-yl]ethyl)-4-(1-oxy-pyrid-4-yl)benzamide;

N-[2-(3-carbamimidoyl-1H-indol-5-yl)-ethyl]-4-(7H-pyrrolo[2,3-d]pyrimidin-6-yl)-benzamide;

N-[2-(3-carbamimidoyl-1H-indol-5-yl)-ethyl]-4-(1H-pyrrolo[3,2-c]pyridin-2-yl)-benzamide;

N-[2-(3-carbamimidoyl-1H-indol-5-yl)-ethyl]-3-chloro-4-(6-oxo-1,6-dihydro-pyridin-3-yl)-benzamide;

N-(2-[3-Carbamimidoylindol-5-yl]ethyl)-4-(6-oxo-1,6-dihydropyrid-3-yl)benzamide;

4-(3-Amino-1,1-dimethyl-propyl)-N-[2-(3-carbamimidoyl-1H-indol-5-yl)-ethyl]-benzamide;

4-(2-Aminomethyl-pyridin-4-yl)-N-[2-(3-carbamimidoyl-1H-indol-5-yl)-ethyl]-benzamide;

4-{4-[2-(3-Carbamimidoy-1H-indol-5-yl)-ethylcarbamoyl]-phenyl-pyridine-2-carboylic acid amide;

N-[2-(3-Carbamimidoy-1H-indol-5-yl-ethyl]-4-(2-(N,N-dimethylaminomethyl)-pyridin-4-yl)benzamide);

N-[2-(3-carbamimidoyl-1H-indol-5-yl)-ethyl]-4-(6-oxo-1,6-dihydro-pyridazin-3-yl)benzamide;

N-[2-(3-carbamimidoyl-1H-indol-5-yl)-ethyl]-4-(6-methoxy-pyridazin-3-yl)-benzamide;

N-[2-(3-carbamimidoyl-1H-indol-5-yl)-ethyl]-4-[ 1-(2-dimethylamino-ethyl)-6-oxo-1,6-dihydro-pyridazin-3-yl]-benzamide;

N-[2-(3-carbamimidoyl-1H-indol-5-yl)-ethyl]-4-[ 1-(3-dimethylamino-propyl)-6-oxo-1,6-dihydro-pyridazin-3-yl]-benzamide;

N-[2-(3-Carbamimidoyl-1H-indol-5-yl)-ethyl]-4-[2-(2-dimethylamino-ethylamino)-pyrimidin-4-yl]-benzamide;

N-[2-(3-Carbamimidoyl-1H-indol-5-yl)-ethyl]-4-[2-methoxy-pyrimidin-4-yl]-benzamide;

N-(2-[3-Carbamimidoylindol-5-yl]ethyl)-4-(1-[2-dimethylaminoethyl]-6-oxo-1,6-dihydropyridin-3-yl)benzamide;

N-[2-(3-Carbamimidoyl-1H-indol-5-yl)ethyl]-4-(6-oxo-piperidin-3-yl)-benzamide;

N-[2-(3-Carbamimidoyl-1H-indol-5-yl)-ethyl]-4-[2-(morpholin-4yl-ethylamino)-pyrimidin-4-yl]-benzamide;

N-[2-(3-Carbamimidoyl-1H-indol-5-yl)-ethyl]-4-[2-(3-dimethylamino-propylamino)-pyrimidin-4-yl]-benzamide;

N-[2-(3-Carbamimidoyl-1H-indol-5-yl)-ethyl]-4-[2-([2-dimethylamino-ethyl]-methyl-amino)-pyrimidin-4-yl]-benzamide;

2-[(4-{4-[2-(3-Carbamimidoyl-1H-indol-5-yl)-ethylcarbamoyl]-phenyl}-pyrimidin-2-yl)-methyl-amino]-ethanesulfonic acid;

N-[2-(3-Carbamimidoyl-1H-indol-5-yl)-ethyl]-4-2-[methyl-(2 (S),3 (R),4 (R),5 (R),6-pentahydroxy-hexyl)-amino]-pyrimidin-4-yl}-benzamide;

N-[2-(3-Carbamimidoyl-1H-indol-5-yl)-ethyl]-4-{2-[methyl-(2 (S),3 (R),4 (S),5 (R),6-pentahydroxy-hexyl)-amino]-pyrimidin-4-yl}-benzamide;

N-[2-(3-Carbamimidoyl-1H-indol-5-yl)-ethyl]-4-[2-(2-hydroxy-1-hydroxymethyl-ethylamino)-pyrimidin-4-yl]-benzamide;

N-[2-(3-Carbamimidoyl-1H-indol-5-yl)-ethyl]-4-[2-(3-imidazol-1-yl-propylamino)-pyrimidin-4-yl]-benzamide;

N-[2-(3-Carbamimidoyl-1H-indol-5-ethyl)-ethyl]-4-{2-[(2-dimethylamino-ethyl)-methyl-amino]-pyrimidin-4-yl}-benzamide;

N-[2-(3-Carbamimidoyl-1H-indol-5-yl)-ethyl]-4-[2-(2-diisopropylamino-ethylamino)-pyrimidin-4-yl]-benzamide;

N-[2-(3-Carbamimidoyl-1H-indol-5-yl)-ethyl]-4-[2-(2-dibutylamino-ethylamino)-pyrimidin-4-yl]-benzamide;

N-[2-(3-Carbamimidoyl-1H-indol-5-y)-ethyl]-4-[2-(3-morpholin-4-y-propylamino)-pyrimidin-4-yl]-benzamide;

N-[2-(3-Carbamimidoyl-1H-indol-5-yl)-ethyl]-4-[2-(3-diethylamino-propylamino)-pyrimidin-4-yl-benzamide;

N-[2-(3-Carbamimidoyl-1H-indol-5-yl)-ethyl]-4-[2-(3-piperidin-1-yl-propylamino)-pyrimidin-4-yl]-benzamide;

N-[2-(3-Carbamimidoyl-1H-indol-5-yl)-ethyl]-4-(2-{[2-(ethyl-methyl-amino)-ethyl]-methyl-amino}-pyrimidin-4-yl)-benzamide;

N-[2-(3-Carbamimidoyl-1H-indol-5-yl)-ethyl]-4-[2-(5-dimethylamino-pentylamino)-pyrimidin-4-yl]-benzamide;

N-[2-(3-Carbamimidoyl-1H-indol-5-yl)-ethyl]-4-[2-(5-morpholin-4-yl-pentylamino)-pyrimidin-4-yl]-benzamide;

N-[2-(3-Carbamimidoyl-1H-indol-5-yl)-ethyl]-4-[2-(5-piperidin-1-yl-pentylamino)-pyrimidin-4-yl]-benzamide;

N-[2-(3-Carbamimidoyl-1H-indol-5-yl)-ethyl]-4-[2-(5-pyrrolidin-1-yl-pentylamino)-pyrimidin-4-yl]-benzamide;

N-[2-(3-Carbamimidoyl-1H-indol-5-yl)-ethyl]-4-(2-oxo-hexahydro-pyrimidin-5-yl)-benzamide;

N-[2-(3-Carbamimidoyl-1H-indol-5-yl)-ethyl]-4-(1,3-dimethyl-2-oxo-hexahydro-pyrimidin-5-yl)-benzamide;

Biphenyl-3,4'-dicarboxylic acid 4'-{[2-(3-carbamimidoyl-1H-indol-5-yl)-ethyl]-amide} 3-[(2-methoxy-ethyl)-amide];
Biphenyl-3,4'-dicarboxylic acid 4'-{[2-(3-carbamimidoyl-1H-indol-5-yl)-ethyl]-amide} 3-[(2-morpholin-4-yl-ethyl)-amide];
N-[2-(3-Carbamimidoyl-1H-indol-5-yl)ethyl]-4-[2-(4-methylpiperazin-1-yl)pyrimidin-4-yl]benzamide;
4-[(4-{4-[2-(3-Carbamimidoyl-1H-indol-5-yl) ethylcarbamoyl]phenyl}pyrimidin-2-yl)methylamino] butyric acid;
N-[2-(3-Carbamimidoyl-1H-indol-5-yl)ethyl]-4-[2-(2,2,2-trifluoroethoxy)pyrimidin-4-yl]benzamide;
N-[2-(3-Carbamimidoyl-1H-indol-5-yl)-ethyl]-4-(2-pyrrolidin-1-ylpyrimidin-4-yl)benzamide;
N-[2-(3-Carbamimidoyl-1H-indol-5-yl)-ethyl]-4-[2-(2-hydroxymethylpyrrolidin-1-yl)-pyrimidin-4-yl] benzamide;
N-[2-(3-Carbamimidoyl-1H-indol-5-y1)-ethyl]-4-[2-(carbamoylmethyl-N-methylamino)-pyrimidin-4-yl] benzamnide;
N-[2-(3-Carbamimidoyl-1H-indol-5-yl)ethyl]-4-[2-(6-pyrrolidin-1-yl-hexylamino)pyrimidin-4-yl] benzamide;
N-[2-(3-Carbamimidoyl-1H-indol-5-yl)ethyl]-4-[2-(6-piperidin-1-ylhexylamino)pyrimidin-4-yl]benzamide;
N-[2-(3-Carbamimidoyl-1H-indol-5-yl)ethyl]-4-[2-(4-piperidin-1-ylbutylamino)pyrimidin-4-yl]benzamide;
N-[2-(3-Carbamimidoyl-1H-indol-5-yl)ethyl]-4-[2-(4-diethylaminobutylamino)pyrimidin-4-yl]benzamide;
N-[2-(3-Carbamimidoyl-1H-indol-5-yl)ethyl]-4-[2-(6-morpholin-4-ylhexylamino)pyrimidin-4-yl]benzamide;
N-[2-(3-Carbamimidoyl-1H-indol-5-yl)ethyl-4-[2-(6-dimethylaminohexylamino)pyrimidin-4-yl]benzamide;
N-[2-(3-Carbamimidoyl-1H-indol-5-yl)ethyl]-4-[2-(4-dimethylaminobutylamino)pyrimidin-4-yl]benzamide;
4-[2-(Bicyclo[2;2;1]hept-2-ylamino)pyrimidin-4-yl]-N-[2-(3-carbamimidoyl-1H-indol-5-yl)ethyl]benzamide;
N-[2-(3-Carbamimidoyl-1H-indol-5-yl)ethyl]-4-{2-[(2-hydroxy-ethyl)-N-methylamino]pyrimidin-4-yl}benzamide;
N-[2-(3-carbamimidoyl-1H-indol-5-yl)-ethyl]-4-(2-morpholin-4-yl-pyrimidin-4-yl)-benzamide;
N-[2-(3-carbamimidoyl-1H-indol-5-yl)-ethyl]-4-[2-(cyclopropylmethyl-amino)-pyrimidin-4-yl]-benzamide;
N-[2-(carbamimidoyl-1H-indol-5-yl)-ethyl]-4-[2-[(2-methoxy-ethyl)-methyl-amino]-pyrimidin-4-yl]-benzamide;
N-[2-(3-carbamimidoyl-1H-indol-5-yl)-ethyl]-4-[2-(3-hydroxy-propylamino)-pyrimidin-4-yl]-benzamide;
N-[2-(3-carbamimidoyl-1H-indol-5-y)-ethyl]-4-[(2-hydroxy-ethyl)-propyl-amino]-pyrimidin-4-yl]-benzamide;
N-[2-(3-Carbamimidoyl-1H-indole-5yl)-ethyl]-4-(2-piperidin-1-yl-pyrimidin-4-yl)benzamide;
N-[2-(3-carbamimidoyl-1H-indol-5-yl)-ethyl]-4-[2-(ethyl-methyl-amino)-pyrimidin-4-yl]-benzamide;
N-[2-(3-carbamimidoyl-1H-indol-5-yl)-ethyl]-4-[2-(4-hydroxy-piperidin-1-yl)-pyrimidin-4-yl]-benzamide;
N-[2-(3-carbamimidoyl-1H-indol-5-yl)-ethyl]-4-[2-(2,3-dihydroxy-propylamino)-pyrimidin-4-yl]-benzamide;

N-[2-(3-carbamimidoyl-1H-indol-1-y)-ethyl]-4-[2-[(2,3-dihydroxy-propyl)-methyl-amino]-pyrimidin-4-yl]-benzamide;
N-[2-(3-carbamimidoyl-1H-indol-5-yl)-ethyl]-4-[2-((s)-2-methoxymethyl-pyrrolidin-1-yl)-pyrimidin-4-yl]-benzamide;
N-[2-(3-carbamimidoyl-1H-indol-5-yl)-ethyl]-4-(2-piperazin-1-yl-pyrimidin-4-yl)-benzamide;
N-[2-(3-carbamimidoyl-1H-indol-5-yl)-4-[2-[2-(2-oxo-imidazolidin-1-yl)-ethylamino]-pyrimidin-4-yl]-benzamide;
N-[2-(3-carbamimidoyl-1H-indol-5-yl)-ethyl]-4-[2-(3-methoxy-propylamino)-pyrimidin-4-yl]-benzamide;
4-[2-(3-carbamimidoyl-1H-indol-5-yl)-ethyl]-4-[2-(2-hydroxy-ethylamino)-pyrimidin-4-yl]-benzamide;
N-[2-(3-Carbamimidoyl-1H-indol-5-yl)-ethyl]-4-[2-(2-methoxyethoxy)-pyrimidin-4-yl]benzamide;
N-[2-(3-Carbamimidoyl-1H-indol-5-yl)ethyl]-4-[2-(1-carbamoylethoxy)pyrimidin-4-yl]benzamide;
N-[2-(3-Carbamimidoyl-1H-indol-5-yl)ethyl]-4-[2-(6-dimethylaminohexyloxy)pyrimidin-4-yl]benzamide;
N-[2-(3-Carbamimidoyl-1H-indol-5-yl)ethyl]-4-[2-(2-pyrrolidin-1-yl-ethoxy)pyrimidin-4-yl]benzamide;
N-[2-(3-Carbamimidoyl-1H-indol-5-yl)ethyl]-4-[2-(2-dimethylaminoethoxy)pyrimidin-4-yl]benzamide;
N-[2-(3-Carbamimidoyl-1H-indol-5-yl)ethyl]-4-(1-oxypyridin-2-yl)benzamide;
2-Dimethylaminoethoxy)biphenyl-4-carboxylic acid [2-(3-carbamimidoyl-1H-indol-5-yl)ethyl]amide;
2'-(3-Dimethylaminopropoxy)biphenyl-4-carboxylic acid [2-(3-carbamimidoyl-1H-indol-5-yl)ethyl]amide;
N-[2-(3-carbamimidoyl-1H-indol-5-yl)-ethyl]-4-(1-oxopyridin-3-yl)-benzamide;
4-[2-(acetylamino-methyl)-pyridin-4-yl]-N-[2-(3-carbamimidoyl-1H-indol-5-yl)-ethyl]-benzamide;
Piperidine-4-carboxylic acid (4-[4-[2-(3-carbamimidoyl-1H-indol-5-yl)-ethylcarbamoyl]-phenyl-]-pyridin-2-ylmethyl)-amide;
N-[2-(3-Carbamimidoyl-1H-indol-5-yl)ethyl]-4-[1-(3-dimethylaminopropyl)-6-oxo-1,6-dihydropyridin-3-yl] benzamide;
4-(2-Amino-1,1-dimethylethyl)-N-(2-[3-carbamimidoylindol-5-yl]ethyl)benzamide; and
N-(2-[3-Carbamimidoylindol-5-yl]ethyl)-4-pyrid-4-ylbenzamide.

29. A pharmaceutical composition comprising a pharmaceutically effective amount of a compound according to claim 1 and a pharmaceutically acceptable carrier.

30. A method for treating a patient suffering from a physiological condition capable of being modulated by inhibiting activity of Factor Xa comprising administering to said patient a pharmaceutically effective amount of a compound according to claim 1.

31. The method according to claim 30 wherein the physiological condition is abnormal thrombus formation, acute myocardial infarction, unstable angina, thromboembolism, acute vessel closure associated with thrombolytic therapy, percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, a risk of pulmonary thromboembolism, or of disseminated systemic intravascular coagulopathy occurring in vascular systems during septic shock 32.

32. The method according to claim 30 wherein the physiological condition is abnormal thrombus formation, acute myocardial infarction, unstable angina, thromboembolism, acute vessel closure associated with thrombolytic therapy, transient ischemic attacks, intermittent claudication or bypass grafting of the coronary or peripheral arteries, restenosis post coronary or venous angioplasty, pathologic thrombus formation occurring in the veins of the lower extremities following abdominal, knee or hip surgery or a risk of pulmonary thromboembolism.

33. The method according to claim 30 wherein the physiological condition is stroke, vessel luminal narrowing, maintenance of vascular access patency in long-term hemodialysis patients, or disseminated systemic intravascular coagulopathy occurring in vascular systems during septic shock, or cancer.

34. A method of inhibiting Factor Xa comprising contacting a Factor Xa inhibitory amount of a compound according to claim 1 with a composition containing Factor Xa.

35. A method of inhibiting the formation of thrombin comprising contacting a Factor Xa inhibitory amount of a compound according to claim 1 with a composition containing Factor Xa.

* * * * *